United States Patent
Andersen et al.

(10) Patent No.: US 9,534,209 B2
(45) Date of Patent: Jan. 3, 2017

(54) METHODS AND TOOLS FOR IDENTIFICATION OF RSK/MSK KINASE INHIBITORS

(71) Applicants: Aarhus Universitet, Århus C (DK); Region Midtjylland, Viborg (DK)

(72) Inventors: Jacob Lauwring Andersen, Århus V (DK); Borbala Gesser, Hasselager (DK); Poul Nissen, Risskov (DK); Lars Iversen, Odense M (DK)

(73) Assignees: Aarhus Universitet, Aarhus (DK); Region Midtjylland, Viborg (DK)

( * ) Notice: Subject to any disclaimer, the term of this patent is extended or adjusted under 35 U.S.C. 154(b) by 73 days.

(21) Appl. No.: 14/431,008

(22) PCT Filed: Sep. 30, 2013

(86) PCT No.: PCT/DK2013/050309
§ 371 (c)(1),
(2) Date: Mar. 25, 2015

(87) PCT Pub. No.: WO2014/048442
PCT Pub. Date: Apr. 3, 2014

(65) Prior Publication Data
US 2015/0247133 A1 Sep. 3, 2015

(30) Foreign Application Priority Data
Sep. 28, 2012 (DK) .................. 2012 70593

(51) Int. Cl.
| | |
|---|---|
| *C12N 9/12* | (2006.01) |
| *C30B 29/58* | (2006.01) |
| *C30B 7/00* | (2006.01) |
| *C40B 30/02* | (2006.01) |
| *G06F 19/12* | (2011.01) |
| *G06F 19/16* | (2011.01) |
| *G06F 19/00* | (2011.01) |

(52) U.S. Cl.
CPC .......... *C12N 9/12* (2013.01); *C12Y 207/11001* (2013.01); *C30B 7/00* (2013.01); *C30B 29/58* (2013.01); *C40B 30/02* (2013.01); *G06F 19/12* (2013.01); *G06F 19/16* (2013.01); *G06F 19/706* (2013.01); *C07K 2319/21* (2013.01)

(58) Field of Classification Search
None
See application file for complete search history.

(56) References Cited

U.S. PATENT DOCUMENTS 4,554,101 A 11/1985 Hopp

OTHER PUBLICATIONS

McPherson, A. Current Approaches to Macromolecular Crystallization. European Journal of Biochemistry. 1990. vol. 189, pp. 1-23.*

Cudney R. Protein Crystallization and Dumb Luck. The Rigaku Journal. 1999. vol. 16, No. 1, pp. 1-7.*

Mrowietz, Ulrich et al., "Dimethylfumarate for psoriasis: more than a dietary curiosity*", Trends in Molecular Medicine, vol. 11, No. 1, Jan. 2005, pp. 43-48.

Afonine, P.V. et al; "The Phenix refinement framework"; CCP4 Newsletter, 42, (2005), p. 1-7.

Alessi, Dario R.; "The protein kinase C inhibitors Ro 31820 and GF 109203X are equally potent inbibitors of MAPKAP kinase 1betal (Rsk-s) and p70 S6 kinase"; FEBS; 1997, p. 121-123.

Altmeyer, P.J—et al; "Antipsoriatic effect of fumaric acid derivatives"; Journal of the American Academy of Dermatology; 1994, p. 977-981.

BG12: "BG 00012, BG-12/Oral Fumarate, FAG201, second-generation fumarate derivative—Fumapharm/Biogen Idec"; Drugs R D 6,; 2005, p. 229-230.

Breuer, K. et al; "Therapy of noninfectious granulomatous skin diseases with fumaric acid esters"; British Journal of Dermatology, 2005, p. 1290-1295.

Brewer, L. et al; "Fumaric acid esters in the management of severe psoriasis"; Clinical Dermatology, 2007, p. 246-249.

Cohen, M. S. et al; "Structural Bioinformaatics-Based Design of Selective, Irreversible Kinase Inhibitors"; Science 208, 1318-1321, May 27, 2005.

Cross, S. A. et al; "Dimethyl Fumarate, an Immune Modulator and Inducer of the Antioxidant Response, Suppresses HIV Replication and Macrophage-Mediated Neurotoxicity: A Novel Candidate for HIV Neuroprotection"; J. Immunol 1987, 5015-5025, (2011).

De Jong, R. et al; "Selective stimulation of T helper 2 cytokine responses by the anti-psoriasis agent monomethylfumarate"; European Journal of Immunol 26; 2067-2074; 1996.

Eberle, F. et al; "Fumaric Acid Esters in Severe Ulcerative Necrobiosis Lipoidica: A Case Report and Evaluation of Current Therapies"; Acta Dermato-Venereologica 90; 104-106; 2010.

Eberlein-König, B. et al; "Disseminated Granuloma Annulare—Treatment with Fumaric Acid Esters"; Dermatology 2005, p. 223-226.

Edgar, Robert C. et al; "MUSCLE: multiple sequence alignment with high accuracy and high throughput"; Nucleic Acids Research, Mar. 19, 2004, vol. 32, No. 5, p. 1792-1797.

Ellrichmann, G. et al; "Efficacy of Fumaric Acid Esters in the R6/2 and YAC128 Models of Huntington's Disease"; PLoS ONe 6, (2011), p. 1-11, e16172.

Emsley, P. et al; "Coot: model-building tools for molecular graphics"; Acta Crystallographica Section D 60, 2126-2132 (2004).

Gambichler, T. et al; "Clearance of necrobiosis lipoidica with fumaric acid esters"; Dermatology 2003; 207:422-424.

Gesser, B. et al; "Dimethylfumarate inhibits MIF-induced proliferation of keratinocytes by inhibiting MSK1 and RSK1 activation and by inducing nuclear p-c-Jun (S63) and p-p53 (S15) expression"; Inflammation Research; Official Journal of: The International Association of Inflammation Societies the European Histamine Research Society.

(Continued)

*Primary Examiner* — Suzanne M Noakes
(74) *Attorney, Agent, or Firm* — Dinsmore & Shohl LLP; Weston Gould

(57) ABSTRACT

The present invention concerns 3D-crystals of complexes of ribosomal S6 kinase (RSK) and mitogen- and stress-activated protein kinase (MSK) proteins and their ligands, as well as methods for crystallization, three-dimensional structure determination and structure assisted methods for identifying ligands of said proteins.

18 Claims, 10 Drawing Sheets

(56) References Cited

OTHER PUBLICATIONS

Gesser, B. et al; "Dimethylfumarate Specifically Inhibits the Mitogen and Stress-Activated Kinases 1 and 2 (MSK1/2): Possible Role for its Anti-Psoriatic Effect"; Journal of Investigative Dermatology 127; 2129-2137 (May 10, 2007).
Ghashghaeinia, M. et al; "Targeting glutathione by dimethylfumarate protects against experimental malaria by enhancing erythorocyte cell membrane scrambling"; American Journal of Physiol Cell Physiol 299; 2010, C791-C804.
Ghoreschi, K. et al; "Fumarates improve psoriasis and multiple sclerosis by inducing type II dendritic cells"; Journal of Experimental Medicine 208, 2291-2302, doi: 10.1084/jem.2010977 (2011).
Guenova, E. et al; "Treatment of Recurrent Aphthous Stomatitis With Fumaric Acid Esters"; Arch Dermatol 147, 282-284; 2011.
Gutzmer, R. et al; "Erfolgreiche Therapie einer Haut- und Lungensarkoidose mit Fumarsäureestern"; Hausartz 55, 553-557; 2004.
Heinz, C et al; "Improvement of Noninfectious Uveitis With Fumaric Acid Esters: Results of a pilot study"; Arch Ophthalmol, vol. 125; 2007.
Hoefnagel, J.J. et al; "Long-term safety aspects of systemic therapy with fumaric acid esters in severe psoriasis"; British Journal of Dermatology, 2003, p. 363-369.
Jensen, C.J. et al; "90-kDa Ribosomal S6 Kinase Is Phosphorylated and Activated by 3-Phosphoinositide-dependelt Protein Kinase-1"; Journal of Biological Chemistry; 1999, p. 27168-76.
Kabsch, Wolfgang; "Automatic Processing of Rotation Diffration Data from Crystals of Initially Unknown Symmetry and Cell Constants"; Journal of Applied Cyrstallography 26, 795-800; 1993.
Kappos, L. et al; "Effect of BG-12 on contrast-enhanced lesions in patients with relapsing-remitting multiple sclerosis:subgroup analyses from the phase 2b study"; Multiple Sclerosis Journal 18; 2012, p. 314-321.
Kappos, L. et al; "Efficacy and safety of oral fumarate in patients with relapsing-remitting multiple sclerosis: a multicentre, randomised, doube-blind, placebo-controlled phase IIb study"; Lancet 2008, vol. 372, p. 1463-77.
Kleine, R. et al; Fumarsäureestertherapei bei einer jungen Patientin mit ausgeprägter Cheilitis granulomatosa; Hautarzt 62, 940-943; 2011.
Kolbach, D.N. et al; "Fumaric acid therapy in psoriasis: Results and side effects of 2 years of treatment", Journal of Academy of Dermatoloty, 1992, p. 769-771.
Kragballe, K. et al; "Increased DNA synthesis of uninvolved psoriatic epidermis is maintained in vitro"; British Journal of Dermatology 112; 263-270; 1985.
Kreuter, A. et al; "Fumaric acid esters in necrobiosis lipoidica: results of a prospective noncontrolled study"; British Journal of Dermatology; 2005; 153; 802-807.
Loewe, R. et al; "Dimethylfumarate imparis melanoma growth and metastasis"; Cancer Research 66, 11888-11896; Dec. 15, 2006.
Malakhova, M. et al; "Structural basis for activation of the autoinhibitory C-terminal kinase domain of p90 RSK2"; Nat. Struc Mol Biol, 2008, p. 112-113.
Malakhova, M. et al; "The Crystal Structure of the Active Form of the C-Terminal Kinase Domain of Mitogen- and Stress-Activated Progein Kinase 1"; Journal of Molecular Biology, Academic Press, United Kingdom; vol. 399, No. 1, May 28, 2010, p. 41-52.
McCoy, A. J. et al; "Phaser crystallographic software"; Journal of Applied Crystallograpy 40, 658-674 (2007).
Medscape Second BG-12 Trial Positive in MS; Accessed on Feb. 1, 2012.
Meili-Butz, S. et al; "Dimethyl fumarate, a small molecule drug for psoriasis, inhibits Nuclear Factor-kB and reduces myocardinal infarct size in rats"; European Journal of Pharmacology; 586, 251-258, doi: 10.1016/j. ejphar (2008).
Meissner, M. et al; "Suppression of VEGFR2 Expression in Human Endothelial Cells by Dimethylfumarate Treatment: Evidence for Anti-Angiogenic Action"; Journal of Investigative Dermatology 131; 1356-1364, (Mar. 24, 2011).
Mrowietz, U. et al; "Treatment of psoriasis with fumaric acid esters: results of a prospective multicentre study"; British Journal of Dermatology, 1998, p. 43-48.

Nguyen, Tam Luong et al; Homology model of RSK2 N-terminal kinase domain, structure based identification of novel SK2 inhibitors, and preliminary common pharmacophore; Bioorganic & Medicinal Chemistry; 14; 6097-6105; 2006.
Nieboer, C et al; "Systemic therapy with fumaric acid derivates: New possibilities in the treatment of psoriasis"; Dermatologica 1977, p. 601-608.
Otkjaer, K. et al; "IL-20 gene expression is induced by IL-1beta through mitogen-activated protein kinase and NF-kappaB-dependent mechanisms" Journal of Investigative Dermatology 127, 1326-1336 (2007).
Peng, H. et al; Dimethyl Fumarate Inhibits Dendritic Cell Maturation via Nuclear Factor kB (NF-kB) and Extracellular Signal-regulated Kinase 1 and 2 (ERK1/2) and Mitogen Stress-activated Kinase 1 (MSK1) Signaling. The Journal of Biological Chemistry vol. 287, No. 33, pp. 28017-28026; 2012.
Rostami-Yazdi, M. et al; "Detection of Metabolites of Fumaric Acid Esters in Human Urine: Implications for Their Mode of Action"; Journal of Investigative Dermatology (2009).
Schilling, S. et al; "Fumaaric acid esters are effective in chronic experimental autoimmune encephalomyelitis and suppress macrophage infiltration"; Clinical & Experimental Immunology 145, 2006, p. 101-107.
Schimrigk, S. et al; "Oral fumaric acid esters for the treatment of active multiple sclerosis: an open-label, baseline-controlled pilot study"; European Journal of Neurology 2006, p. 604-610.
Schulze-Dirks, A. et al; Granuloma annulare disseminatum— erfolgreiche Therapie mit Fumarsäureester; Hautarzt 52, 228-230; 2001.
Schweckendiek, W; "Treatment of psoriasis vulgaris" Med Monatsschr 13; 103-104 (1959).
Seidel, P. et al; Dimethhylfumarate inhibits NF-(kappa)B function at multiple levels to limit airway smooth muscle cell cytokine secretion. Am J Physiol Lung Cell Mol Physiol 297; L326-L339; 2009.
Seidel, P. et al; "DMF inhibits PDGF-BB induced airway smooth muscle cell proliferation through induction of heme-oxygenase-1"; Respiratory Research (2010).
Serafimova, I. M et al; "Reversible targeting of noncatalytic cysteines with chemically tuned electrophiles"; Nature Chemical Biology, vol. 8, No. 5, May 2012, pp. 471-476.
Smith, Jeffrey A. et al; "Identification of the First Specific Inhibitor of p90 Ribosomal S6 Kinase (RSK) Reveals an Unexpected Role for RSK in Cancer Cell Proliferation"; Cancer Research; 1027-1034; 2007.
Thio, H.B. et al; "Long-term systemic therapy with dimethylfumarate and monoethylfumarate (Fumaderm) in psoriasis"; Journal of the European Academy of Dermatology and Venerology, vol. 4, 1995 35-40.
Treumer, F. et al; "Dimethylfumarate Is a Potent Inducer af Apoptosis in Human T Cells"; Journal of Investigative Dermatology 121, 1383-1388; 2003.
Valero, T. et al; "Combination of Dacarbazine and Dimethylfumarate Efficiently Reduces Melanoma Lymph Node Metastasis"; Journal of Investigative Dermatology 130, 1087-1094, 2010.
Vandermeeren, Marc et al; "Dimethylfumarate Is an Inhibitor of Cytokine-Induced E-Selectin, VCAM-1, and ICAM-1 Expression in Human Endothelial Cells"; Biochemical and Biophysical Research Communications 234, 19-23; 1997.
Venten, N. et al; "Treatment of therapy-resistant Alopecia areata with fumaric acid esters"; European Journal of Medical Research; 11, 300-305; Jul. 31, 2006.
Weber, O. et al; "Treatment of Disseminated Granuloma Annulare with Low-dose Fumaric Acid"; Acta Dermato-Venereologica 89; 2009, p. 295-298.
Wilms, H et al; "Dimethylfumarate inhibits microglial and astrocytic inflammation by suppressing the synthesis of nitric oxide, IL-1beta, TNF-alpha and IL-6 in an in-vitro model of brain inflammation"; Journal of Neuroinflammation; 7; 2010, p. 1-8.
Yamazoe, Yuzuru et al; "Dimethylfumarate inhibits tumor cell invasion and metastasis by suppressing the expression and activities of matrix metalloproteinasis in melanoma cells"; Cell Biology International 33; 1087-1094; 2009.

* cited by examiner

| Sequence # | 1 | 2 | 3 | 4 | 5 |
|---|---|---|---|---|---|
| Kinase | mRSK2 | mRSK2 | hRSK1 | hRSK2 | hRSK3 |
| % Identity to #1 | 100,0 | 100,0 | 79,6 | 99,7 | 80,8 |

| Sequence # | 6 | 7 | 8 | 9 | 10 |
|---|---|---|---|---|---|
| Kinase | hRSK4 | hMSK1 | hMSK2 | mRSK1 | mRSK2 |
| % Identity to #1 | 74,6 | 39,0 | 37,7 | 80,2 | 99,7 |

| Sequence # | 11 | 12 | 13 | 14 | 15 |
|---|---|---|---|---|---|
| Kinase | mRSK3 | mRSK4 | mMSK1 | mMSK2 | rRSK1 |
| % Identity to #1 | 80,8 | 71,3 | 33,3 | 37,4 | 79,3 |

| Sequence # | 16 | 17 | 18 | 19 | 20 |
|---|---|---|---|---|---|
| Kinase | rRSK2 | rRSK3 | rRSK4 | rMSK1 | rMSK2 |
| % Identity to #1 | 99,4 | 80,8 | 72,4 | 36,2 | 37,7 |

Fig. 6,

SEQUENCE LISTING

```
<160> NUMBER OF SEQ ID NOS: 20

<210> SEQ ID NO 1
<211> LENGTH: 342
<212> TYPE: PRT
<213> ORGANISM: Mus musculus
<220> FEATURE:
<221> NAME/KEY: MISC_FEATURE
<222> LOCATION: (1)..(342)
<223> OTHER INFORMATION: Murine C-terminal domain of RSK2 used for
      crystallization

<400> SEQUENCE: 1

Gly Gln Thr Val Gly Val His Ser Ile Val Gln Gln Leu His Arg Asn
1               5                   10                  15

Ser Ile Gln Phe Thr Asp Gly Tyr Glu Val Lys Glu Asp Ile Gly Val
            20                  25                  30

Gly Ser Tyr Ser Val Cys Lys Arg Cys Ile His Lys Ala Thr Asn Met
        35                  40                  45

Glu Phe Ala Val Lys Ile Ile Asp Lys Ser Lys Arg Asp Pro Thr Glu
    50                  55                  60

Glu Ile Glu Ile Leu Leu Arg Tyr Gly Gln His Pro Asn Ile Ile Thr
65                  70                  75                  80

Leu Lys Asp Val Tyr Asp Asp Gly Lys Tyr Val Tyr Val Val Thr Glu
                85                  90                  95

Leu Met Lys Gly Gly Glu Leu Leu Asp Lys Ile Leu Arg Gln Lys Phe
            100                 105                 110

Phe Ser Glu Arg Glu Ala Ser Ala Val Leu Phe Thr Ile Thr Lys Thr
        115                 120                 125

Val Glu Tyr Leu His Ala Gln Gly Val Val His Arg Asp Leu Lys Pro
    130                 135                 140

Ser Asn Ile Leu Tyr Val Asp Glu Ser Gly Asn Pro Glu Ser Ile Arg
145                 150                 155                 160

Ile Cys Asp Phe Gly Phe Ala Lys Gln Leu Arg Ala Glu Asn Gly Leu
                165                 170                 175

Leu Met Thr Pro Cys Tyr Thr Ala Asn Phe Val Ala Pro Glu Val Leu
            180                 185                 190

Lys Arg Gln Gly Tyr Asp Ala Ala Cys Asp Ile Trp Ser Leu Gly Val
        195                 200                 205

Leu Leu Tyr Thr Met Leu Thr Gly Tyr Thr Pro Phe Ala Asn Gly Pro
    210                 215                 220

Asp Asp Thr Pro Glu Glu Ile Leu Ala Arg Ile Gly Ser Gly Lys Phe
225                 230                 235                 240

Ser Leu Ser Gly Gly Tyr Trp Asn Ser Val Ser Asp Thr Ala Lys Asp
                245                 250                 255

Leu Val Ser Lys Met Leu His Val Asp Pro His Gln Arg Leu Thr Ala
            260                 265                 270
```

```
Ala Leu Val Leu Arg His Pro Trp Ile Val His Trp Asp Gln Leu Pro
            275                 280                 285

Gln Tyr Gln Leu Asn Arg Gln Asp Ala Pro His Leu Val Lys Gly Ala
        290                 295                 300

Met Ala Ala Thr Tyr Ser Ala Leu Asn Arg Asn Gln Ser Pro Val Leu
305                 310                 315                 320

Glu Pro Val Gly Arg Ser Thr Leu Ala Gln Arg Arg Gly Ile Lys Lys
                325                 330                 335

Ile Thr Ser Thr Ala Leu
            340

<210> SEQ ID NO 2
<211> LENGTH: 341
<212> TYPE: PRT
<213> ORGANISM: Mus musculus
<220> FEATURE:
<221> NAME/KEY: MISC_FEATURE
<222> LOCATION: (1)..(341)
<223> OTHER INFORMATION: Murine C-terminal domain of RSK2 used for
      crystallization, without N-terminal G from TEV protease cleavage
      site

<400> SEQUENCE: 2

Gln Thr Val Gly Val His Ser Ile Val Gln Gln Leu His Arg Asn Ser
1               5                   10                  15

Ile Gln Phe Thr Asp Gly Tyr Glu Val Lys Glu Asp Ile Gly Val Gly
            20                  25                  30

Ser Tyr Ser Val Cys Lys Arg Cys Ile His Lys Ala Thr Asn Met Glu
        35                  40                  45

Phe Ala Val Lys Ile Ile Asp Lys Ser Lys Arg Asp Pro Thr Glu Glu
    50                  55                  60

Ile Glu Ile Leu Leu Arg Tyr Gly Gln His Pro Asn Ile Ile Thr Leu
65                  70                  75                  80

Lys Asp Val Tyr Asp Asp Gly Lys Tyr Val Tyr Val Val Thr Glu Leu
                85                  90                  95

Met Lys Gly Gly Glu Leu Leu Asp Lys Ile Leu Arg Gln Lys Phe Phe
            100                 105                 110

Ser Glu Arg Glu Ala Ser Ala Val Leu Phe Thr Ile Thr Lys Thr Val
        115                 120                 125

Glu Tyr Leu His Ala Gln Gly Val Val His Arg Asp Leu Lys Pro Ser
    130                 135                 140

Asn Ile Leu Tyr Val Asp Glu Ser Gly Asn Pro Glu Ser Ile Arg Ile
145                 150                 155                 160

Cys Asp Phe Gly Phe Ala Lys Gln Leu Arg Ala Glu Asn Gly Leu Leu
                165                 170                 175

Met Thr Pro Cys Tyr Thr Ala Asn Phe Val Ala Pro Glu Val Leu Lys
            180                 185                 190

Arg Gln Gly Tyr Asp Ala Ala Cys Asp Ile Trp Ser Leu Gly Val Leu
        195                 200                 205

Leu Tyr Thr Met Leu Thr Gly Tyr Thr Pro Phe Ala Asn Gly Pro Asp
    210                 215                 220

Asp Thr Pro Glu Glu Ile Leu Ala Arg Ile Gly Ser Gly Lys Phe Ser
225                 230                 235                 240

Leu Ser Gly Gly Tyr Trp Asn Ser Val Ser Asp Thr Ala Lys Asp Leu
                245                 250                 255

Val Ser Lys Met Leu His Val Asp Pro His Gln Arg Leu Thr Ala Ala
            260                 265                 270
```

```
Leu Val Leu Arg His Pro Trp Ile Val His Trp Asp Gln Leu Pro Gln
        275                 280                 285

Tyr Gln Leu Asn Arg Gln Asp Ala Pro His Leu Val Lys Gly Ala Met
290                 295                 300

Ala Ala Thr Tyr Ser Ala Leu Asn Arg Asn Gln Ser Pro Val Leu Glu
305                 310                 315                 320

Pro Val Gly Arg Ser Thr Leu Ala Gln Arg Arg Gly Ile Lys Lys Ile
                325                 330                 335

Thr Ser Thr Ala Leu
            340

<210> SEQ ID NO 3
<211> LENGTH: 735
<212> TYPE: PRT
<213> ORGANISM: Homo sapiens
<220> FEATURE:
<221> NAME/KEY: MISC_FEATURE
<222> LOCATION: (1)..(735)
<223> OTHER INFORMATION: Human RSK1

<400> SEQUENCE: 3

Met Pro Leu Ala Gln Leu Lys Glu Pro Trp Pro Leu Met Glu Leu Val
1               5                   10                  15

Pro Leu Asp Pro Glu Asn Gly Gln Thr Ser Gly Glu Glu Ala Gly Leu
            20                  25                  30

Gln Pro Ser Lys Asp Glu Gly Val Leu Lys Glu Ile Ser Ile Thr His
        35                  40                  45

His Val Lys Ala Gly Ser Glu Lys Ala Asp Pro Ser His Phe Glu Leu
    50                  55                  60

Leu Lys Val Leu Gly Gln Gly Ser Phe Gly Lys Val Phe Leu Val Arg
65                  70                  75                  80

Lys Val Thr Arg Pro Asp Ser Gly His Leu Tyr Ala Met Lys Val Leu
                85                  90                  95

Lys Lys Ala Thr Leu Lys Val Arg Asp Arg Val Arg Thr Lys Met Glu
            100                 105                 110

Arg Asp Ile Leu Ala Asp Val Asn His Pro Phe Val Val Lys Leu His
        115                 120                 125

Tyr Ala Phe Gln Thr Glu Gly Lys Leu Tyr Leu Ile Leu Asp Phe Leu
    130                 135                 140

Arg Gly Gly Asp Leu Phe Thr Arg Leu Ser Lys Glu Val Met Phe Thr
145                 150                 155                 160

Glu Glu Asp Val Lys Phe Tyr Leu Ala Glu Leu Ala Leu Gly Leu Asp
                165                 170                 175

His Leu His Ser Leu Gly Ile Ile Tyr Arg Asp Leu Lys Pro Glu Asn
            180                 185                 190

Ile Leu Leu Asp Glu Glu Gly His Ile Lys Leu Thr Asp Phe Gly Leu
        195                 200                 205

Ser Lys Glu Ala Ile Asp His Glu Lys Lys Ala Tyr Ser Phe Cys Gly
    210                 215                 220

Thr Val Glu Tyr Met Ala Pro Glu Val Val Asn Arg Gln Gly His Ser
225                 230                 235                 240

His Ser Ala Asp Trp Trp Ser Tyr Gly Val Leu Met Phe Glu Met Leu
                245                 250                 255

Thr Gly Ser Leu Pro Phe Gln Gly Lys Asp Arg Lys Glu Thr Met Thr
            260                 265                 270
```

-continued

```
Leu Ile Leu Lys Ala Lys Leu Gly Met Pro Gln Phe Leu Ser Thr Glu
            275                 280                 285

Ala Gln Ser Leu Leu Arg Ala Leu Phe Lys Arg Asn Pro Ala Asn Arg
        290                 295                 300

Leu Gly Ser Gly Pro Asp Gly Ala Glu Glu Ile Lys Arg His Val Phe
305                 310                 315                 320

Tyr Ser Thr Ile Asp Trp Asn Lys Leu Tyr Arg Arg Glu Ile Lys Pro
                325                 330                 335

Pro Phe Lys Pro Ala Val Ala Gln Pro Asp Asp Thr Phe Tyr Phe Asp
            340                 345                 350

Thr Glu Phe Thr Ser Arg Thr Pro Lys Asp Ser Pro Gly Ile Pro Pro
        355                 360                 365

Ser Ala Gly Ala His Gln Leu Phe Arg Gly Phe Ser Phe Val Ala Thr
    370                 375                 380

Gly Leu Met Glu Asp Asp Gly Lys Pro Arg Ala Pro Gln Ala Pro Leu
385                 390                 395                 400

His Ser Val Val Gln Gln Leu His Gly Lys Asn Leu Val Phe Ser Asp
                405                 410                 415

Gly Tyr Val Val Lys Glu Thr Ile Gly Val Gly Ser Tyr Ser Glu Cys
            420                 425                 430

Lys Arg Cys Val His Lys Ala Thr Asn Met Glu Tyr Ala Val Lys Val
        435                 440                 445

Ile Asp Lys Ser Lys Arg Asp Pro Ser Glu Glu Ile Glu Ile Leu Leu
    450                 455                 460

Arg Tyr Gly Gln His Pro Asn Ile Ile Thr Leu Lys Asp Val Tyr Asp
465                 470                 475                 480

Asp Gly Lys His Val Tyr Leu Val Thr Glu Leu Met Arg Gly Gly Glu
                485                 490                 495

Leu Leu Asp Lys Ile Leu Arg Gln Lys Phe Phe Ser Glu Arg Glu Ala
            500                 505                 510

Ser Phe Val Leu His Thr Ile Gly Lys Thr Val Glu Tyr Leu His Ser
        515                 520                 525

Gln Gly Val Val His Arg Asp Leu Lys Pro Ser Asn Ile Leu Tyr Val
    530                 535                 540

Asp Glu Ser Gly Asn Pro Glu Cys Leu Arg Ile Cys Asp Phe Gly Phe
545                 550                 555                 560

Ala Lys Gln Leu Arg Ala Glu Asn Gly Leu Leu Met Thr Pro Cys Tyr
                565                 570                 575

Thr Ala Asn Phe Val Ala Pro Glu Val Leu Lys Arg Gln Gly Tyr Asp
            580                 585                 590

Glu Gly Cys Asp Ile Trp Ser Leu Gly Ile Leu Leu Tyr Thr Met Leu
        595                 600                 605

Ala Gly Tyr Thr Pro Phe Ala Asn Gly Pro Ser Asp Thr Pro Glu Glu
    610                 615                 620

Ile Leu Thr Arg Ile Gly Ser Gly Lys Phe Thr Leu Ser Gly Gly Asn
625                 630                 635                 640

Trp Asn Thr Val Ser Glu Thr Ala Lys Asp Leu Val Ser Lys Met Leu
                645                 650                 655

His Val Asp Pro His Gln Arg Leu Thr Ala Lys Gln Val Leu Gln His
            660                 665                 670

Pro Trp Val Thr Gln Lys Asp Lys Leu Pro Gln Ser Gln Leu Ser His
        675                 680                 685

Gln Asp Leu Gln Leu Val Lys Gly Ala Met Ala Ala Thr Tyr Ser Ala
```

```
              690                 695                 700
Leu Asn Ser Ser Lys Pro Thr Pro Gln Leu Lys Pro Ile Glu Ser Ser
705                 710                 715                 720

Ile Leu Ala Gln Arg Arg Val Arg Lys Leu Pro Ser Thr Thr Leu
                725                 730                 735

<210> SEQ ID NO 4
<211> LENGTH: 740
<212> TYPE: PRT
<213> ORGANISM: Homo sapiens
<220> FEATURE:
<221> NAME/KEY: MISC_FEATURE
<222> LOCATION: (1)..(740)
<223> OTHER INFORMATION: Human RSK2

<400> SEQUENCE: 4

Met Pro Leu Ala Gln Leu Ala Asp Pro Trp Gln Lys Met Ala Val Glu
1               5                   10                  15

Ser Pro Ser Asp Ser Ala Glu Asn Gly Gln Gln Ile Met Asp Glu Pro
            20                  25                  30

Met Gly Glu Glu Glu Ile Asn Pro Gln Thr Glu Glu Val Ser Ile Lys
        35                  40                  45

Glu Ile Ala Ile Thr His His Val Lys Glu Gly His Glu Lys Ala Asp
    50                  55                  60

Pro Ser Gln Phe Glu Leu Leu Lys Val Leu Gly Gln Gly Ser Phe Gly
65                  70                  75                  80

Lys Val Phe Leu Val Lys Lys Ile Ser Gly Ser Asp Ala Arg Gln Leu
                85                  90                  95

Tyr Ala Met Lys Val Leu Lys Lys Ala Thr Leu Lys Val Arg Asp Arg
            100                 105                 110

Val Arg Thr Lys Met Glu Arg Asp Ile Leu Val Glu Val Asn His Pro
        115                 120                 125

Phe Ile Val Lys Leu His Tyr Ala Phe Gln Thr Glu Gly Lys Leu Tyr
    130                 135                 140

Leu Ile Leu Asp Phe Leu Arg Gly Gly Asp Leu Phe Thr Arg Leu Ser
145                 150                 155                 160

Lys Glu Val Met Phe Thr Glu Glu Asp Val Lys Phe Tyr Leu Ala Glu
                165                 170                 175

Leu Ala Leu Ala Leu Asp His Leu His Ser Leu Gly Ile Ile Tyr Arg
            180                 185                 190

Asp Leu Lys Pro Glu Asn Ile Leu Leu Asp Glu Glu Gly His Ile Lys
        195                 200                 205

Leu Thr Asp Phe Gly Leu Ser Lys Glu Ser Ile Asp His Glu Lys Lys
    210                 215                 220

Ala Tyr Ser Phe Cys Gly Thr Val Glu Tyr Met Ala Pro Glu Val Val
225                 230                 235                 240

Asn Arg Arg Gly His Thr Gln Ser Ala Asp Trp Trp Ser Phe Gly Val
                245                 250                 255

Leu Met Phe Glu Met Leu Thr Gly Thr Leu Pro Phe Gln Gly Lys Asp
            260                 265                 270

Arg Lys Glu Thr Met Thr Met Ile Leu Lys Ala Lys Leu Gly Met Pro
        275                 280                 285

Gln Phe Leu Ser Pro Glu Ala Gln Ser Leu Leu Arg Met Leu Phe Lys
    290                 295                 300

Arg Asn Pro Ala Asn Arg Leu Gly Ala Gly Pro Asp Gly Val Glu Glu
305                 310                 315                 320
```

```
Ile Lys Arg His Ser Phe Phe Ser Thr Ile Asp Trp Asn Lys Leu Tyr
            325                 330                 335

Arg Arg Glu Ile His Pro Pro Phe Lys Pro Ala Thr Gly Arg Pro Glu
            340                 345                 350

Asp Thr Phe Tyr Phe Asp Pro Glu Phe Thr Ala Lys Thr Pro Lys Asp
            355                 360                 365

Ser Pro Gly Ile Pro Ser Ala Asn Ala His Gln Leu Phe Arg Gly
    370                 375                 380

Phe Ser Phe Val Ala Ile Thr Ser Asp Asp Glu Ser Gln Ala Met Gln
385                 390                 395                 400

Thr Val Gly Val His Ser Ile Val Gln Gln Leu His Arg Asn Ser Ile
            405                 410                 415

Gln Phe Thr Asp Gly Tyr Glu Val Lys Glu Asp Ile Gly Val Gly Ser
            420                 425                 430

Tyr Ser Val Cys Lys Arg Cys Ile His Lys Ala Thr Asn Met Glu Phe
            435                 440                 445

Ala Val Lys Ile Ile Asp Lys Ser Lys Arg Asp Pro Thr Glu Glu Ile
            450                 455                 460

Glu Ile Leu Leu Arg Tyr Gly Gln His Pro Asn Ile Ile Thr Leu Lys
465                 470                 475                 480

Asp Val Tyr Asp Asp Gly Lys Tyr Val Tyr Val Thr Glu Leu Met
            485                 490                 495

Lys Gly Gly Glu Leu Leu Asp Lys Ile Leu Arg Gln Lys Phe Phe Ser
            500                 505                 510

Glu Arg Glu Ala Ser Ala Val Leu Phe Thr Ile Thr Lys Thr Val Glu
            515                 520                 525

Tyr Leu His Ala Gln Gly Val Val His Arg Asp Leu Lys Pro Ser Asn
            530                 535                 540

Ile Leu Tyr Val Asp Glu Ser Gly Asn Pro Glu Ser Ile Arg Ile Cys
545                 550                 555                 560

Asp Phe Gly Phe Ala Lys Gln Leu Arg Ala Glu Asn Gly Leu Leu Met
            565                 570                 575

Thr Pro Cys Tyr Thr Ala Asn Phe Val Ala Pro Glu Val Leu Lys Arg
            580                 585                 590

Gln Gly Tyr Asp Ala Ala Cys Asp Ile Trp Ser Leu Gly Val Leu Leu
            595                 600                 605

Tyr Thr Met Leu Thr Gly Tyr Thr Pro Phe Ala Asn Gly Pro Asp Asp
            610                 615                 620

Thr Pro Glu Glu Ile Leu Ala Arg Ile Gly Ser Gly Lys Phe Ser Leu
625                 630                 635                 640

Ser Gly Gly Tyr Trp Asn Ser Val Ser Asp Thr Ala Lys Asp Leu Val
            645                 650                 655

Ser Lys Met Leu His Val Asp Pro His Gln Arg Leu Thr Ala Ala Leu
            660                 665                 670

Val Leu Arg His Pro Trp Ile Val His Trp Asp Gln Leu Pro Gln Tyr
            675                 680                 685

Gln Leu Asn Arg Gln Asp Ala Pro His Leu Val Lys Gly Ala Met Ala
            690                 695                 700

Ala Thr Tyr Ser Ala Leu Asn Arg Asn Gln Ser Pro Val Leu Glu Pro
705                 710                 715                 720

Val Gly Arg Ser Thr Leu Ala Gln Arg Arg Gly Ile Lys Lys Ile Thr
            725                 730                 735
```

Ser Thr Ala Leu
        740

<210> SEQ ID NO 5
<211> LENGTH: 733
<212> TYPE: PRT
<213> ORGANISM: Homo sapiens
<220> FEATURE:
<221> NAME/KEY: MISC_FEATURE
<222> LOCATION: (1)..(733)
<223> OTHER INFORMATION: Human RSK3

<400> SEQUENCE: 5

Met Asp Leu Ser Met Lys Lys Phe Ala Val Arg Arg Phe Phe Ser Val
1               5                   10                  15

Tyr Leu Arg Arg Lys Ser Arg Ser Lys Ser Ser Ser Leu Ser Arg Leu
            20                  25                  30

Glu Glu Glu Gly Val Val Lys Glu Ile Asp Ile Ser His His Val Lys
        35                  40                  45

Glu Gly Phe Glu Lys Ala Asp Pro Ser Gln Phe Glu Leu Leu Lys Val
    50                  55                  60

Leu Gly Gln Gly Ser Tyr Gly Lys Val Phe Leu Val Arg Lys Val Lys
65                  70                  75                  80

Gly Ser Asp Ala Gly Gln Leu Tyr Ala Met Lys Val Leu Lys Lys Ala
                85                  90                  95

Thr Leu Lys Val Arg Asp Arg Val Arg Ser Lys Met Glu Arg Asp Ile
            100                 105                 110

Leu Ala Glu Val Asn His Pro Phe Ile Val Lys Leu His Tyr Ala Phe
        115                 120                 125

Gln Thr Glu Gly Lys Leu Tyr Leu Ile Leu Asp Phe Leu Arg Gly Gly
    130                 135                 140

Asp Leu Phe Thr Arg Leu Ser Lys Glu Val Met Phe Thr Glu Glu Asp
145                 150                 155                 160

Val Lys Phe Tyr Leu Ala Glu Leu Ala Leu Ala Leu Asp His Leu His
                165                 170                 175

Ser Leu Gly Ile Ile Tyr Arg Asp Leu Lys Pro Glu Asn Ile Leu Leu
            180                 185                 190

Asp Glu Glu Gly His Ile Lys Ile Thr Asp Phe Gly Leu Ser Lys Glu
        195                 200                 205

Ala Ile Asp His Asp Lys Arg Ala Tyr Ser Phe Cys Gly Thr Ile Glu
    210                 215                 220

Tyr Met Ala Pro Glu Val Val Asn Arg Arg Gly His Thr Gln Ser Ala
225                 230                 235                 240

Asp Trp Trp Ser Phe Gly Val Leu Met Phe Glu Met Leu Thr Gly Ser
                245                 250                 255

Leu Pro Phe Gln Gly Lys Asp Arg Lys Glu Thr Met Ala Leu Ile Leu
            260                 265                 270

Lys Ala Lys Leu Gly Met Pro Gln Phe Leu Ser Gly Glu Ala Gln Ser
        275                 280                 285

Leu Leu Arg Ala Leu Phe Lys Arg Asn Pro Cys Asn Arg Leu Gly Ala
    290                 295                 300

Gly Ile Asp Gly Val Glu Glu Ile Lys Arg His Pro Phe Phe Val Thr
305                 310                 315                 320

Ile Asp Trp Asn Thr Leu Tyr Arg Lys Glu Ile Lys Pro Pro Phe Lys
                325                 330                 335

Pro Ala Val Gly Arg Pro Glu Asp Thr Phe His Phe Asp Pro Glu Phe

```
                        340                 345                 350
Thr Ala Arg Thr Pro Thr Asp Ser Pro Gly Val Pro Pro Ser Ala Asn
                355                 360                 365
Ala His His Leu Phe Arg Gly Phe Ser Phe Val Ala Ser Ser Leu Ile
            370                 375                 380
Gln Glu Pro Ser Gln Gln Asp Leu His Lys Val Pro Val His Pro Ile
385                 390                 395                 400
Val Gln Gln Leu His Gly Asn Asn Ile His Phe Thr Asp Gly Tyr Glu
                405                 410                 415
Ile Lys Glu Asp Ile Gly Val Gly Ser Tyr Ser Val Cys Lys Arg Cys
            420                 425                 430
Val His Lys Ala Thr Asp Thr Glu Tyr Ala Val Lys Ile Ile Asp Lys
        435                 440                 445
Ser Lys Arg Asp Pro Ser Glu Glu Ile Glu Ile Leu Leu Arg Tyr Gly
    450                 455                 460
Gln His Pro Asn Ile Ile Thr Leu Lys Asp Val Tyr Asp Asp Gly Lys
465                 470                 475                 480
Phe Val Tyr Leu Val Met Glu Leu Met Arg Gly Gly Glu Leu Leu Asp
                485                 490                 495
Arg Ile Leu Arg Gln Arg Tyr Phe Ser Glu Arg Glu Ala Ser Asp Val
            500                 505                 510
Leu Cys Thr Ile Thr Lys Thr Met Asp Tyr Leu His Ser Gln Gly Val
        515                 520                 525
Val His Arg Asp Leu Lys Pro Ser Asn Ile Leu Tyr Arg Asp Glu Ser
    530                 535                 540
Gly Ser Pro Glu Ser Ile Arg Val Cys Asp Phe Gly Phe Ala Lys Gln
545                 550                 555                 560
Leu Arg Ala Gly Asn Gly Leu Leu Met Thr Pro Cys Tyr Thr Ala Asn
                565                 570                 575
Phe Val Ala Pro Glu Val Leu Lys Arg Gln Gly Tyr Asp Ala Ala Cys
            580                 585                 590
Asp Ile Trp Ser Leu Gly Ile Leu Leu Tyr Thr Met Leu Ala Gly Phe
        595                 600                 605
Thr Pro Phe Ala Asn Gly Pro Asp Asp Thr Pro Glu Glu Ile Leu Ala
    610                 615                 620
Arg Ile Gly Ser Gly Lys Tyr Ala Leu Ser Gly Gly Asn Trp Asp Ser
625                 630                 635                 640
Ile Ser Asp Ala Ala Lys Asp Val Val Ser Lys Met Leu His Val Asp
                645                 650                 655
Pro His Gln Arg Leu Thr Ala Met Gln Val Leu Lys His Pro Trp Val
            660                 665                 670
Val Asn Arg Glu Tyr Leu Ser Pro Asn Gln Leu Ser Arg Gln Asp Val
        675                 680                 685
His Leu Val Lys Gly Ala Met Ala Ala Thr Tyr Phe Ala Leu Asn Arg
    690                 695                 700
Thr Pro Gln Ala Pro Arg Leu Glu Pro Val Leu Ser Ser Asn Leu Ala
705                 710                 715                 720
Gln Arg Arg Gly Met Lys Arg Leu Thr Ser Thr Arg Leu
                725                 730

<210> SEQ ID NO 6
<211> LENGTH: 745
<212> TYPE: PRT
<213> ORGANISM: Homo sapiens
```

```
<220> FEATURE:
<221> NAME/KEY: MISC_FEATURE
<222> LOCATION: (1)..(745)
<223> OTHER INFORMATION: Human RSK4

<400> SEQUENCE: 6

Met Leu Pro Phe Ala Pro Gln Asp Glu Pro Trp Asp Arg Glu Met Glu
1               5                   10                  15

Val Phe Ser Gly Gly Gly Ala Ser Ser Gly Glu Val Asn Gly Leu Lys
            20                  25                  30

Met Val Asp Glu Pro Met Glu Glu Gly Glu Ala Asp Ser Cys His Asp
        35                  40                  45

Glu Gly Val Val Lys Glu Ile Pro Ile Thr His His Val Lys Glu Gly
    50                  55                  60

Tyr Glu Lys Ala Asp Pro Ala Gln Phe Glu Leu Leu Lys Val Leu Gly
65                  70                  75                  80

Gln Gly Ser Phe Gly Lys Val Phe Leu Val Arg Lys Lys Thr Gly Pro
                85                  90                  95

Asp Ala Gly Gln Leu Tyr Ala Met Lys Val Leu Lys Lys Ala Ser Leu
            100                 105                 110

Lys Val Arg Asp Arg Val Arg Thr Lys Met Glu Arg Asp Ile Leu Val
        115                 120                 125

Glu Val Asn His Pro Phe Ile Val Lys Leu His Tyr Ala Phe Gln Thr
    130                 135                 140

Glu Gly Lys Leu Tyr Leu Ile Leu Asp Phe Leu Arg Gly Gly Asp Val
145                 150                 155                 160

Phe Thr Arg Leu Ser Lys Glu Val Leu Phe Thr Glu Glu Asp Val Lys
                165                 170                 175

Phe Tyr Leu Ala Glu Leu Ala Leu Ala Leu Asp His Leu His Gln Leu
            180                 185                 190

Gly Ile Val Tyr Arg Asp Leu Lys Pro Glu Asn Ile Leu Leu Asp Glu
        195                 200                 205

Ile Gly His Ile Lys Leu Thr Asp Phe Gly Leu Ser Lys Glu Ser Val
    210                 215                 220

Asp Gln Glu Lys Lys Ala Tyr Ser Phe Cys Gly Thr Val Glu Tyr Met
225                 230                 235                 240

Ala Pro Glu Val Val Asn Arg Arg Gly His Ser Gln Ser Ala Asp Trp
                245                 250                 255

Trp Ser Tyr Gly Val Leu Met Phe Glu Met Leu Thr Gly Thr Leu Pro
            260                 265                 270

Phe Gln Gly Lys Asp Arg Asn Glu Thr Met Asn Met Ile Leu Lys Ala
        275                 280                 285

Lys Leu Gly Met Pro Gln Phe Leu Ser Ala Glu Ala Gln Ser Leu Leu
    290                 295                 300

Arg Met Leu Phe Lys Arg Asn Pro Ala Asn Arg Leu Gly Ser Glu Gly
305                 310                 315                 320

Val Glu Glu Ile Lys Arg His Leu Phe Phe Ala Asn Ile Asp Trp Asp
                325                 330                 335

Lys Leu Tyr Lys Arg Glu Val Gln Pro Pro Phe Lys Pro Ala Ser Gly
            340                 345                 350

Lys Pro Asp Asp Thr Phe Cys Phe Asp Pro Glu Phe Thr Ala Lys Thr
        355                 360                 365

Pro Lys Asp Ser Pro Gly Leu Pro Ala Ser Ala Asn Ala His Gln Leu
    370                 375                 380
```

```
Phe Lys Gly Phe Ser Phe Val Ala Thr Ser Ile Ala Glu Glu Tyr Lys
385                 390                 395                 400

Ile Thr Pro Ile Thr Ser Ala Asn Val Leu Pro Ile Val Gln Ile Asn
            405                 410                 415

Gly Asn Ala Ala Gln Phe Gly Glu Val Tyr Glu Leu Lys Glu Asp Ile
        420                 425                 430

Gly Val Gly Ser Tyr Ser Val Cys Lys Arg Cys Ile His Ala Thr Thr
        435                 440                 445

Asn Met Glu Phe Ala Val Lys Ile Ile Asp Lys Ser Lys Arg Asp Pro
450                 455                 460

Ser Glu Glu Ile Glu Ile Leu Met Arg Tyr Gly Gln His Pro Asn Ile
465                 470                 475                 480

Ile Thr Leu Lys Asp Val Phe Asp Asp Gly Arg Tyr Val Tyr Leu Val
            485                 490                 495

Thr Asp Leu Met Lys Gly Gly Glu Leu Leu Asp Arg Ile Leu Lys Gln
            500                 505                 510

Lys Cys Phe Ser Glu Arg Glu Ala Ser Asp Ile Leu Tyr Val Ile Ser
        515                 520                 525

Lys Thr Val Asp Tyr Leu His Cys Gln Gly Val Val His Arg Asp Leu
530                 535                 540

Lys Pro Ser Asn Ile Leu Tyr Met Asp Glu Ser Ala Ser Ala Asp Ser
545                 550                 555                 560

Ile Arg Ile Cys Asp Phe Gly Phe Ala Lys Gln Leu Arg Gly Glu Asn
            565                 570                 575

Gly Leu Leu Leu Thr Pro Cys Tyr Thr Ala Asn Phe Val Ala Pro Glu
        580                 585                 590

Val Leu Met Gln Gln Gly Tyr Asp Ala Ala Cys Asp Ile Trp Ser Leu
        595                 600                 605

Gly Val Leu Phe Tyr Thr Met Leu Ala Gly Tyr Thr Pro Phe Ala Asn
        610                 615                 620

Gly Pro Asn Asp Thr Pro Glu Glu Ile Leu Leu Arg Ile Gly Asn Gly
625                 630                 635                 640

Lys Phe Ser Leu Ser Gly Gly Asn Trp Asp Asn Ile Ser Asp Gly Ala
            645                 650                 655

Lys Asp Leu Leu Ser His Met Leu His Met Asp Pro His Gln Arg Tyr
            660                 665                 670

Thr Ala Glu Gln Ile Leu Lys His Ser Trp Ile Thr His Arg Asp Gln
        675                 680                 685

Leu Pro Asn Asp Gln Pro Lys Arg Asn Asp Val Ser His Val Val Lys
        690                 695                 700

Gly Ala Met Val Ala Thr Tyr Ser Ala Leu Thr His Lys Thr Phe Gln
705                 710                 715                 720

Pro Val Leu Glu Pro Val Ala Ala Ser Ser Leu Ala Gln Arg Arg Ser
            725                 730                 735

Met Lys Lys Arg Thr Ser Thr Gly Leu
            740                 745

<210> SEQ ID NO 7
<211> LENGTH: 802
<212> TYPE: PRT
<213> ORGANISM: Homo sapiens
<220> FEATURE:
<221> NAME/KEY: MISC_FEATURE
<222> LOCATION: (1)..(802)
<223> OTHER INFORMATION: Human MSK1
```

<400> SEQUENCE: 7

```
Met Glu Glu Glu Gly Gly Ser Ser Gly Gly Ala Ala Gly Thr Ser Ala
 1               5                  10                  15
Asp Gly Gly Asp Gly Gly Glu Gln Leu Leu Thr Val Lys His Glu Leu
             20                  25                  30
Arg Thr Ala Asn Leu Thr Gly His Ala Glu Lys Val Gly Ile Glu Asn
         35                  40                  45
Phe Glu Leu Leu Lys Val Leu Gly Thr Gly Ala Tyr Gly Lys Val Phe
 50                  55                  60
Leu Val Arg Lys Ile Ser Gly His Asp Thr Gly Lys Leu Tyr Ala Met
 65                  70                  75                  80
Lys Val Leu Lys Lys Ala Thr Ile Val Gln Lys Ala Lys Thr Thr Glu
                 85                  90                  95
His Thr Arg Thr Glu Arg Gln Val Leu Glu His Ile Arg Gln Ser Pro
             100                 105                 110
Phe Leu Val Thr Leu His Tyr Ala Phe Gln Thr Glu Thr Lys Leu His
         115                 120                 125
Leu Ile Leu Asp Tyr Ile Asn Gly Gly Glu Leu Phe Thr His Leu Ser
130                 135                 140
Gln Arg Glu Arg Phe Thr Glu His Glu Val Gln Ile Tyr Val Gly Glu
145                 150                 155                 160
Ile Val Leu Ala Leu Glu His Leu His Lys Leu Gly Ile Ile Tyr Arg
                165                 170                 175
Asp Ile Lys Leu Glu Asn Ile Leu Leu Asp Ser Asn Gly His Val Val
            180                 185                 190
Leu Thr Asp Phe Gly Leu Ser Lys Glu Phe Val Ala Asp Glu Thr Glu
        195                 200                 205
Arg Ala Tyr Ser Phe Cys Gly Thr Ile Glu Tyr Met Ala Pro Asp Ile
210                 215                 220
Val Arg Gly Gly Asp Ser Gly His Asp Lys Ala Val Asp Trp Trp Ser
225                 230                 235                 240
Leu Gly Val Leu Met Tyr Glu Leu Leu Thr Gly Ala Ser Pro Phe Thr
                245                 250                 255
Val Asp Gly Glu Lys Asn Ser Gln Ala Glu Ile Ser Arg Arg Ile Leu
            260                 265                 270
Lys Ser Glu Pro Pro Tyr Pro Gln Glu Met Ser Ala Leu Ala Lys Asp
        275                 280                 285
Leu Ile Gln Arg Leu Leu Met Lys Asp Pro Lys Lys Arg Leu Gly Cys
290                 295                 300
Gly Pro Arg Asp Ala Asp Glu Ile Lys Glu His Leu Phe Phe Gln Lys
305                 310                 315                 320
Ile Asn Trp Asp Asp Leu Ala Ala Lys Lys Val Pro Ala Pro Phe Lys
                325                 330                 335
Pro Val Ile Arg Asp Glu Leu Asp Val Ser Asn Phe Ala Glu Glu Phe
            340                 345                 350
Thr Glu Met Asp Pro Thr Tyr Ser Pro Ala Ala Leu Pro Gln Ser Ser
        355                 360                 365
Glu Lys Leu Phe Gln Gly Tyr Ser Phe Val Ala Pro Ser Ile Leu Phe
370                 375                 380
Lys Arg Asn Ala Ala Val Ile Asp Pro Leu Gln Phe His Met Gly Val
385                 390                 395                 400
Glu Arg Pro Gly Val Thr Asn Val Ala Arg Ser Ala Met Met Lys Asp
                405                 410                 415
```

```
Ser Pro Phe Tyr Gln His Tyr Asp Leu Asp Leu Lys Asp Lys Pro Leu
            420                 425                 430

Gly Glu Gly Ser Phe Ser Ile Cys Arg Lys Cys Val His Lys Lys Ser
        435                 440                 445

Asn Gln Ala Phe Ala Val Lys Ile Ile Ser Lys Arg Met Glu Ala Asn
        450                 455                 460

Thr Gln Lys Glu Ile Thr Ala Leu Lys Leu Cys Glu Gly His Pro Asn
465                 470                 475                 480

Ile Val Lys Leu His Glu Val Phe His Asp Gln Leu His Thr Phe Leu
                485                 490                 495

Val Met Glu Leu Leu Asn Gly Gly Leu Phe Glu Arg Ile Lys Lys
            500                 505                 510

Lys Lys His Phe Ser Glu Thr Glu Ala Ser Tyr Ile Met Arg Lys Leu
        515                 520                 525

Val Ser Ala Val Ser His Met His Asp Val Gly Val Val His Arg Asp
        530                 535                 540

Leu Lys Pro Glu Asn Leu Leu Phe Thr Asp Glu Asn Asp Asn Leu Glu
545                 550                 555                 560

Ile Lys Ile Ile Asp Phe Gly Phe Ala Arg Leu Lys Pro Pro Asp Asn
                565                 570                 575

Gln Pro Leu Lys Thr Pro Cys Phe Thr Leu His Tyr Ala Ala Pro Glu
        580                 585                 590

Leu Leu Asn Gln Asn Gly Tyr Asp Glu Ser Cys Asp Leu Trp Ser Leu
        595                 600                 605

Gly Val Ile Leu Tyr Thr Met Leu Ser Gly Gln Val Pro Phe Gln Ser
        610                 615                 620

His Asp Arg Ser Leu Thr Cys Thr Ser Ala Val Glu Ile Met Lys Lys
625                 630                 635                 640

Ile Lys Lys Gly Asp Phe Ser Phe Glu Gly Glu Ala Trp Lys Asn Val
                645                 650                 655

Ser Gln Glu Ala Lys Asp Leu Ile Gln Gly Leu Leu Thr Val Asp Pro
        660                 665                 670

Asn Lys Arg Leu Lys Met Ser Gly Leu Arg Tyr Asn Glu Trp Leu Gln
        675                 680                 685

Asp Gly Ser Gln Leu Ser Ser Asn Pro Leu Met Thr Pro Asp Ile Leu
        690                 695                 700

Gly Ser Ser Gly Ala Ala Val His Thr Cys Val Lys Ala Thr Phe His
705                 710                 715                 720

Ala Phe Asn Lys Tyr Lys Arg Glu Gly Phe Cys Leu Gln Asn Val Asp
                725                 730                 735

Lys Ala Pro Leu Ala Lys Arg Arg Lys Met Lys Lys Thr Ser Thr Ser
        740                 745                 750

Thr Glu Thr Arg Ser Ser Ser Glu Ser Ser His Ser Ser Ser Ser
        755                 760                 765

His Ser His Gly Lys Thr Thr Pro Thr Lys Thr Leu Gln Pro Ser Asn
        770                 775                 780

Pro Ala Asp Ser Asn Asn Pro Glu Thr Leu Phe Gln Phe Ser Asp Ser
785                 790                 795                 800

Val Ala

<210> SEQ ID NO 8
<211> LENGTH: 772
<212> TYPE: PRT
```

```
<213> ORGANISM: Homo sapiens
<220> FEATURE:
<221> NAME/KEY: MISC_FEATURE
<222> LOCATION: (1)..(772)
<223> OTHER INFORMATION: Human MSK2

<400> SEQUENCE: 8
```

Met Gly Asp Glu Asp Asp Glu Ser Cys Ala Val Glu Leu Arg Ile
1               5                   10                  15

Thr Glu Ala Asn Leu Thr Gly His Glu Lys Val Ser Val Glu Asn
            20                  25                  30

Phe Glu Leu Leu Lys Val Leu Gly Thr Gly Ala Tyr Gly Lys Val Phe
            35                  40                  45

Leu Val Arg Lys Ala Gly Gly His Asp Ala Gly Lys Leu Tyr Ala Met
        50                  55                  60

Lys Val Leu Arg Lys Ala Ala Leu Val Gln Arg Ala Lys Thr Gln Glu
65                  70                  75                  80

His Thr Arg Thr Glu Arg Ser Val Leu Glu Leu Val Arg Gln Ala Pro
                85                  90                  95

Phe Leu Val Thr Leu His Tyr Ala Phe Gln Thr Asp Ala Lys Leu His
            100                 105                 110

Leu Ile Leu Asp Tyr Val Ser Gly Gly Glu Met Phe Thr His Leu Tyr
        115                 120                 125

Gln Arg Gln Tyr Phe Lys Glu Ala Glu Val Arg Val Tyr Gly Gly Glu
130                 135                 140

Ile Val Leu Ala Leu Glu His Leu His Lys Leu Gly Ile Ile Tyr Arg
145                 150                 155                 160

Asp Leu Lys Leu Glu Asn Val Leu Leu Asp Ser Glu Gly His Ile Val
                165                 170                 175

Leu Thr Asp Phe Gly Leu Ser Lys Glu Phe Leu Thr Glu Glu Lys Glu
            180                 185                 190

Arg Thr Phe Ser Phe Cys Gly Thr Ile Glu Tyr Met Ala Pro Glu Ile
        195                 200                 205

Ile Arg Ser Lys Thr Gly His Gly Lys Ala Val Asp Trp Trp Ser Leu
210                 215                 220

Gly Ile Leu Leu Phe Glu Leu Leu Thr Gly Ala Ser Pro Phe Thr Leu
225                 230                 235                 240

Glu Gly Glu Arg Asn Thr Gln Ala Glu Val Ser Arg Arg Ile Leu Lys
                245                 250                 255

Cys Ser Pro Pro Phe Pro Arg Ile Gly Pro Val Ala Gln Asp Leu
            260                 265                 270

Leu Gln Arg Leu Leu Cys Lys Asp Pro Lys Lys Arg Leu Gly Ala Gly
        275                 280                 285

Pro Gln Gly Ala Gln Glu Val Arg Asn His Pro Phe Phe Gln Gly Leu
290                 295                 300

Asp Trp Val Ala Leu Ala Ala Arg Lys Ile Pro Ala Pro Phe Arg Pro
305                 310                 315                 320

Gln Ile Arg Ser Glu Leu Asp Val Gly Asn Phe Ala Glu Glu Phe Thr
                325                 330                 335

Arg Leu Glu Pro Val Tyr Ser Pro Pro Gly Ser Pro Pro Gly Asp
            340                 345                 350

Pro Arg Ile Phe Gln Gly Tyr Ser Phe Val Ala Pro Ser Ile Leu Phe
        355                 360                 365

Asp His Asn Asn Ala Val Met Thr Asp Gly Leu Glu Ala Pro Gly Ala
370                 375                 380

Gly Asp Arg Pro Gly Arg Ala Ala Val Ala Arg Ser Ala Met Met Gln
385                 390                 395                 400

Asp Ser Pro Phe Phe Gln Gln Tyr Glu Leu Asp Leu Arg Glu Pro Ala
            405                 410                 415

Leu Gly Gln Gly Ser Phe Ser Val Cys Arg Arg Cys Arg Gln Arg Gln
        420                 425                 430

Ser Gly Gln Glu Phe Ala Val Lys Ile Leu Ser Arg Arg Leu Glu Ala
        435                 440                 445

Asn Thr Gln Arg Glu Val Ala Ala Leu Arg Leu Cys Gln Ser His Pro
    450                 455                 460

Asn Val Val Asn Leu His Glu Val His His Asp Gln Leu His Thr Tyr
465                 470                 475                 480

Leu Val Leu Glu Leu Leu Arg Gly Gly Glu Leu Leu Glu His Ile Arg
                485                 490                 495

Lys Lys Arg His Phe Ser Glu Ser Glu Ala Ser Gln Ile Leu Arg Ser
            500                 505                 510

Leu Val Ser Ala Val Ser Phe Met His Glu Glu Ala Gly Val Val His
        515                 520                 525

Arg Asp Leu Lys Pro Glu Asn Ile Leu Tyr Ala Asp Asp Thr Pro Gly
530                 535                 540

Ala Pro Val Lys Ile Ile Asp Phe Gly Phe Ala Arg Leu Arg Pro Gln
545                 550                 555                 560

Ser Pro Gly Val Pro Met Gln Thr Pro Cys Phe Thr Leu Gln Tyr Ala
            565                 570                 575

Ala Pro Glu Leu Leu Ala Gln Gln Gly Tyr Asp Glu Ser Cys Asp Leu
        580                 585                 590

Trp Ser Leu Gly Val Ile Leu Tyr Met Met Leu Ser Gly Gln Val Pro
    595                 600                 605

Phe Gln Gly Ala Ser Gly Gln Gly Gln Ser Gln Ala Ala Glu Ile
    610                 615                 620

Met Cys Lys Ile Arg Glu Gly Arg Phe Ser Leu Asp Gly Glu Ala Trp
625                 630                 635                 640

Gln Gly Val Ser Glu Glu Ala Lys Glu Leu Val Arg Gly Leu Leu Thr
                645                 650                 655

Val Asp Pro Ala Lys Arg Leu Lys Leu Glu Gly Leu Arg Gly Ser Ser
            660                 665                 670

Trp Leu Gln Asp Gly Ser Ala Arg Ser Ser Pro Leu Arg Thr Pro
    675                 680                 685

Asp Val Leu Glu Ser Ser Gly Pro Ala Val Arg Ser Gly Leu Asn Ala
    690                 695                 700

Thr Phe Met Ala Phe Asn Arg Gly Lys Arg Glu Gly Phe Phe Leu Lys
705                 710                 715                 720

Ser Val Glu Asn Ala Pro Leu Ala Lys Arg Arg Lys Gln Lys Leu Arg
            725                 730                 735

Ser Ala Thr Ala Ser Arg Arg Gly Ser Pro Ala Pro Ala Asn Pro Gly
            740                 745                 750

Arg Ala Pro Val Ala Ser Lys Gly Ala Pro Arg Arg Ala Asn Gly Pro
            755                 760                 765

Leu Pro Pro Ser
    770

<210> SEQ ID NO 9
<211> LENGTH: 723

```
<212> TYPE: PRT
<213> ORGANISM: Mus musculus
<220> FEATURE:
<221> NAME/KEY: MISC_FEATURE
<222> LOCATION: (1)..(723)
<223> OTHER INFORMATION: Mouse RSK1

<400> SEQUENCE: 9
```

| | | | | | | | | | | | | | | |
|---|---|---|---|---|---|---|---|---|---|---|---|---|---|---|
| Met | Pro | Leu | Ala | Gln | Leu | Lys | Glu | Pro | Trp | Pro | Leu | Met | Glu | Leu | Val |
| 1 | | | | 5 | | | | | 10 | | | | | 15 | |

| Pro | Leu | Asp | Pro | Glu | Asn | Gly | Gln | Thr | Ser | Gly | Glu | Glu | Ala | Gly | Leu |
|---|---|---|---|---|---|---|---|---|---|---|---|---|---|---|---|
| | | | 20 | | | | | 25 | | | | | 30 | | |

| Gln | Pro | Ser | Lys | Asp | Glu | Ala | Ile | Leu | Lys | Glu | Ile | Ser | Ile | Thr | His |
|---|---|---|---|---|---|---|---|---|---|---|---|---|---|---|---|
| | | 35 | | | | | 40 | | | | | 45 | | | |

| His | Val | Lys | Ala | Gly | Ser | Glu | Lys | Ala | Asp | Pro | Ser | Gln | Phe | Glu | Leu |
|---|---|---|---|---|---|---|---|---|---|---|---|---|---|---|---|
| | 50 | | | | | 55 | | | | | 60 | | | | |

| Leu | Lys | Val | Leu | Gly | Gln | Gly | Ser | Phe | Gly | Lys | Val | Phe | Leu | Val | Arg |
|---|---|---|---|---|---|---|---|---|---|---|---|---|---|---|---|
| 65 | | | | | 70 | | | | | 75 | | | | | 80 |

| Lys | Val | Thr | Arg | Pro | Asp | Ser | Gly | His | Leu | Tyr | Ala | Met | Lys | Val | Leu |
|---|---|---|---|---|---|---|---|---|---|---|---|---|---|---|---|
| | | | | 85 | | | | | 90 | | | | | 95 | |

| Lys | Lys | Ala | Thr | Leu | Lys | Val | Arg | Asp | Arg | Val | Arg | Thr | Lys | Met | Glu |
|---|---|---|---|---|---|---|---|---|---|---|---|---|---|---|---|
| | | | 100 | | | | | 105 | | | | | 110 | | |

| Arg | Asp | Ile | Leu | Ala | Asp | Val | Asn | His | Pro | Phe | Val | Val | Lys | Leu | His |
|---|---|---|---|---|---|---|---|---|---|---|---|---|---|---|---|
| | | 115 | | | | | 120 | | | | | 125 | | | |

| Tyr | Ala | Phe | Gln | Thr | Glu | Gly | Lys | Leu | Tyr | Leu | Ile | Leu | Phe | Leu | Arg |
|---|---|---|---|---|---|---|---|---|---|---|---|---|---|---|---|
| | 130 | | | | | 135 | | | | | 140 | | | | |

| Gly | Gly | Asp | Leu | Phe | Thr | Arg | Leu | Ser | Lys | Glu | Val | Met | Phe | Thr | Glu |
|---|---|---|---|---|---|---|---|---|---|---|---|---|---|---|---|
| 145 | | | | | 150 | | | | | 155 | | | | | 160 |

| Glu | Asp | Val | Lys | Phe | Tyr | Leu | Ala | Glu | Leu | Ala | Leu | Gly | Leu | Asp | His |
|---|---|---|---|---|---|---|---|---|---|---|---|---|---|---|---|
| | | | | 165 | | | | | 170 | | | | | 175 | |

| Leu | His | Ser | Leu | Gly | Ile | Ile | Tyr | Arg | Asp | Leu | Lys | Pro | Glu | Asn | Ile |
|---|---|---|---|---|---|---|---|---|---|---|---|---|---|---|---|
| | | | 180 | | | | | 185 | | | | | 190 | | |

| Leu | Leu | Asp | Glu | Glu | Gly | His | Ile | Lys | Leu | Thr | Asp | Phe | Gly | Leu | Ser |
|---|---|---|---|---|---|---|---|---|---|---|---|---|---|---|---|
| | | 195 | | | | | 200 | | | | | 205 | | | |

| Lys | Glu | Ala | Ile | Asp | His | Glu | Lys | Lys | Ala | Tyr | Ser | Phe | Cys | Gly | Thr |
|---|---|---|---|---|---|---|---|---|---|---|---|---|---|---|---|
| | 210 | | | | | 215 | | | | | 220 | | | | |

| Val | Glu | Tyr | Met | Ala | Pro | Glu | Val | Val | Asn | Arg | Gln | Gly | His | Thr | His |
|---|---|---|---|---|---|---|---|---|---|---|---|---|---|---|---|
| 225 | | | | | 230 | | | | | 235 | | | | | 240 |

| Ser | Ala | Asp | Trp | Trp | Ser | Tyr | Gly | Val | Leu | Met | Gly | Lys | Asp | Arg | Lys |
|---|---|---|---|---|---|---|---|---|---|---|---|---|---|---|---|
| | | | | 245 | | | | | 250 | | | | | 255 | |

| Glu | Thr | Met | Thr | Leu | Ile | Leu | Lys | Ala | Lys | Leu | Gly | Met | Pro | Gln | Phe |
|---|---|---|---|---|---|---|---|---|---|---|---|---|---|---|---|
| | | | 260 | | | | | 265 | | | | | 270 | | |

| Leu | Ser | Thr | Glu | Ala | Gln | Ser | Leu | Leu | Arg | Ala | Leu | Phe | Lys | Arg | Asn |
|---|---|---|---|---|---|---|---|---|---|---|---|---|---|---|---|
| | | 275 | | | | | 280 | | | | | 285 | | | |

| Pro | Ala | Asn | Arg | Leu | Gly | Ser | Gly | Pro | Asp | Gly | Ala | Glu | Glu | Ile | Lys |
|---|---|---|---|---|---|---|---|---|---|---|---|---|---|---|---|
| | 290 | | | | | 295 | | | | | 300 | | | | |

| Arg | His | Ile | Phe | Tyr | Ser | Thr | Ile | Asp | Trp | Asn | Lys | Leu | Tyr | Arg | Arg |
|---|---|---|---|---|---|---|---|---|---|---|---|---|---|---|---|
| 305 | | | | | 310 | | | | | 315 | | | | | 320 |

| Glu | Ile | Lys | Pro | Pro | Phe | Lys | Pro | Ala | Val | Ala | Gln | Pro | Asp | Asp | Thr |
|---|---|---|---|---|---|---|---|---|---|---|---|---|---|---|---|
| | | | | 325 | | | | | 330 | | | | | 335 | |

| Phe | Tyr | Phe | Asp | Thr | Glu | Phe | Thr | Ser | Arg | Thr | Pro | Arg | Asp | Ser | Pro |
|---|---|---|---|---|---|---|---|---|---|---|---|---|---|---|---|
| | | | 340 | | | | | 345 | | | | | 350 | | |

| Gly | Ile | Pro | Pro | Ser | Ala | Gly | Ala | His | Gln | Leu | Phe | Arg | Gly | Phe | Ser |
|---|---|---|---|---|---|---|---|---|---|---|---|---|---|---|---|
| | | 355 | | | | | 360 | | | | | 365 | | | |

| Phe | Val | Ala | Thr | Gly | Leu | Met | Glu | Asp | Asp | Gly | Lys | Pro | Arg | Thr | Thr |

370                 375                 380
Gln Ala Pro Leu His Ser Val Val Gln Gln Leu His Gly Lys Asn Leu
385                 390                 395                 400

Val Phe Ser Asp Gly Tyr Val Val Lys Glu Thr Ile Gly Val Gly Ser
                405                 410                 415

Tyr Ser Val Cys Lys Arg Cys Val His Lys Ala Thr Asn Met Glu Tyr
                420                 425                 430

Ala Val Lys Val Ile Asp Lys Ser Lys Arg Asp Pro Ser Glu Glu Ile
                435                 440                 445

Glu Ile Leu Leu Arg Tyr Gly Gln His Pro Asn Ile Ile Thr Leu Lys
                450                 455                 460

Asp Val Tyr Asp Asp Gly Lys His Val Tyr Leu Val Thr Glu Leu Met
465                 470                 475                 480

Arg Gly Gly Glu Leu Leu Asp Lys Ile Leu Arg Gln Lys Phe Phe Ser
                485                 490                 495

Glu Arg Glu Ala Ser Phe Val Leu His Thr Ile Ser Lys Thr Val Glu
                500                 505                 510

Tyr Leu His Ser Gln Gly Val Val His Arg Asp Leu Lys Pro Ser Asn
                515                 520                 525

Ile Leu Tyr Val Asp Glu Ser Gly Asn Pro Glu Cys Leu Arg Ile Cys
                530                 535                 540

Asp Phe Gly Phe Ala Lys Gln Leu Arg Ala Glu Asn Gly Leu Leu Met
545                 550                 555                 560

Thr Pro Cys Tyr Thr Ala Asn Phe Val Ala Pro Glu Val Leu Lys Arg
                565                 570                 575

Gln Gly Tyr Asp Glu Gly Cys Asp Ile Trp Ser Leu Gly Ile Leu Leu
                580                 585                 590

Tyr Thr Met Leu Ala Gly Tyr Thr Pro Phe Ala Asn Gly Pro Ser Asp
                595                 600                 605

Thr Pro Glu Glu Ile Leu Thr Arg Ile Gly Ser Gly Lys Phe Thr Leu
610                 615                 620

Ser Gly Gly Asn Trp Asn Thr Val Ser Glu Thr Ala Lys Asp Leu Val
625                 630                 635                 640

Ser Lys Met Leu His Val Asp Pro His Gln Arg Leu Thr Ala Lys Gln
                645                 650                 655

Val Leu Gln His Pro Trp Ile Thr Gln Lys Asp Lys Leu Pro Gln Ser
                660                 665                 670

Gln Leu Ser His Gln Asp Leu Gln Leu Val Lys Gly Ala Met Ala Ala
                675                 680                 685

Thr Tyr Ser Ala Leu Asn Ser Ser Lys Pro Thr Pro Gln Leu Lys Pro
690                 695                 700

Ile Glu Ser Ser Ile Leu Ala Gln Arg Arg Val Arg Lys Leu Pro Ser
705                 710                 715                 720

Thr Thr Leu

<210> SEQ ID NO 10
<211> LENGTH: 740
<212> TYPE: PRT
<213> ORGANISM: Mus musculus
<220> FEATURE:
<221> NAME/KEY: MISC_FEATURE
<222> LOCATION: (1)..(740)
<223> OTHER INFORMATION: Mouse RSK2

<400> SEQUENCE: 10

-continued

```
Met Pro Leu Ala Gln Leu Ala Asp Pro Trp Gln Lys Met Ala Val Glu
1               5                   10                  15

Ser Pro Ser Asp Ser Ala Glu Asn Gly Gln Gln Ile Met Asp Glu Pro
            20                  25                  30

Met Gly Glu Glu Glu Ile Asn Pro Gln Thr Glu Glu Gly Ser Ile Lys
        35                  40                  45

Glu Ile Ala Ile Thr His His Val Lys Glu Gly His Glu Lys Ala Asp
50                  55                  60

Pro Ser Gln Phe Glu Leu Leu Lys Val Leu Gly Gln Gly Ser Phe Gly
65                  70                  75                  80

Lys Val Phe Leu Val Lys Lys Ile Ser Gly Ser Asp Ala Arg Gln Leu
                85                  90                  95

Tyr Ala Met Lys Val Leu Lys Lys Ala Thr Leu Lys Val Arg Asp Arg
            100                 105                 110

Val Arg Thr Lys Met Glu Arg Asp Ile Leu Val Glu Val Asn His Pro
        115                 120                 125

Phe Ile Val Lys Leu His Tyr Ala Phe Gln Thr Glu Gly Lys Leu Tyr
    130                 135                 140

Leu Ile Leu Asp Phe Leu Arg Gly Gly Asp Leu Phe Thr Arg Leu Ser
145                 150                 155                 160

Lys Glu Val Met Phe Thr Glu Glu Asp Val Lys Phe Tyr Leu Ala Glu
                165                 170                 175

Leu Ala Leu Ala Leu Asp His Leu His Ser Leu Gly Ile Ile Tyr Arg
            180                 185                 190

Asp Leu Lys Pro Glu Asn Ile Leu Leu Asp Glu Glu Gly His Ile Lys
        195                 200                 205

Leu Thr Asp Phe Gly Leu Ser Lys Glu Ser Ile Asp His Glu Lys Lys
    210                 215                 220

Ala Tyr Ser Phe Cys Gly Thr Val Glu Tyr Met Ala Pro Glu Val Val
225                 230                 235                 240

Asn Arg Arg Gly His Thr Gln Ser Ala Asp Trp Trp Ser Phe Gly Val
                245                 250                 255

Leu Met Phe Glu Met Leu Thr Gly Thr Leu Pro Phe Gln Gly Lys Asp
            260                 265                 270

Arg Lys Glu Thr Met Thr Met Ile Leu Lys Ala Lys Leu Gly Met Pro
        275                 280                 285

Gln Phe Leu Ser Pro Glu Ala Gln Ser Leu Leu Arg Met Leu Phe Lys
    290                 295                 300

Arg Asn Pro Ala Asn Arg Leu Gly Ala Gly Pro Asp Gly Val Glu Glu
305                 310                 315                 320

Ile Lys Arg His Ser Phe Phe Ser Thr Ile Asp Trp Asn Lys Leu Tyr
                325                 330                 335

Arg Arg Glu Ile His Pro Pro Phe Lys Pro Ala Thr Gly Arg Pro Glu
            340                 345                 350

Asp Thr Phe Tyr Phe Asp Pro Glu Phe Thr Ala Lys Thr Pro Lys Asp
        355                 360                 365

Ser Pro Gly Ile Pro Pro Ser Ala Asn Ala His Gln Leu Phe Arg Gly
    370                 375                 380

Phe Ser Phe Val Ala Ile Thr Ser Asp Asp Glu Ser Gln Ala Met Gln
385                 390                 395                 400

Thr Val Gly Val His Ser Ile Val Gln Gln Leu His Arg Asn Ser Ile
                405                 410                 415

Gln Phe Thr Asp Gly Tyr Glu Val Lys Glu Asp Ile Gly Val Gly Ser
```

```
            420                 425                 430
Tyr Ser Val Cys Lys Arg Cys Ile His Lys Ala Thr Asn Met Glu Phe
            435                 440                 445

Ala Val Lys Ile Ile Asp Lys Ser Lys Arg Asp Pro Thr Glu Glu Ile
            450                 455                 460

Glu Ile Leu Leu Arg Tyr Gly Gln His Pro Asn Ile Ile Thr Leu Lys
465                 470                 475                 480

Asp Val Tyr Asp Asp Gly Lys Tyr Val Tyr Val Val Thr Glu Leu Met
            485                 490                 495

Lys Gly Gly Glu Leu Leu Asp Lys Ile Leu Arg Gln Lys Phe Phe Ser
            500                 505                 510

Glu Arg Glu Ala Ser Ala Val Leu Phe Thr Ile Thr Lys Thr Val Glu
            515                 520                 525

Tyr Leu His Ala Gln Gly Val Val His Arg Asp Leu Lys Pro Ser Asn
            530                 535                 540

Ile Leu Tyr Val Asp Glu Ser Gly Asn Pro Glu Ser Ile Arg Ile Cys
545                 550                 555                 560

Asp Phe Gly Phe Ala Lys Gln Leu Arg Ala Glu Asn Gly Leu Leu Met
            565                 570                 575

Thr Pro Cys Tyr Thr Ala Asn Phe Val Ala Pro Glu Val Leu Lys Arg
            580                 585                 590

Gln Gly Tyr Asp Ala Ala Cys Asp Ile Trp Ser Leu Gly Val Leu Leu
            595                 600                 605

Tyr Thr Met Leu Thr Gly Tyr Thr Pro Phe Ala Asn Gly Pro Asp Asp
            610                 615                 620

Thr Pro Glu Glu Ile Leu Ala Arg Ile Gly Ser Gly Lys Phe Ser Leu
625                 630                 635                 640

Ser Gly Gly Tyr Trp Asn Ser Val Ser Asp Thr Ala Lys Asp Leu Val
                    645                 650                 655

Ser Lys Met Leu His Val Asp Pro His Gln Arg Leu Thr Ala Ala Leu
                    660                 665                 670

Val Leu Arg His Pro Trp Ile Val His Trp Asp Gln Leu Pro Gln Tyr
            675                 680                 685

Gln Leu Asn Arg Gln Asp Ala Pro His Leu Val Lys Gly Ala Met Ala
            690                 695                 700

Ala Thr Tyr Ser Ala Leu Asn Arg Asn Gln Ser Pro Val Leu Glu Pro
705                 710                 715                 720

Val Gly Arg Ser Thr Leu Ala Gln Arg Gly Ile Lys Lys Ile Thr
            725                 730                 735

Ser Thr Ala Leu
            740

<210> SEQ ID NO 11
<211> LENGTH: 733
<212> TYPE: PRT
<213> ORGANISM: Mus musculus
<220> FEATURE:
<221> NAME/KEY: MISC_FEATURE
<222> LOCATION: (1)..(733)
<223> OTHER INFORMATION: Mouse RSK3

<400> SEQUENCE: 11

Met Glu Leu Ser Met Lys Lys Phe Thr Val Arg Arg Phe Phe Ser Val
1               5                   10                  15

Tyr Leu Arg Lys Lys Ser Arg Ser Lys Ser Ser Leu Ser Arg Leu
                20                  25                  30
```

-continued

Glu Glu Glu Gly Ile Val Lys Glu Ile Asp Ile Ser Asn His Val Lys
        35                  40                  45

Glu Gly Phe Glu Lys Ala Asp Pro Ser Gln Phe Glu Leu Leu Lys Val
50                  55                  60

Leu Gly Gln Gly Ser Tyr Gly Lys Val Phe Leu Val Arg Lys Val Thr
65                  70                  75                  80

Gly Ser Asp Ala Gly Gln Leu Tyr Ala Met Lys Val Leu Lys Lys Ala
                85                  90                  95

Thr Leu Lys Val Arg Asp Arg Val Arg Ser Lys Met Glu Arg Asp Ile
            100                 105                 110

Leu Ala Glu Val Asn His Pro Phe Ile Val Lys Leu His Tyr Ala Phe
            115                 120                 125

Gln Thr Glu Gly Lys Leu Tyr Leu Ile Leu Asp Phe Leu Arg Gly Gly
        130                 135                 140

Asp Leu Phe Thr Arg Leu Ser Lys Glu Val Met Phe Thr Glu Glu Asp
145                 150                 155                 160

Val Lys Phe Tyr Leu Ala Glu Leu Ala Leu Ala Leu Asp His Leu His
                165                 170                 175

Gly Leu Gly Ile Ile Tyr Arg Asp Leu Lys Pro Glu Asn Ile Leu Leu
            180                 185                 190

Asp Glu Glu Gly His Ile Lys Ile Thr Asp Phe Gly Leu Ser Lys Glu
            195                 200                 205

Ala Thr Asp His Asp Lys Arg Ala Tyr Ser Phe Cys Gly Thr Ile Glu
        210                 215                 220

Tyr Met Ala Pro Glu Val Val Asn Arg Arg Gly His Thr Gln Ser Ala
225                 230                 235                 240

Asp Trp Trp Ser Phe Gly Val Leu Met Phe Glu Met Leu Thr Gly Ser
                245                 250                 255

Leu Pro Phe Gln Gly Lys Asp Arg Lys Glu Thr Met Ala Leu Ile Leu
            260                 265                 270

Lys Ala Lys Leu Gly Met Pro Gln Phe Leu Ser Ala Glu Ala Gln Ser
        275                 280                 285

Leu Leu Arg Ala Leu Phe Lys Arg Asn Pro Cys Asn Arg Leu Gly Ala
        290                 295                 300

Gly Val Asp Gly Val Glu Glu Ile Lys Arg His Pro Phe Phe Val Thr
305                 310                 315                 320

Ile Asp Trp Asn Lys Leu Tyr Arg Lys Glu Ile Lys Pro Pro Phe Lys
                325                 330                 335

Pro Ala Val Gly Arg Pro Glu Asp Thr Phe His Phe Asp Pro Glu Phe
            340                 345                 350

Thr Ala Arg Thr Pro Thr Asp Ser Pro Gly Val Pro Pro Ser Ala Asn
        355                 360                 365

Ala His His Leu Phe Arg Gly Phe Ser Phe Val Ala Ser Ser Leu Val
        370                 375                 380

Gln Glu Pro Ser Gln Gln Asp Val Pro Lys Ala Pro Ile His Pro Ile
385                 390                 395                 400

Val Gln Gln Leu His Gly Asn Asn Ile His Phe Thr Asp Gly Tyr Glu
                405                 410                 415

Ile Lys Glu Asp Ile Gly Val Gly Ser Tyr Ser Val Cys Lys Arg Cys
            420                 425                 430

Val His Lys Ala Thr Asp Ala Glu Tyr Ala Val Lys Ile Ile Asp Lys
        435                 440                 445

```
Ser Lys Arg Asp Pro Ser Glu Ile Glu Ile Leu Arg Tyr Gly
    450                 455                 460

Gln His Pro Asn Ile Ile Thr Leu Lys Asp Val Tyr Asp Asp Gly Lys
465                 470                 475                 480

Tyr Val Tyr Leu Val Met Glu Leu Met Arg Gly Gly Glu Leu Leu Asp
                485                 490                 495

Arg Ile Leu Arg Gln Arg Cys Phe Ser Glu Arg Glu Ala Ser Asp Val
                500                 505                 510

Leu Tyr Thr Ile Ala Arg Thr Met Asp Tyr Leu His Ser Gln Gly Val
            515                 520                 525

Val His Arg Asp Leu Lys Pro Ser Asn Ile Leu Tyr Met Asp Glu Ser
530                 535                 540

Gly Asn Pro Glu Ser Ile Arg Ile Cys Asp Phe Gly Phe Ala Lys Gln
545                 550                 555                 560

Leu Arg Ala Glu Asn Gly Leu Leu Met Thr Pro Cys Tyr Thr Ala Asn
                565                 570                 575

Phe Val Ala Pro Glu Val Leu Lys Arg Gln Gly Tyr Asp Ala Ala Cys
                580                 585                 590

Asp Val Trp Ser Leu Gly Ile Leu Leu Tyr Thr Met Leu Ala Gly Phe
            595                 600                 605

Thr Pro Phe Ala Asn Gly Pro Asp Asp Thr Pro Glu Glu Ile Leu Ala
            610                 615                 620

Arg Ile Gly Ser Gly Lys Tyr Ala Leu Ser Gly Gly Asn Trp Asp Ser
625                 630                 635                 640

Ile Ser Asp Ala Ala Lys Asp Val Val Ser Lys Met Leu His Val Asp
                645                 650                 655

Pro Gln Gln Arg Leu Thr Ala Val Gln Val Leu Lys His Pro Trp Ile
            660                 665                 670

Val Asn Arg Glu Tyr Leu Ser Gln Asn Gln Leu Ser Arg Gln Asp Val
            675                 680                 685

His Leu Val Lys Gly Ala Met Ala Ala Thr Tyr Phe Ala Leu Asn Arg
            690                 695                 700

Thr Pro Gln Ala Pro Arg Leu Glu Pro Val Leu Ser Ser Ser Leu Ala
705                 710                 715                 720

Gln Arg Arg Gly Met Lys Arg Leu Thr Ser Thr Arg Leu
                725                 730

<210> SEQ ID NO 12
<211> LENGTH: 764
<212> TYPE: PRT
<213> ORGANISM: Mus musculus
<220> FEATURE:
<221> NAME/KEY: MISC_FEATURE
<222> LOCATION: (1)..(764)
<223> OTHER INFORMATION: Mouse RSK4

<400> SEQUENCE: 12

Met Leu Pro Phe Ala Pro Val Glu Asp Pro Trp Asp Gln Glu Asp Met
1               5                   10                  15

Glu Val Phe Gly Ser Thr Ser Ser Ser Glu Pro Gln Val Val Phe Thr
            20                  25                  30

Met Lys Asn Ala Ala Thr Val Met Arg Glu His Glu Lys Glu Val
            35                  40                  45

Asn Asp Leu Lys Met Val Asp Glu Pro Met Glu Glu Gly Glu Pro Val
50                  55                  60

Ser Cys Arg Arg Glu Glu Leu Val Lys Glu Val Pro Ile Thr Gln His
```

```
            65                  70                  75                  80
Val Lys Glu Gly Tyr Glu Lys Ala Asp Pro Ala Gln Phe Asp Leu Leu
                        85                  90                  95

Lys Val Leu Gly Gln Gly Ser Phe Gly Lys Val Phe Leu Val Arg Lys
                100                 105                 110

Lys Thr Gly Pro Asp Ala Gly Gln Leu Tyr Ala Met Lys Val Leu Arg
            115                 120                 125

Lys Ala Ser Leu Lys Val Arg Asp Arg Val Arg Thr Lys Met Glu Arg
        130                 135                 140

Asp Ile Leu Val Glu Val Asn His Pro Phe Ile Val Lys Leu His Tyr
145                 150                 155                 160

Ala Phe Gln Thr Glu Gly Lys Leu Tyr Leu Ile Leu Asp Phe Leu Arg
                    165                 170                 175

Gly Gly Asp Val Phe Thr Arg Leu Ser Lys Glu Val Leu Phe Thr Glu
                180                 185                 190

Glu Asp Val Lys Phe Tyr Leu Ala Glu Leu Ala Leu Ala Leu Asp His
            195                 200                 205

Leu His Arg Leu Gly Ile Val Tyr Arg Asp Leu Lys Pro Glu Asn Ile
        210                 215                 220

Leu Leu Asp Glu Ile Gly His Ile Lys Leu Thr Asp Phe Gly Leu Ser
225                 230                 235                 240

Lys Glu Ser Val Asp Gln Glu Lys Lys Ala Tyr Ser Phe Cys Gly Thr
                    245                 250                 255

Val Glu Tyr Met Ala Pro Glu Val Val Asn Arg Arg Ala His Ser Gln
                260                 265                 270

Ser Ala Asp Trp Trp Ser Tyr Gly Val Leu Met Phe Glu Met Leu Thr
            275                 280                 285

Gly Thr Leu Pro Phe Gln Gly Lys Asp Arg Asn Glu Thr Met Asn Met
        290                 295                 300

Ile Leu Lys Ala Lys Leu Gly Met Pro Gln Phe Leu Ser Ala Glu Ala
305                 310                 315                 320

Gln Ser Leu Leu Arg Met Leu Phe Lys Arg Asn Pro Ala Asn Arg Leu
                    325                 330                 335

Gly Ser Glu Gly Val Glu Val Lys Arg His Ala Phe Phe Ala Ser
                340                 345                 350

Ile Asp Trp Asn Lys Leu Tyr Lys Arg Glu Val Gln Pro Pro Phe Arg
            355                 360                 365

Pro Ala Ser Gly Lys Pro Asp Asp Thr Phe Cys Phe Asp Pro Glu Phe
        370                 375                 380

Thr Ala Lys Thr Pro Lys Asp Ser Pro Gly Leu Pro Ala Ser Ala Asn
385                 390                 395                 400

Ala His Gln Leu Phe Lys Gly Phe Ser Phe Val Ala Thr Ser Ile Ala
                    405                 410                 415

Glu Glu Tyr Lys Ile Thr Pro Val Thr Ser Ser Asn Val Leu Pro Ile
                420                 425                 430

Val Gln Ile Asn Gly Asn Ala Ala Gln Phe Ser Glu Ala Tyr Glu Leu
            435                 440                 445

Lys Glu Asp Ile Gly Ile Gly Ser Tyr Ser Val Cys Lys Arg Cys Ile
        450                 455                 460

His Ser Ala Ser Asn Val Glu Phe Ala Val Lys Ile Ile Asp Lys Asn
465                 470                 475                 480

Lys Arg Asp Pro Ser Glu Glu Ile Glu Ile Leu Met Arg Tyr Gly Gln
                    485                 490                 495
```

```
His Pro Asn Ile Ile Ser Leu Lys Glu Val Phe Asp Gly Lys Tyr
                500                 505                 510

Val Tyr Leu Val Thr Asp Leu Met Lys Gly Gly Glu Leu Leu Asp Arg
            515                 520                 525

Ile Leu Lys Lys Lys Cys Phe Ser Glu Gln Glu Ala Ser Asn Val Leu
        530                 535                 540

Tyr Val Ile Thr Lys Thr Val Glu Cys Leu His Ser Gln Gly Val Val
545                 550                 555                 560

His Arg Asp Leu Lys Pro Ser Asn Ile Leu Tyr Met Asp Glu Ser Ala
                565                 570                 575

His Pro Asp Ser Ile Lys Ile Cys Asp Phe Gly Phe Ala Lys Gln Leu
            580                 585                 590

Arg Gly Glu Asn Gly Leu Leu Leu Thr Pro Cys Tyr Thr Ala Asn Phe
        595                 600                 605

Val Ala Pro Glu Val Leu Thr Gln Gln Gly Tyr Asp Ala Ala Cys Asp
610                 615                 620

Ile Trp Ser Leu Gly Val Leu Leu Tyr Thr Met Leu Ala Gly Tyr Thr
625                 630                 635                 640

Pro Phe Ser Asn Gly Pro Asn Asp Thr Pro Glu Glu Ile Leu Leu Arg
                645                 650                 655

Ile Gly Asn Gly Arg Phe Ser Leu Ser Gly Gly Ile Trp Asp Asn Ile
            660                 665                 670

Ser Arg Gly Ala Lys Asp Leu Leu Ser His Met Leu His Met Asp Pro
        675                 680                 685

His Gln Arg Tyr Thr Ala Glu Gln Val Leu Lys His Pro Trp Ile Thr
                690                 695                 700

Gln Arg Glu Gln Leu Pro Arg His Gln Pro Asn Ser Asp Glu Pro Pro
705                 710                 715                 720

Gln Glu Ala Val Ala Ala Pro Tyr Ser Val Leu Ala Arg Asn Pro Asn
                725                 730                 735

Arg His His Pro Ile Leu Glu Pro Val Thr Ala Ser Arg Leu Ala Gln
            740                 745                 750

Arg Arg Asn Met Lys Lys Arg Thr Ser Thr Gly Leu
        755                 760

<210> SEQ ID NO 13
<211> LENGTH: 863
<212> TYPE: PRT
<213> ORGANISM: Mus musculus
<220> FEATURE:
<221> NAME/KEY: MISC_FEATURE
<222> LOCATION: (1)..(863)
<223> OTHER INFORMATION: Mouse MSK1

<400> SEQUENCE: 13

Met Glu Gly Glu Gly Gly Ser Gly Gly Ala Gly Thr Ser Gly Asp
1               5                   10                  15

Ser Gly Asp Gly Gly Glu Gln Leu Leu Thr Val Lys His Glu Leu Arg
            20                  25                  30

Thr Ala Asn Leu Thr Gly His Ala Glu Lys Val Gly Ile Glu Asn Phe
        35                  40                  45

Glu Leu Leu Lys Val Leu Gly Thr Gly Ala Tyr Gly Lys Val Phe Leu
    50                  55                  60

Val Arg Lys Ile Ser Gly His Asp Ala Gly Lys Leu Tyr Ala Met Lys
65                  70                  75                  80
```

Val Leu Lys Lys Ala Thr Ile Val Gln Lys Ala Lys Thr Thr Glu His
                85                  90                  95

Thr Arg Thr Glu Arg Gln Val Leu Glu His Ile Arg Gln Ser Pro Phe
            100                 105                 110

Leu Val Thr Leu His Tyr Ala Phe Gln Thr Glu Thr Lys Leu His Leu
        115                 120                 125

Ile Leu Asp Tyr Ile Asn Gly Gly Glu Leu Phe Thr His Leu Ser Gln
    130                 135                 140

Arg Glu Arg Phe Thr Glu His Glu Val Gln Ile Tyr Val Gly Glu Ile
145                 150                 155                 160

Val Leu Ala Leu Glu His Leu His Lys Leu Gly Ile Ile Tyr Arg Asp
                165                 170                 175

Ile Lys Leu Glu Asn Ile Leu Leu Asp Ser Asn Gly His Val Val Leu
            180                 185                 190

Thr Asp Phe Gly Leu Ser Lys Glu Phe Val Ala Asp Glu Thr Glu Arg
        195                 200                 205

Ala Tyr Ser Phe Cys Gly Thr Ile Glu Tyr Met Ala Pro Asp Ile Val
    210                 215                 220

Arg Gly Gly Asp Ser Gly His Asp Lys Ala Val Asp Trp Trp Ser Leu
225                 230                 235                 240

Gly Val Leu Met Tyr Glu Leu Leu Thr Gly Ala Ser Pro Phe Thr Val
                245                 250                 255

Asp Gly Glu Lys Asn Ser Gln Ala Glu Ile Ser Arg Arg Ile Leu Lys
            260                 265                 270

Ser Glu Pro Pro Tyr Pro Gln Glu Met Ser Thr Val Ala Lys Asp Leu
        275                 280                 285

Leu Gln Arg Leu Leu Met Lys Asp Pro Lys Lys Arg Leu Gly Cys Gly
    290                 295                 300

Pro Arg Asp Ala Glu Glu Ile Lys Glu His Leu Phe Phe Glu Lys Ile
305                 310                 315                 320

Lys Trp Asp Asp Leu Ala Ala Lys Lys Val Pro Ala Pro Phe Lys Pro
                325                 330                 335

Val Ile Arg Asp Glu Leu Asp Val Ser Asn Phe Ala Glu Glu Phe Thr
            340                 345                 350

Glu Met Asp Pro Thr Tyr Ser Pro Ala Ala Leu Pro Gln Ser Ser Glu
        355                 360                 365

Arg Leu Phe Gln Gly Tyr Ser Phe Val Ala Pro Ser Ile Leu Phe Lys
    370                 375                 380

Arg Asn Ala Ala Val Ile Asp Pro Leu Gln Phe His Met Gly Val Asp
385                 390                 395                 400

Arg Pro Gly Val Thr Asn Val Ala Arg Ser Ala Met Met Lys Asp Ser
                405                 410                 415

Pro Phe Tyr Gln His Tyr Asp Leu Asp Leu Lys Asp Lys Pro Leu Gly
            420                 425                 430

Glu Gly Ser Phe Ser Ile Cys Arg Lys Cys Val His Lys Lys Thr Asn
        435                 440                 445

Gln Ala Phe Ala Val Lys Ile Ile Ser Lys Arg Met Glu Ala Asn Thr
    450                 455                 460

Gln Lys Glu Ile Thr Ala Leu Lys Leu Cys Glu Gly His Pro Asn Ile
465                 470                 475                 480

Val Lys Leu His Glu Val Phe His Asp Gln Val Ala Ala Ser Ala Gln
                485                 490                 495

Pro Pro Gly Gln Val Val Leu Cys Ser Leu Leu Leu Ala Leu Leu

```
                    500                 505                 510
        Phe Asn Arg Ser Leu Thr Arg Lys Pro Val Thr Trp Thr Trp Leu Val
                        515                 520                 525
        His Ser Thr Ser Gln Leu Pro Pro Leu Pro Pro Met Pro Glu Ile
                        530                 535                 540
        Val Leu Phe Ile Leu Leu Ser Asp Asn Gly Gln Leu His Thr Phe Leu
        545                 550                 555                 560
        Val Met Glu Leu Leu Asn Gly Gly Glu Leu Phe Glu Arg Ile Lys Arg
                        565                 570                 575
        Lys Lys His Phe Ser Glu Thr Glu Ala Ser Tyr Ile Met Arg Lys Leu
                        580                 585                 590
        Val Ser Ala Val Ser His Met His Asp Val Gly Val Val His Arg Asp
                        595                 600                 605
        Leu Lys Pro Glu Asn Leu Leu Phe Thr Asp Glu Asn Asp Asn Leu Glu
                        610                 615                 620
        Ile Lys Val Ile Asp Phe Gly Phe Ala Arg Leu Lys Pro Pro Asp Asn
        625                 630                 635                 640
        Gln Pro Leu Lys Thr Pro Cys Phe Thr Leu His Tyr Ala Ala Pro Glu
                        645                 650                 655
        Leu Leu Thr His Asn Gly Tyr Asp Glu Ser Cys Asp Leu Trp Ser Leu
                        660                 665                 670
        Gly Val Ile Leu Tyr Thr Met Leu Ser Gly Gln Val Pro Phe Gln Ser
                        675                 680                 685
        His Asp Arg Ser Leu Thr Cys Thr Ser Ala Val Glu Ile Met Lys Lys
                        690                 695                 700
        Ile Lys Lys Gly Asp Phe Ser Phe Glu Gly Glu Ala Trp Lys Asn Val
        705                 710                 715                 720
        Ser Gln Glu Ala Lys Asp Leu Ile Gln Gly Leu Leu Thr Val Asp Pro
                        725                 730                 735
        Asn Lys Arg Leu Lys Met Ser Gly Leu Arg Tyr Asn Glu Trp Leu Gln
                        740                 745                 750
        Asp Gly Ser Gln Leu Ser Ser Asn Pro Leu Met Thr Pro Asp Ile Leu
                        755                 760                 765
        Gly Ser Ser Gly Ala Ala Val His Thr Cys Val Lys Ala Thr Phe His
                        770                 775                 780
        Ala Phe Asn Lys Tyr Lys Arg Glu Gly Phe Cys Leu Gln Asn Val Asp
        785                 790                 795                 800
        Lys Ala Pro Leu Ala Lys Arg Lys Met Lys Arg Thr Ser Thr Ser
                        805                 810                 815
        Thr Glu Thr Arg Ser Ser Ser Ser Glu Ser Ser Arg Ser Ser Ser Ser
                        820                 825                 830
        Gln Ser His Gly Lys Thr Thr Pro Thr Lys Thr Leu Gln Pro Ser Asn
                        835                 840                 845
        Pro Thr Glu Gly Ser Asn Pro Asp Thr Leu Phe Gln Phe Ser Asp
        850                 855                 860

<210> SEQ ID NO 14
<211> LENGTH: 773
<212> TYPE: PRT
<213> ORGANISM: Mus musculus
<220> FEATURE:
<221> NAME/KEY: MISC_FEATURE
<222> LOCATION: (1)..(773)
<223> OTHER INFORMATION: Mouse MSK2

<400> SEQUENCE: 14
```

```
Met Gly Asp Glu Asp Glu Asp Glu Gly Cys Ala Val Glu Leu Gln Ile
1               5                   10                  15

Thr Glu Ala Asn Leu Thr Gly His Glu Glu Lys Val Ser Val Glu Asn
                20                  25                  30

Phe Ala Leu Leu Lys Val Leu Gly Thr Gly Ala Tyr Gly Lys Val Phe
                35                  40                  45

Leu Val Arg Lys Thr Gly Gly His Asp Ala Gly Lys Leu Tyr Ala Met
        50                  55                  60

Lys Val Leu Arg Lys Ala Ala Leu Val Gln Arg Ala Lys Thr Gln Glu
65                  70                  75                  80

His Thr Arg Thr Glu Arg Ser Val Leu Glu Leu Val Arg Gln Ala Pro
                85                  90                  95

Phe Leu Val Thr Leu His Tyr Ala Phe Gln Thr Asp Ala Lys Leu His
                100                 105                 110

Leu Ile Leu Asp Tyr Val Ser Gly Gly Glu Met Phe Thr His Leu Tyr
            115                 120                 125

Gln Arg Gln Tyr Phe Lys Glu Ala Glu Val Arg Val Tyr Gly Gly Glu
        130                 135                 140

Ile Val Leu Ala Leu Glu His Leu His Lys Leu Gly Ile Ile Tyr Arg
145                 150                 155                 160

Asp Leu Lys Leu Glu Asn Val Leu Leu Asp Ser Glu Gly His Ile Val
                165                 170                 175

Leu Thr Asp Phe Gly Leu Ser Lys Glu Phe Leu Thr Glu Glu Lys Glu
            180                 185                 190

Arg Thr Phe Ser Phe Cys Gly Thr Ile Glu Tyr Met Ala Pro Glu Ile
        195                 200                 205

Ile Arg Ser Lys Ala Gly His Gly Lys Ala Val Asp Trp Trp Ser Leu
210                 215                 220

Gly Ile Leu Leu Phe Glu Leu Leu Thr Gly Ala Ser Pro Phe Thr Leu
225                 230                 235                 240

Glu Gly Glu Arg Asn Thr Gln Ala Glu Val Ser Arg Arg Ile Leu Lys
                245                 250                 255

Cys Ser Pro Pro Phe Pro Leu Arg Ile Gly Pro Val Ala Gln Asp Leu
                260                 265                 270

Leu Gln Arg Leu Leu Cys Lys Asp Pro Lys Lys Arg Leu Gly Ala Gly
        275                 280                 285

Pro Gln Gly Ala Gln Glu Val Lys Ser His Pro Phe Phe Gln Gly Leu
290                 295                 300

Asp Trp Val Ala Leu Ala Ala Arg Lys Ile Pro Ala Pro Phe Arg Pro
305                 310                 315                 320

Gln Ile Arg Ser Glu Leu Asp Val Gly Asn Phe Ala Glu Glu Phe Thr
                325                 330                 335

Arg Leu Glu Pro Val Tyr Ser Pro Ala Gly Ser Pro Pro Gly Asp
        340                 345                 350

Pro Arg Ile Phe Gln Gly Tyr Ser Phe Val Ala Pro Ser Ile Leu Phe
        355                 360                 365

Asp His Asn Asn Ala Val Met Ala Asp Val Leu Gln Ala Pro Gly Ala
        370                 375                 380

Gly Tyr Arg Pro Gly Arg Ala Ala Val Ala Arg Ser Ala Met Met Gln
385                 390                 395                 400

Asp Ser Pro Phe Phe Gln Gln Tyr Glu Leu Asp Leu Arg Glu Pro Ala
                405                 410                 415
```

```
Leu Gly Gln Gly Ser Phe Ser Val Cys Arg Arg Cys Arg Gln Arg Gln
            420                 425                 430

Ser Gly Gln Glu Phe Ala Val Lys Ile Leu Ser Arg Arg Leu Glu Glu
        435                 440                 445

Asn Thr Gln Arg Glu Val Ala Ala Leu Arg Leu Cys Gln Ser His Pro
    450                 455                 460

Asn Val Val Asn Leu His Glu Val Leu His Asp Gln Leu His Thr Tyr
465                 470                 475                 480

Leu Val Leu Glu Leu Leu Arg Gly Gly Glu Leu Leu Glu His Ile Arg
                485                 490                 495

Lys Lys Arg Leu Phe Ser Glu Ser Glu Ala Ser Gln Ile Leu Arg Ser
            500                 505                 510

Leu Val Ser Ala Val Ser Phe Met His Glu Glu Ala Gly Val Val His
        515                 520                 525

Arg Asp Leu Lys Pro Glu Asn Ile Leu Tyr Ala Asp Asp Thr Pro Gly
    530                 535                 540

Ala Pro Val Lys Ile Ile Asp Phe Gly Phe Ala Arg Leu Arg Pro Gln
545                 550                 555                 560

Ser Pro Ala Glu Pro Met Gln Thr Pro Cys Phe Thr Leu Gln Tyr Ala
                565                 570                 575

Ala Pro Glu Leu Leu Ala Gln Gln Gly Tyr Asp Glu Ser Cys Asp Leu
            580                 585                 590

Trp Ser Leu Gly Val Ile Leu Tyr Met Met Leu Ser Gly Gln Val Pro
        595                 600                 605

Phe Gln Gly Ala Ser Gly Gln Gly Gly Gln Ser Gln Ala Ala Glu Ile
    610                 615                 620

Met Cys Lys Ile Arg Glu Gly Arg Phe Ser Leu Asp Gly Glu Ala Trp
625                 630                 635                 640

Gln Gly Val Ser Glu Glu Ala Lys Glu Leu Val Arg Gly Leu Leu Thr
                645                 650                 655

Val Asp Pro Ala Lys Arg Leu Lys Leu Glu Gly Leu Arg Ser Ser Ser
            660                 665                 670

Trp Leu Gln Asp Gly Ser Ala Arg Ser Ser Pro Leu Arg Thr Pro
        675                 680                 685

Asp Val Leu Glu Ser Ser Gly Pro Ala Val Arg Ser Gly Leu Asn Ala
690                 695                 700

Thr Phe Met Ala Phe Asn Arg Gly Lys Arg Glu Gly Phe Phe Leu Lys
705                 710                 715                 720

Ser Val Glu Asn Ala Pro Leu Ala Lys Arg Arg Lys Gln Lys Leu Arg
                725                 730                 735

Ser Ala Ala Ala Ser Arg Arg Gly Ser Pro Val Pro Ala Ser Ser Gly
            740                 745                 750

Arg Leu Pro Ala Ser Ala Ala Lys Gly Thr Thr Arg Arg Ala Asn Gly
        755                 760                 765

Pro Leu Ser Pro Ser
        770

<210> SEQ ID NO 15
<211> LENGTH: 735
<212> TYPE: PRT
<213> ORGANISM: Rattus norvegicus
<220> FEATURE:
<221> NAME/KEY: MISC_FEATURE
<222> LOCATION: (1)..(735)
<223> OTHER INFORMATION: Rat RSK1
```

<400> SEQUENCE: 15

```
Met Pro Leu Ala Gln Leu Lys Glu Pro Trp Pro Leu Met Glu Leu Val
1               5                   10                  15

Pro Leu Asp Pro Glu Asn Gly Gln Ala Ser Gly Glu Glu Ala Gly Leu
            20                  25                  30

Gln Pro Ser Lys Asp Glu Gly Ile Leu Lys Glu Ile Ser Ile Thr His
        35                  40                  45

His Val Lys Ala Gly Ser Glu Lys Ala Asp Pro Ser His Phe Glu Leu
    50                  55                  60

Leu Lys Val Leu Gly Gln Gly Ser Phe Gly Lys Val Phe Leu Val Arg
65                  70                  75                  80

Lys Val Thr Arg Pro Asp Asn Gly His Leu Tyr Ala Met Lys Val Leu
                85                  90                  95

Lys Lys Ala Thr Leu Lys Val Arg Asp Arg Val Arg Thr Lys Met Glu
            100                 105                 110

Arg Asp Ile Leu Ala Asp Val Asn His Pro Phe Val Val Lys Leu His
            115                 120                 125

Tyr Ala Phe Gln Thr Glu Gly Lys Leu Tyr Leu Ile Leu Asp Phe Leu
130                 135                 140

Arg Gly Gly Asp Leu Phe Thr Arg Leu Ser Lys Glu Val Met Phe Thr
145                 150                 155                 160

Glu Glu Asp Val Lys Phe Tyr Leu Ala Glu Leu Ala Leu Gly Leu Asp
                165                 170                 175

His Leu His Ser Leu Gly Ile Ile Tyr Arg Asp Leu Lys Pro Glu Asn
            180                 185                 190

Ile Leu Leu Asp Glu Glu Gly His Ile Lys Leu Thr Asp Phe Gly Leu
        195                 200                 205

Ser Lys Glu Ala Ile Asp His Glu Lys Lys Ala Tyr Ser Phe Cys Gly
210                 215                 220

Thr Val Glu Tyr Met Ala Pro Glu Val Val Asn Arg Gln Gly His Thr
225                 230                 235                 240

His Ser Ala Asp Trp Trp Ser Tyr Gly Val Leu Met Phe Glu Met Leu
                245                 250                 255

Thr Gly Ser Leu Pro Phe Gln Gly Lys Asp Arg Lys Glu Thr Met Thr
            260                 265                 270

Leu Ile Leu Lys Ala Lys Leu Gly Met Pro Gln Phe Leu Ser Thr Glu
        275                 280                 285

Ala Gln Ser Leu Leu Arg Ala Leu Phe Lys Arg Asn Pro Ala Asn Arg
290                 295                 300

Leu Gly Ser Gly Pro Asp Gly Ala Glu Glu Ile Lys Arg His Ile Phe
305                 310                 315                 320

Tyr Ser Thr Ile Asp Trp Asn Lys Leu Tyr Arg Arg Glu Ile Lys Pro
                325                 330                 335

Pro Phe Lys Pro Ala Val Ala Gln Pro Asp Asp Thr Phe Tyr Phe Asp
            340                 345                 350

Thr Glu Phe Thr Ser Arg Thr Pro Arg Asp Ser Pro Gly Ile Pro Pro
        355                 360                 365

Ser Ala Gly Ala His Gln Leu Phe Arg Gly Phe Ser Phe Val Ala Thr
370                 375                 380

Gly Leu Met Glu Asp Asp Ser Lys Pro Arg Ala Thr Gln Ala Pro Leu
385                 390                 395                 400

His Ser Val Val Gln Gln Leu His Gly Lys Asn Leu Val Phe Ser Asp
                405                 410                 415
```

```
Gly Tyr Ile Val Lys Glu Thr Ile Gly Val Gly Ser Tyr Ser Val Cys
            420                 425                 430
Lys Arg Cys Val His Lys Ala Thr Asn Met Glu Tyr Ala Val Lys Val
        435                 440                 445
Ile Asp Lys Ser Lys Arg Asp Pro Ser Glu Ile Glu Ile Leu Leu
450                 455                 460
Arg Tyr Gly Gln His Pro Asn Ile Ile Thr Leu Lys Asp Val Tyr Asp
465                 470                 475                 480
Asp Ser Lys His Val Tyr Leu Val Thr Glu Leu Met Arg Gly Gly Glu
                485                 490                 495
Leu Leu Asp Lys Ile Leu Arg Gln Lys Phe Phe Ser Glu Arg Glu Ala
            500                 505                 510
Ser Phe Val Leu Tyr Thr Ile Ser Lys Thr Val Glu Tyr Leu His Ser
        515                 520                 525
Gln Gly Val Val His Arg Asp Leu Lys Pro Ser Asn Ile Leu Tyr Val
    530                 535                 540
Asp Glu Ser Gly Asn Pro Glu Cys Leu Arg Ile Cys Asp Phe Gly Phe
545                 550                 555                 560
Ala Lys Gln Leu Arg Ala Glu Asn Gly Leu Leu Met Thr Pro Cys Tyr
                565                 570                 575
Thr Ala Asn Phe Val Ala Pro Glu Val Leu Lys Arg Gln Gly Tyr Asp
            580                 585                 590
Glu Gly Cys Asp Ile Trp Ser Leu Gly Val Leu Leu Tyr Thr Met Leu
        595                 600                 605
Ala Gly Tyr Thr Pro Phe Ala Asn Gly Pro Ser Asp Thr Pro Glu Glu
    610                 615                 620
Ile Leu Thr Arg Ile Ser Ser Gly Lys Phe Thr Leu Ser Gly Gly Asn
625                 630                 635                 640
Trp Asn Thr Val Ser Glu Thr Ala Lys Asp Leu Val Ser Lys Met Leu
                645                 650                 655
His Val Asp Pro His Gln Arg Leu Thr Ala Lys Gln Val Leu Gln His
            660                 665                 670
Pro Trp Ile Thr Gln Lys Asp Lys Leu Pro Gln Ser Gln Leu Ser His
        675                 680                 685
Gln Asp Leu Gln Leu Val Lys Gly Gly Met Ala Ala Thr Tyr Ser Ala
    690                 695                 700
Leu Ser Ser Ser Lys Pro Thr Pro Gln Leu Lys Pro Ile Glu Ser Ser
705                 710                 715                 720
Ile Leu Ala Gln Arg Arg Val Arg Lys Leu Pro Ser Thr Thr Leu
                725                 730                 735

<210> SEQ ID NO 16
<211> LENGTH: 740
<212> TYPE: PRT
<213> ORGANISM: Rattus norvegicus
<220> FEATURE:
<221> NAME/KEY: MISC_FEATURE
<222> LOCATION: (1)..(740)
<223> OTHER INFORMATION: Rat RSK2

<400> SEQUENCE: 16

Met Pro Leu Ala Gln Leu Ala Asp Pro Trp Gln Lys Met Ala Val Glu
1               5                   10                  15
Ser Pro Ser Asp Ser Ala Glu Asn Gly Gln Gln Ile Met Asp Glu Pro
            20                  25                  30
```

```
Met Gly Glu Glu Ile Asn Pro Gln Thr Glu Gly Ser Ile Lys
             35                  40                  45
Glu Ile Ala Ile Thr His His Val Lys Glu Gly His Glu Lys Ala Asp
 50                  55                  60
Pro Ser Gln Phe Glu Leu Leu Lys Val Leu Gly Gln Gly Ser Phe Gly
 65                  70                  75                  80
Lys Val Phe Leu Val Lys Lys Ile Ser Gly Ser Asp Ala Arg Gln Leu
                 85                  90                  95
Tyr Ala Met Lys Val Leu Lys Lys Ala Thr Leu Lys Val Arg Asp Arg
            100                 105                 110
Val Arg Thr Lys Met Glu Arg Asp Ile Leu Val Glu Val Asn His Pro
            115                 120                 125
Phe Ile Val Lys Leu His Tyr Ala Phe Gln Thr Glu Gly Lys Leu Tyr
            130                 135                 140
Leu Ile Leu Asp Phe Leu Arg Gly Gly Asp Leu Phe Thr Arg Leu Ser
145                 150                 155                 160
Lys Glu Val Met Phe Thr Glu Glu Asp Val Lys Phe Tyr Leu Ala Glu
                165                 170                 175
Leu Ala Leu Ala Leu Asp His Leu His Ser Leu Gly Ile Ile Tyr Arg
            180                 185                 190
Asp Leu Lys Pro Glu Asn Ile Leu Leu Asp Glu Glu Gly His Ile Lys
            195                 200                 205
Leu Thr Asp Phe Gly Leu Ser Lys Glu Ser Ile Asp His Glu Lys Lys
            210                 215                 220
Ala Tyr Ser Phe Cys Gly Thr Val Glu Tyr Met Ala Pro Glu Val Val
225                 230                 235                 240
Asn Arg Arg Gly His Thr Gln Ser Ala Asp Trp Trp Ser Phe Gly Val
                245                 250                 255
Leu Met Phe Glu Met Leu Thr Gly Thr Leu Pro Phe Gln Gly Lys Asp
            260                 265                 270
Arg Lys Glu Thr Met Thr Met Ile Leu Lys Ala Lys Leu Gly Met Pro
            275                 280                 285
Gln Phe Leu Ser Pro Glu Ala Gln Ser Leu Leu Arg Met Leu Phe Lys
            290                 295                 300
Arg Asn Pro Ala Asn Arg Leu Gly Ala Gly Pro Asp Gly Val Glu Glu
305                 310                 315                 320
Ile Lys Arg His Ser Phe Phe Ser Thr Ile Asp Trp Asn Lys Leu Tyr
                325                 330                 335
Arg Arg Glu Ile His Pro Pro Phe Lys Pro Ala Thr Gly Arg Pro Glu
            340                 345                 350
Asp Thr Phe Tyr Phe Asp Pro Glu Phe Thr Ala Lys Thr Pro Lys Asp
            355                 360                 365
Ser Pro Gly Ile Pro Pro Ser Ala Asn Ala His Gln Leu Phe Arg Gly
            370                 375                 380
Phe Ser Phe Val Ala Ile Thr Ser Asp Asp Glu Ser Gln Ala Met Gln
385                 390                 395                 400
Thr Val Gly Val His Ser Ile Val Gln Gln Leu His Arg Asn Ser Ile
                405                 410                 415
Gln Phe Thr Asp Gly Tyr Glu Val Lys Glu Asp Ile Gly Val Gly Ser
            420                 425                 430
Tyr Ser Val Cys Lys Arg Cys Ile His Lys Ala Thr Asn Met Glu Phe
            435                 440                 445
Ala Val Lys Ile Ile Asp Lys Ser Lys Arg Asp Pro Thr Glu Glu Ile
```

```
        450                 455                 460
Glu Ile Leu Leu Arg Tyr Gly Gln His Pro Asn Ile Ile Thr Leu Lys
465                 470                 475                 480

Asp Val Tyr Asp Asp Gly Lys Tyr Val Tyr Val Thr Glu Leu Met
                485                 490                 495

Lys Gly Gly Glu Leu Leu Asp Lys Ile Leu Arg Gln Lys Phe Phe Ser
                500                 505                 510

Glu Arg Glu Ala Ser Ala Val Leu Phe Thr Ile Thr Lys Thr Val Glu
            515                 520                 525

Tyr Leu His Thr Gln Gly Val Val His Arg Asp Leu Lys Pro Ser Asn
        530                 535                 540

Ile Leu Tyr Val Asp Glu Ser Gly Asn Pro Glu Ser Ile Arg Ile Cys
545                 550                 555                 560

Asp Phe Gly Phe Ala Lys Gln Leu Arg Ala Glu Asn Gly Leu Leu Met
                565                 570                 575

Thr Pro Cys Tyr Thr Ala Asn Phe Val Ala Pro Glu Val Leu Lys Arg
                580                 585                 590

Gln Gly Tyr Asp Ala Ala Cys Asp Ile Trp Ser Leu Gly Val Leu Leu
            595                 600                 605

Tyr Thr Met Leu Thr Gly Tyr Thr Pro Phe Ala Asn Gly Pro Asp Asp
        610                 615                 620

Thr Pro Glu Glu Ile Leu Ala Arg Ile Gly Ser Gly Lys Phe Ser Leu
625                 630                 635                 640

Ser Gly Gly Tyr Trp Asn Ser Val Ser Asp Thr Ala Lys Asp Leu Val
                645                 650                 655

Ser Lys Met Leu His Val Asp Pro His Gln Arg Leu Thr Ala Ala Leu
                660                 665                 670

Val Leu Arg His Pro Trp Ile Val His Trp Asp Gln Leu Pro Gln Tyr
            675                 680                 685

Gln Leu Asn Arg Gln Asp Ala Pro His Leu Val Lys Gly Ala Met Ala
        690                 695                 700

Ala Thr Tyr Ser Ala Leu Asn Arg Asn Gln Ser Pro Val Leu Glu Pro
705                 710                 715                 720

Val Gly Arg Ser Thr Leu Ala Gln Arg Arg Gly Ile Lys Lys Ile Thr
                725                 730                 735

Ser Thr Ala Leu
            740

<210> SEQ ID NO 17
<211> LENGTH: 733
<212> TYPE: PRT
<213> ORGANISM: Rattus norvegicus
<220> FEATURE:
<221> NAME/KEY: MISC_FEATURE
<222> LOCATION: (1)..(733)
<223> OTHER INFORMATION: Rat RSK3

<400> SEQUENCE: 17

Met Glu Leu Asn Met Lys Lys Phe Thr Val Arg Arg Phe Phe Ser Val
1               5                   10                  15

Tyr Leu Arg Lys Lys Ser Arg Ser Lys Ser Ser Leu Ser Arg Leu
                20                  25                  30

Glu Glu Glu Gly Ile Val Lys Glu Ile Asp Ile Ser Ser His Val Lys
            35                  40                  45

Glu Gly Phe Glu Lys Ala Asp Pro Ser Gln Phe Glu Leu Leu Lys Val
        50                  55                  60
```

```
Leu Gly Gln Gly Ser Tyr Gly Lys Val Phe Leu Val Arg Lys Val Thr
65                  70                  75                  80

Gly Ser Asp Ala Gly Gln Leu Tyr Ala Met Lys Val Leu Lys Lys Ala
                85                  90                  95

Thr Leu Lys Val Arg Asp Arg Val Arg Ser Lys Met Glu Arg Asp Ile
            100                 105                 110

Leu Ala Glu Val Asn His Pro Phe Ile Val Lys Leu His Tyr Ala Phe
        115                 120                 125

Gln Thr Glu Gly Lys Leu Tyr Leu Ile Leu Asp Phe Leu Arg Gly Gly
    130                 135                 140

Asp Leu Phe Thr Arg Leu Ser Lys Glu Val Met Phe Thr Glu Glu Asp
145                 150                 155                 160

Val Lys Phe Tyr Leu Ala Glu Leu Ala Leu Ala Leu Asp His Leu His
                165                 170                 175

Gly Leu Gly Ile Ile Tyr Arg Asp Leu Lys Pro Glu Asn Ile Leu Leu
                180                 185                 190

Asp Glu Glu Gly His Ile Lys Ile Thr Asp Phe Gly Leu Ser Lys Glu
            195                 200                 205

Ala Ile Asp His Asp Lys Arg Ala Tyr Ser Phe Cys Gly Thr Ile Glu
210                 215                 220

Tyr Met Ala Pro Glu Val Val Asn Arg Arg Gly His Thr Gln Ser Ala
225                 230                 235                 240

Asp Trp Trp Ser Phe Gly Val Leu Met Phe Glu Met Leu Thr Gly Ser
                245                 250                 255

Leu Pro Phe Gln Gly Lys Asp Arg Lys Glu Thr Met Ala Leu Ile Leu
                260                 265                 270

Lys Ala Lys Leu Gly Met Pro Gln Phe Leu Ser Ala Glu Ala Gln Ser
            275                 280                 285

Leu Leu Arg Ala Leu Phe Lys Arg Asn Pro Cys Asn Arg Leu Gly Ala
        290                 295                 300

Gly Val Asp Gly Val Glu Glu Ile Lys Arg His Pro Phe Phe Val Thr
305                 310                 315                 320

Ile Asp Trp Asn Lys Leu Tyr Arg Lys Glu Ile Lys Pro Pro Phe Lys
                325                 330                 335

Pro Ala Val Gly Arg Pro Glu Asp Thr Phe His Phe Asp Pro Glu Phe
                340                 345                 350

Thr Ala Arg Thr Pro Thr Asp Ser Pro Gly Val Pro Pro Ser Ala Asn
            355                 360                 365

Ala His His Leu Phe Arg Gly Phe Ser Phe Val Ala Ser Ser Leu Val
        370                 375                 380

Gln Glu Pro Ser Gln Gln Asp Val Pro Lys Ala Pro Ile His Pro Ile
385                 390                 395                 400

Val Gln Gln Leu His Gly Asn Asn Ile His Phe Thr Asp Gly Tyr Glu
                405                 410                 415

Ile Lys Glu Asp Ile Gly Val Gly Ser Tyr Ser Val Cys Lys Arg Cys
            420                 425                 430

Val His Lys Ala Thr Asp Ala Glu Tyr Ala Val Lys Ile Ile Asp Lys
        435                 440                 445

Ser Lys Arg Asp Pro Ser Glu Glu Ile Glu Ile Leu Leu Arg Tyr Gly
    450                 455                 460

Gln His Pro Asn Ile Ile Thr Leu Lys Asp Val Tyr Asp Asp Gly Lys
465                 470                 475                 480
```

Tyr Val Tyr Leu Val Met Glu Leu Met Arg Gly Gly Glu Leu Leu Asp
            485                 490                 495

Arg Ile Leu Arg Gln Arg Cys Phe Ser Glu Arg Glu Ala Ser Asp Val
        500                 505                 510

Leu Tyr Thr Ile Ala Arg Thr Met Asp Tyr Leu His Ser Gln Gly Val
        515                 520                 525

Val His Arg Asp Leu Lys Pro Ser Asn Ile Leu Tyr Met Asp Glu Ser
        530                 535                 540

Gly Asn Pro Glu Ser Ile Arg Ile Cys Asp Phe Gly Phe Ala Lys Gln
545                 550                 555                 560

Leu Arg Ala Glu Asn Gly Leu Leu Met Thr Pro Cys Tyr Thr Ala Asn
                565                 570                 575

Phe Val Ala Pro Glu Val Leu Lys Arg Gln Gly Tyr Asp Ala Ala Cys
            580                 585                 590

Asp Val Trp Ser Leu Gly Ile Leu Leu Tyr Thr Met Leu Ala Gly Phe
        595                 600                 605

Thr Pro Phe Ala Asn Gly Pro Asp Asp Thr Pro Glu Glu Ile Leu Ala
        610                 615                 620

Arg Ile Gly Ser Gly Lys Tyr Ala Leu Ser Gly Gly Asn Trp Asp Ser
625                 630                 635                 640

Ile Ser Asp Ala Ala Lys Asp Val Val Ser Lys Met Leu His Val Asp
                645                 650                 655

Pro Gln Gln Arg Leu Thr Ala Val Gln Val Leu Lys His Pro Trp Ile
            660                 665                 670

Val Asn Arg Glu Tyr Leu Ser Gln Asn Gln Leu Ser Arg Gln Asp Val
        675                 680                 685

His Leu Val Lys Gly Ala Met Ala Ala Thr Tyr Phe Ala Leu Asn Arg
        690                 695                 700

Thr Pro Gln Ala Pro Arg Leu Glu Pro Val Leu Ser Ser Ser Leu Ala
705                 710                 715                 720

Gln Arg Arg Gly Met Lys Arg Leu Thr Ser Thr Arg Leu
                725                 730

<210> SEQ ID NO 18
<211> LENGTH: 860
<212> TYPE: PRT
<213> ORGANISM: Rattus norvegicus
<220> FEATURE:
<221> NAME/KEY: MISC_FEATURE
<222> LOCATION: (1)..(860)
<223> OTHER INFORMATION: Rat RSK4

<400> SEQUENCE: 18

Met Leu Asn Phe Arg Arg Thr Arg His Thr Pro Ser Gly His Arg Ser
1               5                   10                  15

Asn Ser Ser Leu Asn Leu Phe Cys Cys Phe Pro Phe Gly Cys Arg
            20                  25                  30

Arg Gln Ser Arg Ser Arg Gln Arg Ala Gly Thr Pro Val Val Pro Leu
        35                  40                  45

Leu Arg Tyr Pro Pro Leu Ala Arg Ser Ala Val Thr Gln Arg Glu Ser
        50                  55                  60

Trp Ser Tyr Glu Glu Asp His Glu Pro Ala Gln Gln Ala Gly Cys Met
65                  70                  75                  80

Leu Val Leu Gly Thr Ser Ser Phe Phe Ser Ser Val Pro Glu Ala Ala
                85                  90                  95

Met Leu Pro Phe Ala Pro Val Glu Asp Pro Trp Asp Glu Glu Met Glu

```
            100                 105                 110
Val Phe Gly Ser Gly Thr Ser Ser Ser Glu Pro Gln Ile Val Phe
            115                 120                 125
Thr Met Lys Thr Ala Ala Met Val Ile Arg Gln His Glu His Lys Glu
            130                 135                 140
Val Asn Asp Leu Lys Met Val Asp Glu Pro Met Asp Glu Gly Glu Pro
145                 150                 155                 160
Val Phe Cys Arg Arg Glu Asp Leu Val Lys Glu Ile Pro Ile Thr Gln
                165                 170                 175
His Val Lys Glu Gly Tyr Glu Lys Ala Asp Pro Ala Gln Phe Asp Leu
            180                 185                 190
Leu Lys Val Leu Gly Gln Gly Ser Phe Gly Lys Val Phe Leu Val Arg
            195                 200                 205
Lys Lys Thr Gly Pro Asp Ala Gly Gln Leu Tyr Ala Met Lys Val Leu
            210                 215                 220
Arg Lys Ala Ser Leu Lys Val Arg Asp Arg Val Arg Thr Lys Met Glu
225                 230                 235                 240
Arg Asp Ile Leu Val Glu Val Asn His Pro Phe Ile Val Lys Leu His
                245                 250                 255
Tyr Ala Phe Gln Thr Glu Gly Lys Leu Tyr Leu Ile Leu Asp Phe Leu
            260                 265                 270
Arg Gly Gly Asp Val Phe Thr Arg Leu Ser Lys Glu Val Leu Phe Thr
            275                 280                 285
Glu Glu Asp Val Lys Phe Tyr Leu Ala Glu Leu Ala Leu Ala Leu Asp
            290                 295                 300
His Leu His Arg Leu Gly Ile Val Tyr Arg Asp Leu Lys Pro Glu Asn
305                 310                 315                 320
Ile Leu Leu Asp Glu Ile Gly His Ile Lys Leu Thr Asp Phe Gly Leu
                325                 330                 335
Ser Lys Glu Ser Val Asp Gln Glu Lys Lys Ala Tyr Ser Phe Cys Gly
            340                 345                 350
Thr Val Glu Tyr Met Ala Pro Glu Val Val Asn Arg Arg Gly His Ser
            355                 360                 365
Gln Ser Ala Asp Trp Trp Ser Tyr Gly Val Leu Met Phe Glu Met Leu
            370                 375                 380
Thr Gly Thr Leu Pro Phe Gln Gly Lys Asp Arg Asn Glu Thr Met Asn
385                 390                 395                 400
Met Ile Leu Lys Ala Lys Leu Gly Met Pro Gln Phe Leu Ser Ala Glu
                405                 410                 415
Ala Gln Ser Leu Leu Arg Met Leu Phe Lys Arg Asn Pro Ala Asn Arg
            420                 425                 430
Leu Gly Ser Glu Gly Val Glu Val Lys Arg His Ala Phe Phe Ser
            435                 440                 445
Ser Ile Asp Trp Asn Lys Leu Tyr Lys Arg Glu Val Gln Pro Pro Phe
            450                 455                 460
Arg Pro Ala Ser Gly Lys Pro Asp Asp Thr Phe Cys Phe Asp Pro Glu
465                 470                 475                 480
Phe Thr Ala Lys Thr Pro Lys Asp Ser Pro Gly Leu Pro Ala Ser Ala
                485                 490                 495
Asn Ala His Gln Leu Phe Lys Gly Phe Ser Phe Val Ala Thr Ser Ile
            500                 505                 510
Ala Glu Glu Tyr Lys Ile Thr Pro Val Thr Ser Ser Asn Val Leu Pro
            515                 520                 525
```

```
Ile Val Gln Ile Asn Gly Asn Ala Ala Gln Phe Ser Glu Ala Tyr Glu
    530                 535                 540

Leu Lys Glu Asp Ile Gly Ile Gly Ser Tyr Ser Val Cys Lys Arg Cys
545                 550                 555                 560

Ile His Ser Ala Ser Asn Met Glu Phe Ala Val Lys Ile Ile Asp Lys
                565                 570                 575

Asn Lys Arg Asp Pro Ser Glu Glu Ile Glu Ile Leu Met Arg Tyr Gly
            580                 585                 590

Gln His Pro Asn Ile Ile Ser Leu Lys Glu Val Phe Asp Asp Gly Lys
        595                 600                 605

Tyr Val Tyr Leu Val Thr Asp Leu Met Lys Gly Gly Glu Leu Leu Asp
    610                 615                 620

Arg Ile Leu Lys Lys Lys Cys Phe Ser Glu Gln Glu Ala Ser Asn Val
625                 630                 635                 640

Leu Tyr Val Ile Thr Lys Thr Val Glu Tyr Leu His Ser Gln Gly Val
                645                 650                 655

Val His Arg Asp Leu Lys Pro Ser Asn Ile Leu Tyr Met Asp Glu Ser
            660                 665                 670

Gly His Pro Asp Ser Ile Lys Ile Cys Asp Phe Gly Phe Ala Lys Gln
        675                 680                 685

Leu Arg Gly Glu Asn Gly Leu Leu Leu Thr Pro Cys Tyr Thr Ala Asn
    690                 695                 700

Phe Val Ala Pro Glu Val Leu Thr Gln Gln Gly Tyr Asp Ala Ala Cys
705                 710                 715                 720

Asp Ile Trp Ser Leu Gly Val Leu Leu Tyr Thr Met Leu Ala Gly Tyr
                725                 730                 735

Thr Pro Phe Ser Asn Gly Pro Asn Asp Thr Pro Glu Glu Ile Leu Leu
            740                 745                 750

Arg Ile Gly Asn Gly Arg Phe Ser Leu Ser Gly Gly Ile Trp Asp Asn
        755                 760                 765

Ile Ser Arg Gly Ala Lys Asp Leu Leu Ser His Met Leu His Met Asp
    770                 775                 780

Pro His Gln Arg Tyr Thr Ala Glu Gln Val Leu Lys His Pro Trp Ile
785                 790                 795                 800

Thr Gln Arg Glu Gln Leu Pro Arg His Gln Pro Thr Ser Asp Pro Pro
                805                 810                 815

Pro Gln Glu Ala Val Ala Ala Tyr Ser Val Leu Ala Arg Asn Gln Asn
            820                 825                 830

Asn Arg His Pro Ile Leu Glu Pro Val Ala Ala Ser Arg Leu Ala Gln
        835                 840                 845

Arg Arg Asn Met Lys Lys Arg Thr Ser Thr Gly Leu
    850                 855                 860

<210> SEQ ID NO 19
<211> LENGTH: 775
<212> TYPE: PRT
<213> ORGANISM: Rattus norvegicus
<220> FEATURE:
<221> NAME/KEY: MISC_FEATURE
<222> LOCATION: (1)..(775)
<223> OTHER INFORMATION: Rat MSK1

<400> SEQUENCE: 19

Met Glu Gly Glu Gly Gly Ser Gly Gly Ala Gly Thr Ser Gly Asp
1               5                   10                  15
```

-continued

```
Ser Gly Asp Gly Gly Glu Gln Leu Leu Thr Val Lys His Glu Leu Arg
             20                  25                  30

Thr Ala Asn Leu Thr Gly His Ala Glu Lys Val Gly Ile Glu Asn Phe
         35                  40                  45

Glu Leu Leu Lys Val Leu Gly Thr Gly Ala Tyr Gly Lys Val Phe Leu
 50                  55                  60

Val Arg Lys Ile Ser Gly His Asp Ala Gly Lys Leu Tyr Ala Met Lys
 65                  70                  75                  80

Val Leu Lys Lys Ala Thr Ile Val Gln Lys Ala Lys Thr Thr Glu His
                 85                  90                  95

Thr Arg Thr Glu Arg Gln Val Leu Glu His Ile Arg Gln Ser Pro Phe
            100                 105                 110

Leu Val Thr Leu His Tyr Ala Phe Gln Thr Glu Thr Lys Leu His Leu
            115                 120                 125

Ile Leu Asp Tyr Ile Asn Gly Gly Glu Leu Phe Thr His Leu Ser Gln
            130                 135                 140

Arg Glu Arg Phe Thr Glu His Glu Val Gln Ile Tyr Val Gly Glu Ile
145                 150                 155                 160

Val Leu Ala Leu Glu His Leu His Lys Leu Gly Ile Ile Tyr Arg Asp
                165                 170                 175

Ile Lys Leu Glu Asn Ile Leu Leu Asp Ser Asn Gly His Val Val Leu
            180                 185                 190

Thr Asp Phe Gly Leu Ser Lys Glu Phe Val Ala Asp Glu Ala Glu Arg
            195                 200                 205

Ala Tyr Ser Phe Cys Gly Thr Ile Glu Tyr Met Ala Pro Asp Ile Val
            210                 215                 220

Arg Gly Gly Asp Ser Gly His Asp Lys Gly Met Ser Ser Val Ala Lys
225                 230                 235                 240

Asp Leu Leu Gln Arg Leu Leu Met Lys Asp Pro Lys Lys Arg Leu Gly
                245                 250                 255

Cys Gly Pro Arg Asp Ala Glu Glu Ile Lys Glu His Leu Phe Phe Glu
            260                 265                 270

Lys Ile Asn Trp Asp Asp Leu Ala Ala Lys Lys Val Pro Ala Pro Phe
            275                 280                 285

Lys Pro Val Ile Arg Asp Glu Leu Asp Val Ser Asn Phe Ala Glu Glu
            290                 295                 300

Phe Thr Glu Met Asp Pro Thr Tyr Ser Pro Ala Ala Leu Pro Gln Ser
305                 310                 315                 320

Ser Glu Arg Leu Phe Gln Gly Tyr Ser Phe Val Ala Pro Ser Ile Leu
                325                 330                 335

Phe Lys Arg Asn Ala Ala Val Ile Asp Pro Leu Gln Phe His Met Gly
            340                 345                 350

Val Asp Arg Pro Gly Val Thr Asn Val Ala Arg Ser Ala Met Met Lys
            355                 360                 365

Asp Ser Pro Phe Tyr Gln His Tyr Asp Leu Asp Leu Lys Asp Lys Pro
            370                 375                 380

Leu Gly Glu Gly Ser Phe Ser Ile Cys Arg Lys Cys Val His Lys Lys
385                 390                 395                 400

Thr Asn Gln Ala Phe Ala Val Lys Ile Ile Ser Lys Arg Met Glu Ala
                405                 410                 415

Asn Thr Gln Lys Glu Ile Thr Ala Leu Lys Leu Cys Glu Gly His Pro
            420                 425                 430

Asn Val Val Lys Leu His Glu Val Phe His Asp Gln Leu His Thr Phe
```

-continued

```
                435                 440                 445
Leu Val Met Glu Leu Leu Asn Gly Gly Glu Leu Phe Glu Arg Ile Lys
    450                 455                 460
Lys Lys Lys His Phe Ser Glu Thr Glu Ala Ser Tyr Ile Met Arg Lys
465                 470                 475                 480
Leu Val Ser Ala Val Ser His Met His Asp Val Gly Val Val His Arg
                485                 490                 495
Asp Leu Lys Pro Glu Thr Val Phe His Arg Glu Ile Ser Arg Ser Pro
            500                 505                 510
Val Ile Ser Met Arg Ile Pro Glu Tyr Thr Leu Gln Asn Leu Leu Phe
        515                 520                 525
Thr Asp Glu Asn Asp Asn Leu Glu Ile Lys Val Ile Asp Phe Gly Phe
    530                 535                 540
Ala Arg Leu Lys Pro Pro Asp Asn Gln Pro Leu Lys Thr Pro Cys Phe
545                 550                 555                 560
Thr Leu His Tyr Ala Ala Pro Glu Leu Leu Thr His Asn Gly Tyr Asp
                565                 570                 575
Glu Ser Cys Asp Leu Trp Ser Leu Gly Val Ile Leu Tyr Thr Met Leu
            580                 585                 590
Ser Gly Gln Val Pro Phe Gln Ser His Asp Arg Ser Leu Thr Cys Thr
        595                 600                 605
Ser Ala Val Glu Ile Met Lys Lys Ile Lys Gly Asp Phe Ser Phe
    610                 615                 620
Glu Gly Glu Ala Trp Lys Asn Val Ser Gln Glu Ala Lys Asp Leu Ile
625                 630                 635                 640
Gln Gly Leu Leu Thr Val Asp Pro Asn Lys Arg Leu Lys Met Ser Gly
                645                 650                 655
Leu Arg Tyr Asn Glu Trp Leu Gln Asp Gly Ser Gln Leu Ser Ser Asn
            660                 665                 670
Pro Leu Met Thr Pro Asp Ile Leu Gly Ser Ser Gly Ala Ala Val His
        675                 680                 685
Thr Cys Val Lys Ala Thr Phe His Ala Phe Asn Lys Tyr Lys Arg Glu
    690                 695                 700
Gly Phe Cys Leu Gln Asn Val Asp Lys Ala Pro Leu Ala Lys Arg Arg
705                 710                 715                 720
Lys Met Lys Arg Thr Ser Thr Ser Thr Glu Thr Arg Ser Ser Ser Ser
                725                 730                 735
Glu Ser Ser Arg Ser Ser Ser Ser His Ser His Gly Lys Thr Thr Pro
            740                 745                 750
Thr Lys Thr Leu Gln Pro Ser Asn Pro Thr Glu Gly Ser Asn Pro Asp
        755                 760                 765
Thr Leu Phe Gln Phe Ser Asp
    770                 775
```

<210> SEQ ID NO 20
<211> LENGTH: 773
<212> TYPE: PRT
<213> ORGANISM: Rattus norvegicus
<220> FEATURE:
<221> NAME/KEY: MISC_FEATURE
<222> LOCATION: (1)..(773)
<223> OTHER INFORMATION: Rat MSK2

<400> SEQUENCE: 20

```
Met Gly Asp Glu Asp Glu Asp Glu Gly Cys Ala Val Glu Leu Gln Ile
1               5                   10                  15
```

```
Thr Glu Ala Asn Leu Thr Gly His Glu Glu Lys Val Ser Val Glu Asn
             20                  25                  30

Phe Ala Leu Leu Lys Val Leu Gly Thr Gly Ala Tyr Gly Lys Val Phe
         35                  40                  45

Leu Val Arg Lys Ala Gly Gly His Asp Ala Gly Lys Leu Tyr Ala Met
 50                  55                  60

Lys Val Leu Arg Lys Ala Ala Leu Val Gln Arg Ala Lys Thr Gln Glu
 65                  70                  75                  80

His Thr Arg Thr Glu Arg Ser Val Leu Glu Leu Val Arg Gln Ala Pro
                 85                  90                  95

Phe Leu Val Thr Leu His Tyr Ala Phe Gln Thr Asp Ala Lys Leu His
             100                 105                 110

Leu Ile Leu Asp Tyr Val Ser Gly Gly Glu Met Phe Thr His Leu Tyr
         115                 120                 125

Gln Arg Gln Tyr Phe Lys Glu Ala Glu Val Arg Val Tyr Gly Gly Glu
130                 135                 140

Ile Val Leu Ala Leu Glu His Leu His Lys Leu Gly Ile Ile Tyr Arg
145                 150                 155                 160

Asp Leu Lys Leu Glu Asn Val Leu Leu Asp Ser Glu Gly His Ile Val
                 165                 170                 175

Leu Thr Asp Phe Gly Leu Ser Lys Glu Phe Leu Thr Glu Glu Lys Glu
             180                 185                 190

Arg Thr Phe Ser Phe Cys Gly Thr Ile Glu Tyr Met Ala Pro Glu Ile
         195                 200                 205

Ile Arg Ser Lys Ala Gly His Gly Lys Ala Val Asp Trp Trp Ser Leu
210                 215                 220

Gly Ile Leu Leu Phe Glu Leu Leu Thr Gly Ala Ser Pro Phe Thr Leu
225                 230                 235                 240

Glu Gly Glu Arg Asn Thr Gln Ala Glu Val Ser Arg Arg Ile Leu Lys
                 245                 250                 255

Cys Ser Pro Pro Phe Pro Pro Arg Ile Gly Pro Val Ala Gln Asp Leu
             260                 265                 270

Leu Gln Arg Leu Leu Cys Lys Asp Pro Lys Lys Arg Leu Gly Ala Gly
         275                 280                 285

Pro Gln Gly Ala Gln Glu Val Lys Ser His Leu Phe Phe Gln Gly Leu
290                 295                 300

Asp Trp Val Ala Leu Ala Ala Arg Lys Ile Pro Ala Pro Phe Arg Pro
305                 310                 315                 320

Gln Ile Arg Ser Glu Leu Asp Val Gly Asn Phe Ala Glu Glu Phe Thr
                 325                 330                 335

Arg Leu Glu Pro Val Tyr Ser Pro Ala Gly Ser Pro Pro Pro Gly Asp
             340                 345                 350

Pro Arg Ile Phe Gln Gly Tyr Ser Phe Val Ala Pro Ser Ile Leu Phe
         355                 360                 365

Asp His Asn Asn Ala Val Met Ala Asp Val Leu Ala Ala Pro Gly Ala
370                 375                 380

Gly Tyr Arg Pro Gly Arg Ala Ala Val Ala Arg Ser Ala Met Met Gln
385                 390                 395                 400

Asp Ser Pro Phe Phe Gln Gln Tyr Glu Leu Asp Leu Arg Glu Pro Ala
                 405                 410                 415

Leu Gly Gln Gly Ser Phe Ser Val Cys Arg Arg Cys Arg Gln Arg Gln
             420                 425                 430
```

-continued

Ser Gly Gln Glu Phe Ala Val Lys Ile Leu Ser Arg Arg Leu Glu Glu
        435                 440                 445

Asn Thr Gln Arg Glu Val Ala Ala Leu Arg Leu Cys Gln Ser His Pro
    450                 455                 460

Asn Val Val Asn Leu His Glu Val Leu His Asp Gln Leu His Thr Tyr
465                 470                 475                 480

Leu Val Leu Glu Leu Leu Arg Gly Gly Glu Leu Leu Glu His Ile Arg
                485                 490                 495

Lys Lys Arg Leu Phe Ser Glu Ser Glu Ala Ser Gln Ile Leu Arg Ser
            500                 505                 510

Leu Val Ser Ala Val Ser Phe Met His Glu Glu Ala Gly Val Val His
                515                 520                 525

Arg Asp Leu Lys Pro Glu Asn Ile Leu Tyr Ala Asp Asp Thr Pro Gly
    530                 535                 540

Ala Pro Val Lys Ile Ile Asp Phe Gly Phe Ala Arg Leu Arg Pro Gln
545                 550                 555                 560

Ser Pro Ala Gly Pro Met Gln Thr Pro Cys Phe Thr Leu Gln Tyr Ala
                565                 570                 575

Ala Pro Glu Leu Leu Ala Gln Gln Gly Tyr Asp Glu Ser Cys Asp Leu
            580                 585                 590

Trp Ser Leu Gly Val Ile Leu Tyr Met Met Leu Ser Gly Gln Val Pro
        595                 600                 605

Phe Gln Gly Ala Ser Gly Gln Gly Gly Gln Ser Gln Ala Ala Glu Ile
    610                 615                 620

Met Cys Lys Ile Arg Glu Gly Arg Phe Ser Leu Asp Gly Glu Ala Trp
625                 630                 635                 640

Gln Gly Val Ser Glu Glu Ala Lys Glu Leu Val Arg Gly Leu Leu Thr
                645                 650                 655

Val Asp Pro Ala Lys Arg Leu Lys Leu Glu Gly Leu Arg Ser Ser Ser
            660                 665                 670

Trp Leu Gln Asp Gly Ser Ala Arg Ser Ser Pro Pro Leu Arg Thr Pro
        675                 680                 685

Asp Val Leu Glu Ser Ser Gly Pro Ala Val Arg Ser Gly Leu Asn Ala
    690                 695                 700

Thr Phe Met Ala Phe Asn Arg Gly Lys Arg Glu Gly Phe Phe Leu Lys
705                 710                 715                 720

Ser Val Glu Asn Ala Pro Leu Ala Lys Arg Arg Lys Gln Lys Leu Arg
                725                 730                 735

Ser Ala Ala Ala Ser Arg Arg Gly Ser Pro Val Pro Ala Ser Ser Gly
            740                 745                 750

Arg Leu Pro Ala Ser Ala Ser Lys Gly Thr Thr Arg Arg Ala Asn Gly
        755                 760                 765

Pro Leu Ser Pro Ser
    770

METHODS AND TOOLS FOR IDENTIFICATION OF RSK/MSK KINASE INHIBITORS

FIELD OF INVENTION

The present invention relates to the field of structure assisted drug design. More specifically the present invention relates to the field of identification and development of novel RSK and MSK kinase inhibitors by X-ray crystallographic methods and subsequent in silico, in vitro and in vivo screening methods for identification of candidate inhibitors of RSK/MSK.

BACKGROUND OF INVENTION

Fumaric acid esters (FAE) are a group of compounds beneficial in systemic treatment of psoriasis[1-6] and recently FAEs have also been suggested as a new therapeutic option to treat relapsing remitting multiple sclerosis[7-9].

Various combinations of FAEs for oral treatment of psoriasis have been used for more than 50 years[10,11]. Although a controlled study demonstrated the efficacy of dimethylfumarate (DMF) in psoriasis in 1989[12], it was an empirically composed mixture of dimethylfumarate (DMF) with calcium, magnesium and zinc salts of ethylhydrogen fumarate that was registered as Fumaderm® in Germany in 1994. Fumaderm® has since then become the leading drug for systemic therapy of psoriasis in Germany[11]. One limitation in the use of FAE's is the reported side effects with flushing and gastrointestinal symptoms such as diarrhoea, nausea and cramps. Thus, overall FAE's have been shown to have a favourable long-term safety and clinical-efficacy profile[2] and in particular no long-term toxicity nor a higher risk for infections or malignancies have been observed in more than 100,000 patient years[3].

A second generation fumaric acid derivative (BG-12) was developed as an enteric-coated microtablet to improve gastrointestinal tolerability[13]. BG-12 has shown very promising result in patients with relapsing-remitting multiple sclerosis in a multi-centre, randomized, double-blind, placebo-controlled phase IIb study[9,14] and most recently two phase III clinical trials in patients with relapsing-remitting multiple sclerosis including more than 2600 patients have been reported to confirm these results although the complete data set has not yet been published[15].

Fumaric acid esters have been shown to be effective in several dermatological diseases including: Necrobiosis[16-19], granuloma annulare[18,20-22], alopecia areata[23], cheilitis granulomatosa[18,24], recurrent oral aphthae[25], pityriasis rubra pilaris[18], and annular elastolytic giant cell granuloma[18], as well as a range of non-dermatological diseases: Sarcoldosis[18,26] and non-infectious chronic uveitis[27]. Fumaric acid esters have also shown potential for the use in treatment of cancer[28-30], Huntington's disease[31], malaria[32], human immunodeficiency virus[33], bronchial asthma[34], myocardial infarction[35] and for use as an immunosuppressor in organ transplantation[36].

Despite a clear clinical effect of FAE's in psoriasis and relapsing-remitting multiple sclerosis and numerous in vitro and in vivo studies with FAE's, the precise mechanism of action had not been fully understood. FAEs have been shown to inhibit the expression of TNF-α induced adhesion molecules[37] as well as various cytokines including psoriasis associated cytokines like IL-IP, IL-6, IL-8, IL-20 and TNF-α[38-40]. DMF also suppresses the expression of VEGFR2 in human endothelial cells indicating a possible anti-angiogenic action[41]. Other possible mechanisms causing an anti-psoriatic effect are FAE induced apoptosis of purified human T-cells[42] and a FAE induced shift in the immunological balance from a Th1- towards a Th2-like[43]. Because there is a lack of detectable DMF plasma concentrations after oral intake it has been suggested that there is a reaction of DMF with glutathione (GSH) in the portal vein blood[44]. This hypothesis has recently been supported by novel findings of Ghoreschi and co-workers[45].

Both multiple sclerosis (MS) and psoriasis are considered autoimmune CD4+ T-cell driven disorders with predominance of a Th1 and Th17 phenotype of pathogenic T-cells[46]. Dendritic cells (DCs) are professional antigen-presenting cells (APCs) bridging innate and acquired immunity, recognizing infections, secreting proinflammatory cytokines and orchestrating the maturation of naïve T-cells and to create the cytokine microenvironment regulating T-cell differentiation[47]. FAE have previously been shown to induce a shift in the immunological balance from a Th1- toward a Th2-like response[43] and to inhibit the differentiation of dendritic cells[48]. More recently Ghoreschi at al. 2011[45] suggested that DMF depletes glutathione (GSH) followed by increased hemoxygenase-1 (HO-1) expression and impaired STAT1 phosphorylation. HO-1 interact with AP-1 and NF-κB binding sites in the IL-23p19 promoter inhibiting its expression and IL-23 is a key driver of Th17 maturation. STAT1 inhibition prevented IL-12p35 expression leading to decreased expression of the Th1 driver, IL-12. It was therefore suggested that DMF improved MS and psoriasis through inhibition of Th1 and Th17 responses. In this model, the DMF induced GSH depletion is essential.

In opposition to this, several studies have shown that DMF induces a transient GSH depletion whereas prolonged exposure raised GSH expression[11] and therefore depletion of GSH cannot account for all the effects of DMF seen in MS and psoriasis. However, regulation of T-cell differentiation is important in controlling these two diseases and it is therefore interesting that a recent study[59] has demonstrated DMF mediated inhibition of Th1 and Th17 differentiation through suppression of NF-κB and the p38 MAPK-MSK1 and ERK1/2-MSK1 signalling pathways[39,46]. Both NF-κB and MAPK activation have previously been shown to contribute to LPS mediated DC maturation[49,50]. Although the ERK1/2 MAPK and the NF-κB pathways are independent, they can interact via MSK1. MSK1 enhances NF-κB transcriptional activity through phosphorylation of serine 276 of the NF-κB subunit, p65. Further MSK1 phosphorylates Histone-3 at serine 10 which also enhances NF-κB transcriptional activity. The present inventors and others have previously demonstrated an inhibitory effect of DMF on different signaling pathways including the p38 MAPK-MSK1, ERK1/2-RSK1 and MSK1-NF-κB pathways[36, 39 59].

DMF has previously been shown to block the activation of the Ribosomal S6 Kinase family (composed of RSK1 to RSK4 and the homologous kinases MSK1 and MSK2) by the extracellular signal-regulated kinase (ERK)[39,49].

MSK1/2 and RSK1/2 have overlapping effects on transcription factors like the cAMP-responsive element (CREB), ATF1 and Histone 3[46], while RSK1 to RSK4 separately regulate the phosphorylation of c-Fos, c-Jun and JunB. The complexes of c-Fos, c-Jun and JunB, formed as dimers, bind to the activator 1 (AP-1) site and AP-1 DNA binding activity regulates cell proliferation[54]. The specific inhibitory effect of DMF on RSK1 and MSK1 activation followed by the induction of p-c-Jun (S63) and p-p53 (S15) led to the inhibition of keratinocyte proliferation, partly explaining the anti-psoriatic effect of DMF[46]. The specificity of DMF's inhibitory effect on RSK1 and MSK1 activation was proved by transfection with small interfering RSK1 and MSK1 RNA instead of DMF which showed the same effects on induction of p-c-Jun (S63) and p-p53 (S15)[46].

MSK1/2 and RSK1-4 are activated by pro-inflammatory cytokines and growth factors and their activity is controlled by multiple phosphorylation sites[55,56]. The serine and threonine kinase activity of MSK1/2 and RSK1-4 is dependent on full length activation by phosphorylation at multiple sites in MSK1/2 and RSK1-4[57]. The alignment of the amino acid sequences shows 43% homology between MSK1/2 and RSK1-4[58].

MSKs and RSKs are composed of two kinase domains (a N- and a C-terminal) and are activated by either p38 MAPKs and ERK 1/2 for MSK1/2 or only by ERK1/2 for RSK1-4[55-57]. The activation starts for both MSKs and RSKs in a similar way by phosphorylation of an activation loop in the C-terminal kinase domain. This phosphorylation leads to the activation of the hydrophobic linker loop in the middle part and then the N-terminal kinase domain is phosphorylated. The N-terminal kinase domain binds and phosphorylates substrates. DMF has been shown to fully inhibit activation of specific phosphorylation sites at the C-terminal domain, in the linker loop and in the N-terminal domain and this reduced the kinase activity of the N-terminal domain and thereby downstream substrate activations[39,46,51].

The MSK/RSK kinases are composed of two catalytic domains (an N- and a C-terminal) separated by a ~100 amino acid linker. Each of the catalytic domains is composed of a small N-terminal lobe comprising β-sheets and a larger C-terminal lobe mainly comprising α-helices. ATP and substrate are bound in the interface between the two lobes. The kinases are activated by ERK by phosphorylation of an activation loop in the C-terminal catalytic domain. This phosphorylation leads to the activation of the N-terminal catalytic domain by phosphorylation of the linker region. Phosphorylation of the linker region is abolished by DMF and the activation of the N-terminal kinase domain hereby reduced[39,46]. An apo-structure of the C-terminal kinase domain of murine RSK2 was previously described[47] but does not provide any insights to the binding of ligands (e.g. ATP and substrate). Some RSK2 inhibitors have been identified including Staurosporine like compounds[48], kaemperol-glycosides[49] and [50]s. The majority of the identified RSKs inhibitors are ATP-competitive and bind in the ATP pocket between the two lobes in either one or both of the catalytic domains. An irreversible RSK2 inhibitor of the C-terminal catalytic domain has been developed, covalently binding to a cysteine located in the ATP pocket[51,52].

ATP-competitive inhibitors generally display reduced selectivity due to the numerous ATP-binding pockets in the cell and poor cellular activity due to the high intracellular ATP concentration. The development of an allosteric RSK/MSK inhibitor will reduce off-target effects and increase efficacy. DMF can form covalent adducts with intracellular thiol containing molecules such as GSH, whereas a RSK/MSK selective inhibitor will only undergo covalent interaction once bound in the allosteric pocket.

SUMMARY OF INVENTION

The present inventors have elucidated the structural basis for the mechanism of action of DMF inhibition of the RSK and MSK families of kinases. A 1.9 Å resolution X-ray crystal structure of the C-terminal kinase domain of murine RSK2 co-crystallized with DMF revealed the binding of one DMF molecule to RSK2. A conserved cysteine residue modified by a covalent Michael-addition to DMF defines the binding site (FIG. 1). The binding site is situated in a hinge region (FIG. 2). Comparison with X-ray structures of related kinases revealed that the hinge region will undergo large structural rearrangements during activation, and that covalent modification of the cysteine in the hinge region could abolish this by steric hindrance or by stabilizing the interaction between the C-terminal helix-bundle and the inhibitory αL-helix (FIG. 2). The covalent modification of the conserved cysteine was confirmed by mass spectrometry analysis (FIG. 3). The importance of the binding of DMF to the conserved cysteine in the hinge region was underscored by mutational studies of RSK2 and MSK1 in cell cultures. Mutation of the cysteine, which is conserved across the RSK and MSK families, to a valine abolished the effect of DMF (FIG. 4).

The inventors have thus been able to describe the mechanism behind DMF binding in RSK and MSK families. This has been achieved by the findings of the appropriate conditions for growing highly ordered three-dimensional crystals of the RSK2 protein. Based on these findings, the inventors have developed a method for identifying candidate inhibitors of RSK and MSK proteins.

The basis for identification of ligands according to the present invention is to obtain a crystal of sufficient quality for high resolution X-ray crystallography.

Accordingly, in a main aspect, the present invention concerns a three dimensional crystal of a complex between:
a) one or more fumaric acid ester derivative ligands, and
b) a polypeptide comprising the sequence of SEQ ID NO: 1 (C-terminal kinase domain of murine ribosomal S6 kinase 2), or a biologically active structural and/or functional variant thereof, wherein the biological activity is kinase activity.

In another aspect the present invention concerns a three dimensional crystal of a ribosomal S6 kinase (RSK) or a mitogen- and stress-activated protein kinase (MSK) polypeptide bound to one or more ligands.

More specifically the invention concerns a three dimensional crystal of a polypeptide bound to one or more ligands, wherein the polypeptide has:
a) an amino acid sequence selected from the group consisting of SEQ ID NO. 1, 2, 3, 4, 5, 6, 7, 8, 9, 10, 11, 12, 13, 14, 15, 16, 17, 18. 19 or 20; or
b) a sequence variant of the polypeptide of a), wherein the sequence variant has at least 70% sequence identity to SEQ ID NO. 1, 2, 3, 4, 5, 6, 7, 8, 9, 10, 11, 12, 13, 14, 15, 16, 17, 18. 19 or 20; or
c) a fragment of the polypeptide of a) or b), wherein the fragment comprises at least 200 contiguous amino acids of any one of a) or b), and wherein the biological activity is kinase activity.

Growing of highly ordered protein crystals capable of diffracting X-rays to atomic resolution is far from straight forward. However the present inventors have succeeded in developing a protocol suitable for growing RSK2 crystals.

Hence, in one aspect, the present invention concerns a method for growing the above defined crystal, comprising the steps of:
a) obtaining a composition comprising 2 to 15 mg/mL, such as 5 to 12 mg/mL, such as 5 to 10 mg/mL of a polypeptide selected from the group consisting of SEQ ID NO. 1, 2, 3, 4, 5, 6, 7, 8, 9, 10, 11, 12, 13, 14, 15, 16, 17, 18, 19 and 20 or a fragment or variant thereof, in a suitable buffer,
b) contacting the composition of a) with a ligand, c) allowing time for formation of a protein-ligand complex in solution,
d) mixing the solution comprising the protein-ligand complex of c) with a reservoir solution comprising a precipitant and a buffer,
e) incubating a drop of the mixture of d) under vapour diffusion conditions versus the reservoir solution,
f) obtaining crystals of the protein-ligand complex.

The solution of the structure of RSK2 in complex with DMF has allowed the present inventors to develop a method for screening for candidate compounds capable of binding to RSK2 and homologous kinases, with the aim of inhibiting the kinase activity of these enzymes.

Thus in one aspect the present invention concerns a computer-based method for rational drug design which comprises:
  a) providing the atomic coordinates of the polypeptide as defined by the coordinates of table 3;
  b) providing the structure of a candidate inhibitor molecule; and
  c) fitting the structure of candidate inhibitor molecule to the atomic coordinates of the polypeptide of said table.

In another aspect the invention concerns a computer-based method for identifying a potential inhibitor of the polypeptide selected from the group consisting of SEQ ID NO. 1, 2, 3, 4, 5, 6, 7, 8, 9, 10, 11, 12, 13, 14, 15, 16, 17, 18, 19 and 20 comprising the steps of:
  a) employing a three-dimensional structure of the polypeptide, the three-dimensional structure being defined by atomic coordinate data according to table 3; and
  b) identifying the potential inhibitor by designing or selecting a compound for interaction with the active site.

The invention also concerns a computer readable media with either (a) atomic coordinate data according to table 3 recorded thereon, said data defining the three-dimensional structure of the polypeptide selected from the group consisting of SEQ ID NO. 1, 2, 3, 4, 5, 6, 7, 8, 9, 10, 11, 12, 13, 14, 15, 16, 17, 18, 19 and 20, at least one atom or at least one sub-domain thereof, or (b) structure factor data for the polypeptide selected from the group consisting of SEQ ID NO. 1, 2, 3, 4, 5, 6, 7, 8, 9, 10, 11, 12, 13, 14, 15, 16, 17, 18, 19 and 20 recorded thereon, the structure factor data being derivable from the atomic coordinate data of table 3.

In one aspect the invention concerns a computer-readable data storage medium comprising a data storage material encoded with at least a portion of the structure coordinates set forth in table 3.

In another aspect the invention concerns a method for identifying a ligand capable of binding to the binding site of SEQ ID NO. 1 (C-terminal domain of murine RSK2), said method comprising the steps of:
  a) generating the spatial structure of the binding site on a computer screen using atomic coordinates as presented in table 3 or atomic coordinates selected from a three-dimensional structure that deviates from the three-dimensional structure presented in table 3 by a root mean square deviation over protein backbone atoms of not more than 3 Å,
  b) generating potential ligands with their spatial structure on the computer screen, and
  c) selecting ligands that can bind to at least 1 amino acid residue of the set of binding interaction sites without steric interference.

In yet another aspect the invention concerns a computer-assisted method for identifying a ligand of a polypeptide selected from the group consisting of SEQ ID NO. 1, 2, 3, 4, 5, 6, 7, 8, 9, 10, 11, 12, 13, 14, 15, 16, 17, 18, 19 and 20, using a programmed computer comprising a processor, a data storage system, a data input device and a data output device, comprising the following steps:
  a) inputting into the programmed computer through said input device data comprising:
    atomic coordinates of a subset of the atoms of said polypeptide, thereby generating a criteria data set;
    wherein said atomic coordinates are selected from the three-dimensional structure presented in table 3 or atomic coordinates selected from a three-dimensional structure that deviates from the three-dimensional structure presented table 3 by a root mean square deviation over protein backbone atoms of not more than 3 Å,
  b) comparing, using said processor, the criteria data set to a computer data base of low-molecular weight organic chemical structures and peptide fragments stored in the data storage system; and
  c) selecting from said database, using computer methods, a chemical structure having a portion that is structurally complementary to the criteria data set and being free of steric interference with the polypeptide selected from the group consisting of SEQ ID NO. 1, 2, 3, 4, 5, 6, 7, 8, 9, 10, 11, 12, 13, 14, 15, 16, 17, 18, 19 and 20.

In another aspect the invention concerns a method for identifying a ligand, said method comprising the steps of:
  a) selecting a potential ligand using atomic coordinates in conjunction with computer modelling, wherein said atomic coordinates are the atomic coordinates presented in table 3 or wherein the atomic coordinates are selected from a three-dimensional structure that deviates from the three-dimensional structure presented in any of table 3 by a root mean square deviation over protein backbone atoms of not more than 3 Å, by docking potential ligands into a set of binding interaction sites the binding site of said polypeptide selected from the group consisting of SEQ ID NO. 1, 2, 3, 4, 5, 6, 7, 8, 9, 10, 11, 12, 13, 14, 15, 16, 17, 18, 19 and 20, said binding interaction generated by computer modelling and selecting a potential ligand capable of binding to at least one amino acid in said set of binding interaction sites of said polypeptide selected from the group consisting of SEQ ID NO. 1, 2, 3, 4, 5, 6, 7, 8, 9, 10, 11, 12, 13, 14, 15, 16, 17, 18, 19 and 20,
  b) providing said potential ligand and said polypeptide,
  c) contacting the potential ligand with said polypeptide and
  d) detecting binding of said polypeptide by the potential ligand.

Activation of RSK2 (light grey) by ERK leads to the phosphorylation of a threonine residue in the activation loop (grey). The movement of activation loop has been determined by X-ray crystallography for several kinases and is shown for the related kinase CDK2 (dark grey). The hinge region is undergoing large structural rearrangements during activation and modification of C599 could abolish this by steric hindrance.

Figure 1:
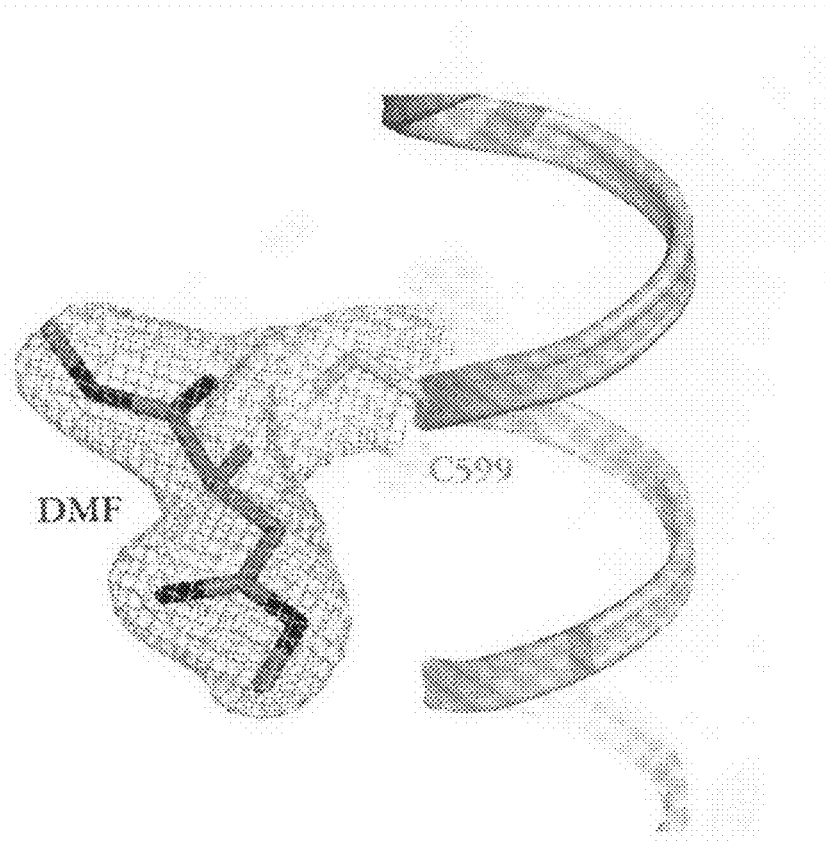
FIG. 1: Atomic structure of RSK2 in complex with dimethyl fumarate (DMF). The covalent modification of cysteine 599 (C599) with DMF in the hinge region of RSK2. The 2Fo-Fc electron density map is contoured at 1.0σ.
Figure 2:
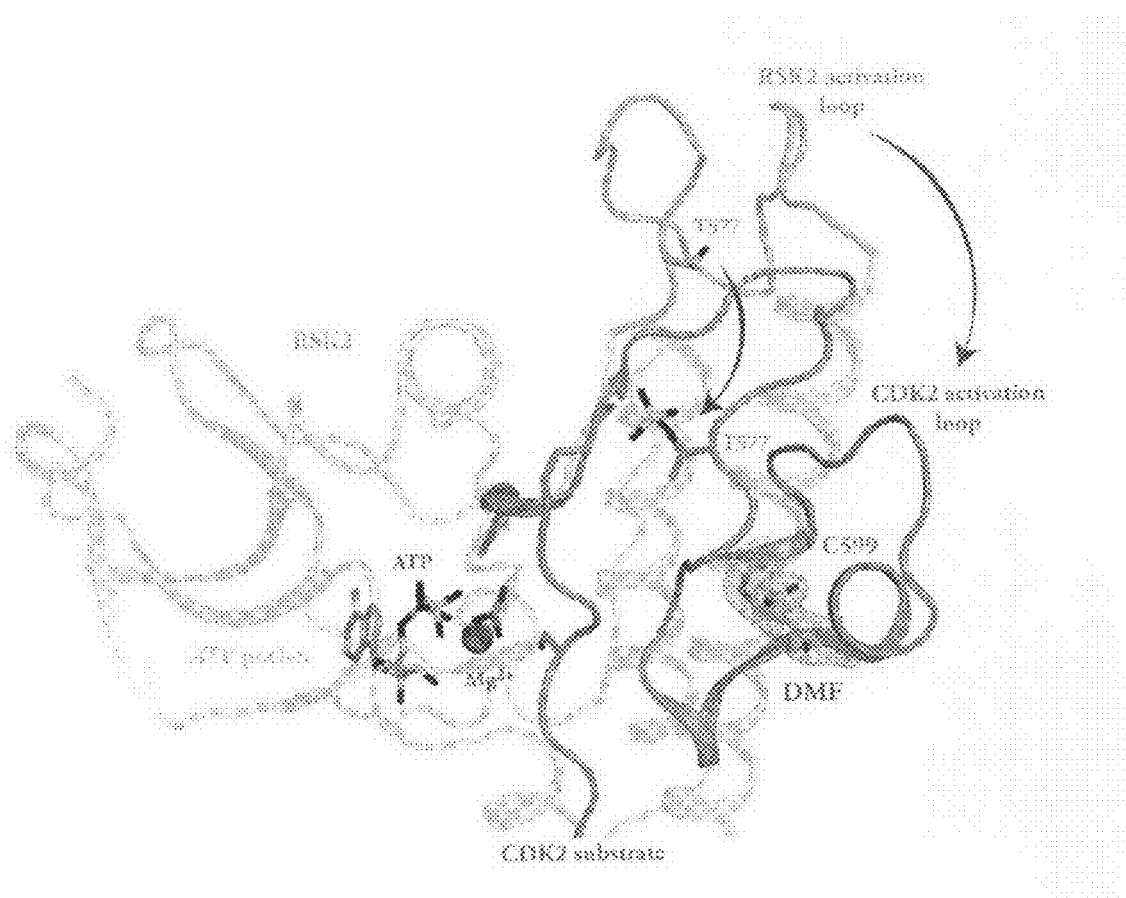
FIG. 2: Mechanism of action of DMF modification of C599.
Figure 3:
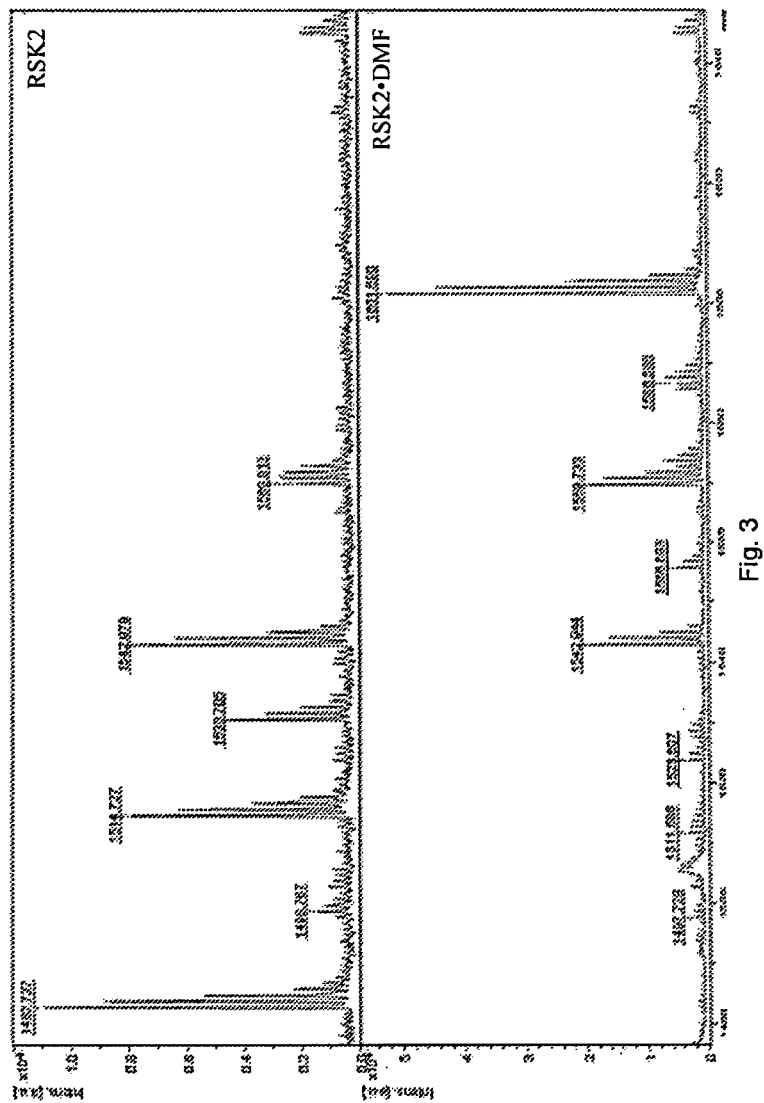

FIG. 3: Mass spectrometric analysis of DMF modification of RSK2 at cysteine 599 (C599). Covalent modification of C599 was identified by chymotrypsin treatment of RSK2. The carbamidomethylated KRQGYDAACDIW peptide of RSK2 containing C599 was identified as 1482.73 and 1514.73 (dioxidized). DMF modification of the peptide was identified as 1569.73 and 1601.69 (dioxidized).

Figure 4:
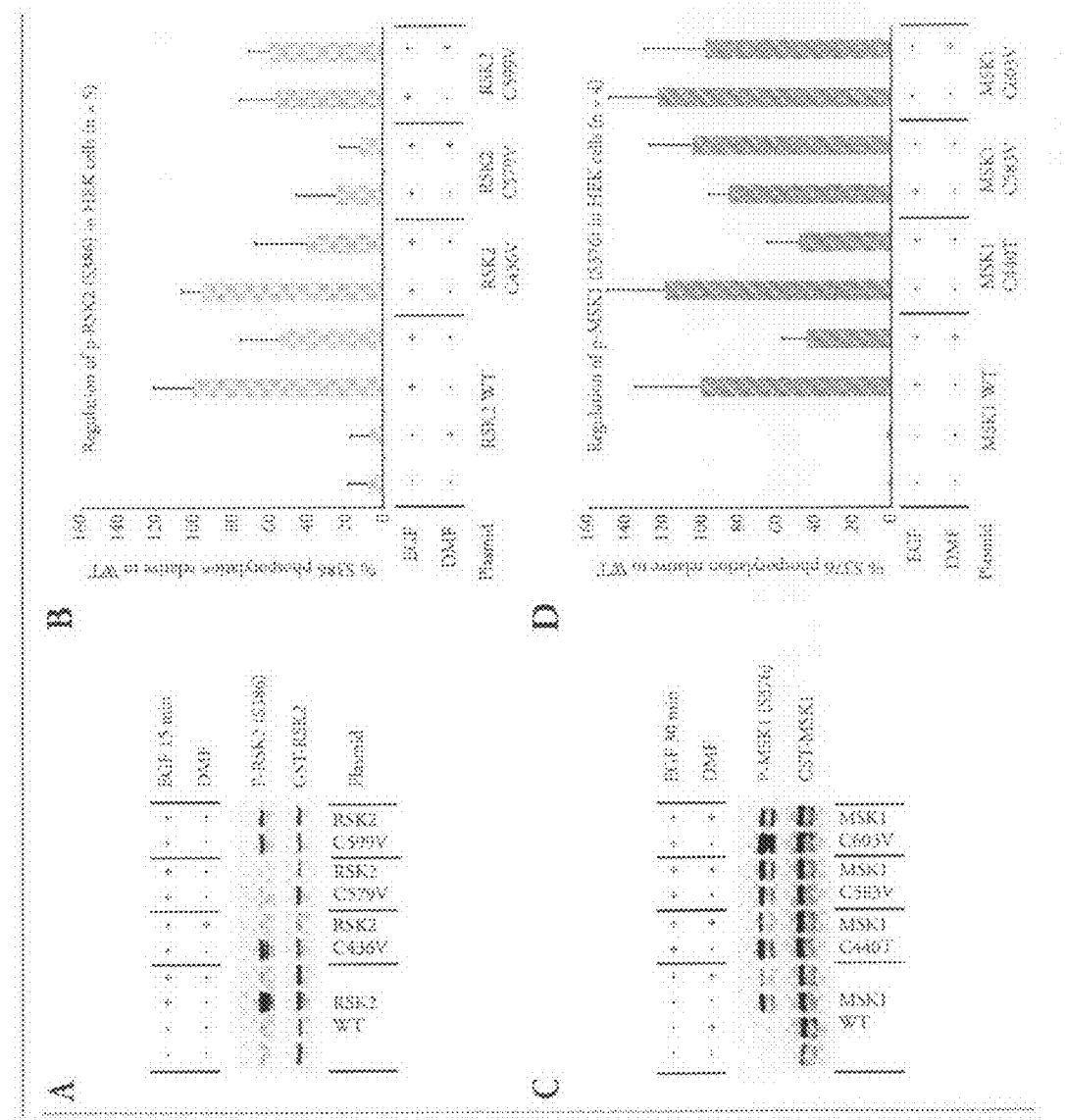

FIG. 4: The importance of the binding of dimethyl fumarate (DMF) to the cysteine in the hinge region (C599) was underscored by mutational studies of RSK2 and MSK1 in HEK 293 cell cultures stimulated by epidermal growth factor (EGF). Mutation studies of RSK2 in cell cultures stimulated by EGF showed that mutation of cysteine (C599) to valine abolished the effect of DMF, as no decrease in the phosphorylation of S386 was observed (representative blot: 4A, statistical analysis: 4B). Mutation of the cysteine corresponding to C599 in MSK1 (C603) to a valine abolished the effect of DMF, as no decrease in the phosphorylation of S376 was observed (representative blot 4C, statistical analysis: 4D).

Figure 5:
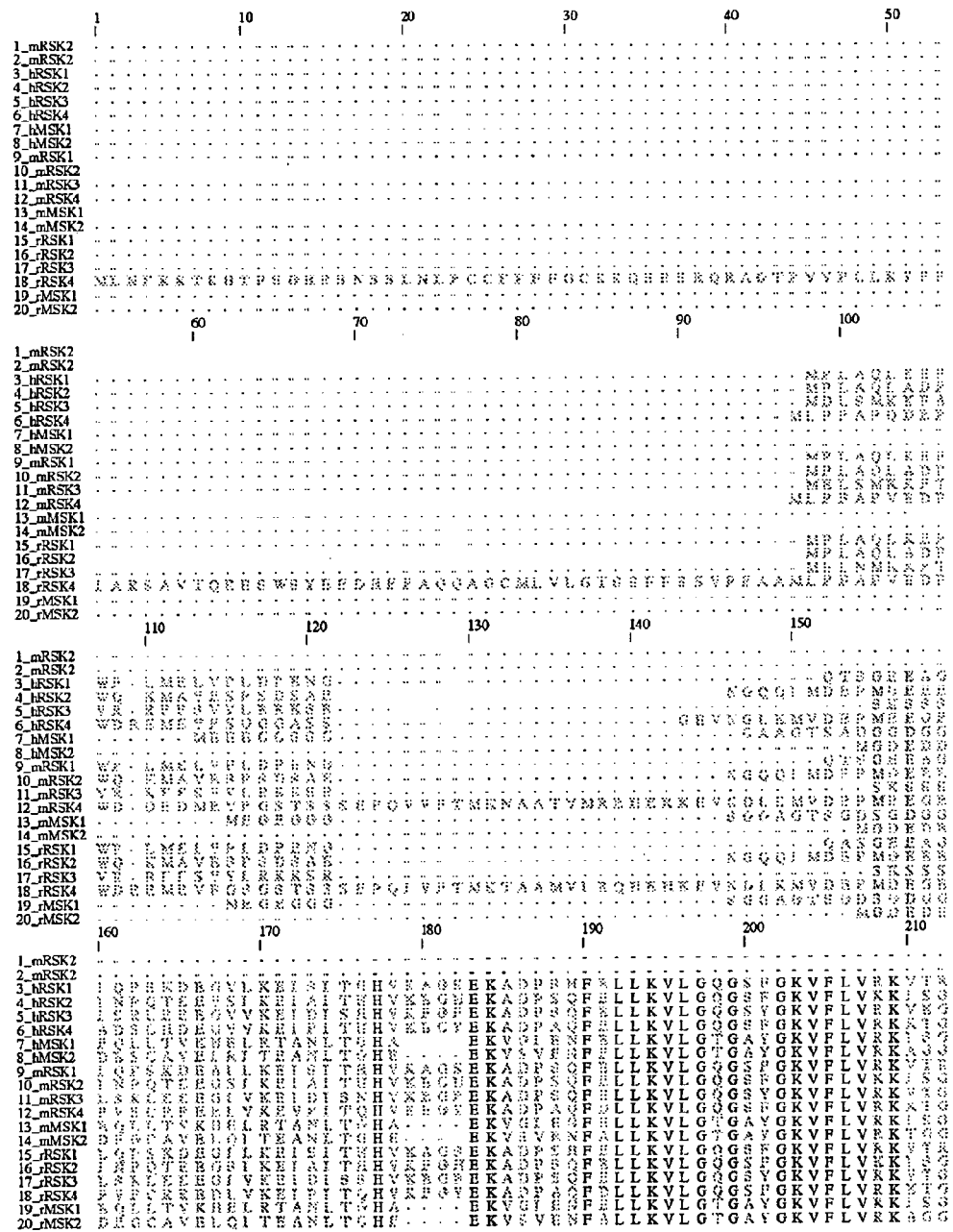

FIG. 5: Multiple sequence alignment of sequence 1-20 aligned in MUSCLE[60]. Fully conserved positions are depicted in black, 50% conserved positions in dark gray and less than 50% conserved positions depicted in light gray.

FIG. 6: Sequence identity matrix.

DETAILED DESCRIPTION OF THE INVENTION

The term "crystal" refers to an ordered state of matter. Proteins, by their nature are difficult to purify to homogeneity. Even highly purified proteins may be chronically heterogeneous due to modifications, the binding of ligands or a host of other effects.

In addition, proteins are crystallized from generally complex solutions that may include not only the target molecule but also buffers, salts, precipitating agents, water and any number of small binding proteins. It is important to note that protein crystals are composed not only of protein, but also of a large percentage of solvents molecules, in particular water. These may vary from 30 to even 90%. Protein crystals may accumulate greater quantities and a diverse range of impurities which cannot be listed here or anticipated in detail. Frequently, heterogeneous masses serve as nucleation centers and the crystals simply grow around them. The skilled person knows that some crystals diffract better than others. Crystals vary in size from a barely observable 20 micron to 1 or more millimeters. Crystals useful for X-ray analysis are typically single, 0.05 mm or larger, and free of cracks and defects.

The term "coordinate" as use herein, refers to the information of the three dimensional organization of the atoms contributing to a protein structure. The final map containing the atomic coordinates of the constituents of the crystal may be stored on a data carrier; typically the data is stored in PDB format. However, crystal coordinates may as well be stored in simple tables or text formats. The PDB format is organized according to the instructions and guidelines given by the Research Collaboratory for Structural Bioinformatics (RCSB).

The term "root mean square deviation" (rmsd) is used as a mean of comparing two closely related structures and relates to a deviation in the distance between related atoms of the two structures after structurally minimizing this distance in an alignment. Related proteins with closely related structures will be characterized by relatively low RMSD values whereas larger differences will result in an increase of the RMSD value.

The term "associating with" or "binding" refers to a condition of proximity between chemical entities or compounds, or portions thereof. The association may be non-covalent—wherein the juxtaposition is energetically favoured by hydrogen bonding or van der Waals or electrostatic interactions- or it may be covalent.

The term "binding pocket", as used herein, refers to a region of a molecule or molecular complex that, as a result of its shape, favourably associates with another molecule, molecular complex, chemical entity or compound.

As used herein the term "complex" refers to the combination of a molecule or a protein, conservative analogues or truncations thereof associated with a chemical entity.

RSK/MSK Crystal

An aspect of the invention relates to a crystal which comprises a RSK/MSK kinase.

Depending on the resolution of a crystal structures larger differences information can be obtained from the data. At a resolution of about 5.5 Å the overall shape of a molecule, such as helices are visible with strong density. At a resolution of about 3.5 Å the overall features of the polypeptide backbone becomes visible (usually with some ambiguities). At a resolution of about 3 Å the side chains are partly resolved and at a resolution of about 2.5 Å the side chains are well resolved. The atoms are located within about 0.4 Å meaning that the lengths of hydrogen bonds calculated from a PDB file (using e.g. for example, by PyMol) have at least this uncertainty. The limit of protein crystallography is normally around 1.5 Å, where atoms are located to about ±0.1 Å. In rare cases do protein crystals diffract better than 1 Å resolution yielding an accuracy of the atomic positions below 0.1 Å, comparable to crystal structures of small molecules.

The crystal of the invention preferably effectively diffracts x-rays for the determination of the atomic coordinates of the protein to a resolution better than 6 Å. More preferably the three dimensional structure determinations can be determined with a resolution of more than 5 Å, such as more than 4 Å or most preferably about 3.5 A using the crystals according to the invention. Most preferably the crystal effectively diffracts x-rays for the determination of the atomic coordinates of the protein to a resolution of 3.6 Å

The space group of the crystal according to the invention is $P4_12_12$ and the cell dimensions are preferably a=b=46.6±4 Å and c=289.5±4 Å. The cell dimensions can vary depending on the specific RSK/MSK comprised by the crystal, quaternary structure and also depending on ligand of choice, and also on the conformation of the RSK/MSK comprised by the crystal.

The inventors have been able to describe the mechanism behind DMF binding in RSK and MSK families by finding the appropriate conditions for growing highly ordered three-dimensional crystals of the RSK2 protein. Based on these findings, the inventors have developed a method for identifying candidate inhibitors of RSK and MSK proteins.

Accordingly, in a main aspect, the present invention concerns a three dimensional crystal of a complex between:
a) one or more fumaric acid ester derivative ligands, and
b) a polypeptide comprising the sequence of SEQ ID NO: 1 (C-terminal kinase domain of murine ribosomal S6 kinase 2), or a biologically active structural and/or functional variant thereof, wherein the biological activity is kinase activity.

In another aspect, the present invention concerns a three dimensional crystal of a ribosomal S6 kinase (RSK) or a mitogen- and stress-activated protein kinase (MSK) polypeptide bound to one or more ligands.

In yet another aspect, the present invention concerns a three dimensional crystal of a polypeptide bound to one or more ligands, wherein the polypeptide has:
  a) an amino acid sequence selected from the group consisting of SEQ ID NO. 1, 2, 3, 4, 5, 6, 7, 8, 9, 10, 11, 12, 13, 14, 15, 16, 17, 18. 19 or 20; or
  b) a sequence variant of the polypeptide of a), wherein the sequence variant has at least 70% sequence identity to SEQ ID NO. 1, 2, 3, 4, 5, 6, 7, 8, 9, 10, 11, 12, 13, 14, 15, 16, 17, 18. 19 or 20; or
  c) a fragment of the polypeptide of a) or b), wherein the fragment comprises at least 200 contiguous amino acids of any one of a) or b), and wherein the biological activity is kinase activity.

The present inventors have found the specific interactions between a fumaric acid ester derivative ligand and the C-terminal kinase domain of murine RSK2, by co-crystallisation. The inventors have found that the ligand is located in a binding site comprising amino acid residues Y197, A200, C201, W204, I235, H263, V264, R269 or L312 of SEQ ID NO. 1.

Based on these findings, the inventors have determined the binding site of fumaric acid ester derivative ligand and analogues thereof in polypeptides homologous to SEQ ID NO: 1 such as polypeptides represented by SEQ ID NOs: 2, 3, 4, 5, 6, 7, 8, 9, 10, 11, 12, 13, 14, 15, 16, 17, 18, 19 and 20.

Thus in one embodiment the ligand is located in a binding site comprising amino acid residues Y196, A199, C200, W203, I234, H262, V263, R268 or L311 of SEQ ID NO. 2.

In another embodiment the one or more ligand(s) is located in a binding site comprising amino acid residues Y591, G594, C595, W598, I629, H657, V658, R663 or L705 of SEQ ID NO. 3.

In yet another embodiment the one or more ligand(s) is located in a binding site comprising amino acid residues Y595, A598, C599, W602, I633, H661, V662, R667 or L710 of SEQ ID NO. 4.

In yet another embodiment the one or more ligand(s) is located in a binding site comprising amino acid residues Y588, A591, C592, W595, 626, H654, V655, R660 or L702 of SEQ ID NO. 5.

In yet another embodiment the one or more ligand(s) is located in a binding site comprising amino acid residues Y599, A602, C603, W606, I637, H665, M666, R671 or L714 of SEQ ID NO. 6.

In yet another embodiment the one or more ligand(s) is located in a binding site comprising amino acid residues Y599, S602, C603, W606, I641, T669, V670, R675 or F722 of SEQ ID NO. 7.

In yet another embodiment the one or more ligand(s) is located in a binding site comprising amino acid residues Y586, S589, C590, W593, I628, T656, V657, R662 or F709 of SEQ ID NO. 8.

In yet another embodiment the one or more ligand(s) is located in a binding site comprising amino acid residues Y580, G583, C584, W587, I618, H646, V647, R652 or L694 of SEQ ID NO. 9.

In yet another embodiment the one or more ligand(s) is located in a binding site comprising amino acid residues Y595, A598, C599, W602, I633, H661, V662, R667, L710 of SEQ ID NO. 10.

In yet another embodiment the one or more ligand(s) is located in a binding site comprising amino acid residues Y588, A591, C592, W595, I626, H654, V655, R660 or L702 of SEQ ID NO. 11.

In yet another embodiment the one or more ligand(s) is located in a binding site comprising amino acid residues Y619, A622, C623, W626, I657, H685, M686, R691 or L731 of SEQ ID NO. 12.

In yet another embodiment the one or more ligand(s) is located in a binding site comprising amino acid residues Y663, S666, C667, W670, I705, T733, V734, R739 or F786 of SEQ ID NO. 13.

In yet another embodiment the one or more ligand(s) is located in a binding site comprising amino acid residues Y586, S589, C590, W593, I628, T656, V657, R662 or F709 of SEQ ID NO. 14.

In yet another embodiment the one or more ligand(s) is located in a binding site comprising amino acid residues Y591, G594, C595, W598, I629, H657, V658, R663 or L705 of SEQ ID NO. 15.

In yet another embodiment the one or more ligand(s) is located in a binding site comprising amino acid residues Y595, A598, C599, W602, I633, H661, V662, R667 or L710 of SEQ ID NO. 16.

In yet another embodiment the one or more ligand(s) is located in a binding site comprising amino acid residues Y588, A591, C592, W595, I626, H654, V655, R660 or L702 of SEQ ID NO. 17.

In yet another embodiment the one or more ligand(s) is located in a binding site comprising amino acid residues Y716, A719, C720, W723, I754 or H782 or M783 or R788 or L828 of SEQ ID NO. 18.

In yet another embodiment the one or more ligand(s) is located in a binding site comprising amino acid residues Y575, A578, C579, W582, I617, T645, V646, R651 and F698 of SEQ ID NO. 19.

In yet another embodiment the one or more ligand(s) is located in a binding site comprising amino acid residues Y586, S589, C590, W593, I628, T656, V657, R662 or F709 of SEQ ID NO. 20.

The polypeptide comprised in the crystal defined herein above, is preferably folded to comprise secondary and tertiary structure.

On the primary structure level, the polypeptide comprised in the crystal as defined herein above, may comprise an affinity tag, such as a polyhistidine tag, a GST tag, a HA tag, a Flag tag, a C-myc tag, a HSV tag, a V5 tag, a maltose binding protein tag, a cellulose binding domain tag or any tag known by those of skill in the art.

The polypeptide comprised in the crystal as defined herein above, may also comprise a polyhistidine tags, such as an N-terminal poly-histidine tag or a C-terminal poly-histidine tag.

The polypeptide comprised by the crystal may furthermore comprise a protease cleavage site allowing the affinity tag; such as a Tobacco Etch Virus protease site; to be removed. The removal of the tag is preferably performed prior to crystallisation such that the affinity tag can be removed to obtain a significantly purse sample comprising the polypeptide of choice.

In one embodiment the ligand, comprised in the crystal defined herein above, is selected from the group consisting of dimethyl fumarate (DMF) and dimethyl fumarate derivatives. The derivatives are e.g. ester derivatives, fumaric acid or succinic acid.

In one embodiment the ligand is a kinase inhibitor. As such, the ligand is capable of inhibiting the biological kinase activity of one or more of the polypeptides selected from the group consisting of SEQ ID NO. 1, 2, 3, 4, 5, 6, 7, 8, 9, 10, 11, 12, 13, 14, 15, 16, 17, 18, 19 and 20.

In a preferred embodiment the crystal as defined herein above is of a tetragonal space group, preferably of space group $P4_12_12$.

In one embodiment, the crystal according to the present invention has the crystal unit cell parameters a=b=46.95 Å±4 Å, c=291.30 Å±4 Å and $\alpha=\beta=\gamma=90°$.

In an embodiment the invention relates to a crystal comprising a ribosomal S6 kinase (RSK) or a mitogen- and stress-activated protein kinase (MSK) polypeptide bound to one or more ligands, wherein the ribosomal S6 kinase (RSK) and the mitogen- and stress-activated protein kinase (MSK) polypeptide is from a mammalian species. In a preferred embodiment the polypeptide is of murine or human origin.

The invention further encompasses ribosomal S6 kinase (RSK) or a mitogen- and stress-activated protein kinase (MSK) polypeptide from different species such human and other animals.

Accordingly, the invention also concerns crystals comprising homologues of a predetermined sequence, which homologues preferably have at least 70% sequence identity, such as 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the a sequence selected from the group consisting of SEQ ID NO. 1, 2, 3, 4, 5, 6, 7, 8, 9, 10, 11, 12, 13, 14, 15, 16, 17, 18. 19 and 20.

The percent identity is determined with the algorithms GAP, BESTFIT, or FASTA in the Wisconsin Genetics Software Package Release 7.0, using default gap weights.

The term "sequence identity" means that two polypeptide sequences are identical (i.e., on a residue-by-residue basis) over the window of comparison. The term "percentage of sequence identity" is calculated by comparing two optimally aligned sequences over the window of comparison, determining the number of positions at which the identical amino acid residues occurs in both sequences to yield the number of matched positions, dividing the number of matched positions by the total number of positions in the window of comparison (i.e., the window size), and multiplying the result by 100 to yield the percentage of sequence identity.

According to the invention the polypeptide comprised by the crystal is not the necessarily a full-length protein. Truncated versions can readily be prepared by conventional methods of molecular biology (Sambrook and Russell, 2001). According to the invention it is preferred that the polypeptide of the crystal comprise more than 75%, more preferred 80%, and mostly preferred more than 90% of the full length protein sequences.

A homologue comprising fragments of the polypeptide preferably includes least 100, contiguous amino acids of a sequence selected from the group consisting of SEQ ID NO. 1, 2, 3, 4, 5, 6, 7, 8, 9, 10, 11, 12, 13, 14, 15, 16, 17, 18. 19 and 20.

Since two polypeptide sequences may each comprise (1) a portion of the complete polypeptide sequence that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window", as used herein, refers to a conceptual segment of at least 20 contiguous peptide positions wherein a polypeptide sequence may be compared to a predetermined sequence of at least 20 contiguous peptides and wherein the portion of the polypeptide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

In a preferred embodiment the crystal includes a homologue of a ribosomal S6 kinase (RSK) or a mitogen- and stress-activated protein kinase (MSK) polypeptide, wherein one ore more of the amino acids residues are conserved or substituted by an amino acid residue with similar properties, e.g. the ribosomal S6 kinase (RSK) or the mitogen- and stress-activated protein kinase (MSK) polypeptide may comprise conserved amino acid substitutions (see below). Preferably more than 1, more than 2, more than 5 AA of the above mentioned AA are conserved or represented by a conserved amino acid substitution. Preferably the ribosomal S6 kinase (RSK) or mitogen- and stress-activated protein kinase (MSK) polypeptide homologue comprised by the crystal comprises all the amino acid residues mentioned herein. Alternatively the ribosomal S6 kinase (RSK) or the mitogen- and stress-activated protein kinase (MSK) polypeptide may comprise conserved amino acid substitutions for one or more of the mentioned amino acid residues.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, homologues are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:
i) Amino acids having polar side chains (Asp, Glu, Lys, Arg, His, Asn, Gln, Ser, Thr, Tyr, and Cys)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphor-containing side chains (Cys, Met),
xi) Neutral, weakly hydrophobic amino acids (Pro, Ala, Gly, Ser, Thr)
xii) Hydrophilic, acidic amino acids (Gin, Asn, Glu, Asp), and
xiii) Hydrophobic amino acids (Leu, Ile, Val)

Accordingly, a homologue or a fragment thereof according to the invention may comprise, within the same homologue of the sequence or fragments thereof, or among different variants of the sequence or fragments thereof, at least one substitution, such as a plurality of substitutions introduced independently of one another.

It is clear from the above outline that the same homologue or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

The polypeptide fragments according to the present invention, including any functional equivalents thereof, may in one embodiment comprise less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues.

The homology between amino acid sequences may be calculated using well known scoring matrices such as any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

In addition to conservative substitutions introduced into any position of a preferred predetermined sequence, or a fragment thereof, it may also be desirable to introduce non-conservative substitutions in any one or more positions of such a sequence.

A non-conservative substitution leading to the formation of a functionally equivalent fragment of SEQ ID NO. 1, 2, 3, 4, 5, 6, 7, 8, 9, 10, 11, 12, 13, 14, 15, 16, 17, 18. 19 and 20 would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Homologues obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take several of the foregoing characteristics into consideration are well known to those of skill in the art and include: arginine and lysine; glutamate and aspartate; serine and threonine; glutamine and asparagine; and valine, leucine and isoleucine.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−0.1); glutamate (+3.0.+− 0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

Method of Growing RSK/MSK Crystal

Growing of a crystal as defined herein above may according to the invention be performed by any suitable method known in the art, such as vapour diffusions methods and/or hanging drops systems known by the person skilled in the art.

As described above the crystal may contain one or more ligands, such as DMF and DMF analogues conveniently added after the purification process and before crystallization is initiated. Alternatively crystals may be submerged in a solution comprising the ligand of choice subsequent to crystallization. Alternatively a composition comprising the ligand may be added to the hanging or sitting drop of the vapour diffusion setup, prior to or subsequent to formation of the crystal.

An aspect of the invention relates to a method of growing a crystal comprising a ribosomal S6 kinase (RSK) or a mitogen- and stress-activated protein kinase (MSK) polypeptide. Such method includes the steps of obtaining a protein composition of sufficient quality for growing of a crystal and growing of the a RSK/MSK crystals. As described herein, both steps can be modulated to optimise the outcome.

Initiation of crystal formation can be nucleated by lowering the solubility of the RSK/MSK. According to the invention PEG is included in the crystallizations environment. PEG is preferably selected from the group of PEGs comprising: PEG 100, PEG 200, PEG 400, PEG 600, PEG 800, PEG 1000, PEG 2000, PEG 3000, PEG 3350, PEG 4000, PEG 5000, PEG 6000, PEG 7000 and PEG 8000.

An aspect of the invention relates to a method for growing a crystal comprising an RSK/MSK and a ligand comprising the steps of:
 a. obtaining a composition comprising an RSK/MSK,
 b. contacting the composition of a) with a ligand of choice thus obtaining a protein:ligand complex composition
 c. subjecting the complex composition of b) to crystallizations environment including PEG 3350 and
 d. obtaining a crystal comprising an RSK/MSK.

The crystallization environment may according to the invention be obtained by mixing a composition comprising an RSK/MSK with a precipitating solution comprising PEG3350. As mentioned above any suitable method of growing crystals may be used, although vapour diffusion from hanging drops is preferred.

In an embodiment the invention relates to a method of growing a crystal comprising a RSK/MSK, comprising the steps of:
 a. obtaining a composition comprising a RSK/MSK,
 b. mixing said composition comprising a RSK/MSK with a precipitating solution comprising PEG3350,
 c. growing RSK/MSK crystals by vapour diffusion from hanging drops
 d. obtaining crystals comprising RSK/MSK.

The precipitating solution used in Example 5 herein comprises 0.1 M Bis-Tris pH 6.5 and 25% (w/v) polyethylene glycol (PEG) 3350, which is the most preferred precipitating solution according to the present invention.

In one aspect the present invention concerns a method for growing a crystal as defined herein above, comprising the steps of:
 a) obtaining a composition comprising 5 to 15 mg/mL of a polypeptide selected from the group consisting of SEQ ID NO. 1, 2, 3, 4, 5, 6, 7, 8, 9, 10, 11, 12, 13, 14, 15, 16, 17, 18, 19 and 20 or a fragment or variant thereof, in a suitable buffer
 b) contacting the composition of a) with a ligand as defined herein above,
 c) allowing time for formation of a protein-ligand complex in solution,
 d) mixing the solution comprising the protein-ligand complex of c) with a reservoir solution comprising a precipitant and a buffer,
 e) incubating a drop of the mixture of d) under vapour diffusion conditions versus the reservoir solution,
 f) obtaining crystals of the protein-ligand complex.

In one embodiment the reservoir solution is an aqueous solution of either 0.1 M Bis-Tris pH 6.5, HEPES pH=7.0 or TrisHCl pH=8.5 and 25% (w/v) polyethylene glycol (PEG) 3350.

In one embodiment of the method, equal volumes of protein-ligand complex and reservoir solution are mixed in step d) above. The equal volumes may e.g. be 0.2-4 µl.

In one embodiment the method is performed at room temperature (18-25° C.).

In another embodiment the method is performed at about 4° C.

The inventors have observed that crystals of improved quality are obtained when the method of growing a crystal further comprises an additive such as an aqueous solution of 0.01-1 M NaF, preferably 0.05 M NaF.

In one embodiment, methionine residues of the polypeptide to be crystallized are replaced by seleno-methionine by conventional molecular biological methods known by those of skill in the art.

In one embodiment the method according to the present invention further comprises the steps of:
 a) isolating an initial precipitate and
 b) growing crystals from the precipitate by vapour diffusion from hanging or sitting drops.

Use of Crystal

Provided that crystals of sufficient quality have been obtained, the crystals may according to the invention be used for X-ray diffraction experiments.

An aspect of the invention relates to the use of RSK/MSK crystals for determination of the three dimensional structure of said RSK/MSK polypeptide.

Before data collection crystals may be if deemed necessary be treated by standard methods for phasing, known in the art. However, in a preferred embodiment phasing is performed by molecular replacement techniques.

Crystals are according to the invention preferably dehydrated by conventional methods such as using cryo-protectants such as sucrose, glycerol and salt etc. Dehydration may be performed by increasing the concentration of the precipitating agent, such as PEG3350 or by controlled humidity around the crystal.

The crystals are mounted in nylon loops and flashed cooled in liquid. Excess mother liquor of the crystallisation mixture can be removed prior to flash cooling by gently touching a glass cover slip with the edge of the loop, Data collection and data processing can be performed by any suitable systems know by the person skilled in the art.

Data may be collected at 100 K on the end stations at e.g. Deutsches Elektronen-Synchrotron (DESY) in Hamburg or the Swiss Light Source SLS in Villigen. Processing may be performed using XDS. Data processing is further described in the examples.

Method Using Information Derived from a Three Dimensional Structure of an RSK/MSK Those of skill in the art will understand that a set of structure coordinates for a protein or protein complex or a portion thereof, is a relative set of points that define a shape in three dimensions. Thus, it is possible that an entirely different set of coordinates could define a similar or identical shape. The variations in coordinates may be generated by mathematical manipulations of the structure coordinates. For example, the structure coordinates set forth in table 3 could be manipulated by crystallographic permutations of the structure coordinates, fractionalization or matrix operations to sets of the structure coordinates or any combination of the above.

Coordinates Stored on Machine Readable Storage Medium

In a further aspect the invention provide a computer-readable data storage medium comprising a data storage material encoded with the structure coordinates, or at least a portion of the structure coordinates set forth in table 3. Examples of such computer readable data storage media are well known to those skilled in the art and include, for example CD-ROM and hard disks such as portable hard disks. Thus, in accordance with the present invention, the structure coordinates of a RSK/MSK, and portions thereof can be stored in a machine-readable storage medium. Such data may be used for a variety of purposes, such as drug discovery and X-ray crystallographic analysis of protein crystal.

The storage medium may be local to a computer as described above, or the storage medium may be located in a net-worked storage medium including the internet, to which remote accessibility is possible.

Three-dimensional structures provide information regarding the spatial localization of the peptide backbone and the side chains of the amino acid residues of the protein complex. Such information cannot be derived from the primary amino acid sequence or from the knowledge of the secondary structure of the protein. The level of order of the crystal determines the level of details that can be obtained. The quality of a three dimensional structure is evaluated by the resolution obtained, which is an expression for the minimum spacing observed in diffraction. As mentioned above the application relates to crystals of high quality e.g. crystals with a resolution of better than 6 Å preferably better than 4 Å, most preferably around 2 Å or better, which is required to have a sufficiently detailed model for selecting potential binding molecules e.g. modulators such as inhibitors of kinase activity.

In order to employ virtual screening (by database docking programs such as Dock, FlexX, Gold, Glide and Maestro programs from Schrödinger, Vina Autodock and Molegro virtual docker) detailed structural information of the molecule is necessary.

Identification of Modulators

According to the invention various strategies can be followed to identify and generate modulators of RSK/MSK based on the structural information described herein. Modulators according to the invention may stimulate or inhibit the overall kinase activity of the RSK/MSK.

Potential modulators are molecules that can bind to the binding site the of same binding site of RSK/MSK as DMF. These modulators can be identified trough virtual screening of chemical databases. Virtual screening are performed with different database docking programs (for instance Dock, FlexX, Gold, Flo, Fred, Glide, LigFit, MOE or MVP, but not limited to these) and used with different scoring functions (e.g. Warren et al., 2005; Jain, 2006; Seifert et al., 2007). The scoring functions may include, but are not limited to force-field scoring functions (affinities estimated by summing Van der Waals and electrostatic interactions of all atoms in the complex between the RSK/MSK and the ligand), empirical scoring functions (counting the number of various interactions, for instance number of hydrogen bonds, hydrophobic-hydrophobic contacts and hydrophilic-hydrophobic contacts, between the RSK/MSK and the ligand), and knowledge based scoring functions (with basis on statistical findings of intermolecular contacts involving certain types of atoms or functional groups). Scoring functions involving terms from any of the two of the mentioned scoring functions may also be combined into a single function used in database virtual screening of chemical libraries.

Identified potential modulators are confirmed by in vitro and in vivo experiments before further developments. The binding of modulators may further be confirmed by x-ray experiments. Even when modulating activity is confirmed further drug development may be required before a compound suitable as a drug is identified.

As seen from the above and the examples the three-dimensional structure described herein has identified a binding site for DMF in RSK2 and specified the amino acid residues involved in phosphorylation. Based on this knowledge potential modulators of a RSK/MSK can be identified. It is preferred that the structure used is the atomic coordinates presented in table 3, but a structure that deviates from the three-dimensional structures as presented in table 3 by a root mean square deviation over protein backbone atoms of not more than 3 Å may like wise used. It is preferred that the deviate is less than 2 Å, more preferably less than 1 Å.

Such methods are preferable performed using computers, whereby the atomic coordinates are introduced into the computer, allowing generation of a model on the computer screen which allows visual selection of binding molecules.

Methods of Selecting or Identifying Potential Modulators

Preferably, potential modulators such as inhibitors are selected by their potential of binding to the binding pocket of the RSK/MSK. Compounds which bind to this pocket or region of the structure can be expected to interfere with the function of the kinase and is thus a potential modulator of the kinase. When selecting a potential modulator by computer modelling, the 3D structure of the kinase is loaded from a data storage device into a computer memory and may be displayed (generated) on a computer screen using a suitable computer program. Preferably, only a subset of interest of the coordinates of the whole structure of the kinase is loaded in the computer memory or displayed on the computer screen. This subset of interest may comprise the coordinates of the binding pocket. This subset may be called a criteria data set; this subset of atoms may be used for designing a modulator such as an inhibitor.

In one aspect the present invention relates to a computer-based method for rational drug design which comprises:

a) providing the atomic coordinates of the polypeptide as defined by the coordinates of a table selected from table 3;

b) providing the structure of a candidate inhibitor molecule; and c) fitting the structure of candidate inhibitor molecule to the atomic coordinates of the polypeptide of said table.

In another aspect the invention concerns a computer-based method for identifying a potential inhibitor of the polypeptide selected from the group consisting of SEQ ID NO. 1, 2, 3, 4, 5, 6, 7, 8, 9, 10, 11, 12, 13, 14, 15, 16, 17, 18, 19 and 20 comprising the steps of:
a) employing a three-dimensional structure of the polypeptide, the three-dimensional structure being defined by atomic coordinate data according to table 3; and
b) identifying the potential inhibitor by designing or selecting a compound for interaction with the active site.

In one embodiment the method further comprises:
a) obtaining or synthesizing the potential inhibitor;
b) contacting the potential inhibitor with the polypeptide selected from the group consisting of SEQ ID NO. 1, 2, 3, 4, 5, 6, 7, 8, 9, 10, 11, 12, 13, 14, 15, 16, 17, 18, 19 and 20 to determine the ability of said inhibitor to interact with said polypeptide.

In another embodiment the method further comprises:
a) obtaining or synthesising said potential inhibitor;
b) forming a complex of said polypeptide selected from the group consisting of SEQ ID NO. 1, 2, 3, 4, 5, 6, 7, 8, 9, 10, 11, 12, 13, 14, 15, 16, 17, 18, 19 and 20; and said potential inhibitor; and
c) analysing said complex by X-ray crystallography to determine the ability of said potential inhibitor to interact with said polypeptide.

In an a further aspect the potential modulators such as inhibitors are identified using a computer, wherein the computer comprise programs and processor capable of utilizing the three dimensional structure information for selecting potential inhibitors bases on a criteria data set which defines target regions of the RSK/MSK. Data bases of potential inhibitors, such as data bases of low molecular weight organic and/or inorganic chemical structures can be stored in the computer, e.g. in a storage system and used by the processor of the computer to identify potential inhibitors which in a region are structurally complementary to the criteria data set and being free of steric interference with the RSK/MSK. Modulators being, in a region, complementary to the criteria data set, can be interpreted as inhibitors capable of accommodating a three-dimensional cavity defined by the criteria data set with out interfering with the structure of the target. Complementary indicates that the RSK/MSK and the modulator interact with each other in an energy favourable way minimizing the availability of polar and charged residues (see below). The storage medium may be local to the computer as described above, or the storage medium may be remote such as a net-worked storage medium including the internet.

The low molecular weight organic chemical structures may include structures such as lipids, nucleic acids, peptides, proteins, antibodies and saccharides.

A computer-assisted method for identifying potential modulators of a RSK/MSK using a programmed computer comprising a processor, a data storage system, a data input devise and a data output device, comprising the following steps:
a. inputting into the programmed computer through said input device data comprising:
atomic coordinates of a subset of the atoms of said RSK/MSK, thereby generating a criteria data set;
wherein said atomic coordinates are selected from the three-dimensional structure presented in table 3 or atomic coordinates selected from a three-dimensional structure that deviates from the three-dimensional structure presented in table 3 by a root mean square deviation over protein backbone atoms of not more than 3 Å,
b. comparing, using said processor, the criteria data set to a computer data base of low-molecular weight organic chemical structures stored in the data storage system; and
c. selecting from said data base, using computer methods, a chemical structure having a portion that is structurally complementary to the criteria data set and being free of steric interference with the RSK/MSK.

In one aspect the present invention comprises a computer readable media with either (a) atomic coordinate data according to table 3 recorded thereon, said data defining the three-dimensional structure of the polypeptide selected from the group consisting of SEQ ID NO. 1, 2, 3, 4, 5, 6, 7, 8, 9, 10, 11, 12, 13, 14, 15, 16, 17, 18, 19 and 20, at least one atom or at least one sub-domain thereof, or (b) structure factor data for the polypeptide selected from the group consisting of SEQ ID NO. 1, 2, 3, 4, 5, 6, 7, 8, 9, 10, 11, 12, 13, 14, 15, 16, 17, 18, 19 and 20 recorded thereon, the structure factor data being derivable from the atomic coordinate data of table 3.

In another aspect the invention concerns a computer-readable data storage medium comprising a data storage material encoded with at least a portion of the structure coordinates set forth in table 3.

In yet another aspect the invention concerns a method for identifying a ligand capable of binding to the binding site of SEQ ID NO. 1 (C-terminal domain of murine RSK2), said method comprising the steps of:
a) generating the spatial structure of the binding site on a computer screen using atomic coordinates as presented in table 3 or atomic coordinates selected from a three-dimensional structure that deviates from the three-dimensional structure presented in table 3 by a root mean square deviation over protein backbone atoms of not more than 3 Å,
b) generating potential ligands with their spatial structure on the computer screen, and
c) selecting ligands that can bind to at least 1 amino acid residue of the set of binding interaction sites without steric interference.

In one aspect the invention relates to a computer-assisted method for identifying a ligand of a polypeptide selected from the group consisting of SEQ ID NO. 1, 2, 3, 4, 5, 6, 7, 8, 9, 10, 11, 12, 13, 14, 15, 16, 17, 18, 19 and 20, using a programmed computer comprising a processor, a data storage system, a data input device and a data output device, comprising the following steps:
a) inputting into the programmed computer through said input device data comprising:
atomic coordinates of a subset of the atoms of said polypeptide, thereby generating a criteria data set;
wherein said atomic coordinates are selected from the three-dimensional structure presented in table 3 or atomic coordinates selected from a three-dimensional structure that deviates from the three-dimensional structure presented table 3 by a root mean square deviation over protein backbone atoms of not more than 3 Å,
b) comparing, using said processor, the criteria data set to a computer data base of low-molecular weight organic chemical structures and peptide fragments stored in the data storage system; and
c) selecting from said database, using computer methods, a chemical structure having a portion that is structurally complementary to the criteria data set and being free of steric interference with the polypeptide selected from the group consisting of SEQ ID NO. 1, 2, 3, 4, 5, 6, 7, 8, 9, 10, 11, 12, 13, 14, 15, 16, 17, 18, 19 and 20.

In yet another aspect the invention relates to a method for identifying a ligand, said method comprising the steps of:
a) selecting a potential ligand using atomic coordinates in conjunction with computer modelling, wherein said atomic coordinates are the atomic coordinates presented in table 3 or wherein the atomic coordinates are selected from a three-dimensional structure that deviates from the three-dimensional structure presented in any of table 3 by a root mean square deviation over protein backbone atoms of not more than 3 Å, by docking potential ligands into a set of binding interaction sites the binding site of said polypeptide selected from the group consisting of SEQ ID NO. 1, 2, 3, 4, 5, 6, 7, 8, 9, 10, 11, 12, 13, 14, 15, 16, 17, 18, 19 and 20, said binding interaction generated by computer modelling and selecting a potential ligand capable of binding to at least one amino acid in said set of binding interaction sites of said polypeptide selected from the group consisting of SEQ ID NO. 1, 2, 3, 4, 5, 6, 7, 8, 9, 10, 11, 12, 13, 14, 15, 16, 17, 18, 19 and 20,
b) providing said potential ligand and said polypeptide,
c) contacting the potential ligand with said polypeptide and
d) detecting binding of said polypeptide by the potential ligand.

In one embodiment the atomic coordinates are determined to a resolution of at least 5 Å, preferably at least 4 Å, more preferably at least 3 Å, more preferably at least 2 Å, more preferably at least 1.5 Å.

In one embodiment the potential inhibitor is selected from the group consisting of non-hydrolyzable peptides and peptide analogues, organic compounds and inorganic compounds.

A potential inhibitor may be designed de novo in conjunction with computer modelling. Models of chemical structures or molecule fragments may be generated on a computer screen using information derived from known low-molecular weight organic chemical structures stored in a computer data base or are built using the general knowledge of an organic chemist regarding bonding types, conformations etc. Suitable computer programs may aid in this process in order to build chemical structures of realistic geometries. Chemical structures or molecule fragments may be selected and/or used to construct a potential inhibitor such that favourable interactions to said subset or criteria data set become possible. The more favourable interactions become possible, the stronger the potential inhibitor will bind to the RSK/MSK. Preferably, favourable interactions to at least one amino acid residues should become possible. Such favourable interactions may occur with any atom of the amino acid residue e.g. atoms of the peptide back-bone or/and atoms of the side chains.

Favourable interactions are any non-covalent attractive forces which may exist between chemical structures such as hydrophobic or van-der-Waals interactions and polar interactions such as hydrogen bonding, salt-bridges etc. Unfavourable interactions such as hydrophobic-hydrophilic interactions should be avoided but may be accepted if they are weaker than the sum of the attractive forces. Steric interference such as clashes or overlaps of portions of the inhibitor being selected or constructed with protein moieties will prevent binding unless resolvable by conformational changes. The binding strength of a potential inhibitor thus created may be assessed by comparing favourable and unfavourable interactions on the computer screen or by using computational methods implemented in commercial computer programs.

Conformational freedom of the potential inhibitor and amino acid side chains of the RSK/MSK should be taken into account. Accessible conformations of a potential inhibitor may be determined using known rules of molecular geometry, notably torsion angles, or computationally using computer programs having implemented procedures of molecular mechanics and/or dynamics or quantum mechanics or combinations thereof.

A potential inhibitor is at least partially complementary to at least a portion of the active site of the RSK/MSK in terms of shape and in terms of hydrophilic or hydrophobic properties.

Databases of chemical structures (e. g. Cambridge structural database or from Chemical Abstracts Service; for a review see: Rusinko (1993) Chem. Des. Auto. News 8, 44-47) may be used to varying extents. In a totally automatic embodiment, all structures in a data base may be compared to the active site or to the binding pockets of the RSK/MSK for complementarity and lack of steric interference computationally using the processor of the computer and a suitable computer program. In this case, computer modelling which comprises manual user interaction at a computer screen may not be necessary. Alternatively, molecular fragments may be selected from a data base and assembled or constructed on a computer screen e. g. manually. Also, the ratio of automation to manual interaction by a person skilled in the art in the process of selecting may vary a lot. As computer programs for drug design and docking of molecules to each other become better, the need for manual interaction decreases.

A preferred approach of selecting or identifying potential inhibitors of RSK/MSKs makes use of the structure of the murine RSK2 of this invention. Analogously to the principles of drug design and computer modelling outlined above, chemical structures or fragments thereof may be selected or constructed based on non-covalent interactions with the potential inhibitor with the binding pocket of the RSK/MSK.

Programs usable for computer modelling include Quanta (Molecular Simulations, Inc.) and Sibyl (Tripos Associates). Other useful programs are Autodock (Scripps Research Institute, La Jolla, described in Goodsell and Olsen (1990) Proteins: Structure, Function and Genetics, 8, 195-201), Dock (University of California, San Francisco, described in: Kuntz et al. (1982) J. Mol. Biol. 161, 269-288.

Methods for Verification of Inhibitors

The activity of identified modulators may be verified by established methods. In vitro verification may be demonstrated by studying binding and inhibition of kinase activity. In vitro verification may be shown by administration of potential inhibitors to cell cultures such as COS cells. In vivo experiments may be performed on mice. The binding is further confirmed by X-ray studies. Such methods are known in the art and an example is described in examples 7-9.

The potential inhibitors can be synthesized according to the methods of organic chemistry. Preferably, compounds from a database have been selected without remodelling, and their synthesis may already be known.

In any event, the synthetic effort needed to find an inhibitor is greatly reduced by the achievements of this invention due to the pre-selection of promising inhibitors by the above methods. Binding of a potential modulator may be determined after contacting the potential inhibitor with the RSK/MSK. This may be done crystallographically by soaking a crystal of the RSK/MSK with the potential inhibitor or by co-crystallisation and determining the crystal structure of the complex. Preferably, binding may be measured in solution according to methods known in the art. More preferably, inhibition of the catalytic activity of the RSK/MSK by the inhibitor is determined e.g. using the assays described in the examples section.

EXAMPLES

Example 1

Sequences

```
SEQ ID NO. 1: Murine C-terminal domain of RSK2
used for crystallization
>RSK2_crystallization
GQTVGVHSIVQQLHRNSIQFTDGYEVKEDIGVGSYSVCKRCIHKA
TNMEFAVKIIDKSKRDPTEEIEILLRYGQHPNIITLKDVYDDGKY
VYVVTELMKGGELLDKILRQKFFSEREASAVLFTITKTVEYLHAQ
GVVHRDLKPSNILYVDESGNPESIRICDFGFAKQLRAENGLLMTP
CYTANFVAPEVLKRQGYDAACDIWSLGVLLYTMLTGYTPFANGPD
DTPEEILARIGSGKFSLSGGYWNSVSDTAKDLVSKMLHVDPHQRL
TAALVLRHPWIVHWDQLPQYQLNRQDAPHLVKGAMAATYSALNRN
QSPVLEPVGRSTLAQRRGIKKITSTAL SEQ ID NO. 2: Murine C-terminal domain of RSK2
used for crystallization, without N-terminal G
from TEV protease cleavage site
>RSK2_crystallization_wo_G
QTVGVHSIVQQLHRNSIQFTDGYEVKEDIGVGSYSVCKRCIHKATN
MEFAVKIIDKSKRDPTEEIEILLRYGQHPNIITLKDVYDDGKYVYV
VTELMKGGELLDKILRQKFFSEREASAVLFTITKTVEYLHAQGVVH
RDLKPSNILYVDESGNPESIRICDFGFAKQLRAENGLLMTPCYTAN
FVAPEVLKRQGYDAACDIWSLGVLLYTMLTGYTPFANGPDDTPEEI
LARIGSGKFSLSGGYWNSVSDTAKDLVSKMLHVDPHQRLTAALVLR
HPWIVHWDQLPQYQLNRQDAPHLVKGAMAATYSALNRNQSPVLEPV
GRSTLAQRRGIKKITSTAL SEQ ID NO. 3: Human RSK1
>RSK1_human(Q15418)
MPLAQLKEPWPLMELVPLDPENGQTSGEEAGLQPSKDEGVLKEISI
THHVKAGSEKADPSHFELLKVLGQGSFGKVFLVRKVTRPDSGHLYA
MKVLKKATLKVRDRVRTKMERDILADVNHPFVVKLHYAFQTEGKLY
LILDFLRGGDLFTRLSKEVMFTEEDVKFYLAELALGLDHLHSLGII
YRDLKPENILLDEEGHIKLTDFGLSKEAIDHEKKAYSFCGTVEYMA
PEVVNRQGHSHSADWWSYGVLMFEMLTGSLPFQGKDRKETMTLILK
AKLGMPQFLSTEAQSLLRALFKRNPANRLGSGPDGAEEIKRHVFYS
TIDWNKLYRREIKPPFKPAVAQPDDTFYFDTEFTSRTPKDSPGIPP
SAGAHQLFRGFSFVATGLMEDDGKPRAPQAPLHSVVQQLHGKNLVF
SDGYVVKETIGVGSYSECKRCVHKATNMEYAVKVIDKSKRDPSEEI
EILLRYGQHPNIITLKDVYDDGKHVYLVTELMRGGELLDKILRQKF
FSEREASFVLHTIGKTVEYLHSQGVVHRDLKPSNILYVDESGNPEC
LRICDFGFAKQLRAENGLLMTPCYTANFVAPEVLKRQGYDEGCDIW
SLGILLYTMLAGYTPFANGPSDTPEEILTRIGSGKFTLSGGNWNTV
SETAKDLVSKMLHVDPHQRLTAKQVLQHPWVTQKDKLPQSQLSHQD
LQLVKGAMAATYSALNSSKPTPQLKPIESSILAQRRVRKLPSTTL SEQ ID NO. 4: Human RSK2
>RSK2_human(P51812)
MPLAQLADPWQKMAVESPSDSAENGQQIMDEPMGEEEINPQTEE
VSIKEIAITHHVKEGHEKADPSQFELLKVLGQGSFGKVFLVKKI
SGSDARQLYAMKVLKKATLKVRDRVRTKMERDILVEVNHPFIVK
LHYAFQTEGKLYLILDFLRGGDLFTRLSKEVMFTEEDVKFYLAE
LALALDHLHSLGIIYRDLKPENILLDEEGHIKLTDFGLSKESID
HEKKAYSFCGTVEYMAPEVVNRRGHTQSADWWSFGVLMFEMLTG
TLPFQGKDRKETMTMILKAKLGMPQFLSPEAQSLLRMLFKRNPA
NRLGAGPDGVEEIKRHSFFSTIDWNKLYRREIHPPFKPATGRPE
DTFYFDPEFTAKTPKDSPGIPPSANAHQLFRGFSFVAITSDDES
QAMQTVGVHSIVQQLHRNSIQFTDGYEVKEDIGVGSYSVCKRCI
HKATNMEFAVKIIDKSKRDPTEEIEILLRYGQHPNIITLKDVYD
DGKYVYVVTELMKGGELLDKILRQKFFSEREASAVLFTITKTVE
YLHAQGVVHRDLKPSNILYVDESGNPESIRICDFGFAKQLRAEN
GLLMTPCYTANFVAPEVLKRQGYDAACDIWSLGVLLYTMLTGYT
PFANGPDDTPEEILARIGSGKFSLSGGYWNSVSDTAKDLVSKML
HVDPHQRLTAALVLRHPWIVHWDQLPQYQLNRQDAPHLVKGAMA
ATYSALNRNQSPVLEPVGRSTLAQRRGIKKITSTAL SEQ ID NO. 5: Human RSK3
>RSK3_human(Q15349)
MDLSMKKFAVRRFFSVYLRRKSRSKSSSLSRLEEEGVVKEIDIS
HHVKEGFEKADPSQFELLKVLGQGSYGKVFLVRKVKGSDAGQLY
AMKVLKKATLKVRDRVRSKMERDILAEVNHPFIVKLHYAFQTEG
KLYLILDFLRGGDLFTRLSKEVMFTEEDVKFYLAELALALDHLH
SLGIIYRDLKPENILLDEEGHIKITDFGLSKEAIDHDKRAYSFC
GTIEYMAPEVVNRRGHTQSADWWVSFGVLMFEMLTGSLPFQGKD
RKETMALILKAKLGMPQFLSGEAQSLLRALFKRNPCNRLGAGID
GVEEIKRHPFFVTIDWNTLYRKEIKPPFKPAVGRPEDTFHFDPE
FTARTPTDSPGVPPSANAHHLFRGFSFVASSLIQEPSQQDLHKV
PVHPIVQQLHGNNIHFTDGYEIKEDIGVGSYSVCKRCVHKATDT
EYAVKIIDKSKRDPSEEIEILLRYGQHPNIITLKDVYDDGKFVY
LVMELMRGGELLDRILRQRYFSEREASDVLCTITKTMDYLHSQG
VVHRDLKPSNILYRDESGSPESIRVCDFGFAKQLRAGNGLLMTP
CYTANFVAPEVLKRQGYDAACDIWSLGILLYTMLAGFTPFANGP
DDTPEEILARIGSGKYALSGGNWDSISDAAKDVVSKMLHVDPHQ
```

```
RLTAMQVLKHPWVVNREYLSPNQLSRQDVHLVKGAMAATYFALN

RTPQAPRLEPVLSSNLAQRRGMKRLTSTRL

SEQ ID NO. 6: Human RSK4
>RSK4_human(Q9UK32)
MLPFAPQDEPWDREMEVFSGGGASSGEVNGLKMVDEPMEEGEA

DSCHDEGVVKEIPITHHVKEGYEKADPAQFELLKVLGQGSFGK

VFLVRKKTGPDAGQLYAMKVLKKASLKVRDRVRTKMERDILVE

VNHPFIVKLHYAFQTEGKLYLILDFLRGGDVFTRLSKEVLFTE

EDVKFYLAELALALDHLHQLGIVYRDLKPENILLDEIGHIKLT

DFGLSKESVDQEKKAYSFCGTVEYMAPEVVNRRGHSQSADWWS

YGVLMFEMLTGTLPFQGKDRNETMNMILKAKLGMPQFLSAEAQ

SLLRMLFKRNPANRLGSEGVEEIKRHLFFANIDWDKLYKREVQ

PPFKPASGKPDDTFCFDPEFTAKTPKDSPGLPASANAHQLFKG

FSFVATSIAEEYKITPITSANVLPIVQINGNAAQFGEVYELKE

DIGVGSYSVCKRCIHATTNMEFAVKIIDKSKRDPSEEIEILMR

YGQHPNIITLKDVFDDGRYVYLVTDLMKGGELLDRILKQKCFS

EREASDILYVISKTVDYLHCQGVVHRDLKPSNILYMDESASAD

SIRICDFGFAKQLRGENGLLLTPCYTANFVAPEVLMQQGYDAA

CDIWSLGVLFYTMLAGYTPFANGPNDTPEEILLRIGNGKFSLS

GGNWDNISDGAKDLLSHMLHMDPHQRYTAEQILKHSWITHRDQ

LPNDQPKRNDVSHVVKGAMVATYSALTHKTFQPVLEPVAASSL

AQRRSMKKRTSTGL

SEQ ID NO. 7: Human MSK1
>MSK1_human(O75582)
MEEEGGSSGGAAGTSADGGDGGEQLLTVKHELRTANLTGHAEK

VGIENFELLKVLGTGAYGKVFLVRKISGHDTGKLYAMKVLKKA

TIVQKAKTTEHTRTERQVLEHIRQSPFLVTLHYAFQTETKLHL
ILDYINGGELFTHLSQRERFTEHEVQIYVGEIVLALEHLHKLG

IIYRDIKLENILLDSNGHVVLTDFGLSKEFVADETERAYSFCG

TIEYMAPDIVRGGDSGHDKAVDWWSLGVLMYELLTGASPFTVD

GEKNSQAEISRRILKSEPPYPQEMSALAKDLIQRLLMKDPKKR

LGCGPRDADEIKEHLFFQKINWDDLAAKKVPAPFKPVIRDELD

VSNFAEEFTEMDPTYSPAALPQSSEKLFQGYSFVAPSILFKRN

AAVIDPLQFHMGVERPGVTNVARSAMMKDSPFYQHYDLDLKDK

PLGEGSFSICRKCVHKKSNQAFAVKIISKRMEANTQKEITALK

LCEGHPNIVKLHEVFHDQLHTFLVMELLNGGELFERIKKKHF

SETEASYIMRKLVSAVSHMHDVGVVHRDLKPENLLFTDENDNL

EIKIIDFGFARLKPPDNQPLKTPCFTLHYAAPELLNQNGYDES

CDLWSLGVILYTMLSGVPFQSHDRSLTCTSAVEIMKKIKKGD

FSFEGEAWKNVSQEAKDLIQGLLTVDPNKRLKMSGLRYNEWLQ

DGSQLSSNPLMTPDILGSSGAAVHTCVKATFHAFNKYKREGFC

LQNVDKAPLAKRRKMKKTSTSTETRSSSSESSHSSSSHSGKT

TPTKTLQPSNPADSNNPETLFQFSDSVA

SEQ ID NO. 8: Human MSK2
>MSK2_human(O75676)
MGDEDDDESCAVELRITEANLTGHEEKVSVENFELLKVLGTGA

YGKVFLVRKAGGHDAGKLYAMKVLRKAALVQRAKTQEHTRTER

SVLELVRQAPFLVTLHYAFQTDAKLHLILDYVSGGEMFTHLYQ

RQYFKEAEVRVYGGEIVLALEHLHKLGIIYRDLKLENVLLDSE

GHIVLTDFGLSKEFLTEEKERTFSFCGTIEYMAPEIIRSKTGH

GKAVDWWSLGILLFELLTGASPFTLEGERNTQAEVSRRILKCS

PPFPPRIGPVAQDLLQRLLCKDPKKRLGAGPQGAQEVRNHPFF

QGLDWVALAARKIPAPFRPQIRSELDVGNFAEEFTRLEPVYSP

PGSPPPGDPRIFQGYSFVAPSILFDHNNAVMTDGLEAPGAGDR

PGRAAVARSAMMQDSPFFQQYELDLREPALGQGSFSVCRRCRQ

RQSGQEFAVKILSRRLEANTQREVAALRLCQSHPNVVNLHEVH

HDQLHTYLVLELLRGGELLEHIRKKRHFSESEASQILRSLVSA

VSFMHEEAGVVHRDLKPENILYADDTPGAPVKIIDFGFARLRP

QSPGVPMQTPCFTLQYAAPELLAQQGYDESCDLWSLGVILYMM

LSGQVPFQGASGQGGQSQAAEIMCKIREGRFSLDGEAWQGVSE

EAKELVRGLLTVDPAKRLKLEGLRGSSWLQDGSARSSPPLRTP

DVLESSGPAVRSGLNATFMAFNRGKREGFFLKSVENAPLAKRR

KQKLRSATASRRGSPAPANPGRAPVASKGAPRRANGPLPPS

SEQ ID NO. 9: Mouse RSK1
>RSK1_mouse(P18653)
MPLAQLKEPWPLMELVPLDPENGQTSGEEAGLQPSKDEAILKE

ISITHHVKAGSEKADPSQFELLKVLGQGSFGKVFLVRKVTRPD

SGHLYAMKVLKKATLKVRDRVRTKMERDILADVNHPFVVKLHY

AFQTEGKLYLILFLRGGDLFTRLSKEVMFTEEDVKFYLAELAL

GLDHLHSLGIIYRDLKPENILLDEEGHIKLTDFGLSKEAIDHE

KKAYSFCGTVEYMAPEVVNRQGHTHSADWWSYGVLMGKDRKET

MTLILKAKLGMPQFLSTEAQSLLRALFKRNPANRLGSGPDAE

EIKRHIFYSTIDWNKLYRREIKPPFKPAVAQPDDTFYFDTEFT

SRTPRDSPGIPPSAGAHQLFRGFSFVATGLMEDDGKPRTTQAP

LHSVVQQLHGKNLVFSDGYVVKETIGVGSYSVCKRCVHKATNM

EYAVKVIDKSKRDPSEEIEILLRYGQHPNIITLKDVYDDGKHV

YLVTELMRGGELLDKILRQKFFSEREASFVLHTISKTVEYLHS

QGVVHRDLKPSNILYVDESGNPECLRICDFGFAKQLRAENGLL

MTPCYTANFVAPEVLKRQGYDEGCDIWSLGILLYTMLAGYTPF

ANGPSDTPEEILTRIGSGKFTLSGGNWNTVSETAKDLVSKMLH

VDPHQRLTAKQVLQHPWITQKDKLPQSQLSHQDLQLVKGAMAA

TYSALNSSKPTPQLKPIESSILAQRRVRKLPSTTL

SEQ ID NO. 10: Mouse RSK2
>RSK2_mouse(P18654)
MPLAQLADPWQKMAVESPSDSAENGQQIMDEPMGEEEINPQTE

EGSIKEIAITHHVKEGHEKADPSQFELLKVLGQGSFGKVFLVK
```

KISGSDARQLYAMKVLKKATLKVRDRVRTKMERDILVEVNHPF

IVKLHYAFQTEGKLYLILDFLRGGDLFTRLSKEVMFTEEDVKF

YLAELALALDHLSLGIIYRDLKPENILLDEEGHIKLTDFGLS

KESIDHEKKAYSFCGTVEYMAPEVVNRRGHTQSADWWSFGVLM

FEMLTGTLPFQGKDRKETMTMILKAKLGMPQFLSPEAQSLLRM

LFKRNPANRLGAGPDGVEEIKRHSFFSTIDWNKLYRREIHPPF

KPATGRPEDTFYFDPEFTAKTPKDSPGIPPSANAHQLFRGFSF

VAITSDDESQAMQTVGVHSIVQQLHRNSIQFTDGYEVKEDIGV

GSYSVCKRCIHKATNMEFAVKIIDKSKRDPTEEIEILLRYGQH

PNIITLKDVYDDGKYVYVVTELMKGGELLDKILRQKFFSEREA

SAVLFTITKTVEYLHAQGVVHRDLKPSNILYVDESGNPESIRI

CDFGFAKQLRAENGLLMTPCYTANFVAPEVLKRQGYDAACDIW

SLGVLLYTMLTGYTPFANGPDDTPEEILARIGSGKFSLSGGYW

NSVSDTAKDLVSKMLHVDPHQRLTAALVLRHPWIVHWDQLPQY

QLNRQDAPHLVKGAMAATYSALNRNQSPVLEPVGRSTLAQRRG

IKKITSTAL

SEQ ID NO. 11: Mouse RSK3
>RSK3_mouse(Q9WUT3)
MELSMKKFTVRRFFSVYLRKKSRSKSSSLSRLEEEGIVKEIDI

SNHVKEGFEKADPSQFELLKVLGQGSYGKVFLVRKVTGSDAGQ

LYAMKVLKKATLKVRDRVRSKMERDILAEVNHPFIVKLHYAFQ

TEGKLYLILDFLRGGDLFTRLSKEVMFTEEDVKFYLAELALAL

DHLHGLGIIYRDLKPENILLDEEGHIKITDFGLSKEATDHDKR

AYSFCGTIEYMAPEVVNRRGHTQSADWWSFGVLMFEMLTGSLP

FQGKDRKETMALILKAKLGMPQFLSAEAQSLLRALFKRNPCNR

LGAGVDGVEEIKRHPFFVTIDWNKLYRKEIKPPFKPAVGRPED

TFHFDPEFTARTPTDSPGVPPSANAHHLFRGFSFVASSLVQEP

SQQDVPKAPIHPIVQQLHGNNIHFTDGYEIKEDIGVGSYSVCK

RCVHKATDAEYAVKIIDKSKRDPSEEIEILLRYGQHPNIITLK

DVYDDGKYVYLVMELMRGGELLDRILRQRCFSEREASDVLYTI

ARTMDYLHSQGVVHRDLKPSNILYMDESGNPESIRICDFGFAK

QLRAENGLLMTPCYTANFVAPEVLKRQGYDAACDVWSLGILLY

TMLAGFTPFANGPDDTPEEILARIGSGKYALSGGNWDSISDAA

KDVVSKMLHVDPQQRLTAVQVLKHPWIVNREYLSQNQLSRQDV

HLVKGAMAATYFALNRTPQAPRLEPVLSSSLAQRRGMKRLTSTRL

SEQ ID NO. 12: Mouse RSK4
>RSK4_mouse(Q7TPS0)
MLPFAPVEDPWDQEDMEVFGSTSSSEPQVVFTMKNAATVMREH

ERKEVNDLKMVDEPMEEGEPVSCRREELVKEVPITQHVKEGYE

KADPAQFDLLKVLGQGSFGKVFLVRKKTGPDAGQLYAMKVLRK

ASLKVRDRVRTKMERDILVEVNHPFIVKLHYAFQTEGKLYLIL

DFLRGGDVFTRLSKEVLFTEEDVKFYLAELALALDHLHRLGIV

YRDLKPENILLDEIGHIKLTDFGLSKESVDQEKKAYSFCGTVE

YMAPEVVNRRAHSQSADWWSYGVLMFEMLTGTLPFQGKDRNET

MNMILKAKLGMPQFLSAEAQSLLRMLFKRNPANRLGSEGVEEV

KRHAFFASIDWNKLYKREVQPPFRPASGKPDDTFCFDPEFTAK

TPKDSPGLPASANAHQLFKGFSFVATSIAEEYKITPVTSSNVL

PIVQINGNAAQFSEAYELKEDIGIGSYSVCKRCIHSASNVEFA

VKIIDKNKRDPSEEIEILMRYGQHPNIISLKEVFDDGKYVYLV

TDLMKGGELLDRILKKKCFSEQEASNVLYVITKTVECLHSQGV

VHRDLKPSNILYMDESAHPDSIKICDFGFAKQLRGENGLLLTP

CYTANFVAPEVLTQQGYDAACDIWSLGVLLYTMLAGYTPFSNG

PNDTPEEILLRIGNGRFSLSGGIWDNISRGAKDLLSHMLHMDP

HQRYTAEQVLKHPWITQREQLPRHQPNSDEPPQEAVAAPYSVL

ARNPNRHHPILEPVTASRLAQRRNMKKRTSTGL

SEQ ID NO. 13: Mouse MSK1
>MSK1_mouse(Q8C050)
MEGEGGGSGGAGTSGDSGDGGEQLLTVKHELRTANLTGHAEKV

GIENFELLKVLGTGAYGKVFLVRKISGHDAGKLYAMKVLKKAT

IVQKAKTTEHTRTERQVLEHIRQSPFLVTLHYAFQTETKLHLI

LDYINGGELFTHLSQRERFTEHEVQIYVGEIVLALEHLHKLGI

IYRDIKLENILLDSNGHVVLTDFGLSKEFVADETERAYSFCGT

IEYMAPDIVRGGDSGHDKAVDWWSLGVLMYELLTGASPFTVDG

EKNSQAEISRRILKSEPPYPQEMSTVAKDLLQRLLMKDPKKRL

GCGPRDAEEIKEHLFFEKIKWDDLAAKKVPAPFKPVIRDELDV

SNFAEEFTEMDPTYSPAALPQSSERLFQGYSFVAPSILFKRNA

AVIDPLQFHMGVDRPGVTNVARSAMMKDSPFYQHYDLDLKDKP

LGEGSFSICRKCVHKKTNQAFAVKIISKRMEANTQKEITALKL

CEGHPNIVKLHEVFHDQVAASAQPPGQVVLCSLLLLALLFNRS

LTRKPVTVVTWLVHSTSQLPPLPPPMPEIVLFILLSDNGQLHT

FLVMELLNGGELFERIKRKKHFSETEASYIMRKLVSAVSHMHD

VGVVHRDLKPENLLFTDENDNLEIKVIDFGFARLKPPDNQPLK

TPCFTLHYAAPELLTHNGYDESCDLWSLGVILYTMLSGQVPFQ

SHDRSLTCTSAVEIMKKIKKGDFSFEGEAWKNVSQEAKDLIQG

LLTVDPNKRLKMSGLRYNEWLQDGSQLSSNPLMTPDILGSSGA

AVHTCVKATFHAFNKYKREGFCLQNVDKAPLAKRRKMKRTSTS

TETRSSSSESSRSSSSQSHGKTTPTKTLQPSNPTEGSNPDTLF

QFSD

SEQ ID NO. 14: Mouse MSK2
>MSK2_mouse(Q9Z2B9)
MGDEDEDEGCAVELQITEANLTGHEEKVSVENFALLKVLGTGA

YGKVFLVRKTGGHDAGKLYAMKVLRKAALVQRAKTQEHTRTER

SVLELVRQAPFLVTLHYAFQTDAKLHLILDYVSGGEMFTHLYQ

ERQYFKAEVRVYGGEIVLALEHLHKLGIIYRDLKLENVLLDSE

EGHIVLTDFGLSKEFLTEEKERTFSFCGTIYMAPEIIRSKAGH
GKAVDWWSLGILLLFELLTGASPFTLEGERNTQAEVSRRILKCS
APPFPLRIGPVQDLLQRLLCKDPKKRLGAGPQGAQEVKSHPFF
QGLDWVALAARKIPAPFRPQIRSELDVGNFAEEFTRLEPVYSP
AGSPPPGDPRIFQGYSFVAPSILFDHNNAVMADVLQAPGAGYR
PGRAAVARSAMMQDSPFFQQYELDLREPALGQGSFSVCRRCRQ
RQSGQEFAVKILSRRLEENTQREVAALRLCQSHPNVVNLHEVL
HDQLHTYLVLELLRGGELLEHIRKKRLFSESEASQILRSLVSA
VSFMHEEAGVVHRDLKPENILYADDTPGAPVKIIDFGFARLRP
QSPAEPMQTPCFTLQYAAPELLAQQGYDESCDLWSLGVILYMM
LSGQVPFQGASGQGGQSQAAEIMCKIREGRFSLDGEAWQGVSE
EAKELVRGLLTVDPAKRLKLEGLRSSSWLQDGSARSSPPLRTP
DVLESSGPAVRSGLNATFMAFNRGKREGFFLKSVENAPLAKRR
KQKLRSAAASRRGSPVPASSGRLPASAAKGTTRRANGPLSPS

SEQ ID NO. 15: Rat RSK1
>RSK1_rat(Q63531)
MPLAQLKEPWPLMELVPLDPENGQASGEEAGLQPSKDEGILKE
ISITHHVKAGSEKADPSHFELLKVLGQGSFGKVFLVRKVTRPD
NGHLYAMKVLKKATLKVRDRVRTKMERDILADVNHPFVVKLHY
AFQTEGKLYLILDFLRGGDLFTRLSKEVMFTEEDVKFYLAELA
LGLDHLHSLGIIYRDLKPENILLDEEGHIKLTDFGLSKEAIDH
EKKAYSFCGTVEYMAPEVVNRQGHTHSADWWSYGVLMFEMLTG
SLPFQGKDRKETMTLILKAKLGMPQFLSTEAQSLLRALFKRNP
ANRLGSGPDGAEEIKRHIFYSTIDWNKLYRREIKPPFKPAVAQ
PDDTFYFDTEFTSRTPRDSPGIPPSAGAHQLFRGFSFVATGLM
EDDSKPRATQAPLHSVVQQLHGKNLVFSDGYIVKETIGVGSYS
VCKRCVHKATNMEYAVKVIDKSKRDPSEEIEILLRYGQHPNII
TLKDVYDDSKHVYLVTELMRGGELLDKILRQKFFSEREASFVL
YTISKTVEYLHSQGVVHRDLKPSNILYVDESGNPECLRICDFG
FAKQLRAENGLLMTPCYTANFVAPEVLKRQGYDEGCDIWSLGV
LLYTMLAGYTPFANGPSDTPEEILTRISSGKFTLSGGNWNTVS
ETAKDLVSKMLHVDPHQRLTAKQVLQHPWITQKDKLPQSQLSH
QDLQLVKGGMAATYSALSSSKPTPQLKPIESSILAQRRVRKLP
STTL SEQ ID NO. 16: Rat RSK2
>RSK2_rat(NP_001178933.1)
MPLAQLADPWQKMAVESPSDSAENGQQIMDEPMGEEEINPQT
EEGSIKEIAITHHVKEGHEKADPSQFELLKVLGQGSFGKVFL
VKKISGSDARQLYAMKVLKKATLKVRDRVRTKMERDILVEVN
HPFIVKLHYAFQTEGKLYLILDFLRGGDLFTRLSKEVMFTEE
DVKFYLAELALALDHLHSLGIIYRDLKPENILLDEEGHIKLT
DFGLSKESIDHEKKAYSFCGTVEYMAPEVVNRRGHTQSADWW
SFGVLMFEMLTGTLPFQGKDRKETMTMILKAKLGMPQFLSPE
AQSLLRMLFKRNPANRLGAGPDGVEEIKRHSFFSTIDWNKLY
RREIHPPFKPATGRPEDTFYFDPEFTAKTPKDSPGIPPSANA
HQLFRGFSFVAITSDDESQAMQTVGVHSIVQQLHRNSIQFTD
GYEVKEDIGVGSYSVCKRCIHKATNMEFAVKIIDKSKRDPTE
EIEILLRYGQHPNIITLKDVYDDGKYVYVVTELMKGGELLDK
ILRQKFFSEREASAVLFTITKTVEYLHTQGVVHRDLKPSNIL
YVDESGNPESIRICDFGFAKQLRAENGLLMTPCYTANFVAPE
VLKRQGYDAACDIWSLGVLLYTMLTGYTPFANGPDDTPEEIL
ARIGSGKFSLSGGYWNSVSDTAKDLVSKMLHVDPHQRLTAAL
VLRHPWIVHWDQLPQYQLNRQDAPHLVKGAMAATYSALNRNQ
SPVLEPVGRSTLAQRRGIKKITSTAL SEQ ID NO. 17: Rat RSK3
>RSK3_rat(NP_476469.1)
MELNMKKFTVRRFFSVYLRKKSRSKSSSLSRLEEEGIVKEID
ISSHVKEGFEKADPSQFELLKVLGQGSYGKVFLVRKVTGSDA
GQLYAMKVLKKATLKVRDRVRSKMERDILAEVNHPFIVKLHY
AFQTEGKLYLILDFLRGGDLFTRLSKEVMFTEEDVKFYLAEL
ALALDHLHGLGIIYRDLKPENILLDEEGHIKITDFGLSKEAI
DHDKRAYSFCGTIEYMAPEVVNRRGHTQSADWWSFGVLMFEM
LTGSLPFQGKDRKETMALILKAKLGMPQFLSAEAQSLLRALF
KRNPCNRLGAGVDGVEEIKRHPFFVTIDWNKLYRKEIKPPFK
PAVGRPEDTFHFDPEFTARTPTDSPGVPPSANAHHLFRGFSF
VASSLVQEPSQQDVPKAPIHPIVQQLHGNNIHFTDGYEIKED
IGVGSYSVCKRCVHKATDAEYAVKIIDKSKRDPSEEIEILLR
YGQHPNIITLKDVYDDGKYVYLVMELMRGGELLDRILRQRCF
SEREASDVLYTIARTMDYLHSQGVVHRDLKPSNILYMDESGN
PESIRICDFGFAKQLRAENGLLMTPCYTANFVAPEVLKRQGY
DAACDVWSLGILLYTMLAGFTPFANGPDDTPEEILARIGSGK
YALSGGNWDSISDAAKDVVSKMLHVDPQQRLTAVQVLKHPWI
VNREYLSQNQLSRQDVHLVKGAMAATYFALNRTPQAPRLEPV
LSSSLAQRRGMKRLTSTRL SEQ ID NO. 18: Rat RSK4
>RSK4_rat(NP_001178650.1)
MLNFRRTRHTPSGHRSNSSLNLFCCFPFFGCRRQSRSRQRAG
TPVVPLLRYPPLARSAVTQRESWSYEEDHEPAQQAGCMLVLG
TSSFFSSVPEAAMLPFAPVEDPWDEEMEVFGSGSTSSSEPQI
VFTMKTAAMVIRQHEHKEVNDLKMVDEPMDEGEPVFCRREDL
VKEIPITQHVKEGYEKADPAQFDLLKVLGQGSFGKVFLVRKK
TGPDAGQLYAMKVLRKASLKVRDRVRTKMERDILVEVNHPFI
VKLHYAFQTEGKLYLILDFLRGGDVFTRLSKEVLFTEEDVKF
YLAELALALDHLHRLGIVYRDLKPENILLDEIGHIKLTDFGL -continued

SKESVDQEKKAYSFCGTVEYMAPEVVNRRGHSQSADWWSYGV

LMFEMLTGTLPFQGKDRNETMNMILKAKLGMPQFLSAEAQSL

KLRMLFKRNPANRLGSEGVEEVKRHAFFSSIDWNKLYKREVQ

PPFRPASGPDDTFCFDPEFTAKTPKDSPGLPASANAHQLFKG

FSFVATSIAEEYKITPVTSSNVLPIVQINGNAAQFSEAYELK

EDIGIGSYSVCKRCIHSASNMEFAVKIIDKNKRDPSEEIEIL

MRYGQHPNIISLKEVFDDGKYVYLVTDLMKGGELLDRILKKK

CFSEQEASNVLYVITKTVEYLHSQGVVHRDLKPSNILYMDES

GHPDSIKICDFGFAKQLRGENGLLLTPCYTANFVAPEVLTQQ

GYDAACDIWSLGVLLYTMLAGYTPFSNGPNDTPEEILLRIGN

GRFSLSGGIWDNISRGAKDLLSHMLHMDPHQRYTAEQVLKHP

WITQREQLPRHQPTSDDPPQEAVAAAYSVLARNQNRHPILEP

VAASRLAQRRNMKKRTSTGL

SEQ ID NO. 19: Rat MSK1
>MSK1_rat(NP_001101518.1)
MEGEGGGSGGAGTSGDSGDGGEQLLTVKHELRTANLTGHAEK

VGIENFELLKVLGTGAYGKVFLVRKISGHDAGKLYAMKVLKK

ATIVQKAKTTEHTRTERQVLEHIRQSPFLVTLHYAFQTETKL

HLILDYINGGELFTHLSQRERFTEHEVQIYVGEIVLALEHLH

KLGIIYRDIKLENILLDSNGHVVLTDFGLSKEFVADEAERAY

SFCGTIEYMAPDIVRGGDSGHDKGMSSVAKDLLQRLLMKDPK

KRLGCGPRDAEEIKEHLFFEKINWDDLAAKKVPAPFKPVIRD

ELDVSNFAEEFTEMDPTYSPAALPQSSERLFQGYSFVAPSIL

FKRNAAVIDPLQFHMGVDRPGVTNVARSAMMKDSPFYQHYDL

DLKDKPLGEGSFSICRKCVHKKTNQAFAVKIISKRMEANTQK

EITALKLCEGHPNVVKLHEVFHDQLHTFLVMELLNGGELFER

IKKKKHFSETEASYIMRKLVSAVSHMHDVGVVHRDLKPETVF

IHREISRSPVISMRIPEYTLQNLLFTDENDNLEKVIDFGFAR

LKPPDNQPLKTPCFTLHYAAPELLTHNGYDESCDLWSLGVIL

YTMLSGQVPFQSHDRSLTCTSAVEIMKKIKKGDFSFEGEAWK

NVSQEAKDLIQGLLTVDPNKRLKMSGLRYNEWLQDGSQLSSN

PLMTPDILGSSGAAVHTCVKATFHAFNKYKREGFCLQNVDKA

PLAKRRKMKRTSTSTETRSSSSESSRSSSSHSHGKTTPTKTL

QPSNPTEGSNPDTLFQFSD

SEQ ID NO. 20: Rat MSK2
>MSK2_rat(NP_001101987.2)
MGDEDEDEGCAVELQITEANLTGHEEKVSVENFALLKVLGTG

AYGKVFLVRKAGGHDAGKLYAMKVLRKAALVQRAKTQEHTRT

ERSVLELVRQAPFLVTLHYAFQTDAKLHLILDYVSGGEMFTH

LYQRQYFKEAEVRVYGGEIVLALEHLHKLGIIYRDLKLENVL

LDSEGHIVLTDFGLSKEFLTEEKERTFSFCGTIEYMAPEIIR

SKAGHGKAVDWWSLGILLFELLTGASPFTLEGERNTQAEVSR

-continued

RILKCSPPFPPRIGPVAQDLLQRLLCKDPKKRLGAGPQGAQE

VKSHLFFQGLDWVALAARKIPAPFRPQIRSELDVGNFAEEFT

RLEPVYSPAGSPPPGDPRIFQGYSFVAPSILFDHNNAVMADV

LAAPGAGYRPGRAAVARSAMMQDSPFFQQYELDLREPALGQG

SFSVCRRCRQRQSGQEFAVKILSRRLEENTQREVAALRLCQS

HPNVVNLHEVLHDQLHTYLVLELLRGGELLEHIRKKRLFSES

EASQILRSLVSAVSFMHEEAGVVHRDLKPENILYADDTPGAP

VKIIDFGFARLRPQSPAGPMQTPCFTLQYAAPELLAQQGYDE

SCDLWSLGVILYMMLSGQVPFQGASGQGGQSQAAEIMCKIRE

GRFSLDGEAWQGVSEEAKELVRGLLTVDPAKRLKLEGLRSSS

WLQDGSARSSPPLRTPDVLESSGPAVRSGLNATFMAFNRGKR

EGFFLKSVENAPLAKRRKQKLRSAAASRRGSPVPASSGRLPA

SASKGTTRRANGPLSPS

Example 2

Ribosomal S6 Kinase 2 Expression and Purification

A construct of the C-terminal kinase domain of murine Ribosomal S6 Kinase 2 (RSK2) (residues 400-740; SEQ ID NO. 2) including a N-terminal polyhistidine tag (His$_8$), a linker (DYDIPTT) (SEQ ID NO: 21) and a Tobacco Etch Virus (TEV) protease site (ENLYFQG) (SEQ ID NO: 22) in the expressed kinase was designed and ordered from Genscript. The synthesised gene was subcloned into pET-22b (Novagen) by the vendor resulting in RSK2-pET-22b. BI21 (DE3) Rosetta was transformed with RSK2-pET-22b and plated on lysogeny broth (LB) agar plates supplemented with 50 µg/ml ampicillin (Amp) and 35 µg/ml Chloramphenicol (Cam). 5 colonies were used for inoculation of a 20 ml LB overnight culture supplemented with 100 µg/ml Amp and 35 µg/ml Cam. 2 liters of LB, supplemented with 100 µg/ml Amp and 35 µg/ml Cam, was inoculated with the overnight culture and grown at 37° C. Expression was induced with 0.1 mM isopropyl β-D-1-thiogalactopyranoside at an optical density of $A_{600\ nm}$=0.8 and the temperature was lowered to 20° C. for 3 h and further lowered to 12° C. for 20 hours. 8 g cells were harvested from 2 l of culture and resuspended in 100 ml of lysis-buffer (50 mM Tris-HCl, 100 mM NaCl and 5 mM β-mercaptoethanol, pH 7.5). Cells were lysed by high-pressure homogenisation (three times at 15.000 psi) in lysis-buffer supplemented with 1 mM PMSF and 5 µg/ml DNase I. The lysate was cleared of cell debris and aggregates by centrifugation at 25.000 g for 45 minutes. 5 ml of Ni$^{2+}$-beads slurry (Ni-sepharose 6 Fast Flow, GE Healthcare) were washed in equilibration-buffer (20 mM Tris-HCl, 100 mM NaCl, 5 mM β-mercaptoethanol, pH 7.5) and incubated with supernatant for 1 h at room temperature. The supernatant and Ni$^{2+}$-beads were poured into a Poly-Prep column (Bio-Rad) and washed with 100 ml equilibration-buffer. RSK2 was eluted in two times 5 ml elution-buffer (20 mM TrisHCl, 100 mM NaCl, 5 mM β-mercaptoethanol, 500 mM imidazole, pH 7.5). The eluate was supplemented with 1 mg of recombinant TEV and immediately dialysed against 1 l of equilibration-buffer overnight at room temperature. Digested and dialysed RSK2 was loaded on the Ni-beads in the Poly-Prep column and RSK2 was collected in the flow through. RSK2 was concentrated by ultrafiltration (Vivaspin 6, 30 kDa cutoff). Protein concentration was evaluated by spectrophotometry (Nanodrop, Thermo Fisher Scientific) assuming $\epsilon_{RSK2}$=44350 cm$^{-1}$ M$^{-1}$ and $M_{RSK2}$=38.4 kDa. Size exclusion chromatography (SEC) was performed on a Superdex 200 10/300 GL (GE Healthcare) column in SEC-buffer (10 mM TrisHCl, 50 mM NaCl, 5 mM β-mercaptoethanol, pH 8.0) at room temperature. Fractions containing RSK2 were concentrated by ultrafiltration to 10 mg/ml (Vivaspin 6, 30 kDa cut off) and during concentration the buffer was exchanged to 10 mM TrisHCl pH 8.0, 10 mM β-mercaptoethanol. RSK2 was aliquoted, flash frozen in liquid N$_2$ and stored at −80° C. RSK2 purity was evaluated by SDS-PAGE using a 15% separation gel. RSK2 was dialysed into reactions buffer (10 mM TrisHCl pH 8.0 and 5 mM Tris(2-carboxyethyl)phosphine (TCEP)) in a slide-A-lyzer (Thermo Fisher) prior to reaction with dimethyl fumarate for ligand assays and crystallisation. The purification procedure resulted >95% pure and stable RSK2 evaluated by SDS-PAGE and mass spectrometry.

Example 3

Crystallisation

The RSK2-DMF complex was formed by mixing RSK2 (SEQ ID NO: 1) (8 mg/ml) dialysed into reaction buffer with 5 mM DMF and incubating 30 min at room temperature. Aggregated RSK2 was removed by centrifugation at 15.000 g for 5 min. Initial screening was performed using Index screen (Hampton Research) where 1 µl RSK2 was mixed with 1 µl reservoir solution and equilibrated against 500 µl reservoir using the sitting-drop vapour-diffusion method at 19° C. An initial crystal hit was obtained in condition #43 (0.1 M Bis-Tris pH 6.5 and 25% (w/v) polyethylene glycol (PEG) 3350). The size and diffraction properties of the crystals were optimized with Additive Screen HT (Hampton Research) with condition #19 (0.05 M NaF). Crystals were reproducibly obtained in the described condition in a size suitable for data collection.

Example 4

Data Collection, Processing and Refinement

Crystals were mounted in nylon loops from mother liquor supplemented with 20% (v/v) Ethylene glycol and flash cooled in liquid N$_2$. A complete data-set was collected at 100 K on the X06SA beamline at the Swiss Light Source (Paul Scherrer Institute). The diffraction images were processed using XDS[53]. Molecular replacement was performed with the program PHASER[54] and a search model derived from PDB ID 2QR8[47]. Rigid body refinement, refinement and calculation of omit maps were performed in the PHENIX suite[55]. Model building and analysis was performed with Coot[56]. A complete data set scaling to 1.9 Å resolution with good statistics was collected. Phases were obtained by molecular replacement and the structure of RSK2 with DMF bound was refined to acceptable geometry and R-factors.

TABLE 1

| Data statistics | |
| --- | --- |
| Beamline | X06SA (SLS) |
| Wavelength (Å) | 0.9 |
| Resolution range | 47.0-1.9 |
| Space group | P4$_1$2$_1$2 |
| Unit cell parameters (Å) | a = b = 47.0 and c = 291.9 |
| Mosaicity (°) | 0.1 |
| Unique reflections | 27094 |
| Multiplicity | 8.6 |
| Mean I/σ(I) | 23.3 (2.3) |
| Completeness (%) | 99.4 (96.5) |
| R$_{meas}$ (%) | 3.7 (88.8) |
| R$_{p.i.m}$ | 1.3 (32.1) |
| Molecules per asymmetric unit | 1 |
| Solvent content (%) | 48.7 |
| Matthews coefficient (Å$^3$ Da$^{-1}$) | 2.39 |

TABLE 2

| Refinement statistics | |
| --- | --- |
| R/R$_{free}$ (%) | 19.5/24.6 |
| Bond length (Å)/bond angle (°) | 0.007/1.043 |
| Overall B factor from Wilson plot (Å$^2$) | 42.2 |
| B-factors (Å$^2$) | |
| Protein | 64.1 |
| Dimethyl fumarate | 61.8 |
| Waters | 58.8 |
| Ramachandran plot (%) | |
| Most favored region | 96.0 |
| Allowed region | 3.3 |
| Outlier region | 0.7 |

TABLE 3

| Atomic coordinates of RSK2 model (pdb file) | | | | | | | | | | |
| --- | --- | --- | --- | --- | --- | --- | --- | --- | --- | --- |
| ATOM | 1 | O | VAL | A | 408 | −29.990 | 9.813 | 6.893 | 1.00 | 129.22 | O |
| ATOM | 2 | N | VAL | A | 408 | −27.851 | 11.711 | 6.085 | 1.00 | 124.97 | N |
| ATOM | 3 | CA | VAL | A | 408 | −28.040 | 10.345 | 5.612 | 1.00 | 126.54 | C |
| ATOM | 4 | C | VAL | A | 408 | −29.506 | 9.936 | 5.765 | 1.00 | 131.99 | C |
| ATOM | 5 | CB | VAL | A | 408 | −27.165 | 9.353 | 6.413 | 1.00 | 118.17 | C |
| ATOM | 6 | CG1 | VAL | A | 408 | −25.860 | 10.007 | 6.844 | 1.00 | 106.36 | C |
| ATOM | 7 | CG2 | VAL | A | 408 | −26.904 | 8.090 | 5.601 | 1.00 | 118.04 | C |
| ATOM | 8 | O | GLN | A | 409 | −31.963 | 10.617 | 2.848 | 1.00 | 136.09 | O |
| ATOM | 9 | N | GLN | A | 409 | −30.224 | 9.729 | 4.657 | 1.00 | 135.16 | N |
| ATOM | 10 | CA | GLN | A | 409 | −29.717 | 9.877 | 3.291 | 1.00 | 133.31 | C |
| ATOM | 11 | C | GLN | A | 409 | −30.875 | 10.288 | 2.374 | 1.00 | 136.40 | C |
| ATOM | 12 | CB | GLN | A | 409 | −29.127 | 8.549 | 2.803 | 1.00 | 129.08 | C |
| ATOM | 13 | CG | GLN | A | 409 | −27.798 | 8.673 | 2.079 | 1.00 | 125.42 | C |
| ATOM | 14 | CD | GLN | A | 409 | −27.959 | 9.036 | 0.621 | 1.00 | 124.14 | C |
| ATOM | 15 | OE1 | GLN | A | 409 | −28.921 | 8.625 | −0.030 | 1.00 | 125.64 | O |
| ATOM | 16 | NE2 | GLN | A | 409 | −27.023 | 9.817 | 0.099 | 1.00 | 120.76 | N |

TABLE 3-continued

Atomic coordinates of RSK2 model (pdb file)

| ATOM | 17 | O | GLN | A | 410 | −33.283 | 8.719 | −0.475 | 1.00 | 144.07 | O |
|---|---|---|---|---|---|---|---|---|---|---|---|
| ATOM | 18 | N | GLN | A | 410 | −30.647 | 10.271 | 1.065 | 1.00 | 140.18 | N |
| ATOM | 19 | CA | GLN | A | 410 | −31.736 | 10.454 | 0.112 | 1.00 | 139.98 | C |
| ATOM | 20 | C | GLN | A | 410 | −32.115 | 9.110 | −0.497 | 1.00 | 139.47 | C |
| ATOM | 21 | CB | GLN | A | 410 | −31.361 | 11.454 | −0.986 | 1.00 | 142.41 | C |
| ATOM | 22 | CG | GLN | A | 410 | −32.392 | 12.571 | −1.204 | 1.00 | 144.67 | C |
| ATOM | 23 | CD | GLN | A | 410 | −33.708 | 12.085 | −1.811 | 1.00 | 144.58 | C |
| ATOM | 24 | OE1 | GLN | A | 410 | −33.788 | 10.985 | −2.363 | 1.00 | 148.55 | O |
| ATOM | 25 | NE2 | GLN | A | 410 | −34.746 | 12.911 | −1.711 | 1.00 | 138.39 | N |
| ATOM | 26 | O | LEU | A | 411 | −31.217 | 5.801 | 0.419 | 1.00 | 116.84 | O |
| ATOM | 27 | N | LEU | A | 411 | −31.124 | 8.402 | −1.032 | 1.00 | 133.05 | N |
| ATOM | 28 | CA | LEU | A | 411 | −31.361 | 7.085 | −1.615 | 1.00 | 129.09 | C |
| ATOM | 29 | C | LEU | A | 411 | −31.887 | 6.096 | −0.575 | 1.00 | 128.15 | C |
| ATOM | 30 | CB | LEU | A | 411 | −30.094 | 6.536 | −2.278 | 1.00 | 125.31 | C |
| ATOM | 31 | CG | LEU | A | 411 | −29.563 | 7.270 | −3.512 | 1.00 | 119.72 | C |
| ATOM | 32 | CD2 | LEU | A | 411 | −30.698 | 7.854 | −4.339 | 1.00 | 113.47 | C |
| ATOM | 33 | CD1 | LEU | A | 411 | −28.699 | 6.335 | −4.353 | 1.00 | 116.24 | C |
| ATOM | 34 | O | HIS | A | 412 | −33.887 | 2.696 | −1.271 | 1.00 | 132.76 | O |
| ATOM | 35 | N | HIS | A | 412 | −33.097 | 5.598 | −0.816 | 1.00 | 133.67 | N |
| ATOM | 36 | CA | HIS | A | 412 | −33.767 | 4.673 | 0.092 | 1.00 | 136.06 | C |
| ATOM | 37 | C | HIS | A | 412 | −34.500 | 3.602 | −0.703 | 1.00 | 135.41 | C |
| ATOM | 38 | CB | HIS | A | 412 | −34.786 | 5.423 | 0.954 | 1.00 | 136.48 | C |
| ATOM | 39 | CG | HIS | A | 412 | −34.177 | 6.427 | 1.880 | 1.00 | 137.17 | C |
| ATOM | 40 | ND1 | HIS | A | 412 | −32.946 | 6.243 | 2.473 | 1.00 | 137.23 | N |
| ATOM | 41 | CD2 | HIS | A | 412 | −34.631 | 7.625 | 2.319 | 1.00 | 137.64 | C |
| ATOM | 42 | CE1 | HIS | A | 412 | −32.669 | 7.283 | 3.237 | 1.00 | 138.79 | C |
| ATOM | 43 | NE2 | HIS | A | 412 | −33.674 | 8.137 | 3.160 | 1.00 | 139.12 | N |
| ATOM | 44 | O | ARG | A | 413 | −38.732 | 3.025 | −0.154 | 1.00 | 137.84 | O |
| ATOM | 45 | N | ARG | A | 413 | −35.825 | 3.737 | −0.716 | 1.00 | 136.48 | N |
| ATOM | 46 | CA | ARG | A | 413 | −36.740 | 2.908 | −1.495 | 1.00 | 135.59 | C |
| ATOM | 47 | C | ARG | A | 413 | −38.167 | 3.369 | −1.193 | 1.00 | 137.33 | C |
| ATOM | 48 | CB | ARG | A | 413 | −36.578 | 1.425 | −1.155 | 1.00 | 133.58 | C |
| ATOM | 49 | CG | ARG | A | 413 | −37.300 | 0.490 | −2.108 | 1.00 | 131.73 | C |
| ATOM | 50 | CD | ARG | A | 413 | −36.824 | −0.947 | −1.941 | 1.00 | 132.45 | C |
| ATOM | 51 | NE | ARG | A | 413 | −37.033 | −1.451 | −0.584 | 1.00 | 134.15 | N |
| ATOM | 52 | CZ | ARG | A | 413 | −38.081 | −2.177 | −0.204 | 1.00 | 132.79 | C |
| ATOM | 53 | NH1 | ARG | A | 413 | −39.029 | −2.495 | −1.077 | 1.00 | 132.54 | N |
| ATOM | 54 | NH2 | ARG | A | 413 | −38.179 | −2.590 | 1.053 | 1.00 | 129.67 | N |
| ATOM | 55 | O | ASN | A | 414 | −41.028 | 2.572 | −2.299 | 1.00 | 126.87 | O |
| ATOM | 56 | N | ASN | A | 414 | −38.737 | 4.159 | −2.098 | 1.00 | 136.05 | N |
| ATOM | 57 | CA | ASN | A | 414 | −40.064 | 4.746 | −1.901 | 1.00 | 132.80 | C |
| ATOM | 58 | C | ASN | A | 414 | −41.224 | 3.755 | −2.015 | 1.00 | 126.57 | C |
| ATOM | 59 | CB | ASN | A | 414 | −40.284 | 5.902 | −2.889 | 1.00 | 134.06 | C |
| ATOM | 60 | CG | ASN | A | 414 | −39.865 | 7.246 | −2.324 | 1.00 | 135.51 | C |
| ATOM | 61 | OD1 | ASN | A | 414 | −40.271 | 7.622 | −1.224 | 1.00 | 136.08 | O |
| ATOM | 62 | ND2 | ASN | A | 414 | −39.050 | 7.980 | −3.077 | 1.00 | 132.85 | N |
| ATOM | 63 | O | SER | A | 415 | −44.266 | 2.791 | −4.246 | 1.00 | 110.34 | O |
| ATOM | 64 | N | SER | A | 415 | −42.432 | 4.257 | −1.776 | 1.00 | 118.82 | N |
| ATOM | 65 | CA | SER | A | 415 | −43.660 | 3.507 | −2.025 | 1.00 | 111.36 | C |
| ATOM | 66 | C | SER | A | 415 | −44.043 | 3.727 | −3.481 | 1.00 | 111.15 | C |
| ATOM | 67 | CB | SER | A | 415 | −44.784 | 4.043 | −1.137 | 1.00 | 106.30 | C |
| ATOM | 68 | OG | SER | A | 415 | −45.997 | 3.346 | −1.362 | 1.00 | 104.38 | O |
| ATOM | 69 | O | ILE | A | 416 | −42.161 | 5.349 | −6.030 | 1.00 | 78.90 | O |
| ATOM | 70 | N | ILE | A | 416 | −44.109 | 5.004 | −3.831 | 1.00 | 104.49 | N |
| ATOM | 71 | CA | ILE | A | 416 | −44.409 | 5.467 | −5.169 | 1.00 | 93.98 | C |
| ATOM | 72 | C | ILE | A | 416 | −43.340 | 5.019 | −6.165 | 1.00 | 69.29 | C |
| ATOM | 73 | CB | ILE | A | 416 | −44.510 | 6.984 | −5.169 | 1.00 | 101.27 | C |
| ATOM | 74 | CG1 | ILE | A | 416 | −43.408 | 7.568 | −4.282 | 1.00 | 108.71 | C |
| ATOM | 75 | CG2 | ILE | A | 416 | −45.870 | 7.416 | −4.643 | 1.00 | 98.29 | C |
| ATOM | 76 | CD1 | ILE | A | 416 | −43.294 | 9.084 | −4.296 | 1.00 | 110.46 | C |
| ATOM | 77 | N | GLN | A | 417 | −43.757 | 4.256 | −7.167 | 1.00 | 94.62 | N |
| ATOM | 78 | CA | GLN | A | 417 | −42.838 | 3.785 | −8.197 | 1.00 | 77.33 | C |
| ATOM | 79 | C | GLN | A | 417 | −42.767 | 4.760 | −9.373 | 1.00 | 80.01 | C |
| ATOM | 80 | O | GLN | A | 417 | −43.716 | 5.505 | −9.653 | 1.00 | 64.65 | O |
| ATOM | 81 | CB | GLN | A | 417 | −43.252 | 2.394 | −8.680 | 1.00 | 83.50 | C |
| ATOM | 82 | CG | GLN | A | 417 | −43.323 | 1.354 | −7.579 | 1.00 | 87.24 | C |
| ATOM | 83 | CD | GLN | A | 417 | −42.318 | 0.232 | −7.767 | 1.00 | 97.42 | C |
| ATOM | 84 | OE1 | GLN | A | 417 | −41.173 | 0.466 | −8.150 | 1.00 | 98.83 | O |
| ATOM | 85 | NE2 | GLN | A | 417 | −42.752 | −1.000 | −7.515 | 1.00 | 105.59 | N |
| ATOM | 86 | N | PHE | A | 418 | −41.631 | 4.750 | −10.057 | 1.00 | 71.46 | N |
| ATOM | 87 | CA | PHE | A | 418 | −41.440 | 5.607 | −11.210 | 1.00 | 69.51 | C |
| ATOM | 88 | C | PHE | A | 418 | −42.492 | 5.309 | −12.269 | 1.00 | 67.13 | C |
| ATOM | 89 | O | PHE | A | 418 | −42.974 | 6.213 | −12.945 | 1.00 | 66.63 | O |
| ATOM | 90 | CB | PHE | A | 418 | −40.039 | 5.413 | −11.784 | 1.00 | 72.46 | C |
| ATOM | 91 | CG | PHE | A | 418 | −39.821 | 6.113 | −13.089 | 1.00 | 69.66 | C |
| ATOM | 92 | CD1 | PHE | A | 418 | −39.833 | 7.498 | −13.158 | 1.00 | 65.59 | C |
| ATOM | 93 | CD2 | PHE | A | 418 | −39.595 | 5.388 | −14.246 | 1.00 | 64.89 | C |
| ATOM | 94 | CE1 | PHE | A | 418 | −39.625 | 8.150 | −14.365 | 1.00 | 63.62 | C |

TABLE 3-continued

Atomic coordinates of RSK2 model (pdb file)

| ATOM | 95  | CE2 | PHE | A | 418 | −39.385 | 6.031  | −15.449 | 1.00 | 74.14  | C |
|------|-----|-----|-----|---|-----|---------|--------|---------|------|--------|---|
| ATOM | 96  | CZ  | PHE | A | 418 | −39.403 | 7.416  | −15.511 | 1.00 | 71.95  | C |
| ATOM | 97  | N   | THR | A | 419 | −42.859 | 4.036  | −12.380 | 1.00 | 74.14  | N |
| ATOM | 98  | CA  | THR | A | 419 | −43.819 | 3.560  | −13.375 | 1.00 | 80.84  | C |
| ATOM | 99  | C   | THR | A | 419 | −45.224 | 4.103  | −13.127 | 1.00 | 81.68  | C |
| ATOM | 100 | O   | THR | A | 419 | −46.078 | 4.083  | −14.016 | 1.00 | 93.16  | O |
| ATOM | 101 | CB  | THR | A | 419 | −43.896 | 2.015  | −13.366 | 1.00 | 92.79  | C |
| ATOM | 102 | OG1 | THR | A | 419 | −42.582 | 1.465  | −13.222 | 1.00 | 101.76 | O |
| ATOM | 103 | CG2 | THR | A | 419 | −44.523 | 1.493  | −14.647 | 1.00 | 94.97  | C |
| ATOM | 104 | N   | ASP | A | 420 | −45.460 | 4.586  | −11.915 | 1.00 | 73.49  | N |
| ATOM | 105 | CA  | ASP | A | 420 | −46.790 | 5.027  | −11.519 | 1.00 | 82.79  | C |
| ATOM | 106 | C   | ASP | A | 420 | −47.118 | 6.433  | −11.996 | 1.00 | 82.88  | C |
| ATOM | 107 | O   | ASP | A | 420 | −48.253 | 6.713  | −12.382 | 1.00 | 86.87  | O |
| ATOM | 108 | CB  | ASP | A | 420 | −46.938 | 4.945  | −10.004 | 1.00 | 84.17  | C |
| ATOM | 109 | CG  | ASP | A | 420 | −46.853 | 3.529  | −9.496  | 0.35 | 81.78  | C |
| ATOM | 110 | OD1 | ASP | A | 420 | −47.368 | 2.621  | −10.180 | 1.00 | 82.62  | O |
| ATOM | 111 | OD2 | ASP | A | 420 | −46.261 | 3.323  | −8.421  | 1.00 | 76.57  | O |
| ATOM | 112 | N   | GLY | A | 421 | −46.123 | 7.314  | −11.965 | 1.00 | 71.47  | N |
| ATOM | 113 | CA  | GLY | A | 421 | −46.316 | 8.689  | −12.390 | 1.00 | 72.52  | C |
| ATOM | 114 | C   | GLY | A | 421 | −45.795 | 8.994  | −13.783 | 1.00 | 67.40  | C |
| ATOM | 115 | O   | GLY | A | 421 | −46.120 | 10.037 | −14.365 | 1.00 | 67.06  | O |
| ATOM | 116 | N   | TYR | A | 422 | −44.990 | 8.086  | −14.331 | 1.00 | 57.07  | N |
| ATOM | 117 | CA  | TYR | A | 422 | −44.384 | 8.318  | −15.641 | 1.00 | 60.05  | C |
| ATOM | 118 | C   | TYR | A | 422 | −44.606 | 7.177  | −16.620 | 1.00 | 64.60  | C |
| ATOM | 119 | O   | TYR | A | 422 | −44.629 | 6.008  | −16.233 | 1.00 | 59.66  | O |
| ATOM | 120 | CB  | TYR | A | 422 | −42.882 | 8.583  | −15.488 | 1.00 | 55.61  | C |
| ATOM | 121 | CG  | TYR | A | 422 | −42.566 | 9.836  | −14.705 | 1.00 | 52.03  | C |
| ATOM | 122 | CD1 | TYR | A | 422 | −42.328 | 11.046 | −15.352 | 1.00 | 57.30  | C |
| ATOM | 123 | CD2 | TYR | A | 422 | −42.512 | 9.814  | −13.317 | 1.00 | 57.96  | C |
| ATOM | 124 | CE1 | TYR | A | 422 | −42.038 | 12.197 | −14.631 | 1.00 | 41.10  | C |
| ATOM | 125 | CE2 | TYR | A | 422 | −42.229 | 10.952 | −12.594 | 1.00 | 53.76  | C |
| ATOM | 126 | CZ  | TYR | A | 422 | −41.997 | 12.139 | −13.252 | 1.00 | 46.21  | C |
| ATOM | 127 | OH  | TYR | A | 422 | −41.715 | 13.266 | −12.529 | 1.00 | 48.13  | O |
| ATOM | 128 | N   | GLU | A | 423 | −44.779 | 7.533  | −17.889 | 1.00 | 64.97  | N |
| ATOM | 129 | CA  | GLU | A | 423 | −44.781 | 6.566  | −18.979 | 1.00 | 71.15  | C |
| ATOM | 130 | C   | GLU | A | 423 | −43.432 | 6.629  | −19.677 | 1.00 | 74.66  | C |
| ATOM | 131 | O   | GLU | A | 423 | −43.031 | 7.675  | −20.183 | 1.00 | 73.44  | O |
| ATOM | 132 | CB  | GLU | A | 423 | −45.898 | 6.858  | −19.992 | 1.00 | 76.67  | C |
| ATOM | 133 | CG  | GLU | A | 423 | −47.302 | 6.769  | −19.422 | 1.00 | 90.10  | C |
| ATOM | 134 | CD  | GLU | A | 423 | −48.347 | 7.360  | −20.346 | 1.00 | 95.73  | C |
| ATOM | 135 | OE1 | GLU | A | 423 | −49.516 | 7.483  | −19.917 | 1.00 | 103.18 | O |
| ATOM | 136 | OE2 | GLU | A | 423 | −47.997 | 7.702  | −21.498 | 1.00 | 91.66  | O |
| ATOM | 137 | N   | VAL | A | 424 | −42.732 | 5.505  | −19.698 | 1.00 | 70.20  | N |
| ATOM | 138 | CA  | VAL | A | 424 | −41.428 | 5.427  | −20.337 | 1.00 | 67.69  | C |
| ATOM | 139 | C   | VAL | A | 424 | −41.562 | 5.327  | −21.853 | 1.00 | 72.98  | C |
| ATOM | 140 | O   | VAL | A | 424 | −42.348 | 4.534  | −22.375 | 1.00 | 77.26  | O |
| ATOM | 141 | CB  | VAL | A | 424 | −40.628 | 4.221  | −19.793 | 1.00 | 70.59  | C |
| ATOM | 142 | CG1 | VAL | A | 424 | −39.482 | 3.850  | −20.721 | 1.00 | 68.34  | C |
| ATOM | 143 | CG2 | VAL | A | 424 | −40.117 | 4.525  | −18.394 | 1.00 | 66.58  | C |
| ATOM | 144 | N   | LYS | A | 425 | −40.790 | 6.136  | −22.562 | 1.00 | 68.02  | N |
| ATOM | 145 | CA  | LYS | A | 425 | −40.808 | 6.079  | −24.010 | 1.00 | 73.63  | C |
| ATOM | 146 | C   | LYS | A | 425 | −39.445 | 5.707  | −24.583 | 1.00 | 76.36  | C |
| ATOM | 147 | O   | LYS | A | 425 | −38.695 | 4.927  | −23.989 | 1.00 | 81.23  | O |
| ATOM | 148 | CB  | LYS | A | 425 | −41.321 | 7.400  | −24.592 | 1.00 | 73.69  | C |
| ATOM | 149 | CG  | LYS | A | 425 | −42.784 | 7.667  | −24.274 | 1.00 | 77.85  | C |
| ATOM | 150 | CD  | LYS | A | 425 | −43.652 | 6.484  | −24.691 | 1.00 | 84.09  | C |
| ATOM | 151 | CE  | LYS | A | 425 | −45.126 | 6.725  | −24.412 | 1.00 | 83.50  | C |
| ATOM | 152 | NZ  | LYS | A | 425 | −45.947 | 5.519  | −24.725 | 1.00 | 88.52  | N |
| ATOM | 153 | N   | GLU | A | 426 | −39.142 | 6.283  | −25.739 | 1.00 | 75.33  | N |
| ATOM | 154 | CA  | GLU | A | 426 | −37.965 | 5.950  | −26.535 | 1.00 | 76.64  | C |
| ATOM | 155 | C   | GLU | A | 426 | −36.659 | 6.233  | −25.809 | 1.00 | 77.88  | C |
| ATOM | 156 | O   | GLU | A | 426 | −36.622 | 7.022  | −24.869 | 1.00 | 70.53  | O |
| ATOM | 157 | CB  | GLU | A | 426 | −38.011 | 6.762  | −27.831 | 1.00 | 68.53  | C |
| ATOM | 158 | CG  | GLU | A | 426 | −39.126 | 7.816  | −27.818 | 1.00 | 58.09  | C |
| ATOM | 159 | CD  | GLU | A | 426 | −38.631 | 9.204  | −28.151 | 1.00 | 73.18  | C |
| ATOM | 160 | OE1 | GLU | A | 426 | −37.398 | 9.400  | −28.213 | 1.00 | 87.31  | O |
| ATOM | 161 | OE2 | GLU | A | 426 | −39.478 | 10.100 | −28.352 | 1.00 | 78.58  | O |
| ATOM | 162 | N   | ASP | A | 427 | −35.584 | 5.592  | −26.263 | 1.00 | 84.75  | N |
| ATOM | 163 | CA  | ASP | A | 427 | −34.242 | 5.907  | −25.782 | 1.00 | 81.34  | C |
| ATOM | 164 | C   | ASP | A | 427 | −33.802 | 7.262  | −26.314 | 1.00 | 69.87  | C |
| ATOM | 165 | O   | ASP | A | 427 | −34.156 | 7.643  | −27.429 | 1.00 | 79.90  | O |
| ATOM | 166 | CB  | ASP | A | 427 | −33.236 | 4.850  | −26.249 | 1.00 | 90.94  | C |
| ATOM | 167 | CG  | ASP | A | 427 | −33.479 | 3.492  | −25.627 | 1.00 | 99.76  | C |
| ATOM | 168 | OD1 | ASP | A | 427 | −32.890 | 3.214  | −24.562 | 1.00 | 96.02  | O |
| ATOM | 169 | OD2 | ASP | A | 427 | −34.249 | 2.699  | −26.208 | 1.00 | 107.76 | O |
| ATOM | 170 | N   | ILE | A | 428 | −33.027 | 7.991  | −25.519 | 1.00 | 67.31  | N |
| ATOM | 171 | CA  | ILE | A | 428 | −32.446 | 9.247  | −25.984 | 1.00 | 75.99  | C |
| ATOM | 172 | C   | ILE | A | 428 | −30.930 | 9.156  | −25.992 | 1.00 | 75.26  | C |

TABLE 3-continued

Atomic coordinates of RSK2 model (pdb file)

| ATOM | 173 | O | ILE | A | 428 | −30.260 | 9.859 | −26.745 | 1.00 | 87.11 | O |
|---|---|---|---|---|---|---|---|---|---|---|---|
| ATOM | 174 | CB | ILE | A | 428 | −32.814 | 10.441 | −25.084 | 1.00 | 79.16 | C |
| ATOM | 175 | CG1 | ILE | A | 428 | −34.257 | 10.356 | −24.600 | 1.00 | 85.42 | C |
| ATOM | 176 | CG2 | ILE | A | 428 | −32.567 | 11.759 | −25.813 | 1.00 | 75.68 | C |
| ATOM | 177 | CD1 | ILE | A | 428 | −34.579 | 11.425 | −23.579 | 1.00 | 79.00 | C |
| ATOM | 178 | N | GLY | A | 429 | −30.385 | 8.303 | −25.133 | 1.00 | 79.96 | N |
| ATOM | 179 | CA | GLY | A | 429 | −28.946 | 8.182 | −25.031 | 1.00 | 89.62 | C |
| ATOM | 180 | C | GLY | A | 429 | −28.474 | 6.935 | −24.318 | 1.00 | 101.29 | C |
| ATOM | 181 | O | GLY | A | 429 | −29.235 | 5.993 | −24.089 | 1.00 | 102.80 | O |
| ATOM | 182 | N | VAL | A | 430 | −27.197 | 6.943 | −23.957 | 1.00 | 106.38 | N |
| ATOM | 183 | CA | VAL | A | 430 | −26.553 | 5.787 | −23.365 | 1.00 | 106.87 | C |
| ATOM | 184 | C | VAL | A | 430 | −25.480 | 6.265 | −22.395 | 1.00 | 116.42 | C |
| ATOM | 185 | O | VAL | A | 430 | −25.110 | 7.440 | −22.391 | 1.00 | 122.79 | O |
| ATOM | 186 | CB | VAL | A | 430 | −25.895 | 4.921 | −24.457 | 1.00 | 99.37 | C |
| ATOM | 187 | CG1 | VAL | A | 430 | −24.593 | 5.561 | −24.928 | 1.00 | 103.44 | C |
| ATOM | 188 | CG2 | VAL | A | 430 | −25.661 | 3.496 | −23.966 | 1.00 | 93.65 | C |
| ATOM | 189 | N | GLY | A | 431 | −24.997 | 5.354 | −21.562 | 1.00 | 116.25 | N |
| ATOM | 190 | CA | GLY | A | 431 | −23.838 | 5.614 | −20.738 | 1.00 | 115.28 | C |
| ATOM | 191 | C | GLY | A | 431 | −22.939 | 4.395 | −20.710 | 1.00 | 116.92 | C |
| ATOM | 192 | O | GLY | A | 431 | −21.753 | 4.509 | −20.414 | 1.00 | 126.27 | O |
| ATOM | 193 | N | SER | A | 432 | −23.513 | 3.239 | −21.050 | 1.00 | 112.47 | N |
| ATOM | 194 | CA | SER | A | 432 | −22.921 | 1.914 | −20.795 | 1.00 | 114.55 | C |
| ATOM | 195 | C | SER | A | 432 | −22.923 | 1.605 | −19.290 | 1.00 | 117.46 | C |
| ATOM | 196 | O | SER | A | 432 | −22.469 | 0.543 | −18.855 | 1.00 | 120.57 | O |
| ATOM | 197 | CB | SER | A | 432 | −21.523 | 1.752 | −21.418 | 1.00 | 112.91 | C |
| ATOM | 198 | OG | SER | A | 432 | −20.966 | 0.476 | −21.134 | 1.00 | 110.75 | O |
| ATOM | 199 | N | TYR | A | 433 | −23.445 | 2.553 | −18.512 | 1.00 | 113.77 | N |
| ATOM | 200 | CA | TYR | A | 433 | −23.690 | 2.386 | −17.086 | 1.00 | 108.07 | C |
| ATOM | 201 | C | TYR | A | 433 | −25.099 | 2.887 | −16.842 | 1.00 | 100.32 | C |
| ATOM | 202 | O | TYR | A | 433 | −25.743 | 2.541 | −15.848 | 1.00 | 92.34 | O |
| ATOM | 203 | CB | TYR | A | 433 | −22.717 | 3.225 | −16.257 | 1.00 | 114.16 | C |
| ATOM | 204 | CG | TYR | A | 433 | −21.526 | 3.750 | −17.027 | 1.00 | 123.59 | C |
| ATOM | 205 | CD2 | TYR | A | 433 | −21.417 | 5.101 | −17.343 | 1.00 | 121.36 | C |
| ATOM | 206 | CD1 | TYR | A | 433 | −20.500 | 2.897 | −17.423 | 1.00 | 128.94 | C |
| ATOM | 207 | CE2 | TYR | A | 433 | −20.320 | 5.586 | −18.043 | 1.00 | 125.82 | C |
| ATOM | 208 | CE1 | TYR | A | 433 | −19.406 | 3.370 | −18.127 | 1.00 | 132.24 | C |
| ATOM | 209 | CZ | TYR | A | 433 | −19.319 | 4.712 | −18.435 | 1.00 | 132.44 | C |
| ATOM | 210 | OH | TYR | A | 433 | −18.225 | 5.178 | −19.133 | 1.00 | 139.72 | O |
| ATOM | 211 | N | SER | A | 434 | −25.563 | 3.714 | −17.773 | 1.00 | 95.53 | N |
| ATOM | 212 | CA | SER | A | 434 | −26.863 | 4.355 | −17.675 | 1.00 | 95.37 | C |
| ATOM | 213 | C | SER | A | 434 | −27.562 | 4.359 | −19.025 | 1.00 | 93.72 | C |
| ATOM | 214 | O | SER | A | 434 | −26.923 | 4.409 | −20.074 | 1.00 | 96.30 | O |
| ATOM | 215 | CB | SER | A | 434 | −26.702 | 5.801 | −17.212 | 1.00 | 97.16 | C |
| ATOM | 216 | OG | SER | A | 434 | −26.126 | 6.589 | −18.241 | 1.00 | 104.36 | O |
| ATOM | 217 | N | VAL | A | 435 | −28.886 | 4.311 | −18.983 | 1.00 | 84.71 | N |
| ATOM | 218 | CA | VAL | A | 435 | −29.692 | 4.549 | −20.162 | 1.00 | 76.32 | C |
| ATOM | 219 | C | VAL | A | 435 | −30.497 | 5.812 | −19.896 | 1.00 | 68.29 | C |
| ATOM | 220 | O | VAL | A | 435 | −31.002 | 6.010 | −18.790 | 1.00 | 62.06 | O |
| ATOM | 221 | CB | VAL | A | 435 | −30.650 | 3.378 | −20.438 | 1.00 | 76.43 | C |
| ATOM | 222 | CG1 | VAL | A | 435 | −31.331 | 3.560 | −21.790 | 1.00 | 80.88 | C |
| ATOM | 223 | CG2 | VAL | A | 435 | −29.901 | 2.062 | −20.392 | 1.00 | 85.57 | C |
| ATOM | 224 | N | CYS | A | 436 | −30.586 | 6.682 | −20.893 | 1.00 | 60.43 | N |
| ATOM | 225 | CA | CYS | A | 436 | −31.444 | 7.856 | −20.798 | 1.00 | 55.26 | C |
| ATOM | 226 | C | CYS | A | 436 | −32.658 | 7.653 | −21.704 | 1.00 | 60.74 | C |
| ATOM | 227 | O | CYS | A | 436 | −32.512 | 7.289 | −22.873 | 1.00 | 69.02 | O |
| ATOM | 228 | CB | CYS | A | 436 | −30.673 | 9.128 | −21.179 | 1.00 | 55.04 | C |
| ATOM | 229 | SG | CYS | A | 436 | −29.358 | 9.598 | −20.011 | 1.00 | 71.96 | S |
| ATOM | 230 | N | LYS | A | 437 | −33.856 | 7.857 | −21.162 | 1.00 | 51.36 | N |
| ATOM | 231 | CA | LYS | A | 437 | −35.077 | 7.704 | −21.956 | 1.00 | 59.33 | C |
| ATOM | 232 | C | LYS | A | 437 | −35.978 | 8.929 | −21.856 | 1.00 | 64.38 | C |
| ATOM | 233 | O | LYS | A | 437 | −35.846 | 9.745 | −20.939 | 1.00 | 50.87 | O |
| ATOM | 234 | CB | LYS | A | 437 | −35.860 | 6.445 | −21.554 | 1.00 | 59.09 | C |
| ATOM | 235 | CG | LYS | A | 437 | −35.125 | 5.137 | −21.785 | 1.00 | 66.28 | C |
| ATOM | 236 | CD | LYS | A | 437 | −36.023 | 3.948 | −21.480 | 1.00 | 79.01 | C |
| ATOM | 237 | CE | LYS | A | 437 | −35.224 | 2.655 | −21.324 | 1.00 | 87.75 | C |
| ATOM | 238 | NZ | LYS | A | 437 | −34.439 | 2.320 | −22.546 | 1.00 | 99.02 | N |
| ATOM | 239 | N | ARG | A | 438 | −36.878 | 9.067 | −22.825 | 1.00 | 61.60 | N |
| ATOM | 240 | CA | ARG | A | 438 | −37.890 | 10.104 | −22.767 | 1.00 | 54.91 | C |
| ATOM | 241 | C | ARG | A | 438 | −39.050 | 9.559 | −21.958 | 1.00 | 59.97 | C |
| ATOM | 242 | O | ARG | A | 438 | −39.383 | 8.375 | −22.057 | 1.00 | 59.81 | O |
| ATOM | 243 | CB | ARG | A | 438 | −38.373 | 10.474 | −24.182 | 1.00 | 55.49 | C |
| ATOM | 244 | CG | ARG | A | 438 | −39.289 | 11.702 | −24.215 | 1.00 | 54.37 | C |
| ATOM | 245 | CD | ARG | A | 438 | −39.628 | 12.148 | −25.651 | 1.00 | 58.13 | C |
| ATOM | 246 | NE | ARG | A | 438 | −40.372 | 11.108 | −26.355 | 1.00 | 68.81 | N |
| ATOM | 247 | CZ | ARG | A | 438 | −41.695 | 10.993 | −26.336 | 1.00 | 69.10 | C |
| ATOM | 248 | NH1 | ARG | A | 438 | −42.428 | 11.874 | −25.665 | 1.00 | 66.58 | N |
| ATOM | 249 | NH2 | ARG | A | 438 | −42.283 | 9.999 | −26.990 | 1.00 | 65.48 | N |
| ATOM | 250 | N | CYS | A | 439 | −39.676 | 10.404 | −21.152 | 1.00 | 50.98 | N |

TABLE 3-continued

Atomic coordinates of RSK2 model (pdb file)

| ATOM | 251 | CA | CYS | A | 439 | −40.852 | 9.942 | −20.424 | 1.00 | 52.78 | C |
|---|---|---|---|---|---|---|---|---|---|---|---|
| ATOM | 252 | C | CYS | A | 439 | −41.964 | 10.978 | −20.409 | 1.00 | 49.77 | C |
| ATOM | 253 | O | CYS | A | 439 | −41.746 | 12.156 | −20.707 | 1.00 | 52.56 | O |
| ATOM | 254 | CB | CYS | A | 439 | −40.494 | 9.514 | −18.987 | 1.00 | 44.44 | C |
| ATOM | 255 | SG | CYS | A | 439 | −39.621 | 10.747 | −18.032 | 1.00 | 52.40 | S |
| ATOM | 256 | N | ILE | A | 440 | −43.158 | 10.518 | −20.052 | 1.00 | 57.09 | N |
| ATOM | 257 | CA | ILE | A | 440 | −44.318 | 11.384 | −19.948 | 1.00 | 58.28 | C |
| ATOM | 258 | C | ILE | A | 440 | −44.865 | 11.364 | −18.533 | 1.00 | 59.77 | C |
| ATOM | 259 | O | ILE | A | 440 | −45.177 | 10.305 | −17.982 | 1.00 | 60.90 | O |
| ATOM | 260 | CB | ILE | A | 440 | −45.431 | 10.957 | −20.921 | 1.00 | 57.51 | C |
| ATOM | 261 | CG1 | ILE | A | 440 | −44.928 | 11.040 | −22.364 | 1.00 | 58.48 | C |
| ATOM | 262 | CG2 | ILE | A | 440 | −46.674 | 11.820 | −20.717 | 1.00 | 60.16 | C |
| ATOM | 263 | CD1 | ILE | A | 440 | −45.929 | 10.553 | −23.391 | 1.00 | 70.13 | C |
| ATOM | 264 | N | HIS | A | 441 | −44.962 | 12.546 | −17.943 | 1.00 | 58.16 | N |
| ATOM | 265 | CA | HIS | A | 441 | −45.571 | 12.705 | −16.635 | 1.00 | 53.79 | C |
| ATOM | 266 | C | HIS | A | 441 | −47.088 | 12.582 | −16.807 | 1.00 | 60.37 | C |
| ATOM | 267 | O | HIS | A | 441 | −47.714 | 13.405 | −17.479 | 1.00 | 53.35 | O |
| ATOM | 268 | CB | HIS | A | 441 | −45.185 | 14.070 | −16.066 | 1.00 | 52.16 | C |
| ATOM | 269 | CG | HIS | A | 441 | −45.691 | 14.323 | −14.681 | 1.00 | 51.33 | C |
| ATOM | 270 | ND1 | HIS | A | 441 | −46.546 | 15.362 | −14.379 | 1.00 | 59.37 | N |
| ATOM | 271 | CD2 | HIS | A | 441 | −45.463 | 13.673 | −13.516 | 1.00 | 52.68 | C |
| ATOM | 272 | CE1 | HIS | A | 441 | −46.817 | 15.345 | −13.088 | 1.00 | 67.68 | C |
| ATOM | 273 | NE2 | HIS | A | 441 | −46.169 | 14.333 | −12.540 | 1.00 | 60.97 | N |
| ATOM | 274 | N | LYS | A | 442 | −47.668 | 11.542 | −16.217 | 1.00 | 54.74 | N |
| ATOM | 275 | CA | LYS | A | 442 | −49.057 | 11.173 | −16.500 | 1.00 | 60.99 | C |
| ATOM | 276 | C | LYS | A | 442 | −50.072 | 12.258 | −16.139 | 1.00 | 67.21 | C |
| ATOM | 277 | O | LYS | A | 442 | −51.038 | 12.480 | −16.865 | 1.00 | 68.41 | O |
| ATOM | 278 | CB | LYS | A | 442 | −49.419 | 9.859 | −15.797 | 1.00 | 65.74 | C |
| ATOM | 279 | CG | LYS | A | 442 | −48.686 | 8.634 | −16.323 | 1.00 | 72.12 | C |
| ATOM | 280 | CD | LYS | A | 442 | −49.151 | 7.372 | −15.605 | 1.00 | 83.09 | C |
| ATOM | 281 | CE | LYS | A | 442 | −48.388 | 6.137 | −16.063 | 1.00 | 85.39 | C |
| ATOM | 282 | NZ | LYS | A | 442 | −48.763 | 4.921 | −15.285 | 1.00 | 86.32 | N |
| ATOM | 283 | N | ALA | A | 443 | −49.842 | 12.942 | −15.024 | 1.00 | 61.15 | N |
| ATOM | 284 | CA | ALA | A | 443 | −50.805 | 13.923 | −14.528 | 1.00 | 72.33 | C |
| ATOM | 285 | C | ALA | A | 443 | −50.882 | 15.210 | −15.365 | 1.00 | 77.29 | C |
| ATOM | 286 | O | ALA | A | 443 | −51.799 | 16.019 | −15.176 | 1.00 | 66.81 | O |
| ATOM | 287 | CB | ALA | A | 443 | −50.515 | 14.255 | −13.062 | 1.00 | 71.67 | C |
| ATOM | 288 | N | THR | A | 444 | −49.930 | 15.402 | −16.281 | 1.00 | 60.62 | N |
| ATOM | 289 | CA | THR | A | 444 | −49.833 | 16.664 | −17.016 | 1.00 | 57.97 | C |
| ATOM | 290 | C | THR | A | 444 | −49.606 | 16.482 | −18.515 | 1.00 | 58.96 | C |
| ATOM | 291 | O | THR | A | 444 | −49.828 | 17.412 | −19.291 | 1.00 | 59.34 | O |
| ATOM | 292 | CB | THR | A | 444 | −48.678 | 17.540 | −16.483 | 1.00 | 64.74 | C |
| ATOM | 293 | OG1 | THR | A | 444 | −47.433 | 16.863 | −16.684 | 1.00 | 64.46 | O |
| ATOM | 294 | CG2 | THR | A | 444 | −48.859 | 17.840 | −15.007 | 1.00 | 62.15 | C |
| ATOM | 295 | N | ASN | A | 445 | −49.170 | 15.283 | −18.905 | 1.00 | 52.64 | N |
| ATOM | 296 | CA | ASN | A | 445 | −48.735 | 14.992 | −20.277 | 1.00 | 54.81 | C |
| ATOM | 297 | C | ASN | A | 445 | −47.513 | 15.794 | −20.742 | 1.00 | 57.65 | C |
| ATOM | 298 | O | ASN | A | 445 | −47.220 | 15.835 | −21.935 | 1.00 | 57.93 | O |
| ATOM | 299 | CB | ASN | A | 445 | −49.894 | 15.099 | −21.284 | 1.00 | 55.25 | C |
| ATOM | 300 | CG | ASN | A | 445 | −50.912 | 13.993 | −21.107 | 1.00 | 64.89 | C |
| ATOM | 301 | OD1 | ASN | A | 445 | −50.552 | 12.821 | −21.011 | 1.00 | 62.09 | O |
| ATOM | 302 | ND2 | ASN | A | 445 | −52.193 | 14.360 | −21.050 | 1.00 | 65.82 | N |
| ATOM | 303 | N | MET | A | 446 | −46.802 | 16.411 | −19.794 | 1.00 | 50.37 | N |
| ATOM | 304 | CA | MET | A | 446 | −45.534 | 17.083 | −20.082 | 1.00 | 49.19 | C |
| ATOM | 305 | C | MET | A | 446 | −44.473 | 16.026 | −20.297 | 1.00 | 52.80 | C |
| ATOM | 306 | O | MET | A | 446 | −44.559 | 14.941 | −19.725 | 1.00 | 56.14 | O |
| ATOM | 307 | CB | MET | A | 446 | −45.086 | 17.939 | −18.892 | 1.00 | 51.22 | C |
| ATOM | 308 | CG | MET | A | 446 | −45.887 | 19.199 | −18.646 | 1.00 | 60.86 | C |
| ATOM | 309 | SD | MET | A | 446 | −45.083 | 20.278 | −17.436 | 1.00 | 63.35 | S |
| ATOM | 310 | CE | MET | A | 446 | −43.496 | 20.535 | −18.227 | 1.00 | 67.46 | C |
| ATOM | 311 | N | GLU | A | 447 | −43.439 | 16.340 | −21.070 | 1.00 | 55.19 | N |
| ATOM | 312 | CA | GLU | A | 447 | −42.391 | 15.356 | −21.267 | 1.00 | 47.79 | C |
| ATOM | 313 | C | GLU | A | 447 | −41.091 | 15.744 | −20.582 | 1.00 | 59.74 | C |
| ATOM | 314 | O | GLU | A | 447 | −40.802 | 16.922 | −20.390 | 1.00 | 55.30 | O |
| ATOM | 315 | CB | GLU | A | 447 | −42.179 | 15.031 | −22.747 | 1.00 | 63.68 | C |
| ATOM | 316 | CG | GLU | A | 447 | −41.847 | 16.205 | −23.623 | 1.00 | 75.17 | C |
| ATOM | 317 | CD | GLU | A | 447 | −41.925 | 15.853 | −25.095 | 1.00 | 86.42 | C |
| ATOM | 318 | OE1 | GLU | A | 447 | −42.459 | 14.771 | −25.426 | 1.00 | 92.85 | O |
| ATOM | 319 | OE2 | GLU | A | 447 | −41.449 | 16.656 | −25.921 | 1.00 | 85.00 | O |
| ATOM | 320 | N | PHE | A | 448 | −40.321 | 14.725 | −20.210 | 1.00 | 53.82 | N |
| ATOM | 321 | CA | PHE | A | 448 | −39.084 | 14.894 | −19.465 | 1.00 | 43.61 | C |
| ATOM | 322 | C | PHE | A | 448 | −38.123 | 13.821 | −19.915 | 1.00 | 51.93 | C |
| ATOM | 323 | O | PHE | A | 448 | −38.496 | 12.930 | −20.681 | 1.00 | 56.07 | O |
| ATOM | 324 | CB | PHE | A | 448 | −39.342 | 14.725 | −17.954 | 1.00 | 45.84 | C |
| ATOM | 325 | CG | PHE | A | 448 | −40.247 | 15.764 | −17.381 | 1.00 | 45.48 | C |
| ATOM | 326 | CD2 | PHE | A | 448 | −41.601 | 15.508 | −17.209 | 1.00 | 47.68 | C |
| ATOM | 327 | CD1 | PHE | A | 448 | −39.751 | 17.006 | −17.026 | 1.00 | 48.85 | C |
| ATOM | 328 | CE2 | PHE | A | 448 | −42.444 | 16.475 | −16.690 | 1.00 | 56.72 | C |

TABLE 3-continued

Atomic coordinates of RSK2 model (pdb file)

| ATOM | 329 | CE1 | PHE | A | 448 | −40.590 | 17.980 | −16.508 | 1.00 | 45.35 | C |
|---|---|---|---|---|---|---|---|---|---|---|---|
| ATOM | 330 | CZ | PHE | A | 448 | −41.940 | 17.713 | −16.340 | 1.00 | 47.55 | C |
| ATOM | 331 | N | ALA | A | 449 | −36.886 | 13.913 | −19.430 | 1.00 | 45.79 | N |
| ATOM | 332 | CA | ALA | A | 449 | −35.896 | 12.879 | −19.643 | 1.00 | 42.74 | C |
| ATOM | 333 | C | ALA | A | 449 | −35.719 | 12.126 | −18.329 | 1.00 | 49.88 | C |
| ATOM | 334 | O | ALA | A | 449 | −35.834 | 12.712 | −17.254 | 1.00 | 51.49 | O |
| ATOM | 335 | CB | ALA | A | 449 | −34.557 | 13.488 | −20.082 | 1.00 | 39.71 | C |
| ATOM | 336 | N | VAL | A | 450 | −35.441 | 10.830 | −18.418 | 1.00 | 50.99 | N |
| ATOM | 337 | CA | VAL | A | 450 | −35.091 | 10.059 | −17.234 | 1.00 | 48.59 | C |
| ATOM | 338 | C | VAL | A | 450 | −33.782 | 9.306 | −17.481 | 1.00 | 55.02 | C |
| ATOM | 339 | O | VAL | A | 450 | −33.621 | 8.650 | −18.505 | 1.00 | 56.43 | O |
| ATOM | 340 | CB | VAL | A | 450 | −36.231 | 9.104 | −16.810 | 1.00 | 59.91 | C |
| ATOM | 341 | CG1 | VAL | A | 450 | −36.601 | 8.142 | −17.937 | 1.00 | 59.40 | C |
| ATOM | 342 | CG2 | VAL | A | 450 | −35.851 | 8.354 | −15.540 | 1.00 | 60.84 | C |
| ATOM | 343 | N | LYS | A | 451 | −32.833 | 9.452 | −16.563 | 1.00 | 55.75 | N |
| ATOM | 344 | CA | LYS | A | 451 | −31.585 | 8.693 | −16.622 | 1.00 | 54.89 | C |
| ATOM | 345 | C | LYS | A | 451 | −31.744 | 7.527 | −15.670 | 1.00 | 59.06 | C |
| ATOM | 346 | O | LYS | A | 451 | −32.024 | 7.715 | −14.487 | 1.00 | 58.38 | O |
| ATOM | 347 | CB | LYS | A | 451 | −30.384 | 9.571 | −16.234 | 1.00 | 49.98 | C |
| ATOM | 348 | CG | LYS | A | 451 | −29.023 | 8.861 | −16.139 | 1.00 | 57.09 | C |
| ATOM | 349 | CD | LYS | A | 451 | −27.909 | 9.905 | −16.036 | 1.00 | 55.25 | C |
| ATOM | 350 | CE | LYS | A | 451 | −26.530 | 9.295 | −15.931 | 1.00 | 66.78 | C |
| ATOM | 351 | NZ | LYS | A | 451 | −25.481 | 10.367 | −15.900 | 1.00 | 65.48 | N |
| ATOM | 352 | N | ILE | A | 452 | −31.612 | 6.318 | −16.198 | 1.00 | 61.83 | N |
| ATOM | 353 | CA | ILE | A | 452 | −31.817 | 5.117 | −15.404 | 1.00 | 61.31 | C |
| ATOM | 354 | C | ILE | A | 452 | −30.461 | 4.484 | −15.106 | 1.00 | 60.73 | C |
| ATOM | 355 | O | ILE | A | 452 | −29.738 | 4.093 | −16.022 | 1.00 | 61.90 | O |
| ATOM | 356 | CB | ILE | A | 452 | −32.724 | 4.120 | −16.142 | 1.00 | 67.27 | C |
| ATOM | 357 | CG1 | ILE | A | 452 | −34.044 | 4.798 | −16.529 | 1.00 | 66.46 | C |
| ATOM | 358 | CG2 | ILE | A | 452 | −32.973 | 2.890 | −15.287 | 1.00 | 62.64 | C |
| ATOM | 359 | CD1 | ILE | A | 452 | −34.980 | 3.910 | −17.310 | 1.00 | 74.38 | C |
| ATOM | 360 | N | ILE | A | 453 | −30.120 | 4.395 | −13.822 | 1.00 | 66.39 | N |
| ATOM | 361 | CA | ILE | A | 453 | −28.763 | 4.036 | −13.413 | 1.00 | 68.34 | C |
| ATOM | 362 | C | ILE | A | 453 | −28.690 | 2.705 | −12.666 | 1.00 | 71.49 | C |
| ATOM | 363 | O | ILE | A | 453 | −29.328 | 2.521 | −11.629 | 1.00 | 69.68 | O |
| ATOM | 364 | CB | ILE | A | 453 | −28.136 | 5.137 | −12.536 | 1.00 | 64.85 | C |
| ATOM | 365 | CG1 | ILE | A | 453 | −28.179 | 6.485 | −13.262 | 1.00 | 64.84 | C |
| ATOM | 366 | CG2 | ILE | A | 453 | −26.700 | 4.771 | −12.161 | 1.00 | 71.83 | C |
| ATOM | 367 | CD1 | ILE | A | 453 | −27.822 | 7.652 | −12.371 | 1.00 | 61.37 | C |
| ATOM | 368 | N | ASP | A | 454 | −27.893 | 1.785 | −13.200 | 1.00 | 78.51 | N |
| ATOM | 369 | CA | ASP | A | 454 | −27.735 | 0.456 | −12.619 | 1.00 | 77.54 | C |
| ATOM | 370 | C | ASP | A | 454 | −26.870 | 0.551 | −11.363 | 1.00 | 75.79 | C |
| ATOM | 371 | O | ASP | A | 454 | −25.670 | 0.818 | −11.444 | 1.00 | 74.79 | O |
| ATOM | 372 | CB | ASP | A | 454 | −27.082 | −0.481 | −13.645 | 1.00 | 83.82 | C |
| ATOM | 373 | CG | ASP | A | 454 | −27.346 | −1.954 | −13.360 | 1.00 | 91.61 | C |
| ATOM | 374 | OD1 | ASP | A | 454 | −27.494 | −2.331 | −12.175 | 1.00 | 92.56 | O |
| ATOM | 375 | OD2 | ASP | A | 454 | −27.398 | −2.740 | −14.332 | 1.00 | 89.93 | O |
| ATOM | 376 | N | LYS | A | 455 | −27.481 | 0.338 | −10.202 | 1.00 | 74.78 | N |
| ATOM | 377 | CA | LYS | A | 455 | −26.773 | 0.454 | −8.934 | 1.00 | 82.72 | C |
| ATOM | 378 | C | LYS | A | 455 | −25.659 | −0.587 | −8.811 | 1.00 | 89.08 | C |
| ATOM | 379 | O | LYS | A | 455 | −24.697 | −0.389 | −8.070 | 1.00 | 86.34 | O |
| ATOM | 380 | CB | LYS | A | 455 | −27.760 | 0.327 | −7.772 | 1.00 | 83.92 | C |
| ATOM | 381 | CG | LYS | A | 455 | −28.996 | 1.186 | −7.963 | 1.00 | 71.26 | C |
| ATOM | 382 | CD | LYS | A | 455 | −29.934 | 1.108 | −6.768 | 1.00 | 81.16 | C |
| ATOM | 383 | CE | LYS | A | 455 | −29.306 | 1.742 | −5.542 | 1.00 | 81.96 | C |
| ATOM | 384 | NZ | LYS | A | 455 | −30.214 | 1.679 | −4.372 | 1.00 | 87.51 | N |
| ATOM | 385 | N | SER | A | 456 | −25.800 | −1.688 | −9.546 | 1.00 | 94.12 | N |
| ATOM | 386 | CA | SER | A | 456 | −24.789 | −2.743 | −9.583 | 1.00 | 94.31 | C |
| ATOM | 387 | C | SER | A | 456 | −23.486 | −2.189 | −10.125 | 1.00 | 91.92 | C |
| ATOM | 388 | O | SER | A | 456 | −22.404 | −2.517 | −9.639 | 1.00 | 95.44 | O |
| ATOM | 389 | CB | SER | A | 456 | −25.243 | −3.880 | −10.498 | 1.00 | 92.72 | C |
| ATOM | 390 | OG | SER | A | 456 | −26.595 | −4.223 | −10.259 | 1.00 | 98.18 | O |
| ATOM | 391 | N | LYS | A | 457 | −23.607 | −1.340 | −11.137 | 1.00 | 86.55 | N |
| ATOM | 392 | CA | LYS | A | 457 | −22.454 | −0.831 | −11.861 | 1.00 | 94.15 | C |
| ATOM | 393 | C | LYS | A | 457 | −21.993 | 0.529 | −11.336 | 1.00 | 100.55 | C |
| ATOM | 394 | O | LYS | A | 457 | −20.807 | 0.850 | −11.398 | 1.00 | 102.15 | O |
| ATOM | 395 | CB | LYS | A | 457 | −22.773 | −0.768 | −13.362 | 1.00 | 96.45 | C |
| ATOM | 396 | CG | LYS | A | 457 | −21.690 | −0.141 | −14.227 | 1.00 | 102.62 | C |
| ATOM | 397 | CD | LYS | A | 457 | −21.811 | −0.589 | −15.679 | 1.00 | 106.18 | C |
| ATOM | 398 | CE | LYS | A | 457 | −21.244 | −1.992 | −15.882 | 1.00 | 106.69 | C |
| ATOM | 399 | NZ | LYS | A | 457 | −19.756 | −2.025 | −15.781 | 1.00 | 105.49 | N |
| ATOM | 400 | N | ARG | A | 458 | −22.921 | 1.321 | −10.803 | 1.00 | 101.66 | N |
| ATOM | 401 | CA | ARG | A | 458 | −22.589 | 2.680 | −10.375 | 1.00 | 96.12 | C |
| ATOM | 402 | C | ARG | A | 458 | −23.343 | 3.163 | −9.137 | 1.00 | 94.82 | C |
| ATOM | 403 | O | ARG | A | 458 | −24.507 | 2.824 | −8.929 | 1.00 | 102.55 | O |
| ATOM | 404 | CB | ARG | A | 458 | −22.829 | 3.669 | −11.516 | 1.00 | 89.09 | C |
| ATOM | 405 | CG | ARG | A | 458 | −21.679 | 4.625 | −11.745 | 1.00 | 89.74 | C |
| ATOM | 406 | CD | ARG | A | 458 | −22.113 | 5.775 | −12.620 | 1.00 | 96.43 | C |

TABLE 3-continued

Atomic coordinates of RSK2 model (pdb file)

| ATOM | 407 | NE | ARG | A | 458 | −22.638 | 6.874 | −11.820 | 1.00 | 95.51 | N |
|---|---|---|---|---|---|---|---|---|---|---|---|
| ATOM | 408 | CZ | ARG | A | 458 | −23.518 | 7.766 | −12.259 | 1.00 | 87.97 | C |
| ATOM | 409 | NH1 | ARG | A | 458 | −23.994 | 7.687 | −13.497 | 1.00 | 93.08 | N |
| ATOM | 410 | NH2 | ARG | A | 458 | −23.927 | 8.732 | −11.452 | 1.00 | 81.58 | N |
| ATOM | 411 | N | ASP | A | 459 | −22.664 | 3.967 | −8.323 | 1.00 | 82.22 | N |
| ATOM | 412 | CA | ASP | A | 459 | −23.292 | 4.636 | −7.188 | 1.00 | 77.58 | C |
| ATOM | 413 | C | ASP | A | 459 | −23.530 | 6.103 | −7.540 | 1.00 | 71.42 | C |
| ATOM | 414 | O | ASP | A | 459 | −22.588 | 6.898 | −7.585 | 1.00 | 65.83 | O |
| ATOM | 415 | CB | ASP | A | 459 | −22.407 | 4.531 | −5.948 | 1.00 | 88.42 | C |
| ATOM | 416 | CG | ASP | A | 459 | −22.831 | 5.484 | −4.850 | 1.00 | 104.95 | C |
| ATOM | 417 | OD2 | ASP | A | 459 | −21.943 | 6.015 | −4.150 | 1.00 | 114.81 | O |
| ATOM | 418 | OD1 | ASP | A | 459 | −24.051 | 5.708 | −4.684 | 1.00 | 107.23 | O |
| ATOM | 419 | N | PRO | A | 460 | −24.795 | 6.470 | −7.788 | 1.00 | 71.37 | N |
| ATOM | 420 | CA | PRO | A | 460 | −25.107 | 7.806 | −8.301 | 1.00 | 70.59 | C |
| ATOM | 421 | C | PRO | A | 460 | −25.310 | 8.842 | −7.203 | 1.00 | 70.26 | C |
| ATOM | 422 | O | PRO | A | 460 | −25.804 | 9.931 | −7.497 | 1.00 | 66.16 | O |
| ATOM | 423 | CB | PRO | A | 460 | −26.432 | 7.592 | −9.044 | 1.00 | 80.09 | C |
| ATOM | 424 | CG | PRO | A | 460 | −26.894 | 6.186 | −8.689 | 1.00 | 84.98 | C |
| ATOM | 425 | CD | PRO | A | 460 | −26.015 | 5.676 | −7.593 | 1.00 | 83.22 | C |
| ATOM | 426 | N | THR | A | 461 | −24.935 | 8.513 | −5.971 | 1.00 | 69.86 | N |
| ATOM | 427 | CA | THR | A | 461 | −25.155 | 9.411 | −4.840 | 1.00 | 68.13 | C |
| ATOM | 428 | C | THR | A | 461 | −24.556 | 10.803 | −5.085 | 1.00 | 65.89 | C |
| ATOM | 429 | O | THR | A | 461 | −25.250 | 11.812 | −4.950 | 1.00 | 57.94 | O |
| ATOM | 430 | CB | THR | A | 461 | −24.649 | 8.792 | −3.524 | 1.00 | 72.44 | C |
| ATOM | 431 | OG1 | THR | A | 461 | −25.398 | 7.598 | −3.256 | 1.00 | 75.61 | O |
| ATOM | 432 | CG2 | THR | A | 461 | −24.833 | 9.763 | −2.354 | 1.00 | 68.03 | C |
| ATOM | 433 | N | GLU | A | 462 | −23.288 | 10.848 | −5.482 | 1.00 | 60.65 | N |
| ATOM | 434 | CA | GLU | A | 462 | −22.614 | 12.106 | −5.801 | 1.00 | 66.55 | C |
| ATOM | 435 | C | GLU | A | 462 | −23.362 | 12.917 | −6.860 | 1.00 | 68.97 | C |
| ATOM | 436 | O | GLU | A | 462 | −23.633 | 14.119 | −6.685 | 1.00 | 55.09 | O |
| ATOM | 437 | CB | GLU | A | 462 | −21.197 | 11.824 | −6.289 | 1.00 | 70.12 | C |
| ATOM | 438 | CG | GLU | A | 462 | −20.353 | 13.058 | −6.469 | 1.00 | 62.35 | C |
| ATOM | 439 | CD | GLU | A | 462 | −19.641 | 13.476 | −5.195 | 1.00 | 72.12 | C |
| ATOM | 440 | OE1 | GLU | A | 462 | −20.296 | 13.581 | −4.138 | 1.00 | 83.00 | O |
| ATOM | 441 | OE2 | GLU | A | 462 | −18.415 | 13.696 | −5.251 | 1.00 | 81.98 | O |
| ATOM | 442 | N | GLU | A | 463 | −23.696 | 12.257 | −7.961 | 1.00 | 60.55 | N |
| ATOM | 443 | CA | GLU | A | 463 | −24.376 | 12.922 | −9.050 | 1.00 | 52.65 | C |
| ATOM | 444 | C | GLU | A | 463 | −25.707 | 13.502 | −8.597 | 1.00 | 48.90 | C |
| ATOM | 445 | O | GLU | A | 463 | −26.054 | 14.643 | −8.928 | 1.00 | 52.09 | O |
| ATOM | 446 | CB | GLU | A | 463 | −24.606 | 11.956 | −10.208 | 1.00 | 51.77 | C |
| ATOM | 447 | CG | GLU | A | 463 | −25.390 | 12.595 | −11.362 | 1.00 | 52.72 | C |
| ATOM | 448 | CD | GLU | A | 463 | −25.436 | 11.712 | −12.586 | 1.00 | 56.33 | C |
| ATOM | 449 | OE1 | GLU | A | 463 | −25.053 | 10.525 | −12.476 | 1.00 | 63.63 | O |
| ATOM | 450 | OE2 | GLU | A | 463 | −25.838 | 12.201 | −13.660 | 1.00 | 53.95 | O |
| ATOM | 451 | N | ILE | A | 464 | −26.461 | 12.722 | −7.833 | 1.00 | 48.69 | N |
| ATOM | 452 | CA | ILE | A | 464 | −27.773 | 13.190 | −7.385 | 1.00 | 50.41 | C |
| ATOM | 453 | C | ILE | A | 464 | −27.647 | 14.338 | −6.379 | 1.00 | 58.61 | C |
| ATOM | 454 | O | ILE | A | 464 | −28.420 | 15.298 | −6.440 | 1.00 | 49.15 | O |
| ATOM | 455 | CB | ILE | A | 464 | −28.620 | 12.027 | −6.813 | 1.00 | 57.14 | C |
| ATOM | 456 | CG1 | ILE | A | 464 | −28.946 | 11.027 | −7.928 | 1.00 | 63.03 | C |
| ATOM | 457 | CG2 | ILE | A | 464 | −29.907 | 12.536 | −6.161 | 1.00 | 56.16 | C |
| ATOM | 458 | CD1 | ILE | A | 464 | −29.321 | 9.659 | −7.407 | 1.00 | 74.54 | C |
| ATOM | 459 | N | GLU | A | 465 | −26.666 | 14.259 | −5.473 | 1.00 | 54.90 | N |
| ATOM | 460 | CA | GLU | A | 465 | −26.466 | 15.333 | −4.490 | 1.00 | 50.87 | C |
| ATOM | 461 | C | GLU | A | 465 | −26.150 | 16.661 | −5.176 | 1.00 | 48.57 | C |
| ATOM | 462 | O | GLU | A | 465 | −26.665 | 17.709 | −4.773 | 1.00 | 48.92 | O |
| ATOM | 463 | CB | GLU | A | 465 | −25.355 | 14.986 | −3.487 | 1.00 | 54.40 | C |
| ATOM | 464 | CG | GLU | A | 465 | −25.791 | 14.129 | −2.314 | 1.00 | 63.82 | C |
| ATOM | 465 | CD | GLU | A | 465 | −24.655 | 13.847 | −1.339 | 0.49 | 76.57 | C |
| ATOM | 466 | OE1 | GLU | A | 465 | −24.908 | 13.180 | −0.312 | 0.92 | 90.73 | O |
| ATOM | 467 | OE2 | GLU | A | 465 | −23.509 | 14.286 | −1.598 | 1.00 | 70.74 | O |
| ATOM | 468 | N | ILE | A | 466 | −25.303 | 16.610 | −6.204 | 1.00 | 47.17 | N |
| ATOM | 469 | CA | ILE | A | 466 | −24.967 | 17.803 | −6.998 | 1.00 | 48.23 | C |
| ATOM | 470 | C | ILE | A | 466 | −26.171 | 18.383 | −7.723 | 1.00 | 53.44 | C |
| ATOM | 471 | O | ILE | A | 466 | −26.426 | 19.598 | −7.671 | 1.00 | 51.83 | O |
| ATOM | 472 | CB | ILE | A | 466 | −23.840 | 17.509 | −8.008 | 1.00 | 52.07 | C |
| ATOM | 473 | CG1 | ILE | A | 466 | −22.541 | 17.225 | −7.245 | 1.00 | 62.18 | C |
| ATOM | 474 | CG2 | ILE | A | 466 | −23.681 | 18.674 | −9.005 | 1.00 | 47.93 | C |
| ATOM | 475 | CD1 | ILE | A | 466 | −21.428 | 16.644 | −8.110 | 1.00 | 53.91 | C |
| ATOM | 476 | N | LEU | A | 467 | −26.913 | 17.526 | −8.411 | 1.00 | 47.25 | N |
| ATOM | 477 | CA | LEU | A | 467 | −28.133 | 17.988 | −9.079 | 1.00 | 52.09 | C |
| ATOM | 478 | C | LEU | A | 467 | −29.155 | 18.583 | −8.118 | 1.00 | 50.45 | C |
| ATOM | 479 | O | LEU | A | 467 | −29.789 | 19.608 | −8.421 | 1.00 | 43.92 | O |
| ATOM | 480 | CB | LEU | A | 467 | −28.755 | 16.855 | −9.899 | 1.00 | 47.63 | C |
| ATOM | 481 | CG | LEU | A | 467 | −27.864 | 16.451 | −11.080 | 1.00 | 52.32 | C |
| ATOM | 482 | CD1 | LEU | A | 467 | −28.375 | 15.177 | −11.733 | 1.00 | 59.11 | C |
| ATOM | 483 | CD2 | LEU | A | 467 | −27.769 | 17.595 | −12.109 | 1.00 | 44.29 | C |
| ATOM | 484 | N | LEU | A | 468 | −29.329 | 17.943 | −6.963 | 1.00 | 48.34 | N |

TABLE 3-continued

Atomic coordinates of RSK2 model (pdb file)

| ATOM | 485 | CA | LEU | A | 468 | −30.285 | 18.424 | −5.967 | 1.00 | 52.39 | C |
|---|---|---|---|---|---|---|---|---|---|---|---|
| ATOM | 486 | C | LEU | A | 468 | −29.873 | 19.784 | −5.436 | 1.00 | 61.76 | C |
| ATOM | 487 | O | LEU | A | 468 | −30.702 | 20.649 | −5.194 | 1.00 | 52.52 | O |
| ATOM | 488 | CB | LEU | A | 468 | −30.361 | 17.452 | −4.782 | 1.00 | 55.16 | C |
| ATOM | 489 | CG | LEU | A | 468 | −31.263 | 16.235 | −4.932 | 1.00 | 57.96 | C |
| ATOM | 490 | CD1 | LEU | A | 468 | −31.004 | 15.231 | −3.816 | 1.00 | 63.91 | C |
| ATOM | 491 | CD2 | LEU | A | 468 | −32.720 | 16.684 | −4.925 | 1.00 | 58.07 | C |
| ATOM | 492 | N | ARG | A | 469 | −28.574 | 19.955 | −5.235 | 1.00 | 50.11 | N |
| ATOM | 493 | CA | ARG | A | 469 | −28.065 | 21.151 | −4.603 | 1.00 | 56.51 | C |
| ATOM | 494 | C | ARG | A | 469 | −27.933 | 22.305 | −5.599 | 1.00 | 50.64 | C |
| ATOM | 495 | O | ARG | A | 469 | −28.168 | 23.463 | −5.249 | 1.00 | 55.06 | O |
| ATOM | 496 | CB | ARG | A | 469 | −26.723 | 20.810 | −3.953 | 1.00 | 57.11 | C |
| ATOM | 497 | CG | ARG | A | 469 | −25.930 | 21.963 | −3.416 | 1.00 | 69.90 | C |
| ATOM | 498 | CD | ARG | A | 469 | −26.675 | 22.816 | −2.438 | 0.81 | 74.27 | C |
| ATOM | 499 | NE | ARG | A | 469 | −25.755 | 23.626 | −1.644 | 1.00 | 72.10 | N |
| ATOM | 500 | CZ | ARG | A | 469 | −25.642 | 23.525 | −0.325 | 0.60 | 82.44 | C |
| ATOM | 501 | NH1 | ARG | A | 469 | −26.398 | 22.651 | 0.324 | 1.00 | 77.85 | N |
| ATOM | 502 | NH2 | ARG | A | 469 | −24.786 | 24.291 | 0.341 | 1.00 | 82.68 | N |
| ATOM | 503 | N | TYR | A | 470 | −27.577 | 21.994 | −6.842 | 1.00 | 46.40 | N |
| ATOM | 504 | CA | TYR | A | 470 | −27.164 | 23.045 | −7.776 | 1.00 | 44.03 | C |
| ATOM | 505 | C | TYR | A | 470 | −28.002 | 23.108 | −9.055 | 1.00 | 46.92 | C |
| ATOM | 506 | O | TYR | A | 470 | −27.820 | 24.005 | −9.869 | 1.00 | 52.37 | O |
| ATOM | 507 | CB | TYR | A | 470 | −25.673 | 22.886 | −8.129 | 1.00 | 45.04 | C |
| ATOM | 508 | CG | TYR | A | 470 | −24.751 | 22.817 | −6.915 | 1.00 | 51.79 | C |
| ATOM | 509 | CD1 | TYR | A | 470 | −24.536 | 23.934 | −6.112 | 1.00 | 57.95 | C |
| ATOM | 510 | CD2 | TYR | A | 470 | −24.082 | 21.638 | −6.585 | 1.00 | 43.71 | C |
| ATOM | 511 | CE1 | TYR | A | 470 | −23.692 | 23.882 | −4.997 | 1.00 | 63.92 | C |
| ATOM | 512 | CE2 | TYR | A | 470 | −23.235 | 21.576 | −5.465 | 1.00 | 48.30 | C |
| ATOM | 513 | CZ | TYR | A | 470 | −23.042 | 22.702 | −4.680 | 1.00 | 65.52 | C |
| ATOM | 514 | OH | TYR | A | 470 | −22.210 | 22.645 | −3.567 | 1.00 | 61.32 | O |
| ATOM | 515 | N | GLY | A | 471 | −28.931 | 22.172 | −9.217 | 1.00 | 50.89 | N |
| ATOM | 516 | CA | GLY | A | 471 | −29.740 | 22.097 | −10.424 | 1.00 | 50.86 | C |
| ATOM | 517 | C | GLY | A | 471 | −30.671 | 23.275 | −10.582 | 1.00 | 49.87 | C |
| ATOM | 518 | O | GLY | A | 471 | −31.245 | 23.495 | −11.649 | 1.00 | 45.60 | O |
| ATOM | 519 | N | GLN | A | 472 | −30.839 | 24.039 | −9.510 | 1.00 | 41.16 | N |
| ATOM | 520 | CA | GLN | A | 472 | −31.718 | 25.196 | −9.561 | 1.00 | 50.99 | C |
| ATOM | 521 | C | GLN | A | 472 | −31.034 | 26.369 | −10.282 | 1.00 | 43.25 | C |
| ATOM | 522 | O | GLN | A | 472 | −31.676 | 27.371 | −10.599 | 1.00 | 44.06 | O |
| ATOM | 523 | CB | GLN | A | 472 | −32.145 | 25.586 | −8.144 | 1.00 | 62.29 | C |
| ATOM | 524 | CG | GLN | A | 472 | −33.624 | 25.774 | −7.993 | 1.00 | 79.77 | C |
| ATOM | 525 | CD | GLN | A | 472 | −33.980 | 27.228 | −7.961 | 1.00 | 89.01 | C |
| ATOM | 526 | OE1 | GLN | A | 472 | −33.100 | 28.084 | −8.049 | 0.46 | 92.48 | O |
| ATOM | 527 | NE2 | GLN | A | 472 | −35.266 | 27.527 | −7.827 | 1.00 | 86.85 | N |
| ATOM | 528 | N | HIS | A | 473 | −29.727 | 26.247 | −10.516 | 1.00 | 39.97 | N |
| ATOM | 529 | CA | HIS | A | 473 | −29.030 | 27.225 | −11.340 | 1.00 | 43.28 | C |
| ATOM | 530 | C | HIS | A | 473 | −29.716 | 27.260 | −12.706 | 1.00 | 42.87 | C |
| ATOM | 531 | O | HIS | A | 473 | −30.001 | 26.208 | −13.281 | 1.00 | 38.41 | O |
| ATOM | 532 | CB | HIS | A | 473 | −27.553 | 26.838 | −11.492 | 1.00 | 39.48 | C |
| ATOM | 533 | CG | HIS | A | 473 | −26.704 | 27.925 | −12.079 | 1.00 | 48.46 | C |
| ATOM | 534 | ND1 | HIS | A | 473 | −26.778 | 28.295 | −13.407 | 1.00 | 43.36 | N |
| ATOM | 535 | CD2 | HIS | A | 473 | −25.784 | 28.742 | −11.511 | 1.00 | 47.22 | C |
| ATOM | 536 | CE1 | HIS | A | 473 | −25.928 | 29.284 | −13.632 | 1.00 | 46.09 | C |
| ATOM | 537 | NE2 | HIS | A | 473 | −25.320 | 29.579 | −12.497 | 1.00 | 47.66 | N |
| ATOM | 538 | N | PRO | A | 474 | −29.997 | 28.467 | −13.223 | 1.00 | 45.01 | N |
| ATOM | 539 | CA | PRO | A | 474 | −30.657 | 28.620 | −14.528 | 1.00 | 49.68 | C |
| ATOM | 540 | C | PRO | A | 474 | −29.984 | 27.880 | −15.677 | 1.00 | 39.78 | C |
| ATOM | 541 | O | PRO | A | 474 | −30.659 | 27.488 | −16.631 | 1.00 | 39.20 | O |
| ATOM | 542 | CB | PRO | A | 474 | −30.597 | 30.130 | −14.782 | 1.00 | 48.62 | C |
| ATOM | 543 | CG | PRO | A | 474 | −29.558 | 30.650 | −13.846 | 1.00 | 59.65 | C |
| ATOM | 544 | CD | PRO | A | 474 | −29.664 | 29.774 | −12.632 | 1.00 | 50.42 | C |
| ATOM | 545 | N | ASN | A | 475 | −28.675 | 27.689 | −15.610 | 1.00 | 40.34 | N |
| ATOM | 546 | CA | ASN | A | 475 | −27.974 | 27.087 | −16.744 | 1.00 | 36.71 | C |
| ATOM | 547 | C | ASN | A | 475 | −27.396 | 25.716 | −16.422 | 1.00 | 42.93 | C |
| ATOM | 548 | O | ASN | A | 475 | −26.477 | 25.254 | −17.090 | 1.00 | 41.20 | O |
| ATOM | 549 | CB | ASN | A | 475 | −26.872 | 28.042 | −17.230 | 1.00 | 35.01 | C |
| ATOM | 550 | CG | ASN | A | 475 | −27.443 | 29.376 | −17.726 | 1.00 | 38.36 | C |
| ATOM | 551 | OD1 | ASN | A | 475 | −27.277 | 30.413 | −17.082 | 1.00 | 40.20 | O |
| ATOM | 552 | ND2 | ASN | A | 475 | −28.112 | 29.343 | −18.872 | 1.00 | 39.98 | N |
| ATOM | 553 | N | ILE | A | 476 | −27.914 | 25.084 | −15.375 | 1.00 | 40.72 | N |
| ATOM | 554 | CA | ILE | A | 476 | −27.533 | 23.709 | −15.064 | 1.00 | 39.99 | C |
| ATOM | 555 | C | ILE | A | 476 | −28.795 | 22.905 | −15.285 | 1.00 | 42.96 | C |
| ATOM | 556 | O | ILE | A | 476 | −29.872 | 23.399 | −15.002 | 1.00 | 38.88 | O |
| ATOM | 557 | CB | ILE | A | 476 | −27.049 | 23.565 | −13.597 | 1.00 | 37.95 | C |
| ATOM | 558 | CG1 | ILE | A | 476 | −25.664 | 24.220 | −13.435 | 1.00 | 35.69 | C |
| ATOM | 559 | CG2 | ILE | A | 476 | −26.984 | 22.081 | −13.176 | 1.00 | 38.69 | C |
| ATOM | 560 | CD1 | ILE | A | 476 | −25.140 | 24.226 | −11.984 | 1.00 | 37.93 | C |
| ATOM | 561 | N | ILE | A | 477 | −28.677 | 21.689 | −15.813 | 1.00 | 39.45 | N |
| ATOM | 562 | CA | ILE | A | 477 | −29.857 | 20.859 | −16.058 | 1.00 | 43.04 | C |

TABLE 3-continued

Atomic coordinates of RSK2 model (pdb file)

| ATOM | 563 | C | ILE | A | 477 | −30.676 | 20.676 | −14.768 | 1.00 | 38.05 | C |
|---|---|---|---|---|---|---|---|---|---|---|---|
| ATOM | 564 | O | ILE | A | 477 | −30.127 | 20.381 | −13.718 | 1.00 | 41.98 | O |
| ATOM | 565 | CB | ILE | A | 477 | −29.475 | 19.491 | −16.664 | 1.00 | 42.65 | C |
| ATOM | 566 | CG1 | ILE | A | 477 | −30.743 | 18.678 | −16.947 | 1.00 | 48.52 | C |
| ATOM | 567 | CG2 | ILE | A | 477 | −28.497 | 18.757 | −15.746 | 1.00 | 42.13 | C |
| ATOM | 568 | CD1 | ILE | A | 477 | −30.566 | 17.552 | −17.922 | 1.00 | 53.26 | C |
| ATOM | 569 | N | THR | A | 478 | −31.987 | 20.887 | −14.845 | 1.00 | 42.06 | N |
| ATOM | 570 | CA | THR | A | 478 | −32.801 | 20.930 | −13.640 | 1.00 | 43.17 | C |
| ATOM | 571 | C | THR | A | 478 | −33.378 | 19.560 | −13.308 | 1.00 | 45.99 | C |
| ATOM | 572 | O | THR | A | 478 | −33.995 | 18.911 | −14.151 | 1.00 | 45.38 | O |
| ATOM | 573 | CB | THR | A | 478 | −33.955 | 21.945 | −13.822 | 1.00 | 41.75 | C |
| ATOM | 574 | OG1 | THR | A | 478 | −33.418 | 23.178 | −14.322 | 1.00 | 48.64 | O |
| ATOM | 575 | CG2 | THR | A | 478 | −34.676 | 22.197 | −12.511 | 1.00 | 46.58 | C |
| ATOM | 576 | N | LEU | A | 479 | −33.172 | 19.123 | −12.075 | 1.00 | 43.86 | N |
| ATOM | 577 | CA | LEU | A | 479 | −33.709 | 17.856 | −11.600 | 1.00 | 41.82 | C |
| ATOM | 578 | C | LEU | A | 479 | −35.194 | 18.035 | −11.297 | 1.00 | 48.73 | C |
| ATOM | 579 | O | LEU | A | 479 | −35.594 | 19.035 | −10.700 | 1.00 | 51.65 | O |
| ATOM | 580 | CB | LEU | A | 479 | −32.954 | 17.425 | −10.334 | 1.00 | 43.94 | C |
| ATOM | 581 | CG | LEU | A | 479 | −33.328 | 16.102 | −9.672 | 1.00 | 58.09 | C |
| ATOM | 582 | CD1 | LEU | A | 479 | −33.002 | 14.960 | −10.600 | 1.00 | 58.82 | C |
| ATOM | 583 | CD2 | LEU | A | 479 | −32.585 | 15.947 | −8.349 | 1.00 | 64.71 | C |
| ATOM | 584 | N | LYS | A | 480 | −36.018 | 17.079 | −11.718 | 1.00 | 46.92 | N |
| ATOM | 585 | CA | LYS | A | 480 | −37.466 | 17.191 | −11.536 | 1.00 | 48.73 | C |
| ATOM | 586 | C | LYS | A | 480 | −37.980 | 16.129 | −10.580 | 1.00 | 53.19 | C |
| ATOM | 587 | O | LYS | A | 480 | −38.898 | 16.377 | −9.795 | 1.00 | 59.82 | O |
| ATOM | 588 | CB | LYS | A | 480 | −38.190 | 17.086 | −12.883 | 1.00 | 55.66 | C |
| ATOM | 589 | CG | LYS | A | 480 | −37.857 | 18.210 | −13.861 | 1.00 | 57.07 | C |
| ATOM | 590 | CD | LYS | A | 480 | −38.345 | 19.547 | −13.329 | 1.00 | 69.87 | C |
| ATOM | 591 | CE | LYS | A | 480 | −38.040 | 20.684 | −14.283 | 1.00 | 67.88 | C |
| ATOM | 592 | NZ | LYS | A | 480 | −38.851 | 21.891 | −13.950 | 1.00 | 64.50 | N |
| ATOM | 593 | N | ASP | A | 481 | −37.375 | 14.947 | −10.625 | 1.00 | 51.81 | N |
| ATOM | 594 | CA | ASP | A | 481 | −37.831 | 13.840 | −9.784 | 1.00 | 52.35 | C |
| ATOM | 595 | C | ASP | A | 481 | −36.746 | 12.777 | −9.673 | 1.00 | 55.41 | C |
| ATOM | 596 | O | ASP | A | 481 | −35.905 | 12.665 | −10.562 | 1.00 | 52.69 | O |
| ATOM | 597 | CB | ASP | A | 481 | −39.093 | 13.223 | −10.390 | 1.00 | 54.32 | C |
| ATOM | 598 | CG | ASP | A | 481 | −40.073 | 12.766 | −9.347 | 1.00 | 73.81 | C |
| ATOM | 599 | OD2 | ASP | A | 481 | −41.281 | 12.716 | −9.663 | 1.00 | 73.53 | O |
| ATOM | 600 | OD1 | ASP | A | 481 | −39.640 | 12.456 | −8.217 | 1.00 | 85.58 | O |
| ATOM | 601 | N | VAL | A | 482 | −36.749 | 12.020 | −8.571 | 1.00 | 60.38 | N |
| ATOM | 602 | CA | VAL | A | 482 | −35.809 | 10.903 | −8.397 | 1.00 | 67.21 | C |
| ATOM | 603 | C | VAL | A | 482 | −36.476 | 9.705 | −7.750 | 1.00 | 56.10 | C |
| ATOM | 604 | O | VAL | A | 482 | −37.225 | 9.855 | −6.792 | 1.00 | 59.10 | O |
| ATOM | 605 | CB | VAL | A | 482 | −34.584 | 11.249 | −7.511 | 1.00 | 69.73 | C |
| ATOM | 606 | CG1 | VAL | A | 482 | −33.476 | 10.226 | −7.737 | 1.00 | 72.17 | C |
| ATOM | 607 | CG2 | VAL | A | 482 | −34.060 | 12.634 | −7.807 | 1.00 | 57.40 | C |
| ATOM | 608 | N | TYR | A | 483 | −36.195 | 8.514 | −8.269 | 1.00 | 67.98 | N |
| ATOM | 609 | CA | TYR | A | 483 | −36.724 | 7.280 | −7.686 | 1.00 | 71.55 | C |
| ATOM | 610 | C | TYR | A | 483 | −35.618 | 6.246 | −7.519 | 1.00 | 69.96 | C |
| ATOM | 611 | O | TYR | A | 483 | −34.660 | 6.226 | −8.291 | 1.00 | 62.86 | O |
| ATOM | 612 | CB | TYR | A | 483 | −37.826 | 6.689 | −8.568 | 1.00 | 71.50 | C |
| ATOM | 613 | CG | TYR | A | 483 | −39.048 | 7.562 | −8.711 | 1.00 | 64.53 | C |
| ATOM | 614 | CD2 | TYR | A | 483 | −40.203 | 7.292 | −7.995 | 1.00 | 68.30 | C |
| ATOM | 615 | CD1 | TYR | A | 483 | −39.049 | 8.653 | −9.576 | 1.00 | 72.47 | C |
| ATOM | 616 | CE2 | TYR | A | 483 | −41.328 | 8.088 | −8.129 | 1.00 | 76.04 | C |
| ATOM | 617 | CE1 | TYR | A | 483 | −40.165 | 9.454 | −9.715 | 1.00 | 65.74 | C |
| ATOM | 618 | CZ | TYR | A | 483 | −41.299 | 9.167 | −8.995 | 1.00 | 73.06 | C |
| ATOM | 619 | OH | TYR | A | 483 | −42.405 | 9.967 | −9.141 | 1.00 | 78.92 | O |
| ATOM | 620 | N | ASP | A | 484 | −35.771 | 5.384 | −6.516 | 1.00 | 71.80 | N |
| ATOM | 621 | CA | ASP | A | 484 | −34.839 | 4.282 | −6.265 | 1.00 | 75.00 | C |
| ATOM | 622 | C | ASP | A | 484 | −35.664 | 3.047 | −5.924 | 1.00 | 78.32 | C |
| ATOM | 623 | O | ASP | A | 484 | −36.348 | 3.023 | −4.902 | 1.00 | 80.96 | O |
| ATOM | 624 | CB | ASP | A | 484 | −33.897 | 4.635 | −5.102 | 1.00 | 84.63 | C |
| ATOM | 625 | CG | ASP | A | 484 | −32.790 | 3.593 | −4.882 | 1.00 | 86.73 | C |
| ATOM | 626 | OD1 | ASP | A | 484 | −33.068 | 2.375 | −4.909 | 1.00 | 82.15 | O |
| ATOM | 627 | OD2 | ASP | A | 484 | −31.624 | 3.999 | −4.675 | 1.00 | 85.87 | O |
| ATOM | 628 | N | ASP | A | 485 | −35.612 | 2.027 | −6.778 | 1.00 | 80.31 | N |
| ATOM | 629 | CA | ASP | A | 485 | −36.388 | 0.808 | −6.546 | 1.00 | 92.15 | C |
| ATOM | 630 | C | ASP | A | 485 | −35.536 | −0.312 | −5.949 | 1.00 | 92.91 | C |
| ATOM | 631 | O | ASP | A | 485 | −35.969 | −1.462 | −5.874 | 1.00 | 98.29 | O |
| ATOM | 632 | CB | ASP | A | 485 | −37.107 | 0.345 | −7.827 | 1.00 | 98.54 | C |
| ATOM | 633 | CG | ASP | A | 485 | −36.152 | −0.107 | −8.926 | 1.00 | 99.27 | C |
| ATOM | 634 | OD1 | ASP | A | 485 | −34.920 | −0.014 | −8.749 | 1.00 | 106.70 | O |
| ATOM | 635 | OD2 | ASP | A | 485 | −36.645 | −0.551 | −9.986 | 1.00 | 94.46 | O |
| ATOM | 636 | N | GLY | A | 486 | −34.326 | 0.042 | −5.525 | 1.00 | 81.70 | N |
| ATOM | 637 | CA | GLY | A | 486 | −33.403 | −0.913 | −4.937 | 1.00 | 90.27 | C |
| ATOM | 638 | C | GLY | A | 486 | −32.407 | −1.457 | −5.945 | 1.00 | 102.70 | C |
| ATOM | 639 | O | GLY | A | 486 | −31.321 | −1.907 | −5.575 | 1.00 | 107.24 | O |
| ATOM | 640 | N | LYS | A | 487 | −32.777 | −1.396 | −7.223 | 1.00 | 94.67 | N |

TABLE 3-continued

Atomic coordinates of RSK2 model (pdb file)

| ATOM | 641 | CA  | LYS | A | 487 | −31.996 | −1.998  | −8.299  | 1.00 | 88.63  | C |
|------|-----|-----|-----|---|-----|---------|---------|---------|------|--------|---|
| ATOM | 642 | C   | LYS | A | 487 | −31.520 | −0.918  | −9.264  | 1.00 | 90.58  | C |
| ATOM | 643 | O   | LYS | A | 487 | −30.413 | −0.982  | −9.814  | 1.00 | 84.16  | O |
| ATOM | 644 | CB  | LYS | A | 487 | −32.865 | −3.021  | −9.033  | 1.00 | 101.52 | C |
| ATOM | 645 | CG  | LYS | A | 487 | −32.106 | −4.084  | −9.808  | 1.00 | 109.57 | C |
| ATOM | 646 | CD  | LYS | A | 487 | −33.037 | −5.234  | −10.190 | 1.00 | 114.84 | C |
| ATOM | 647 | CE  | LYS | A | 487 | −34.361 | −4.719  | −10.746 | 1.00 | 116.43 | C |
| ATOM | 648 | NZ  | LYS | A | 487 | −35.169 | −5.804  | −11.363 | 1.00 | 119.11 | N |
| ATOM | 649 | N   | TYR | A | 488 | −32.368 | 0.085   | −9.455  | 1.00 | 85.44  | N |
| ATOM | 650 | CA  | TYR | A | 488 | −32.056 | 1.204   | −10.333 | 1.00 | 84.35  | C |
| ATOM | 651 | C   | TYR | A | 488 | −32.425 | 2.521   | −9.684  | 1.00 | 77.33  | C |
| ATOM | 652 | O   | TYR | A | 488 | −33.377 | 2.605   | −8.907  | 1.00 | 79.24  | O |
| ATOM | 653 | CB  | TYR | A | 488 | −32.825 | 1.092   | −11.649 | 1.00 | 78.92  | C |
| ATOM | 654 | CG  | TYR | A | 488 | −32.504 | −0.130  | −12.469 | 1.00 | 77.26  | C |
| ATOM | 655 | CD2 | TYR | A | 488 | −33.306 | −1.263  | −12.404 | 1.00 | 74.50  | C |
| ATOM | 656 | CD1 | TYR | A | 488 | −31.409 | −0.146  | −13.321 | 1.00 | 78.85  | C |
| ATOM | 657 | CE2 | TYR | A | 488 | −33.020 | −2.380  | −13.157 | 1.00 | 82.19  | C |
| ATOM | 658 | CE1 | TYR | A | 488 | −31.115 | −1.260  | −14.080 | 1.00 | 83.30  | C |
| ATOM | 659 | CZ  | TYR | A | 488 | −31.923 | −2.372  | −13.995 | 1.00 | 84.09  | C |
| ATOM | 660 | OH  | TYR | A | 488 | −31.633 | −3.480  | −14.750 | 1.00 | 96.40  | O |
| ATOM | 661 | N   | VAL | A | 489 | −31.669 | 3.558   | −10.016 | 1.00 | 79.97  | N |
| ATOM | 662 | CA  | VAL | A | 489 | −32.059 | 4.903   | −9.644  | 1.00 | 76.44  | C |
| ATOM | 663 | C   | VAL | A | 489 | −32.621 | 5.601   | −10.882 | 1.00 | 65.93  | C |
| ATOM | 664 | O   | VAL | A | 489 | −32.016 | 5.562   | −11.949 | 1.00 | 59.53  | O |
| ATOM | 665 | CB  | VAL | A | 489 | −30.877 | 5.696   | −9.073  | 1.00 | 78.01  | C |
| ATOM | 666 | CG1 | VAL | A | 489 | −31.376 | 6.959   | −8.402  | 1.00 | 81.11  | C |
| ATOM | 667 | CG2 | VAL | A | 489 | −30.109 | 4.840   | −8.078  | 1.00 | 77.45  | C |
| ATOM | 668 | N   | TYR | A | 490 | −33.792 | 6.212   | −10.745 | 1.00 | 66.59  | N |
| ATOM | 669 | CA  | TYR | A | 490 | −34.398 | 6.942   | −11.862 | 1.00 | 59.90  | C |
| ATOM | 670 | C   | TYR | A | 490 | −34.275 | 8.433   | −11.615 | 1.00 | 52.54  | C |
| ATOM | 671 | O   | TYR | A | 490 | −34.881 | 8.968   | −10.695 | 1.00 | 57.84  | O |
| ATOM | 672 | CB  | TYR | A | 490 | −35.874 | 6.550   | −12.040 | 1.00 | 63.28  | C |
| ATOM | 673 | CG  | TYR | A | 490 | −36.072 | 5.065   | −12.267 | 1.00 | 75.15  | C |
| ATOM | 674 | CD1 | TYR | A | 490 | −36.005 | 4.167   | −11.207 | 1.00 | 83.38  | C |
| ATOM | 675 | CD2 | TYR | A | 490 | −36.305 | 4.559   | −13.539 | 1.00 | 72.60  | C |
| ATOM | 676 | CE1 | TYR | A | 490 | −36.171 | 2.806   | −11.405 | 1.00 | 91.85  | C |
| ATOM | 677 | CE2 | TYR | A | 490 | −36.476 | 3.198   | −13.748 | 1.00 | 77.55  | C |
| ATOM | 678 | CZ  | TYR | A | 490 | −36.406 | 2.325   | −12.675 | 1.00 | 90.48  | C |
| ATOM | 679 | OH  | TYR | A | 490 | −36.575 | 0.968   | −12.867 | 1.00 | 88.94  | O |
| ATOM | 680 | N   | VAL | A | 491 | −33.479 | 9.097   | −12.439 | 1.00 | 50.54  | N |
| ATOM | 681 | CA  | VAL | A | 491 | −33.250 | 10.527  | −12.304 | 1.00 | 48.91  | C |
| ATOM | 682 | C   | VAL | A | 491 | −34.014 | 11.295  | −13.394 | 1.00 | 45.41  | C |
| ATOM | 683 | O   | VAL | A | 491 | −33.634 | 11.257  | −14.566 | 1.00 | 51.80  | O |
| ATOM | 684 | CB  | VAL | A | 491 | −31.746 | 10.825  | −12.412 | 1.00 | 50.49  | C |
| ATOM | 685 | CG1 | VAL | A | 491 | −31.482 | 12.317  | −12.298 | 1.00 | 46.86  | C |
| ATOM | 686 | CG2 | VAL | A | 491 | −30.983 | 10.047  | −11.347 | 1.00 | 61.41  | C |
| ATOM | 687 | N   | VAL | A | 492 | −35.099 | 11.966  | −13.013 | 1.00 | 48.62  | N |
| ATOM | 688 | CA  | VAL | A | 492 | −35.911 | 12.683  | −13.991 | 1.00 | 50.81  | C |
| ATOM | 689 | C   | VAL | A | 492 | −35.501 | 14.146  | −14.073 | 1.00 | 50.74  | C |
| ATOM | 690 | O   | VAL | A | 492 | −35.442 | 14.842  | −13.049 | 1.00 | 50.26  | O |
| ATOM | 691 | CB  | VAL | A | 492 | −37.414 | 12.608  | −13.646 | 1.00 | 56.70  | C |
| ATOM | 692 | CG1 | VAL | A | 492 | −38.245 | 13.147  | −14.812 | 1.00 | 47.88  | C |
| ATOM | 693 | CG2 | VAL | A | 492 | −37.807 | 11.183  | −13.310 | 1.00 | 52.04  | C |
| ATOM | 694 | N   | THR | A | 493 | −35.216 | 14.610  | −15.287 | 1.00 | 43.88  | N |
| ATOM | 695 | CA  | THR | A | 493 | −34.808 | 15.996  | −15.504 | 1.00 | 48.36  | C |
| ATOM | 696 | C   | THR | A | 493 | −35.568 | 16.653  | −16.641 | 1.00 | 50.05  | C |
| ATOM | 697 | O   | THR | A | 493 | −36.340 | 16.001  | −17.344 | 1.00 | 46.86  | O |
| ATOM | 698 | CB  | THR | A | 493 | −33.321 | 16.091  | −15.862 | 1.00 | 51.29  | C |
| ATOM | 699 | OG1 | THR | A | 493 | −33.123 | 15.647  | −17.214 | 1.00 | 48.07  | O |
| ATOM | 700 | CG2 | THR | A | 493 | −32.484 | 15.249  | −14.895 | 1.00 | 44.37  | C |
| ATOM | 701 | N   | GLU | A | 494 | −35.356 | 17.951  | −16.825 | 1.00 | 45.27  | N |
| ATOM | 702 | CA  | GLU | A | 494 | −35.906 | 18.599  | −18.010 | 1.00 | 54.57  | C |
| ATOM | 703 | C   | GLU | A | 494 | −35.299 | 17.927  | −19.241 | 1.00 | 41.67  | C |
| ATOM | 704 | O   | GLU | A | 494 | −34.154 | 17.448  | −19.206 | 1.00 | 44.74  | O |
| ATOM | 705 | CB  | GLU | A | 494 | −35.661 | 20.116  | −18.013 | 1.00 | 54.80  | C |
| ATOM | 706 | CG  | GLU | A | 494 | −34.266 | 20.548  | −17.596 | 1.00 | 60.23  | C |
| ATOM | 707 | CD  | GLU | A | 494 | −34.131 | 22.062  | −17.513 | 1.00 | 60.87  | C |
| ATOM | 708 | OE1 | GLU | A | 494 | −35.121 | 22.759  | −17.819 | 1.00 | 48.52  | O |
| ATOM | 709 | OE2 | GLU | A | 494 | −33.040 | 22.562  | −17.145 | 1.00 | 43.04  | O |
| ATOM | 710 | N   | LEU | A | 495 | −36.114 | 17.833  | −20.288 | 1.00 | 44.34  | N |
| ATOM | 711 | CA  | LEU | A | 495 | −35.732 | 17.240  | −21.564 | 1.00 | 52.01  | C |
| ATOM | 712 | C   | LEU | A | 495 | −35.170 | 18.333  | −22.474 | 1.00 | 49.14  | C |
| ATOM | 713 | O   | LEU | A | 495 | −35.839 | 19.327  | −22.737 | 1.00 | 41.11  | O |
| ATOM | 714 | CB  | LEU | A | 495 | −36.969 | 16.618  | −22.222 | 1.00 | 53.75  | C |
| ATOM | 715 | CG  | LEU | A | 495 | −36.813 | 15.930  | −23.579 | 1.00 | 49.77  | C |
| ATOM | 716 | CD1 | LEU | A | 495 | −35.921 | 14.714  | −23.445 | 1.00 | 52.36  | C |
| ATOM | 717 | CD2 | LEU | A | 495 | −38.175 | 15.545  | −24.152 | 1.00 | 45.56  | C |
| ATOM | 718 | N   | MET | A | 496 | −33.940 | 18.160  | −22.936 | 1.00 | 43.99  | N |

TABLE 3-continued

Atomic coordinates of RSK2 model (pdb file)

| ATOM | 719 | CA  | MET | A | 496 | −33.329 | 19.135 | −23.819 | 1.00 | 46.37 | C |
|------|-----|-----|-----|---|-----|---------|--------|---------|------|-------|---|
| ATOM | 720 | C   | MET | A | 496 | −33.924 | 18.948 | −25.206 | 1.00 | 57.98 | C |
| ATOM | 721 | O   | MET | A | 496 | −33.797 | 17.879 | −25.809 | 1.00 | 54.49 | O |
| ATOM | 722 | CB  | MET | A | 496 | −31.813 | 18.932 | −23.905 | 1.00 | 40.46 | C |
| ATOM | 723 | CG  | MET | A | 496 | −31.060 | 19.087 | −22.581 | 1.00 | 56.19 | C |
| ATOM | 724 | SD  | MET | A | 496 | −31.337 | 20.682 | −21.779 | 1.00 | 48.97 | S |
| ATOM | 725 | CE  | MET | A | 496 | −32.293 | 20.107 | −20.397 | 1.00 | 57.78 | C |
| ATOM | 726 | N   | LYS | A | 497 | −34.585 | 19.975 | −25.714 | 1.00 | 40.94 | N |
| ATOM | 727 | CA  | LYS | A | 497 | −35.167 | 19.860 | −27.047 | 1.00 | 45.17 | C |
| ATOM | 728 | C   | LYS | A | 497 | −34.495 | 20.737 | −28.113 | 1.00 | 49.87 | C |
| ATOM | 729 | O   | LYS | A | 497 | −34.962 | 20.807 | −29.250 | 1.00 | 50.66 | O |
| ATOM | 730 | CB  | LYS | A | 497 | −36.675 | 20.099 | −26.970 | 1.00 | 56.71 | C |
| ATOM | 731 | CG  | LYS | A | 497 | −37.398 | 18.916 | −26.346 | 1.00 | 55.20 | C |
| ATOM | 732 | CD  | LYS | A | 497 | −38.627 | 19.340 | −25.593 | 1.00 | 70.78 | C |
| ATOM | 733 | CE  | LYS | A | 497 | −39.857 | 19.274 | −26.456 | 1.00 | 80.50 | C |
| ATOM | 734 | NZ  | LYS | A | 497 | −41.051 | 19.011 | −25.602 | 1.00 | 73.66 | N |
| ATOM | 735 | N   | GLY | A | 498 | −33.386 | 21.384 | −27.762 | 1.00 | 39.67 | N |
| ATOM | 736 | CA  | GLY | A | 498 | −32.716 | 22.262 | −28.716 | 1.00 | 45.22 | C |
| ATOM | 737 | C   | GLY | A | 498 | −31.396 | 21.703 | −29.239 | 1.00 | 44.27 | C |
| ATOM | 738 | O   | GLY | A | 498 | −30.691 | 22.370 | −29.983 | 1.00 | 46.01 | O |
| ATOM | 739 | N   | GLY | A | 499 | −31.053 | 20.490 | −28.829 | 1.00 | 41.63 | N |
| ATOM | 740 | CA  | GLY | A | 499 | −29.872 | 19.821 | −29.350 | 1.00 | 47.76 | C |
| ATOM | 741 | C   | GLY | A | 499 | −28.587 | 20.297 | −28.699 | 1.00 | 45.86 | C |
| ATOM | 742 | O   | GLY | A | 499 | −28.606 | 21.118 | −27.771 | 1.00 | 47.81 | O |
| ATOM | 743 | N   | GLU | A | 500 | −27.467 | 19.748 | −29.161 | 1.00 | 43.83 | N |
| ATOM | 744 | CA  | GLU | A | 500 | −26.159 | 20.146 | −28.669 | 1.00 | 39.42 | C |
| ATOM | 745 | C   | GLU | A | 500 | −25.818 | 21.560 | −29.142 | 1.00 | 39.03 | C |
| ATOM | 746 | O   | GLU | A | 500 | −26.126 | 21.945 | −30.266 | 1.00 | 41.02 | O |
| ATOM | 747 | CB  | GLU | A | 500 | −25.076 | 19.146 | −29.104 | 1.00 | 50.27 | C |
| ATOM | 748 | CG  | GLU | A | 500 | −25.262 | 17.730 | −28.529 | 1.00 | 57.75 | C |
| ATOM | 749 | CD  | GLU | A | 500 | −24.260 | 16.704 | −29.076 | 1.00 | 65.28 | C |
| ATOM | 750 | OE1 | GLU | A | 500 | −23.227 | 17.095 | −29.673 | 1.00 | 59.91 | O |
| ATOM | 751 | OE2 | GLU | A | 500 | −24.510 | 15.491 | −28.906 | 1.00 | 57.79 | O |
| ATOM | 752 | N   | LEU | A | 501 | −25.137 | 22.313 | −28.283 | 1.00 | 38.16 | N |
| ATOM | 753 | CA  | LEU | A | 501 | −24.861 | 23.719 | −28.532 | 1.00 | 41.41 | C |
| ATOM | 754 | C   | LEU | A | 501 | −24.048 | 23.854 | −29.794 | 1.00 | 46.27 | C |
| ATOM | 755 | O   | LEU | A | 501 | −24.397 | 24.605 | −30.707 | 1.00 | 40.55 | O |
| ATOM | 756 | CB  | LEU | A | 501 | −24.054 | 24.294 | −27.361 | 1.00 | 47.68 | C |
| ATOM | 757 | CG  | LEU | A | 501 | −23.764 | 25.793 | −27.409 | 1.00 | 50.83 | C |
| ATOM | 758 | CD1 | LEU | A | 501 | −24.726 | 26.543 | −26.518 | 1.00 | 47.57 | C |
| ATOM | 759 | CD2 | LEU | A | 501 | −22.318 | 26.081 | −27.012 | 1.00 | 50.02 | C |
| ATOM | 760 | N   | LEU | A | 502 | −22.969 | 23.092 | −29.854 | 1.00 | 47.06 | N |
| ATOM | 761 | CA  | LEU | A | 502 | −22.070 | 23.155 | −30.994 | 1.00 | 61.68 | C |
| ATOM | 762 | C   | LEU | A | 502 | −22.771 | 22.814 | −32.299 | 1.00 | 57.22 | C |
| ATOM | 763 | O   | LEU | A | 502 | −22.587 | 23.491 | −33.308 | 1.00 | 65.34 | O |
| ATOM | 764 | CB  | LEU | A | 502 | −20.880 | 22.226 | −30.760 | 1.00 | 60.29 | C |
| ATOM | 765 | CG  | LEU | A | 502 | −19.557 | 22.750 | −31.285 | 1.00 | 49.20 | C |
| ATOM | 766 | CD1 | LEU | A | 502 | −19.431 | 24.233 | −30.970 | 1.00 | 39.55 | C |
| ATOM | 767 | CD2 | LEU | A | 502 | −18.436 | 21.930 | −30.685 | 1.00 | 39.02 | C |
| ATOM | 768 | N   | ASP | A | 503 | −23.590 | 21.770 | −32.281 | 1.00 | 50.82 | N |
| ATOM | 769 | CA  | ASP | A | 503 | −24.339 | 21.383 | −33.461 | 1.00 | 58.10 | C |
| ATOM | 770 | C   | ASP | A | 503 | −25.160 | 22.534 | −34.017 | 1.00 | 62.01 | C |
| ATOM | 771 | O   | ASP | A | 503 | −25.243 | 22.722 | −35.225 | 1.00 | 57.67 | O |
| ATOM | 772 | CB  | ASP | A | 503 | −25.254 | 20.198 | −33.156 | 1.00 | 70.69 | C |
| ATOM | 773 | CG  | ASP | A | 503 | −24.754 | 18.905 | −33.766 | 1.00 | 84.33 | C |
| ATOM | 774 | OD1 | ASP | A | 503 | −24.178 | 18.964 | −34.879 | 1.00 | 82.05 | O |
| ATOM | 775 | OD2 | ASP | A | 503 | −24.938 | 17.836 | −33.134 | 1.00 | 78.88 | O |
| ATOM | 776 | N   | LYS | A | 504 | −25.761 | 23.314 | −33.131 | 1.00 | 47.11 | N |
| ATOM | 777 | CA  | LYS | A | 504 | −26.582 | 24.430 | −33.574 | 1.00 | 41.50 | C |
| ATOM | 778 | C   | LYS | A | 504 | −25.726 | 25.605 | −34.073 | 1.00 | 34.69 | C |
| ATOM | 779 | O   | LYS | A | 504 | −25.974 | 26.154 | −35.145 | 1.00 | 39.09 | O |
| ATOM | 780 | CB  | LYS | A | 504 | −27.517 | 24.849 | −32.444 | 1.00 | 51.11 | C |
| ATOM | 781 | CG  | LYS | A | 504 | −28.532 | 23.758 | −32.138 | 1.00 | 59.48 | C |
| ATOM | 782 | CD  | LYS | A | 504 | −29.400 | 23.530 | −33.385 | 1.00 | 59.78 | C |
| ATOM | 783 | CE  | LYS | A | 504 | −29.979 | 22.121 | −33.461 | 1.00 | 53.56 | C |
| ATOM | 784 | NZ  | LYS | A | 504 | −31.204 | 22.145 | −34.326 | 1.00 | 58.33 | N |
| ATOM | 785 | N   | ILE | A | 505 | −24.704 | 25.946 | −33.296 | 1.00 | 38.17 | N |
| ATOM | 786 | CA  | ILE | A | 505 | −23.808 | 27.068 | −33.598 | 1.00 | 43.13 | C |
| ATOM | 787 | C   | ILE | A | 505 | −22.992 | 26.848 | −34.885 | 1.00 | 43.49 | C |
| ATOM | 788 | O   | ILE | A | 505 | −22.812 | 27.768 | −35.674 | 1.00 | 42.56 | O |
| ATOM | 789 | CB  | ILE | A | 505 | −22.884 | 27.334 | −32.365 | 1.00 | 44.16 | C |
| ATOM | 790 | CG1 | ILE | A | 505 | −23.693 | 27.977 | −31.243 | 1.00 | 45.64 | C |
| ATOM | 791 | CG2 | ILE | A | 505 | −21.682 | 28.229 | −32.695 | 1.00 | 43.62 | C |
| ATOM | 792 | CD1 | ILE | A | 505 | −22.893 | 28.175 | −29.971 | 1.00 | 49.46 | C |
| ATOM | 793 | N   | LEU | A | 506 | −22.503 | 25.632 | −35.102 | 1.00 | 43.11 | N |
| ATOM | 794 | CA  | LEU | A | 506 | −21.689 | 25.362 | −36.291 | 1.00 | 47.49 | C |
| ATOM | 795 | C   | LEU | A | 506 | −22.502 | 25.392 | −37.579 | 1.00 | 49.85 | C |
| ATOM | 796 | O   | LEU | A | 506 | −21.947 | 25.584 | −38.672 | 1.00 | 43.51 | O |

TABLE 3-continued

Atomic coordinates of RSK2 model (pdb file)

| ATOM | 797 | CB | LEU | A | 506 | −20.980 | 24.019 | −36.171 | 1.00 | 40.84 | C |
|---|---|---|---|---|---|---|---|---|---|---|---|
| ATOM | 798 | CG | LEU | A | 506 | −19.883 | 23.953 | −35.108 | 1.00 | 43.79 | C |
| ATOM | 799 | CD1 | LEU | A | 506 | −19.263 | 22.559 | −35.119 | 1.00 | 39.75 | C |
| ATOM | 800 | CD2 | LEU | A | 506 | −18.840 | 25.035 | −35.365 | 1.00 | 43.93 | C |
| ATOM | 801 | N | ARG | A | 507 | −23.812 | 25.186 | −37.459 | 1.00 | 42.71 | N |
| ATOM | 802 | CA | ARG | A | 507 | −24.686 | 25.238 | −38.628 | 1.00 | 50.81 | C |
| ATOM | 803 | C | ARG | A | 507 | −25.262 | 26.625 | −38.883 | 1.00 | 60.25 | C |
| ATOM | 804 | O | ARG | A | 507 | −26.035 | 26.803 | −39.820 | 1.00 | 57.38 | O |
| ATOM | 805 | CB | ARG | A | 507 | −25.827 | 24.223 | −38.508 | 1.00 | 51.12 | C |
| ATOM | 806 | CG | ARG | A | 507 | −25.358 | 22.796 | −38.568 | 1.00 | 57.10 | C |
| ATOM | 807 | CD | ARG | A | 507 | −26.394 | 21.843 | −38.018 | 1.00 | 69.33 | C |
| ATOM | 808 | NE | ARG | A | 507 | −25.837 | 20.504 | −37.861 | 1.00 | 74.26 | N |
| ATOM | 809 | CZ | ARG | A | 507 | −25.738 | 19.634 | −38.860 | 1.00 | 63.10 | C |
| ATOM | 810 | NH1 | ARG | A | 507 | −25.217 | 18.427 | −38.658 | 1.00 | 51.88 | N |
| ATOM | 811 | NH2 | ARG | A | 507 | −26.159 | 19.975 | −40.070 | 1.00 | 74.46 | N |
| ATOM | 812 | N | GLN | A | 508 | −24.896 | 27.605 | −38.060 | 1.00 | 50.01 | N |
| ATOM | 813 | CA | GLN | A | 508 | −25.326 | 28.997 | −38.307 | 1.00 | 47.42 | C |
| ATOM | 814 | C | GLN | A | 508 | −24.298 | 29.794 | −39.097 | 1.00 | 54.12 | C |
| ATOM | 815 | O | GLN | A | 508 | −23.222 | 30.085 | −38.580 | 1.00 | 56.49 | O |
| ATOM | 816 | CB | GLN | A | 508 | −25.566 | 29.721 | −36.980 | 1.00 | 52.02 | C |
| ATOM | 817 | CG | GLN | A | 508 | −26.776 | 29.255 | −36.211 | 1.00 | 60.94 | C |
| ATOM | 818 | CD | GLN | A | 508 | −27.054 | 30.135 | −35.011 | 1.00 | 74.19 | C |
| ATOM | 819 | OE1 | GLN | A | 508 | −26.615 | 31.283 | −34.957 | 1.00 | 81.70 | O |
| ATOM | 820 | NE2 | GLN | A | 508 | −27.784 | 29.603 | −34.042 | 1.00 | 80.80 | N |
| ATOM | 821 | N | LYS | A | 509 | −24.630 | 30.201 | −40.320 | 1.00 | 47.51 | N |
| ATOM | 822 | CA | LYS | A | 509 | −23.649 | 30.894 | −41.153 | 1.00 | 60.66 | C |
| ATOM | 823 | C | LYS | A | 509 | −23.365 | 32.312 | −40.684 | 1.00 | 61.81 | C |
| ATOM | 824 | O | LYS | A | 509 | −22.298 | 32.863 | −40.966 | 1.00 | 53.39 | O |
| ATOM | 825 | CB | LYS | A | 509 | −24.059 | 30.903 | −42.628 | 1.00 | 71.75 | C |
| ATOM | 826 | CG | LYS | A | 509 | −23.565 | 29.698 | −43.409 | 1.00 | 87.43 | C |
| ATOM | 827 | CD | LYS | A | 509 | −24.376 | 28.458 | −43.078 | 1.00 | 96.37 | C |
| ATOM | 828 | CE | LYS | A | 509 | −23.737 | 27.214 | −43.657 | 1.00 | 96.42 | C |
| ATOM | 829 | NZ | LYS | A | 509 | −23.375 | 27.413 | −45.079 | 1.00 | 98.30 | N |
| ATOM | 830 | N | PHE | A | 510 | −24.303 | 32.902 | −39.952 | 1.00 | 51.35 | N |
| ATOM | 831 | CA | PHE | A | 510 | −24.177 | 34.324 | −39.625 | 1.00 | 51.65 | C |
| ATOM | 832 | C | PHE | A | 510 | −23.748 | 34.564 | −38.179 | 1.00 | 61.44 | C |
| ATOM | 833 | O | PHE | A | 510 | −23.906 | 35.648 | −37.625 | 1.00 | 64.41 | O |
| ATOM | 834 | CB | PHE | A | 510 | −25.456 | 35.059 | −40.005 | 1.00 | 47.78 | C |
| ATOM | 835 | CG | PHE | A | 510 | −25.655 | 35.128 | −41.492 | 1.00 | 50.13 | C |
| ATOM | 836 | CD2 | PHE | A | 510 | −26.369 | 34.141 | −42.160 | 1.00 | 53.82 | C |
| ATOM | 837 | CD1 | PHE | A | 510 | −25.070 | 36.139 | −42.228 | 1.00 | 49.66 | C |
| ATOM | 838 | CE2 | PHE | A | 510 | −26.526 | 34.192 | −43.536 | 1.00 | 53.67 | C |
| ATOM | 839 | CE1 | PHE | A | 510 | −25.235 | 36.201 | −43.627 | 1.00 | 52.20 | C |
| ATOM | 840 | CZ | PHE | A | 510 | −25.959 | 35.222 | −44.269 | 1.00 | 58.34 | C |
| ATOM | 841 | N | PHE | A | 511 | −23.144 | 33.541 | −37.602 | 1.00 | 48.60 | N |
| ATOM | 842 | CA | PHE | A | 511 | −22.689 | 33.575 | −36.218 | 1.00 | 46.62 | C |
| ATOM | 843 | C | PHE | A | 511 | −21.472 | 34.506 | −36.112 | 1.00 | 42.18 | C |
| ATOM | 844 | O | PHE | A | 511 | −20.626 | 34.534 | −37.022 | 1.00 | 54.94 | O |
| ATOM | 845 | CB | PHE | A | 511 | −22.340 | 32.149 | −35.803 | 1.00 | 48.69 | C |
| ATOM | 846 | CG | PHE | A | 511 | −22.078 | 31.981 | −34.342 | 1.00 | 47.80 | C |
| ATOM | 847 | CD1 | PHE | A | 511 | −23.124 | 31.939 | −33.440 | 1.00 | 52.34 | C |
| ATOM | 848 | CD2 | PHE | A | 511 | −20.777 | 31.835 | −33.873 | 1.00 | 57.48 | C |
| ATOM | 849 | CE1 | PHE | A | 511 | −22.881 | 31.769 | −32.088 | 1.00 | 52.74 | C |
| ATOM | 850 | CE2 | PHE | A | 511 | −20.526 | 31.668 | −32.529 | 1.00 | 51.55 | C |
| ATOM | 851 | CZ | PHE | A | 511 | −21.582 | 31.635 | −31.631 | 1.00 | 48.56 | C |
| ATOM | 852 | N | SER | A | 512 | −21.388 | 35.275 | −35.025 | 1.00 | 53.47 | N |
| ATOM | 853 | CA | SER | A | 512 | −20.327 | 36.280 | −34.853 | 1.00 | 47.54 | C |
| ATOM | 854 | C | SER | A | 512 | −19.599 | 36.114 | −33.525 | 1.00 | 49.01 | C |
| ATOM | 855 | O | SER | A | 512 | −20.075 | 35.421 | −32.647 | 1.00 | 42.40 | O |
| ATOM | 856 | CB | SER | A | 512 | −20.917 | 37.694 | −34.903 | 1.00 | 52.74 | C |
| ATOM | 857 | OG | SER | A | 512 | −21.831 | 37.891 | −33.826 | 1.00 | 56.71 | O |
| ATOM | 858 | N | GLU | A | 513 | −18.450 | 36.773 | −33.375 | 1.00 | 46.85 | N |
| ATOM | 859 | CA | GLU | A | 513 | −17.726 | 36.781 | −32.105 | 1.00 | 49.81 | C |
| ATOM | 860 | C | GLU | A | 513 | −18.583 | 37.290 | −30.948 | 1.00 | 52.64 | C |
| ATOM | 861 | O | GLU | A | 513 | −18.469 | 36.813 | −29.808 | 1.00 | 43.22 | O |
| ATOM | 862 | CB | GLU | A | 513 | −16.467 | 37.653 | −32.207 | 1.00 | 52.85 | C |
| ATOM | 863 | CG | GLU | A | 513 | −15.359 | 37.063 | −33.046 | 1.00 | 61.32 | C |
| ATOM | 864 | CD | GLU | A | 513 | −14.037 | 37.772 | −32.827 | 1.00 | 63.66 | C |
| ATOM | 865 | OE1 | GLU | A | 513 | −13.749 | 38.182 | −31.673 | 1.00 | 55.10 | O |
| ATOM | 866 | OE2 | GLU | A | 513 | −13.284 | 37.923 | −33.811 | 1.00 | 51.31 | O |
| ATOM | 867 | N | ARG | A | 514 | −19.416 | 38.280 | −31.241 | 1.00 | 45.58 | N |
| ATOM | 868 | CA | ARG | A | 514 | −20.311 | 38.849 | −30.245 | 1.00 | 51.99 | C |
| ATOM | 869 | C | ARG | A | 514 | −21.194 | 37.764 | −29.651 | 1.00 | 50.00 | C |
| ATOM | 870 | O | ARG | A | 514 | −21.372 | 37.665 | −28.433 | 1.00 | 45.21 | O |
| ATOM | 871 | CB | ARG | A | 514 | −21.187 | 39.912 | −30.897 | 1.00 | 54.99 | C |
| ATOM | 872 | CG | ARG | A | 514 | −21.976 | 40.753 | −29.926 | 1.00 | 79.96 | C |
| ATOM | 873 | CD | ARG | A | 514 | −21.246 | 42.048 | −29.636 | 1.00 | 91.72 | C |
| ATOM | 874 | NE | ARG | A | 514 | −21.080 | 42.864 | −30.835 | 1.00 | 98.18 | N |

TABLE 3-continued

Atomic coordinates of RSK2 model (pdb file)

| ATOM | 875 | CZ | ARG | A | 514 | −21.848 | 43.905 | −31.144 | 1.00 | 102.81 | C |
|---|---|---|---|---|---|---|---|---|---|---|---|
| ATOM | 876 | NH1 | ARG | A | 514 | −22.838 | 44.265 | −30.338 | 1.00 | 97.13 | N |
| ATOM | 877 | NH2 | ARG | A | 514 | −21.623 | 44.589 | −32.256 | 1.00 | 108.98 | N |
| ATOM | 878 | N | GLU | A | 515 | −21.754 | 36.942 | −30.522 | 1.00 | 46.44 | N |
| ATOM | 879 | CA | GLU | A | 515 | −22.570 | 35.831 | −30.064 | 1.00 | 45.26 | C |
| ATOM | 880 | C | GLU | A | 515 | −21.766 | 34.723 | −29.390 | 1.00 | 47.88 | C |
| ATOM | 881 | O | GLU | A | 515 | −22.263 | 34.075 | −28.477 | 1.00 | 41.64 | O |
| ATOM | 882 | CB | GLU | A | 515 | −23.414 | 35.275 | −31.216 | 1.00 | 53.07 | C |
| ATOM | 883 | CG | GLU | A | 515 | −24.664 | 36.114 | −31.465 | 1.00 | 67.46 | C |
| ATOM | 884 | CD | GLU | A | 515 | −25.237 | 36.706 | −30.166 | 1.00 | 93.12 | C |
| ATOM | 885 | OE1 | GLU | A | 515 | −25.936 | 35.982 | −29.419 | 1.00 | 97.39 | O |
| ATOM | 886 | OE2 | GLU | A | 515 | −24.991 | 37.903 | −29.890 | 1.00 | 99.77 | O |
| ATOM | 887 | N | ALA | A | 516 | −20.534 | 34.496 | −29.844 | 1.00 | 46.76 | N |
| ATOM | 888 | CA | ALA | A | 516 | −19.698 | 33.469 | −29.229 | 1.00 | 39.69 | C |
| ATOM | 889 | C | ALA | A | 516 | −19.356 | 33.881 | −27.797 | 1.00 | 42.62 | C |
| ATOM | 890 | O | ALA | A | 516 | −19.323 | 33.044 | −26.898 | 1.00 | 36.58 | O |
| ATOM | 891 | CB | ALA | A | 516 | −18.418 | 33.240 | −30.036 | 1.00 | 39.68 | C |
| ATOM | 892 | N | SER | A | 517 | −19.110 | 35.175 | −27.609 | 1.00 | 39.35 | N |
| ATOM | 893 | CA | SER | A | 517 | −18.799 | 35.730 | −26.303 | 1.00 | 40.22 | C |
| ATOM | 894 | C | SER | A | 517 | −19.980 | 35.609 | −25.355 | 1.00 | 43.04 | C |
| ATOM | 895 | O | SER | A | 517 | −19.807 | 35.200 | −24.210 | 1.00 | 40.22 | O |
| ATOM | 896 | CB | SER | A | 517 | −18.358 | 37.193 | −26.433 | 1.00 | 47.11 | C |
| ATOM | 897 | OG | SER | A | 517 | −17.956 | 37.713 | −25.176 | 1.00 | 49.04 | O |
| ATOM | 898 | N | ALA | A | 518 | −21.180 | 35.949 | −25.826 | 1.00 | 42.31 | N |
| ATOM | 899 | CA | ALA | A | 518 | −22.369 | 35.784 | −24.987 | 1.00 | 44.87 | C |
| ATOM | 900 | C | ALA | A | 518 | −22.528 | 34.328 | −24.528 | 1.00 | 45.63 | C |
| ATOM | 901 | O | ALA | A | 518 | −22.824 | 34.061 | −23.356 | 1.00 | 43.17 | O |
| ATOM | 902 | CB | ALA | A | 518 | −23.640 | 36.280 | −25.705 | 1.00 | 46.44 | C |
| ATOM | 903 | N | VAL | A | 519 | −22.319 | 33.388 | −25.445 | 1.00 | 38.24 | N |
| ATOM | 904 | CA | VAL | A | 519 | −22.393 | 31.968 | −25.102 | 1.00 | 40.27 | C |
| ATOM | 905 | C | VAL | A | 519 | −21.317 | 31.520 | −24.114 | 1.00 | 42.86 | C |
| ATOM | 906 | O | VAL | A | 519 | −21.618 | 30.857 | −23.108 | 1.00 | 41.53 | O |
| ATOM | 907 | CB | VAL | A | 519 | −22.326 | 31.088 | −26.366 | 1.00 | 38.82 | C |
| ATOM | 908 | CG1 | VAL | A | 519 | −22.028 | 29.632 | −25.993 | 1.00 | 41.43 | C |
| ATOM | 909 | CG2 | VAL | A | 519 | −23.624 | 31.217 | −27.173 | 1.00 | 46.53 | C |
| ATOM | 910 | N | LEU | A | 520 | −20.059 | 31.869 | −24.379 | 1.00 | 37.30 | N |
| ATOM | 911 | CA | LEU | A | 520 | −19.003 | 31.516 | −23.438 | 1.00 | 44.12 | C |
| ATOM | 912 | C | LEU | A | 520 | −19.248 | 32.141 | −22.058 | 1.00 | 39.46 | C |
| ATOM | 913 | O | LEU | A | 520 | −18.998 | 31.507 | −21.034 | 1.00 | 36.62 | O |
| ATOM | 914 | CB | LEU | A | 520 | −17.614 | 31.904 | −23.975 | 1.00 | 35.95 | C |
| ATOM | 915 | CG | LEU | A | 520 | −16.438 | 31.436 | −23.108 | 1.00 | 53.96 | C |
| ATOM | 916 | CD1 | LEU | A | 520 | −16.456 | 29.921 | −22.929 | 1.00 | 42.20 | C |
| ATOM | 917 | CD2 | LEU | A | 520 | −15.094 | 31.892 | −23.687 | 1.00 | 58.16 | C |
| ATOM | 918 | N | PHE | A | 521 | −19.736 | 33.375 | −22.031 | 1.00 | 38.19 | N |
| ATOM | 919 | CA | PHE | A | 521 | −19.982 | 34.057 | −20.759 | 1.00 | 41.94 | C |
| ATOM | 920 | C | PHE | A | 521 | −20.979 | 33.271 | −19.917 | 1.00 | 50.33 | C |
| ATOM | 921 | O | PHE | A | 521 | −20.730 | 33.001 | −18.743 | 1.00 | 41.44 | O |
| ATOM | 922 | CB | PHE | A | 521 | −20.527 | 35.477 | −20.988 | 1.00 | 39.48 | C |
| ATOM | 923 | CG | PHE | A | 521 | −21.111 | 36.112 | −19.743 | 1.00 | 50.05 | C |
| ATOM | 924 | CD1 | PHE | A | 521 | −20.281 | 36.640 | −18.757 | 1.00 | 48.93 | C |
| ATOM | 925 | CD2 | PHE | A | 521 | −22.489 | 36.179 | −19.559 | 1.00 | 50.85 | C |
| ATOM | 926 | CE1 | PHE | A | 521 | −20.818 | 37.225 | −17.604 | 1.00 | 56.13 | C |
| ATOM | 927 | CE2 | PHE | A | 521 | −23.029 | 36.755 | −18.415 | 1.00 | 53.14 | C |
| ATOM | 928 | CZ | PHE | A | 521 | −22.191 | 37.284 | −17.436 | 1.00 | 58.43 | C |
| ATOM | 929 | N | THR | A | 522 | −22.115 | 32.927 | −20.525 | 1.00 | 44.17 | N |
| ATOM | 930 | CA | THR | A | 522 | −23.164 | 32.179 | −19.835 | 1.00 | 39.19 | C |
| ATOM | 931 | C | THR | A | 522 | −22.647 | 30.857 | −19.280 | 1.00 | 43.18 | C |
| ATOM | 932 | O | THR | A | 522 | −22.882 | 30.496 | −18.109 | 1.00 | 38.43 | O |
| ATOM | 933 | CB | THR | A | 522 | −24.331 | 31.915 | −20.789 | 1.00 | 46.53 | C |
| ATOM | 934 | OG1 | THR | A | 522 | −24.933 | 33.169 | −21.128 | 1.00 | 43.18 | O |
| ATOM | 935 | CG2 | THR | A | 522 | −25.369 | 31.010 | −20.137 | 1.00 | 43.99 | C |
| ATOM | 936 | N | ILE | A | 523 | −21.906 | 30.143 | −20.109 | 1.00 | 35.82 | N |
| ATOM | 937 | CA | ILE | A | 523 | −21.339 | 28.865 | −19.681 | 1.00 | 38.56 | C |
| ATOM | 938 | C | ILE | A | 523 | −20.274 | 29.036 | −18.617 | 1.00 | 44.89 | C |
| ATOM | 939 | O | ILE | A | 523 | −20.266 | 28.308 | −17.626 | 1.00 | 38.18 | O |
| ATOM | 940 | CB | ILE | A | 523 | −20.754 | 28.091 | −20.878 | 1.00 | 39.30 | C |
| ATOM | 941 | CG1 | ILE | A | 523 | −21.878 | 27.752 | −21.878 | 1.00 | 40.35 | C |
| ATOM | 942 | CG2 | ILE | A | 523 | −20.008 | 26.842 | −20.394 | 1.00 | 36.07 | C |
| ATOM | 943 | CD1 | ILE | A | 523 | −21.353 | 27.295 | −23.291 | 1.00 | 40.97 | C |
| ATOM | 944 | N | THR | A | 524 | −19.371 | 29.991 | −18.806 | 1.00 | 39.97 | N |
| ATOM | 945 | CA | THR | A | 524 | −18.260 | 30.128 | −17.867 | 1.00 | 40.42 | C |
| ATOM | 946 | C | THR | A | 524 | −18.751 | 30.649 | −16.510 | 1.00 | 44.05 | C |
| ATOM | 947 | O | THR | A | 524 | −18.200 | 30.309 | −15.462 | 1.00 | 43.70 | O |
| ATOM | 948 | CB | THR | A | 524 | −17.170 | 31.053 | −18.419 | 1.00 | 41.81 | C |
| ATOM | 949 | OG1 | THR | A | 524 | −16.774 | 30.579 | −19.713 | 1.00 | 44.20 | O |
| ATOM | 950 | CG2 | THR | A | 524 | −15.951 | 31.081 | −17.481 | 1.00 | 44.47 | C |
| ATOM | 951 | N | LYS | A | 525 | −19.791 | 31.472 | −16.531 | 1.00 | 36.44 | N |
| ATOM | 952 | CA | LYS | A | 525 | −20.404 | 31.962 | −15.286 | 1.00 | 46.98 | C |

TABLE 3-continued

Atomic coordinates of RSK2 model (pdb file)

| ATOM | 953 | C | LYS | A | 525 | −20.898 | 30.800 | −14.437 | 1.00 | 45.64 | C |
|---|---|---|---|---|---|---|---|---|---|---|---|
| ATOM | 954 | O | LYS | A | 525 | −20.820 | 30.812 | −13.194 | 1.00 | 45.88 | O |
| ATOM | 955 | CB | LYS | A | 525 | −21.600 | 32.843 | −15.624 | 1.00 | 48.44 | C |
| ATOM | 956 | CG | LYS | A | 525 | −21.391 | 34.295 | −15.366 | 1.00 | 60.84 | C |
| ATOM | 957 | CD | LYS | A | 525 | −21.428 | 34.553 | −13.891 | 1.00 | 68.50 | C |
| ATOM | 958 | CE | LYS | A | 525 | −20.968 | 35.953 | −13.572 | 1.00 | 83.23 | C |
| ATOM | 959 | NZ | LYS | A | 525 | −21.031 | 36.208 | −12.109 | 1.00 | 85.81 | N |
| ATOM | 960 | N | THR | A | 526 | −21.427 | 29.801 | −15.129 | 1.00 | 44.01 | N |
| ATOM | 961 | CA | THR | A | 526 | −21.996 | 28.628 | −14.492 | 1.00 | 43.39 | C |
| ATOM | 962 | C | THR | A | 526 | −20.889 | 27.774 | −13.911 | 1.00 | 44.97 | C |
| ATOM | 963 | O | THR | A | 526 | −21.013 | 27.229 | −12.807 | 1.00 | 45.05 | O |
| ATOM | 964 | CB | THR | A | 526 | −22.800 | 27.814 | −15.519 | 1.00 | 49.47 | C |
| ATOM | 965 | OG1 | THR | A | 526 | −23.815 | 28.654 | −16.092 | 1.00 | 42.80 | O |
| ATOM | 966 | CG2 | THR | A | 526 | −23.449 | 26.615 | −14.860 | 1.00 | 42.52 | C |
| ATOM | 967 | N | VAL | A | 527 | −19.804 | 27.655 | −14.663 | 1.00 | 37.84 | N |
| ATOM | 968 | CA | VAL | A | 527 | −18.632 | 26.882 | −14.222 | 1.00 | 36.68 | C |
| ATOM | 969 | C | VAL | A | 527 | −17.952 | 27.579 | −13.048 | 1.00 | 47.43 | C |
| ATOM | 970 | O | VAL | A | 527 | −17.495 | 26.930 | −12.093 | 1.00 | 47.77 | O |
| ATOM | 971 | CB | VAL | A | 527 | −17.657 | 26.652 | −15.408 | 1.00 | 35.64 | C |
| ATOM | 972 | CG1 | VAL | A | 527 | −16.314 | 26.071 | −14.938 | 1.00 | 37.07 | C |
| ATOM | 973 | CG2 | VAL | A | 527 | −18.297 | 25.754 | −16.478 | 1.00 | 37.19 | C |
| ATOM | 974 | N | GLU | A | 528 | −17.910 | 28.908 | −13.088 | 1.00 | 43.21 | N |
| ATOM | 975 | CA | GLU | A | 528 | −17.279 | 29.641 | −11.988 | 1.00 | 50.31 | C |
| ATOM | 976 | C | GLU | A | 528 | −18.038 | 29.406 | −10.692 | 1.00 | 51.84 | C |
| ATOM | 977 | O | GLU | A | 528 | −17.430 | 29.253 | −9.633 | 1.00 | 50.06 | O |
| ATOM | 978 | CB | GLU | A | 528 | −17.203 | 31.148 | −12.270 | 1.00 | 47.88 | C |
| ATOM | 979 | CG | GLU | A | 528 | −16.447 | 31.917 | −11.166 | 1.00 | 57.92 | C |
| ATOM | 980 | CD | GLU | A | 528 | −16.781 | 33.397 | −11.141 | 1.00 | 67.13 | C |
| ATOM | 981 | OE1 | GLU | A | 528 | −15.849 | 34.213 | −10.958 | 1.00 | 67.89 | O |
| ATOM | 982 | OE2 | GLU | A | 528 | −17.975 | 33.747 | −11.305 | 1.00 | 61.15 | O |
| ATOM | 983 | N | TYR | A | 529 | −19.368 | 29.395 | −10.786 | 1.00 | 46.83 | N |
| ATOM | 984 | CA | TYR | A | 529 | −20.220 | 29.162 | −9.619 | 1.00 | 53.15 | C |
| ATOM | 985 | C | TYR | A | 529 | −19.960 | 27.780 | −9.028 | 1.00 | 55.04 | C |
| ATOM | 986 | O | TYR | A | 529 | −19.759 | 27.634 | −7.821 | 1.00 | 55.31 | O |
| ATOM | 987 | CB | TYR | A | 529 | −21.694 | 29.292 | −10.001 | 1.00 | 45.52 | C |
| ATOM | 988 | CG | TYR | A | 529 | −22.635 | 28.812 | −8.921 | 1.00 | 53.63 | C |
| ATOM | 989 | CD1 | TYR | A | 529 | −22.818 | 29.550 | −7.750 | 1.00 | 59.08 | C |
| ATOM | 990 | CD2 | TYR | A | 529 | −23.333 | 27.621 | −9.057 | 1.00 | 50.42 | C |
| ATOM | 991 | CE1 | TYR | A | 529 | −23.678 | 29.119 | −6.750 | 1.00 | 57.32 | C |
| ATOM | 992 | CE2 | TYR | A | 529 | −24.203 | 27.181 | −8.054 | 1.00 | 56.34 | C |
| ATOM | 993 | CZ | TYR | A | 529 | −24.368 | 27.936 | −6.905 | 1.00 | 56.15 | C |
| ATOM | 994 | OH | TYR | A | 529 | −25.220 | 27.519 | −5.908 | 1.00 | 55.99 | O |
| ATOM | 995 | N | LEU | A | 530 | −19.965 | 26.773 | −9.896 | 1.00 | 48.63 | N |
| ATOM | 996 | CA | LEU | A | 530 | −19.684 | 25.390 | −9.507 | 1.00 | 52.33 | C |
| ATOM | 997 | C | LEU | A | 530 | −18.319 | 25.216 | −8.830 | 1.00 | 54.36 | C |
| ATOM | 998 | O | LEU | A | 530 | −18.209 | 24.638 | −7.736 | 1.00 | 51.02 | O |
| ATOM | 999 | CB | LEU | A | 530 | −19.803 | 24.489 | −10.748 | 1.00 | 45.87 | C |
| ATOM | 1000 | CG | LEU | A | 530 | −21.254 | 24.229 | −11.162 | 1.00 | 51.27 | C |
| ATOM | 1001 | CD1 | LEU | A | 530 | −21.335 | 23.569 | −12.535 | 1.00 | 45.59 | C |
| ATOM | 1002 | CD2 | LEU | A | 530 | −21.964 | 23.381 | −10.123 | 1.00 | 50.70 | C |
| ATOM | 1003 | N | HIS | A | 531 | −17.276 | 25.740 | −9.461 | 1.00 | 46.41 | N |
| ATOM | 1004 | CA | HIS | A | 531 | −15.926 | 25.615 | −8.902 | 1.00 | 48.23 | C |
| ATOM | 1005 | C | HIS | A | 531 | −15.822 | 26.262 | −7.528 | 1.00 | 54.40 | C |
| ATOM | 1006 | O | HIS | A | 531 | −15.128 | 25.757 | −6.649 | 1.00 | 54.69 | O |
| ATOM | 1007 | CB | HIS | A | 531 | −14.883 | 26.220 | −9.835 | 1.00 | 48.87 | C |
| ATOM | 1008 | CG | HIS | A | 531 | −14.622 | 25.400 | −11.061 | 1.00 | 45.72 | C |
| ATOM | 1009 | ND1 | HIS | A | 531 | −13.768 | 25.810 | −12.065 | 1.00 | 49.30 | N |
| ATOM | 1010 | CD2 | HIS | A | 531 | −15.107 | 24.194 | −11.450 | 1.00 | 40.60 | C |
| ATOM | 1011 | CE1 | HIS | A | 531 | −13.726 | 24.888 | −13.011 | 1.00 | 49.55 | C |
| ATOM | 1012 | NE2 | HIS | A | 531 | −14.531 | 23.899 | −12.665 | 1.00 | 43.23 | N |
| ATOM | 1013 | N | ALA | A | 532 | −16.526 | 27.376 | −7.353 | 1.00 | 53.41 | N |
| ATOM | 1014 | CA | ALA | A | 532 | −16.520 | 28.102 | −6.087 | 1.00 | 60.53 | C |
| ATOM | 1015 | C | ALA | A | 532 | −17.285 | 27.357 | −5.001 | 1.00 | 56.21 | C |
| ATOM | 1016 | O | ALA | A | 532 | −17.040 | 27.553 | −3.800 | 1.00 | 58.08 | O |
| ATOM | 1017 | CB | ALA | A | 532 | −17.113 | 29.488 | −6.288 | 1.00 | 63.00 | C |
| ATOM | 1018 | N | GLN | A | 533 | −18.235 | 26.524 | −5.415 | 1.00 | 54.01 | N |
| ATOM | 1019 | CA | GLN | A | 533 | −19.009 | 25.730 | −4.465 | 1.00 | 58.16 | C |
| ATOM | 1020 | C | GLN | A | 533 | −18.304 | 24.402 | −4.199 | 1.00 | 61.04 | C |
| ATOM | 1021 | O | GLN | A | 533 | −18.774 | 23.567 | −3.429 | 1.00 | 57.30 | O |
| ATOM | 1022 | CB | GLN | A | 533 | −20.418 | 25.494 | −4.996 | 1.00 | 61.67 | C |
| ATOM | 1023 | CG | GLN | A | 533 | −21.219 | 26.778 | −5.176 | 1.00 | 52.37 | C |
| ATOM | 1024 | CD | GLN | A | 533 | −21.390 | 27.540 | −3.882 | 1.00 | 69.76 | C |
| ATOM | 1025 | OE1 | GLN | A | 533 | −21.541 | 26.946 | −2.814 | 1.00 | 69.15 | O |
| ATOM | 1026 | NE2 | GLN | A | 533 | −21.359 | 28.864 | −3.968 | 1.00 | 81.08 | N |
| ATOM | 1027 | N | GLY | A | 534 | −17.159 | 24.227 | −4.845 | 1.00 | 55.01 | N |
| ATOM | 1028 | CA | GLY | A | 534 | −16.353 | 23.033 | −4.674 | 1.00 | 61.08 | C |
| ATOM | 1029 | C | GLY | A | 534 | −16.694 | 21.897 | −5.623 | 1.00 | 58.88 | C |
| ATOM | 1030 | O | GLY | A | 534 | −16.373 | 20.742 | −5.343 | 1.00 | 58.80 | O |

TABLE 3-continued

Atomic coordinates of RSK2 model (pdb file)

| ATOM | 1031 | N   | VAL | A | 535 | −17.338 | 22.210 | −6.748  | 1.00 | 50.49 | N |
|------|------|-----|-----|---|-----|---------|--------|---------|------|-------|---|
| ATOM | 1032 | CA  | VAL | A | 535 | −17.756 | 21.176 | −7.685  | 1.00 | 43.48 | C |
| ATOM | 1033 | C   | VAL | A | 535 | −16.954 | 21.277 | −8.979  | 1.00 | 46.58 | C |
| ATOM | 1034 | O   | VAL | A | 535 | −16.913 | 22.341 | −9.592  | 1.00 | 46.53 | O |
| ATOM | 1035 | CB  | VAL | A | 535 | −19.266 | 21.298 | −8.028  | 1.00 | 43.49 | C |
| ATOM | 1036 | CG1 | VAL | A | 535 | −19.664 | 20.297 | −9.103  | 1.00 | 44.34 | C |
| ATOM | 1037 | CG2 | VAL | A | 535 | −20.102 | 21.111 | −6.796  | 1.00 | 50.39 | C |
| ATOM | 1038 | N   | VAL | A | 536 | −16.291 | 20.183 | −9.367  | 1.00 | 52.70 | N |
| ATOM | 1039 | CA  | VAL | A | 536 | −15.681 | 20.067 | −10.699 | 1.00 | 48.52 | C |
| ATOM | 1040 | C   | VAL | A | 536 | −16.511 | 19.117 | −11.568 | 1.00 | 47.75 | C |
| ATOM | 1041 | O   | VAL | A | 536 | −16.985 | 18.086 | −11.092 | 1.00 | 46.09 | O |
| ATOM | 1042 | CB  | VAL | A | 536 | −14.223 | 19.569 | −10.636 | 1.00 | 44.76 | C |
| ATOM | 1043 | CG1 | VAL | A | 536 | −13.325 | 20.670 | −10.148 | 1.00 | 47.35 | C |
| ATOM | 1044 | CG2 | VAL | A | 536 | −14.100 | 18.343 | −9.740  | 1.00 | 46.95 | C |
| ATOM | 1045 | N   | HIS | A | 537 | −16.690 | 19.473 | −12.836 | 1.00 | 44.14 | N |
| ATOM | 1046 | CA  | HIS | A | 537 | −17.547 | 18.714 | −13.744 | 1.00 | 47.47 | C |
| ATOM | 1047 | C   | HIS | A | 537 | −16.869 | 17.433 | −14.242 | 1.00 | 50.85 | C |
| ATOM | 1048 | O   | HIS | A | 537 | −17.455 | 16.355 | −14.160 | 1.00 | 46.13 | O |
| ATOM | 1049 | CB  | HIS | A | 537 | −18.002 | 19.576 | −14.932 | 1.00 | 45.24 | C |
| ATOM | 1050 | CG  | HIS | A | 537 | −19.057 | 18.924 | −15.775 | 1.00 | 43.14 | C |
| ATOM | 1051 | ND1 | HIS | A | 537 | −18.777 | 17.902 | −16.658 | 1.00 | 37.01 | N |
| ATOM | 1052 | CD2 | HIS | A | 537 | −20.396 | 19.134 | −15.856 | 1.00 | 40.94 | C |
| ATOM | 1053 | CE1 | HIS | A | 537 | −19.893 | 17.518 | −17.251 | 1.00 | 44.97 | C |
| ATOM | 1054 | NE2 | HIS | A | 537 | −20.889 | 18.248 | −16.781 | 1.00 | 42.17 | N |
| ATOM | 1055 | N   | ARG | A | 538 | −15.649 | 17.560 | −14.769 | 1.00 | 45.32 | N |
| ATOM | 1056 | CA  | ARG | A | 538 | −14.817 | 16.411 | −15.149 | 1.00 | 45.72 | C |
| ATOM | 1057 | C   | ARG | A | 538 | −15.207 | 15.728 | −16.479 | 1.00 | 39.75 | C |
| ATOM | 1058 | O   | ARG | A | 538 | −14.466 | 14.883 | −16.991 | 1.00 | 48.52 | O |
| ATOM | 1059 | CB  | ARG | A | 538 | −14.695 | 15.387 | −14.006 | 1.00 | 50.00 | C |
| ATOM | 1060 | CG  | ARG | A | 538 | −14.168 | 15.975 | −12.687 | 1.00 | 51.59 | C |
| ATOM | 1061 | CD  | ARG | A | 538 | −13.922 | 14.914 | −11.603 | 1.00 | 53.43 | C |
| ATOM | 1062 | NE  | ARG | A | 538 | −12.834 | 14.004 | −11.964 | 1.00 | 72.80 | N |
| ATOM | 1063 | CZ  | ARG | A | 538 | −13.016 | 12.750 | −12.369 | 1.00 | 74.44 | C |
| ATOM | 1064 | NH1 | ARG | A | 538 | −14.247 | 12.259 | −12.461 | 1.00 | 66.10 | N |
| ATOM | 1065 | NH2 | ARG | A | 538 | −11.971 | 11.987 | −12.678 | 1.00 | 69.84 | N |
| ATOM | 1066 | N   | ASP | A | 539 | −16.353 | 16.085 | −17.040 | 1.00 | 45.64 | N |
| ATOM | 1067 | CA  | ASP | A | 539 | −16.720 | 15.563 | −18.359 | 1.00 | 45.45 | C |
| ATOM | 1068 | C   | ASP | A | 539 | −17.336 | 16.668 | −19.216 | 1.00 | 49.98 | C |
| ATOM | 1069 | O   | ASP | A | 539 | −18.368 | 16.472 | −19.861 | 1.00 | 40.78 | O |
| ATOM | 1070 | CB  | ASP | A | 539 | −17.708 | 14.393 | −18.214 | 1.00 | 65.97 | C |
| ATOM | 1071 | CG  | ASP | A | 539 | −17.884 | 13.602 | −19.509 | 1.00 | 64.04 | C |
| ATOM | 1072 | OD1 | ASP | A | 539 | −16.911 | 13.508 | −20.286 | 1.00 | 57.98 | O |
| ATOM | 1073 | OD2 | ASP | A | 539 | −18.994 | 13.073 | −19.750 | 1.00 | 66.09 | O |
| ATOM | 1074 | N   | LEU | A | 540 | −16.704 | 17.834 | −19.221 | 1.00 | 39.27 | N |
| ATOM | 1075 | CA  | LEU | A | 540 | −17.328 | 19.027 | −19.794 | 1.00 | 34.55 | C |
| ATOM | 1076 | C   | LEU | A | 540 | −17.090 | 19.156 | −21.296 | 1.00 | 43.81 | C |
| ATOM | 1077 | O   | LEU | A | 540 | −16.753 | 20.222 | −21.808 | 1.00 | 43.35 | O |
| ATOM | 1078 | CB  | LEU | A | 540 | −16.889 | 20.278 | −19.023 | 1.00 | 41.00 | C |
| ATOM | 1079 | CG  | LEU | A | 540 | −17.625 | 21.607 | −19.167 | 1.00 | 41.07 | C |
| ATOM | 1080 | CD1 | LEU | A | 540 | −19.155 | 21.441 | −18.934 | 1.00 | 42.09 | C |
| ATOM | 1081 | CD2 | LEU | A | 540 | −17.035 | 22.600 | −18.175 | 1.00 | 39.69 | C |
| ATOM | 1082 | N   | LYS | A | 541 | −17.296 | 18.060 | −22.012 | 1.00 | 38.50 | N |
| ATOM | 1083 | CA  | LYS | A | 541 | −17.196 | 18.101 | −23.469 | 1.00 | 41.16 | C |
| ATOM | 1084 | C   | LYS | A | 541 | −18.387 | 18.803 | −24.091 | 1.00 | 44.52 | C |
| ATOM | 1085 | O   | LYS | A | 541 | −19.461 | 18.880 | −23.476 | 1.00 | 41.51 | O |
| ATOM | 1086 | CB  | LYS | A | 541 | −17.010 | 16.695 | −24.045 | 1.00 | 47.70 | C |
| ATOM | 1087 | CG  | LYS | A | 541 | −18.039 | 15.670 | −23.628 | 1.00 | 48.98 | C |
| ATOM | 1088 | CD  | LYS | A | 541 | −17.495 | 14.262 | −23.877 | 1.00 | 46.93 | C |
| ATOM | 1089 | CE  | LYS | A | 541 | −18.591 | 13.215 | −23.770 | 1.00 | 55.15 | C |
| ATOM | 1090 | NZ  | LYS | A | 541 | −18.042 | 11.850 | −24.011 | 1.00 | 52.19 | N |
| ATOM | 1091 | N   | PRO | A | 542 | −18.198 | 19.351 | −25.306 | 1.00 | 39.77 | N |
| ATOM | 1092 | CA  | PRO | A | 542 | −19.266 | 20.060 | −26.021 | 1.00 | 38.27 | C |
| ATOM | 1093 | C   | PRO | A | 542 | −20.588 | 19.293 | −26.067 | 1.00 | 39.32 | C |
| ATOM | 1094 | O   | PRO | A | 542 | −21.661 | 19.902 | −25.995 | 1.00 | 40.92 | O |
| ATOM | 1095 | CB  | PRO | A | 542 | −18.689 | 20.221 | −27.437 | 1.00 | 46.04 | C |
| ATOM | 1096 | CG  | PRO | A | 542 | −17.213 | 20.401 | −27.194 | 1.00 | 45.41 | C |
| ATOM | 1097 | CD  | PRO | A | 542 | −16.880 | 19.550 | −25.954 | 1.00 | 36.60 | C |
| ATOM | 1098 | N   | SER | A | 543 | −20.540 | 17.972 | −26.172 | 1.00 | 35.93 | N |
| ATOM | 1099 | CA  | SER | A | 543 | −21.807 | 17.254 | −26.310 | 1.00 | 41.15 | C |
| ATOM | 1100 | C   | SER | A | 543 | −22.586 | 17.228 | −24.986 | 1.00 | 38.51 | C |
| ATOM | 1101 | O   | SER | A | 543 | −23.728 | 16.769 | −24.946 | 1.00 | 45.59 | O |
| ATOM | 1102 | CB  | SER | A | 543 | −21.580 | 15.843 | −26.844 | 1.00 | 44.01 | C |
| ATOM | 1103 | OG  | SER | A | 543 | −20.717 | 15.125 | −25.976 | 1.00 | 47.33 | O |
| ATOM | 1104 | N   | ASN | A | 544 | −21.979 | 17.712 | −23.903 | 1.00 | 35.63 | N |
| ATOM | 1105 | CA  | ASN | A | 544 | −22.703 | 17.782 | −22.630 | 1.00 | 38.84 | C |
| ATOM | 1106 | C   | ASN | A | 544 | −23.248 | 19.181 | −22.353 | 1.00 | 39.85 | C |
| ATOM | 1107 | O   | ASN | A | 544 | −23.682 | 19.482 | −21.243 | 1.00 | 42.61 | O |
| ATOM | 1108 | CB  | ASN | A | 544 | −21.842 | 17.275 | −21.474 | 1.00 | 37.11 | C |

TABLE 3-continued

Atomic coordinates of RSK2 model (pdb file)

| ATOM | 1109 | CG | ASN | A | 544 | −21.804 | 15.766 | −21.437 | 1.00 | 41.09 | C |
|---|---|---|---|---|---|---|---|---|---|---|---|
| ATOM | 1110 | OD1 | ASN | A | 544 | −22.745 | 15.121 | −21.914 | 1.00 | 41.04 | O |
| ATOM | 1111 | ND2 | ASN | A | 544 | −20.733 | 15.195 | −20.901 | 1.00 | 38.70 | N |
| ATOM | 1112 | N | ILE | A | 545 | −23.196 | 20.037 | −23.367 | 1.00 | 34.27 | N |
| ATOM | 1113 | CA | ILE | A | 545 | −23.695 | 21.400 | −23.228 | 1.00 | 36.15 | C |
| ATOM | 1114 | C | ILE | A | 545 | −24.764 | 21.569 | −24.274 | 1.00 | 47.98 | C |
| ATOM | 1115 | O | ILE | A | 545 | −24.480 | 21.523 | −25.468 | 1.00 | 38.44 | O |
| ATOM | 1116 | CB | ILE | A | 545 | −22.576 | 22.435 | −23.420 | 1.00 | 39.43 | C |
| ATOM | 1117 | CG1 | ILE | A | 545 | −21.481 | 22.193 | −22.378 | 1.00 | 43.27 | C |
| ATOM | 1118 | CG2 | ILE | A | 545 | −23.142 | 23.866 | −23.318 | 1.00 | 36.12 | C |
| ATOM | 1119 | CD1 | ILE | A | 545 | −20.379 | 23.225 | −22.389 | 1.00 | 41.93 | C |
| ATOM | 1120 | N | LEU | A | 546 | −26.005 | 21.726 | −23.828 | 1.00 | 34.70 | N |
| ATOM | 1121 | CA | LEU | A | 546 | −27.139 | 21.673 | −24.744 | 1.00 | 34.93 | C |
| ATOM | 1122 | C | LEU | A | 546 | −28.020 | 22.908 | −24.623 | 1.00 | 38.13 | C |
| ATOM | 1123 | O | LEU | A | 546 | −27.867 | 23.710 | −23.707 | 1.00 | 37.41 | O |
| ATOM | 1124 | CB | LEU | A | 546 | −28.017 | 20.442 | −24.461 | 1.00 | 41.33 | C |
| ATOM | 1125 | CG | LEU | A | 546 | −27.575 | 18.972 | −24.572 | 1.00 | 56.63 | C |
| ATOM | 1126 | CD1 | LEU | A | 546 | −28.513 | 18.214 | −25.501 | 1.00 | 58.32 | C |
| ATOM | 1127 | CD2 | LEU | A | 546 | −26.171 | 18.781 | −25.042 | 1.00 | 57.44 | C |
| ATOM | 1128 | N | TYR | A | 547 | −28.957 | 23.028 | −25.553 | 1.00 | 37.22 | N |
| ATOM | 1129 | CA | TYR | A | 547 | −29.983 | 24.052 | −25.526 | 1.00 | 37.77 | C |
| ATOM | 1130 | C | TYR | A | 547 | −31.290 | 23.384 | −25.122 | 1.00 | 45.37 | C |
| ATOM | 1131 | O | TYR | A | 547 | −31.650 | 22.353 | −25.685 | 1.00 | 43.34 | O |
| ATOM | 1132 | CB | TYR | A | 547 | −30.172 | 24.629 | −26.931 | 1.00 | 38.98 | C |
| ATOM | 1133 | CG | TYR | A | 547 | −29.188 | 25.701 | −27.334 | 1.00 | 47.12 | C |
| ATOM | 1134 | CD1 | TYR | A | 547 | −29.118 | 26.912 | −26.646 | 1.00 | 42.91 | C |
| ATOM | 1135 | CD2 | TYR | A | 547 | −28.356 | 25.521 | −28.430 | 1.00 | 45.73 | C |
| ATOM | 1136 | CE1 | TYR | A | 547 | −28.234 | 27.918 | −27.042 | 1.00 | 45.84 | C |
| ATOM | 1137 | CE2 | TYR | A | 547 | −27.466 | 26.510 | −28.828 | 1.00 | 47.52 | C |
| ATOM | 1138 | CZ | TYR | A | 547 | −27.411 | 27.706 | −28.137 | 1.00 | 51.98 | C |
| ATOM | 1139 | OH | TYR | A | 547 | −26.518 | 28.675 | −28.543 | 1.00 | 43.91 | O |
| ATOM | 1140 | N | VAL | A | 548 | −32.003 | 23.954 | −24.152 | 1.00 | 42.14 | N |
| ATOM | 1141 | CA | VAL | A | 548 | −33.238 | 23.331 | −23.685 | 1.00 | 42.26 | C |
| ATOM | 1142 | C | VAL | A | 548 | −34.370 | 23.520 | −24.702 | 1.00 | 42.94 | C |
| ATOM | 1143 | O | VAL | A | 548 | −35.285 | 22.681 | −24.799 | 1.00 | 44.13 | O |
| ATOM | 1144 | CB | VAL | A | 548 | −33.675 | 23.846 | −22.266 | 1.00 | 49.20 | C |
| ATOM | 1145 | CG1 | VAL | A | 548 | −34.041 | 25.320 | −22.302 | 1.00 | 45.56 | C |
| ATOM | 1146 | CG2 | VAL | A | 548 | −34.851 | 23.030 | −21.739 | 1.00 | 44.53 | C |
| ATOM | 1147 | N | ASP | A | 549 | −34.304 | 24.611 | −25.465 | 1.00 | 46.19 | N |
| ATOM | 1148 | CA | ASP | A | 549 | −35.294 | 24.865 | −26.514 | 1.00 | 47.80 | C |
| ATOM | 1149 | C | ASP | A | 549 | −34.630 | 25.378 | −27.792 | 1.00 | 50.65 | C |
| ATOM | 1150 | O | ASP | A | 549 | −33.401 | 25.402 | −27.888 | 1.00 | 45.39 | O |
| ATOM | 1151 | CB | ASP | A | 549 | −36.377 | 25.833 | −26.018 | 1.00 | 52.66 | C |
| ATOM | 1152 | CG | ASP | A | 549 | −35.798 | 27.112 | −25.442 | 1.00 | 58.17 | C |
| ATOM | 1153 | OD2 | ASP | A | 549 | −36.241 | 27.532 | −24.357 | 1.00 | 68.78 | O |
| ATOM | 1154 | OD1 | ASP | A | 549 | −34.898 | 27.703 | −26.072 | 1.00 | 51.79 | O |
| ATOM | 1155 | N | GLU | A | 550 | −35.435 | 25.797 | −28.765 | 1.00 | 49.97 | N |
| ATOM | 1156 | CA | GLU | A | 550 | −34.894 | 26.260 | −30.040 | 1.00 | 64.81 | C |
| ATOM | 1157 | C | GLU | A | 550 | −34.825 | 27.779 | −30.159 | 1.00 | 62.88 | C |
| ATOM | 1158 | O | GLU | A | 550 | −34.710 | 28.308 | −31.259 | 1.00 | 67.05 | O |
| ATOM | 1159 | CB | GLU | A | 550 | −35.718 | 25.706 | −31.206 | 1.00 | 70.31 | C |
| ATOM | 1160 | CG | GLU | A | 550 | −35.640 | 24.197 | −31.394 | 1.00 | 85.28 | C |
| ATOM | 1161 | CD | GLU | A | 550 | −36.508 | 23.710 | −32.548 | 1.00 | 94.03 | C |
| ATOM | 1162 | OE1 | GLU | A | 550 | −37.345 | 24.493 | −33.051 | 1.00 | 93.69 | O |
| ATOM | 1163 | OE2 | GLU | A | 550 | −36.353 | 22.539 | −32.954 | 1.00 | 99.55 | O |
| ATOM | 1164 | N | SER | A | 551 | −34.892 | 28.484 | −29.036 | 1.00 | 53.77 | N |
| ATOM | 1165 | CA | SER | A | 551 | −34.913 | 29.948 | −29.058 | 1.00 | 57.03 | C |
| ATOM | 1166 | C | SER | A | 551 | −33.571 | 30.555 | −29.474 | 1.00 | 55.17 | C |
| ATOM | 1167 | O | SER | A | 551 | −33.498 | 31.717 | −29.871 | 1.00 | 64.24 | O |
| ATOM | 1168 | CB | SER | A | 551 | −35.281 | 30.476 | −27.680 | 1.00 | 62.75 | C |
| ATOM | 1169 | OG | SER | A | 551 | −34.307 | 30.054 | −26.733 | 1.00 | 57.19 | O |
| ATOM | 1170 | N | GLY | A | 552 | −32.507 | 29.769 | −29.353 | 1.00 | 50.27 | N |
| ATOM | 1171 | CA | GLY | A | 552 | −31.168 | 30.225 | −29.675 | 1.00 | 54.00 | C |
| ATOM | 1172 | C | GLY | A | 552 | −30.534 | 31.187 | −28.683 | 1.00 | 65.76 | C |
| ATOM | 1173 | O | GLY | A | 552 | −29.424 | 31.678 | −28.919 | 1.00 | 57.85 | O |
| ATOM | 1174 | N | ASN | A | 553 | −31.212 | 31.468 | −27.571 | 1.00 | 49.89 | N |
| ATOM | 1175 | CA | ASN | A | 553 | −30.652 | 32.419 | −26.612 | 1.00 | 58.58 | C |
| ATOM | 1176 | C | ASN | A | 553 | −29.808 | 31.787 | −25.502 | 1.00 | 52.87 | C |
| ATOM | 1177 | O | ASN | A | 553 | −30.070 | 30.664 | −25.067 | 1.00 | 47.25 | O |
| ATOM | 1178 | CB | ASN | A | 553 | −31.732 | 33.343 | −26.042 | 1.00 | 77.46 | C |
| ATOM | 1179 | CG | ASN | A | 553 | −33.078 | 32.686 | −25.972 | 1.00 | 92.84 | C |
| ATOM | 1180 | OD1 | ASN | A | 553 | −33.205 | 31.560 | −25.492 | 1.00 | 103.27 | O |
| ATOM | 1181 | ND2 | ASN | A | 553 | −34.102 | 33.378 | −26.468 | 1.00 | 88.37 | N |
| ATOM | 1182 | N | PRO | A | 554 | −28.772 | 32.511 | −25.060 | 1.00 | 58.43 | N |
| ATOM | 1183 | CA | PRO | A | 554 | −27.857 | 32.010 | −24.030 | 1.00 | 57.78 | C |
| ATOM | 1184 | C | PRO | A | 554 | −28.582 | 31.493 | −22.782 | 1.00 | 54.27 | C |
| ATOM | 1185 | O | PRO | A | 554 | −28.130 | 30.517 | −22.202 | 1.00 | 52.47 | O |
| ATOM | 1186 | CB | PRO | A | 554 | −26.998 | 33.232 | −23.714 | 1.00 | 58.37 | C |

TABLE 3-continued

Atomic coordinates of RSK2 model (pdb file)

| ATOM | 1187 | CG | PRO | A | 554 | −26.972 | 33.995 | −25.004 | 1.00 | 53.90 | C |
|---|---|---|---|---|---|---|---|---|---|---|---|
| ATOM | 1188 | CD | PRO | A | 554 | −28.354 | 33.829 | −25.577 | 1.00 | 58.41 | C |
| ATOM | 1189 | N | GLU | A | 555 | −29.710 | 32.104 | −22.412 | 1.00 | 48.66 | N |
| ATOM | 1190 | CA | GLU | A | 555 | −30.493 | 31.671 | −21.243 | 1.00 | 52.53 | C |
| ATOM | 1191 | C | GLU | A | 555 | −31.014 | 30.227 | −21.351 | 1.00 | 53.94 | C |
| ATOM | 1192 | O | GLU | A | 555 | −31.375 | 29.606 | −20.353 | 1.00 | 54.14 | O |
| ATOM | 1193 | CB | GLU | A | 555 | −31.679 | 32.615 | −21.012 | 1.00 | 57.21 | C |
| ATOM | 1194 | CG | GLU | A | 555 | −31.312 | 34.093 | −20.812 | 1.00 | 83.20 | C |
| ATOM | 1195 | CD | GLU | A | 555 | −31.000 | 34.841 | −22.111 | 1.00 | 92.07 | C |
| ATOM | 1196 | OE1 | GLU | A | 555 | −30.976 | 36.092 | −22.080 | 1.00 | 102.94 | O |
| ATOM | 1197 | OE2 | GLU | A | 555 | −30.772 | 34.199 | −23.162 | 1.00 | 76.11 | O |
| ATOM | 1198 | N | SER | A | 556 | −31.072 | 29.700 | −22.566 | 1.00 | 48.17 | N |
| ATOM | 1199 | CA | SER | A | 556 | −31.601 | 28.355 | −22.778 | 1.00 | 39.93 | C |
| ATOM | 1200 | C | SER | A | 556 | −30.486 | 27.302 | −22.770 | 1.00 | 41.41 | C |
| ATOM | 1201 | O | SER | A | 556 | −30.743 | 26.121 | −22.980 | 1.00 | 40.15 | O |
| ATOM | 1202 | CB | SER | A | 556 | −32.363 | 28.288 | −24.103 | 1.00 | 49.56 | C |
| ATOM | 1203 | OG | SER | A | 556 | −31.436 | 28.348 | −25.168 | 1.00 | 50.24 | O |
| ATOM | 1204 | N | ILE | A | 557 | −29.253 | 27.729 | −22.523 | 1.00 | 32.46 | N |
| ATOM | 1205 | CA | ILE | A | 557 | −28.130 | 26.779 | −22.422 | 1.00 | 30.87 | C |
| ATOM | 1206 | C | ILE | A | 557 | −28.198 | 25.971 | −21.119 | 1.00 | 32.44 | C |
| ATOM | 1207 | O | ILE | A | 557 | −28.531 | 26.517 | −20.059 | 1.00 | 40.14 | O |
| ATOM | 1208 | CB | ILE | A | 557 | −26.802 | 27.561 | −22.452 | 1.00 | 37.79 | C |
| ATOM | 1209 | CG1 | ILE | A | 557 | −26.618 | 28.235 | −23.826 | 1.00 | 47.87 | C |
| ATOM | 1210 | CG2 | ILE | A | 557 | −25.628 | 26.651 | −22.107 | 1.00 | 34.88 | C |
| ATOM | 1211 | CD1 | ILE | A | 557 | −25.493 | 29.264 | −23.841 | 1.00 | 49.44 | C |
| ATOM | 1212 | N | ARG | A | 558 | −27.880 | 24.675 | −21.177 | 1.00 | 32.27 | N |
| ATOM | 1213 | CA | ARG | A | 558 | −27.791 | 23.872 | −19.958 | 1.00 | 32.43 | C |
| ATOM | 1214 | C | ARG | A | 558 | −26.527 | 23.048 | −20.005 | 1.00 | 33.83 | C |
| ATOM | 1215 | O | ARG | A | 558 | −26.253 | 22.398 | −21.019 | 1.00 | 38.67 | O |
| ATOM | 1216 | CB | ARG | A | 558 | −28.970 | 22.909 | −19.854 | 1.00 | 38.59 | C |
| ATOM | 1217 | CG | ARG | A | 558 | −30.329 | 23.603 | −19.810 | 1.00 | 37.48 | C |
| ATOM | 1218 | CD | ARG | A | 558 | −30.551 | 24.318 | −18.470 | 1.00 | 38.91 | C |
| ATOM | 1219 | NE | ARG | A | 558 | −31.939 | 24.812 | −18.403 | 1.00 | 43.84 | N |
| ATOM | 1220 | CZ | ARG | A | 558 | −32.345 | 25.977 | −18.893 | 1.00 | 49.79 | C |
| ATOM | 1221 | NH1 | ARG | A | 558 | −31.488 | 26.790 | −19.496 | 1.00 | 46.05 | N |
| ATOM | 1222 | NH2 | ARG | A | 558 | −33.617 | 26.333 | −18.783 | 1.00 | 48.40 | N |
| ATOM | 1223 | N | ILE | A | 559 | −25.768 | 23.100 | −18.922 | 1.00 | 35.09 | N |
| ATOM | 1224 | CA | ILE | A | 559 | −24.711 | 22.125 | −18.695 | 1.00 | 36.16 | C |
| ATOM | 1225 | C | ILE | A | 559 | −25.347 | 20.855 | −18.128 | 1.00 | 44.08 | C |
| ATOM | 1226 | O | ILE | A | 559 | −26.093 | 20.905 | −17.143 | 1.00 | 41.39 | O |
| ATOM | 1227 | CB | ILE | A | 559 | −23.662 | 22.666 | −17.706 | 1.00 | 41.29 | C |
| ATOM | 1228 | CG1 | ILE | A | 559 | −23.055 | 23.966 | −18.256 | 1.00 | 40.26 | C |
| ATOM | 1229 | CG2 | ILE | A | 559 | −22.578 | 21.612 | −17.434 | 1.00 | 39.41 | C |
| ATOM | 1230 | CD1 | ILE | A | 559 | −21.866 | 24.481 | −17.408 | 1.00 | 40.73 | C |
| ATOM | 1231 | N | CYS | A | 560 | −25.056 | 19.721 | −18.760 | 1.00 | 40.80 | N |
| ATOM | 1232 | CA | CYS | A | 560 | −25.665 | 18.444 | −18.404 | 1.00 | 40.65 | C |
| ATOM | 1233 | C | CYS | A | 560 | −24.626 | 17.387 | −18.054 | 1.00 | 45.22 | C |
| ATOM | 1234 | O | CYS | A | 560 | −23.412 | 17.627 | −18.130 | 1.00 | 45.70 | O |
| ATOM | 1235 | CB | CYS | A | 560 | −26.505 | 17.905 | −19.567 | 1.00 | 39.51 | C |
| ATOM | 1236 | SG | CYS | A | 560 | −27.752 | 19.073 | −20.235 | 1.00 | 46.36 | S |
| ATOM | 1237 | N | ASP | A | 561 | −25.135 | 16.211 | −17.694 | 1.00 | 45.35 | N |
| ATOM | 1238 | CA | ASP | A | 561 | −24.333 | 15.038 | −17.320 | 1.00 | 45.53 | C |
| ATOM | 1239 | C | ASP | A | 561 | −23.283 | 15.266 | −16.236 | 1.00 | 49.18 | C |
| ATOM | 1240 | O | ASP | A | 561 | −22.086 | 15.444 | −16.505 | 1.00 | 43.19 | O |
| ATOM | 1241 | CB | ASP | A | 561 | −23.704 | 14.367 | −18.545 | 1.00 | 51.99 | C |
| ATOM | 1242 | CG | ASP | A | 561 | −23.315 | 12.912 | −18.277 | 1.00 | 62.55 | C |
| ATOM | 1243 | OD1 | ASP | A | 561 | −23.353 | 12.476 | −17.104 | 1.00 | 62.28 | O |
| ATOM | 1244 | OD2 | ASP | A | 561 | −22.963 | 12.201 | −19.242 | 1.00 | 65.81 | O |
| ATOM | 1245 | N | PHE | A | 562 | −23.735 | 15.194 | −14.997 | 1.00 | 40.57 | N |
| ATOM | 1246 | CA | PHE | A | 562 | −22.857 | 15.339 | −13.853 | 1.00 | 44.10 | C |
| ATOM | 1247 | C | PHE | A | 562 | −22.455 | 13.975 | −13.291 | 1.00 | 46.83 | C |
| ATOM | 1248 | O | PHE | A | 562 | −22.116 | 13.847 | −12.114 | 1.00 | 46.88 | O |
| ATOM | 1249 | CB | PHE | A | 562 | −23.550 | 16.207 | −12.797 | 1.00 | 43.23 | C |
| ATOM | 1250 | CG | PHE | A | 562 | −23.568 | 17.669 | −13.154 | 1.00 | 42.71 | C |
| ATOM | 1251 | CD1 | PHE | A | 562 | −24.466 | 18.159 | −14.100 | 1.00 | 44.38 | C |
| ATOM | 1252 | CD2 | PHE | A | 562 | −22.662 | 18.543 | −12.575 | 1.00 | 47.62 | C |
| ATOM | 1253 | CE1 | PHE | A | 562 | −24.478 | 19.513 | −14.445 | 1.00 | 41.33 | C |
| ATOM | 1254 | CE2 | PHE | A | 562 | −22.658 | 19.890 | −12.905 | 1.00 | 44.19 | C |
| ATOM | 1255 | CZ | PHE | A | 562 | −23.570 | 20.381 | −13.842 | 1.00 | 41.25 | C |
| ATOM | 1256 | N | GLY | A | 563 | −22.480 | 12.958 | −14.146 | 1.00 | 47.72 | N |
| ATOM | 1257 | CA | GLY | A | 563 | −22.160 | 11.604 | −13.726 | 1.00 | 51.84 | C |
| ATOM | 1258 | C | GLY | A | 563 | −20.697 | 11.378 | −13.387 | 1.00 | 58.31 | C |
| ATOM | 1259 | O | GLY | A | 563 | −20.343 | 10.336 | −12.833 | 1.00 | 56.03 | O |
| ATOM | 1260 | N | PHE | A | 564 | −19.843 | 12.342 | −13.726 | 1.00 | 55.96 | N |
| ATOM | 1261 | CA | PHE | A | 564 | −18.411 | 12.245 | −13.412 | 1.00 | 58.81 | C |
| ATOM | 1262 | C | PHE | A | 564 | −17.950 | 13.369 | −12.476 | 1.00 | 54.14 | C |
| ATOM | 1263 | O | PHE | A | 564 | −16.788 | 13.416 | −12.059 | 1.00 | 53.61 | O |
| ATOM | 1264 | CB | PHE | A | 564 | −17.577 | 12.235 | −14.699 | 1.00 | 59.65 | C |

TABLE 3-continued

Atomic coordinates of RSK2 model (pdb file)

| ATOM | 1265 | CG | PHE | A | 564 | −17.717 | 10.966 | −15.506 | 1.00 | 63.33 | C |
|---|---|---|---|---|---|---|---|---|---|---|---|
| ATOM | 1266 | CD2 | PHE | A | 564 | −18.454 | 10.947 | −16.685 | 1.00 | 69.59 | C |
| ATOM | 1267 | CD1 | PHE | A | 564 | −17.102 | 9.795 | −15.088 | 1.00 | 74.64 | C |
| ATOM | 1268 | CE2 | PHE | A | 564 | −18.573 | 9.786 | −17.425 | 1.00 | 74.43 | C |
| ATOM | 1269 | CE1 | PHE | A | 564 | −17.217 | 8.630 | −15.823 | 1.00 | 79.79 | C |
| ATOM | 1270 | CZ | PHE | A | 564 | −17.952 | 8.624 | −16.992 | 1.00 | 83.51 | C |
| ATOM | 1271 | N | ALA | A | 565 | −18.878 | 14.259 | −12.138 | 1.00 | 47.63 | N |
| ATOM | 1272 | CA | ALA | A | 565 | −18.603 | 15.392 | −11.269 | 1.00 | 47.12 | C |
| ATOM | 1273 | C | ALA | A | 565 | −18.259 | 14.966 | −9.842 | 1.00 | 56.32 | C |
| ATOM | 1274 | O | ALA | A | 565 | −18.648 | 13.887 | −9.398 | 1.00 | 56.40 | O |
| ATOM | 1275 | CB | ALA | A | 565 | −19.783 | 16.351 | −11.272 | 1.00 | 42.94 | C |
| ATOM | 1276 | N | LYS | A | 566 | −17.541 | 15.836 | −9.134 | 1.00 | 48.04 | N |
| ATOM | 1277 | CA | LYS | A | 566 | −17.068 | 15.552 | −7.777 | 1.00 | 51.73 | C |
| ATOM | 1278 | C | LYS | A | 566 | −17.153 | 16.806 | −6.895 | 1.00 | 54.53 | C |
| ATOM | 1279 | O | LYS | A | 566 | −16.734 | 17.891 | −7.306 | 1.00 | 51.84 | O |
| ATOM | 1280 | CB | LYS | A | 566 | −15.633 | 15.002 | −7.830 | 1.00 | 57.20 | C |
| ATOM | 1281 | CG | LYS | A | 566 | −14.995 | 14.769 | −6.463 | 1.00 | 77.28 | C |
| ATOM | 1282 | CD | LYS | A | 566 | −13.690 | 13.995 | −6.585 | 1.00 | 89.41 | C |
| ATOM | 1283 | CE | LYS | A | 566 | −12.941 | 13.942 | −5.259 | 1.00 | 88.49 | C |
| ATOM | 1284 | NZ | LYS | A | 566 | −12.533 | 15.306 | −4.799 | 1.00 | 76.89 | N |
| ATOM | 1285 | N | GLN | A | 567 | −17.732 | 16.653 | −5.702 | 1.00 | 54.40 | N |
| ATOM | 1286 | C | GLN | A | 567 | −16.485 | 17.591 | −3.780 | 1.00 | 60.19 | C |
| ATOM | 1287 | O | GLN | A | 567 | −16.165 | 16.520 | −3.247 | 1.00 | 57.51 | O |
| ATOM | 1288 | CA | GLN | A | 567 | −17.721 | 17.689 | −4.673 | 1.00 | 60.39 | C |
| ATOM | 1289 | CB | GLN | A | 567 | −18.975 | 17.605 | −3.784 | 1.00 | 62.20 | C |
| ATOM | 1290 | CG | GLN | A | 567 | −20.259 | 18.043 | −4.482 | 1.00 | 70.67 | C |
| ATOM | 1291 | CD | GLN | A | 567 | −21.292 | 18.661 | −3.539 | 1.00 | 76.68 | C |
| ATOM | 1292 | OE1 | GLN | A | 567 | −21.102 | 19.766 | −3.023 | 1.00 | 84.12 | O |
| ATOM | 1293 | NE2 | GLN | A | 567 | −22.394 | 17.951 | −3.320 | 1.00 | 74.69 | N |
| ATOM | 1294 | N | LEU | A | 568 | −15.807 | 18.718 | −3.593 | 1.00 | 58.91 | N |
| ATOM | 1295 | CA | LEU | A | 568 | −14.680 | 18.784 | −2.674 | 1.00 | 57.17 | C |
| ATOM | 1296 | C | LEU | A | 568 | −15.174 | 18.507 | −1.265 | 1.00 | 66.72 | C |
| ATOM | 1297 | O | LEU | A | 568 | −16.110 | 19.153 | −0.791 | 1.00 | 63.65 | O |
| ATOM | 1298 | CB | LEU | A | 568 | −14.066 | 20.176 | −2.713 | 1.00 | 65.48 | C |
| ATOM | 1299 | CG | LEU | A | 568 | −12.843 | 20.398 | −1.832 | 1.00 | 65.02 | C |
| ATOM | 1300 | CD1 | LEU | A | 568 | −11.690 | 19.515 | −2.294 | 1.00 | 59.83 | C |
| ATOM | 1301 | CD2 | LEU | A | 568 | −12.455 | 21.867 | −1.845 | 1.00 | 65.66 | C |
| ATOM | 1302 | N | ARG | A | 569 | −14.562 | 17.547 | −0.587 | 1.00 | 66.91 | N |
| ATOM | 1303 | CA | ARG | A | 569 | −14.944 | 17.292 | 0.793 | 1.00 | 71.81 | C |
| ATOM | 1304 | C | ARG | A | 569 | −13.782 | 16.813 | 1.633 | 1.00 | 78.11 | C |
| ATOM | 1305 | O | ARG | A | 569 | −12.740 | 16.419 | 1.113 | 1.00 | 74.26 | O |
| ATOM | 1306 | CB | ARG | A | 569 | −16.138 | 16.336 | 0.884 | 1.00 | 84.77 | C |
| ATOM | 1307 | CG | ARG | A | 569 | −15.849 | 14.892 | 0.590 | 1.00 | 95.70 | C |
| ATOM | 1308 | CD | ARG | A | 569 | −17.107 | 14.070 | 0.804 | 1.00 | 99.08 | C |
| ATOM | 1309 | NE | ARG | A | 569 | −18.194 | 14.545 | −0.046 | 1.00 | 100.93 | N |
| ATOM | 1310 | CZ | ARG | A | 569 | −19.357 | 13.921 | −0.201 | 1.00 | 106.80 | C |
| ATOM | 1311 | NH1 | ARG | A | 569 | −19.592 | 12.785 | 0.440 | 1.00 | 112.79 | N |
| ATOM | 1312 | NH2 | ARG | A | 569 | −20.283 | 14.431 | −1.003 | 1.00 | 105.02 | N |
| ATOM | 1313 | N | ALA | A | 570 | −13.960 | 16.879 | 2.944 | 1.00 | 72.57 | N |
| ATOM | 1314 | CA | ALA | A | 570 | −12.893 | 16.551 | 3.874 | 1.00 | 76.58 | C |
| ATOM | 1315 | C | ALA | A | 570 | −12.902 | 15.067 | 4.195 | 1.00 | 84.62 | C |
| ATOM | 1316 | O | ALA | A | 570 | −13.820 | 14.338 | 3.798 | 1.00 | 79.53 | O |
| ATOM | 1317 | CB | ALA | A | 570 | −13.054 | 17.361 | 5.153 | 1.00 | 105.03 | C |
| ATOM | 1318 | N | GLU | A | 571 | −11.878 | 14.639 | 4.931 | 1.00 | 85.03 | N |
| ATOM | 1319 | CA | GLU | A | 571 | −11.724 | 13.250 | 5.349 | 1.00 | 98.07 | C |
| ATOM | 1320 | C | GLU | A | 571 | −12.995 | 12.719 | 6.019 | 1.00 | 102.66 | C |
| ATOM | 1321 | O | GLU | A | 571 | −13.475 | 11.637 | 5.683 | 1.00 | 95.27 | O |
| ATOM | 1322 | CB | GLU | A | 571 | −10.527 | 13.118 | 6.297 | 1.00 | 105.29 | C |
| ATOM | 1323 | CG | GLU | A | 571 | −10.110 | 11.683 | 6.598 | 1.00 | 118.99 | C |
| ATOM | 1324 | CD | GLU | A | 571 | −9.623 | 11.493 | 8.030 | 1.00 | 130.50 | C |
| ATOM | 1325 | OE1 | GLU | A | 571 | −10.380 | 10.915 | 8.843 | 1.00 | 131.68 | O |
| ATOM | 1326 | OE2 | GLU | A | 571 | −8.486 | 11.912 | 8.344 | 1.00 | 136.05 | O |
| ATOM | 1327 | N | ASN | A | 572 | −13.542 | 13.498 | 6.950 | 1.00 | 108.49 | N |
| ATOM | 1328 | CA | ASN | A | 572 | −14.750 | 13.120 | 7.686 | 1.00 | 107.07 | C |
| ATOM | 1329 | C | ASN | A | 572 | −16.011 | 12.968 | 6.831 | 1.00 | 101.18 | C |
| ATOM | 1330 | O | ASN | A | 572 | −16.950 | 12.284 | 7.233 | 1.00 | 93.98 | O |
| ATOM | 1331 | CB | ASN | A | 572 | −15.009 | 14.107 | 8.828 | 1.00 | 117.49 | C |
| ATOM | 1332 | CG | ASN | A | 572 | −14.373 | 15.454 | 8.582 | 1.00 | 124.43 | C |
| ATOM | 1333 | OD1 | ASN | A | 572 | −13.353 | 15.551 | 7.904 | 1.00 | 126.22 | O |
| ATOM | 1334 | ND2 | ASN | A | 572 | −14.968 | 16.502 | 9.135 | 1.00 | 127.99 | N |
| ATOM | 1335 | N | GLY | A | 573 | −16.023 | 13.595 | 5.656 | 1.00 | 90.77 | N |
| ATOM | 1336 | CA | GLY | A | 573 | −17.176 | 13.537 | 4.778 | 1.00 | 92.37 | C |
| ATOM | 1337 | C | GLY | A | 573 | −17.813 | 14.900 | 4.575 | 1.00 | 94.91 | C |
| ATOM | 1338 | O | GLY | A | 573 | −18.674 | 15.062 | 3.709 | 1.00 | 84.61 | O |
| ATOM | 1339 | N | LEU | A | 574 | −17.372 | 15.878 | 5.367 | 1.00 | 88.53 | N |
| ATOM | 1340 | CA | LEU | A | 574 | −17.926 | 17.234 | 5.353 | 1.00 | 75.67 | C |
| ATOM | 1341 | C | LEU | A | 574 | −17.738 | 17.936 | 4.016 | 1.00 | 86.74 | C |
| ATOM | 1342 | O | LEU | A | 574 | −16.619 | 18.026 | 3.504 | 1.00 | 77.05 | O |

TABLE 3-continued

Atomic coordinates of RSK2 model (pdb file)

| ATOM | 1343 | CB  | LEU | A | 574 | −17.270 | 18.085 | 6.445  | 1.00 | 78.80  | C |
|------|------|-----|-----|---|-----|---------|--------|--------|------|--------|---|
| ATOM | 1344 | CG  | LEU | A | 574 | −18.064 | 18.262 | 7.735  | 1.00 | 82.03  | C |
| ATOM | 1345 | CD1 | LEU | A | 574 | −17.283 | 19.118 | 8.736  | 1.00 | 85.28  | C |
| ATOM | 1346 | CD2 | LEU | A | 574 | −19.426 | 18.871 | 7.416  | 1.00 | 88.71  | C |
| ATOM | 1347 | N   | LEU | A | 575 | −18.829 | 18.452 | 3.461  | 1.00 | 81.20  | N |
| ATOM | 1348 | CA  | LEU | A | 575 | −18.741 | 19.230 | 2.242  | 1.00 | 76.18  | C |
| ATOM | 1349 | C   | LEU | A | 575 | −17.964 | 20.527 | 2.445  | 1.00 | 70.95  | C |
| ATOM | 1350 | O   | LEU | A | 575 | −18.118 | 21.216 | 3.447  | 1.00 | 80.30  | O |
| ATOM | 1351 | CB  | LEU | A | 575 | −20.129 | 19.465 | 1.647  | 1.00 | 87.45  | C |
| ATOM | 1352 | CG  | LEU | A | 575 | −20.663 | 18.129 | 1.119  | 1.00 | 95.28  | C |
| ATOM | 1353 | CD1 | LEU | A | 575 | −22.015 | 18.265 | 0.465  | 1.00 | 99.82  | C |
| ATOM | 1354 | CD2 | LEU | A | 575 | −19.670 | 17.524 | 0.147  | 1.00 | 97.21  | C |
| ATOM | 1355 | N   | MET | A | 576 | −17.116 | 20.842 | 1.472  | 1.00 | 74.81  | N |
| ATOM | 1356 | CA  | MET | A | 576 | −16.179 | 21.943 | 1.607  | 1.00 | 76.51  | C |
| ATOM | 1357 | C   | MET | A | 576 | −16.169 | 22.799 | 0.335  | 1.00 | 80.73  | C |
| ATOM | 1358 | O   | MET | A | 576 | −16.444 | 22.315 | −0.766 | 1.00 | 70.70  | O |
| ATOM | 1359 | CB  | MET | A | 576 | −14.781 | 21.382 | 1.865  | 1.00 | 85.50  | C |
| ATOM | 1360 | CG  | MET | A | 576 | −13.932 | 22.189 | 2.814  | 1.00 | 96.95  | C |
| ATOM | 1361 | SD  | MET | A | 576 | −14.569 | 22.149 | 4.499  | 1.00 | 115.63 | S |
| ATOM | 1362 | CE  | MET | A | 576 | −14.856 | 20.399 | 4.701  | 1.00 | 122.51 | C |
| ATOM | 1363 | N   | THR | A | 577 | −15.868 | 24.081 | 0.496  | 1.00 | 98.30  | N |
| ATOM | 1364 | CA  | THR | A | 577 | −15.692 | 24.974 | −0.644 | 1.00 | 99.19  | C |
| ATOM | 1365 | C   | THR | A | 577 | −14.221 | 25.349 | −0.681 | 1.00 | 95.27  | C |
| ATOM | 1366 | O   | THR | A | 577 | −13.569 | 25.369 | 0.368  | 1.00 | 96.92  | O |
| ATOM | 1367 | CB  | THR | A | 577 | −16.546 | 26.250 | −0.503 | 1.00 | 100.21 | C |
| ATOM | 1368 | OG1 | THR | A | 577 | −16.010 | 27.081 | 0.537  | 1.00 | 90.26  | O |
| ATOM | 1369 | CG2 | THR | A | 577 | −17.997 | 25.897 | −0.180 | 1.00 | 100.60 | C |
| ATOM | 1370 | N   | PRO | A | 578 | −13.684 | 25.645 | −1.876 | 1.00 | 83.35  | N |
| ATOM | 1371 | CA  | PRO | A | 578 | −12.257 | 25.982 | −1.961 | 1.00 | 80.34  | C |
| ATOM | 1372 | C   | PRO | A | 578 | −11.954 | 27.304 | −1.265 | 1.00 | 90.97  | C |
| ATOM | 1373 | O   | PRO | A | 578 | −10.785 | 27.647 | −1.081 | 1.00 | 99.53  | O |
| ATOM | 1374 | CB  | PRO | A | 578 | −12.007 | 26.112 | −3.472 | 1.00 | 70.55  | C |
| ATOM | 1375 | CG  | PRO | A | 578 | −13.162 | 25.446 | −4.120 | 1.00 | 67.94  | C |
| ATOM | 1376 | CD  | PRO | A | 578 | −14.324 | 25.648 | −3.201 | 1.00 | 73.80  | C |
| ATOM | 1377 | N   | CYS | A | 579 | −12.996 | 28.036 | −0.887 | 1.00 | 86.36  | N |
| ATOM | 1378 | CA  | CYS | A | 579 | −12.816 | 29.288 | −0.165 | 1.00 | 100.63 | C |
| ATOM | 1379 | C   | CYS | A | 579 | −12.648 | 29.075 | 1.348  | 1.00 | 100.99 | C |
| ATOM | 1380 | O   | CYS | A | 579 | −11.906 | 29.806 | 2.012  | 1.00 | 87.07  | O |
| ATOM | 1381 | CB  | CYS | A | 579 | −13.983 | 30.236 | −0.449 | 1.00 | 106.64 | C |
| ATOM | 1382 | SG  | CYS | A | 579 | −13.589 | 31.968 | −0.114 | 1.00 | 183.45 | S |
| ATOM | 1383 | N   | TYR | A | 580 | −13.339 | 28.074 | 1.886  | 1.00 | 102.40 | N |
| ATOM | 1384 | CA  | TYR | A | 580 | −13.170 | 27.698 | 3.286  | 1.00 | 108.15 | C |
| ATOM | 1385 | C   | TYR | A | 580 | −12.816 | 26.222 | 3.416  | 1.00 | 118.71 | C |
| ATOM | 1386 | O   | TYR | A | 580 | −13.697 | 25.361 | 3.415  | 1.00 | 121.05 | O |
| ATOM | 1387 | CB  | TYR | A | 580 | −14.436 | 27.992 | 4.092  | 1.00 | 102.03 | C |
| ATOM | 1388 | CG  | TYR | A | 580 | −14.308 | 27.673 | 5.570  | 1.00 | 98.77  | C |
| ATOM | 1389 | CD2 | TYR | A | 580 | −14.681 | 26.431 | 6.072  | 1.00 | 89.57  | C |
| ATOM | 1390 | CD1 | TYR | A | 580 | −13.817 | 28.617 | 6.463  | 1.00 | 103.54 | C |
| ATOM | 1391 | CE2 | TYR | A | 580 | −14.572 | 26.143 | 7.418  | 1.00 | 104.48 | C |
| ATOM | 1392 | CE1 | TYR | A | 580 | −13.704 | 28.336 | 7.815  | 1.00 | 103.38 | C |
| ATOM | 1393 | CZ  | TYR | A | 580 | −14.081 | 27.098 | 8.286  | 1.00 | 105.34 | C |
| ATOM | 1394 | OH  | TYR | A | 580 | −13.965 | 26.808 | 9.629  | 1.00 | 109.68 | O |
| ATOM | 1395 | N   | THR | A | 581 | −11.522 | 25.938 | 3.520  | 1.00 | 122.25 | N |
| ATOM | 1396 | CA  | THR | A | 581 | −11.051 | 24.581 | 3.760  | 1.00 | 119.54 | C |
| ATOM | 1397 | C   | THR | A | 581 | −10.329 | 24.536 | 5.096  | 1.00 | 121.14 | C |
| ATOM | 1398 | O   | THR | A | 581 | −9.456  | 23.696 | 5.320  | 1.00 | 118.96 | O |
| ATOM | 1399 | CB  | THR | A | 581 | −10.107 | 24.084 | 2.640  | 1.00 | 113.94 | C |
| ATOM | 1400 | OG1 | THR | A | 581 | −9.173  | 25.117 | 2.302  | 1.00 | 123.30 | O |
| ATOM | 1401 | CG2 | THR | A | 581 | −10.899 | 23.694 | 1.395  | 1.00 | 90.62  | C |
| ATOM | 1402 | N   | ALA | A | 582 | −10.718 | 25.436 | 5.995  | 1.00 | 123.46 | N |
| ATOM | 1403 | CA  | ALA | A | 582 | −10.076 | 25.550 | 7.303  | 1.00 | 126.36 | C |
| ATOM | 1404 | C   | ALA | A | 582 | −10.292 | 24.325 | 8.200  | 1.00 | 130.02 | C |
| ATOM | 1405 | O   | ALA | A | 582 | −10.078 | 24.385 | 9.413  | 1.00 | 124.41 | O |
| ATOM | 1406 | CB  | ALA | A | 582 | −10.518 | 26.828 | 8.010  | 1.00 | 125.72 | C |
| ATOM | 1407 | N   | ASN | A | 583 | −10.730 | 23.224 | 7.594  | 1.00 | 129.78 | N |
| ATOM | 1408 | CA  | ASN | A | 583 | −10.701 | 21.916 | 8.228  | 1.00 | 135.26 | C |
| ATOM | 1409 | C   | ASN | A | 583 | −9.512  | 21.152 | 7.670  | 1.00 | 130.65 | C |
| ATOM | 1410 | O   | ASN | A | 583 | −8.510  | 21.752 | 7.272  | 1.00 | 124.90 | O |
| ATOM | 1411 | CB  | ASN | A | 583 | −11.990 | 21.143 | 7.945  | 1.00 | 133.32 | C |
| ATOM | 1412 | CG  | ASN | A | 583 | −13.223 | 21.870 | 8.434  | 1.00 | 138.30 | C |
| ATOM | 1413 | OD1 | ASN | A | 583 | −13.232 | 23.095 | 8.541  | 1.00 | 144.00 | O |
| ATOM | 1414 | ND2 | ASN | A | 583 | −14.274 | 21.117 | 8.738  | 1.00 | 137.18 | N |
| ATOM | 1415 | N   | PHE | A | 584 | −9.620  | 19.829 | 7.626  | 1.00 | 127.92 | N |
| ATOM | 1416 | CA  | PHE | A | 584 | −8.585  | 19.032 | 6.984  | 1.00 | 122.55 | C |
| ATOM | 1417 | C   | PHE | A | 584 | −9.053  | 18.415 | 5.670  | 1.00 | 107.35 | C |
| ATOM | 1418 | O   | PHE | A | 584 | −9.850  | 17.472 | 5.654  | 1.00 | 100.95 | O |
| ATOM | 1419 | CB  | PHE | A | 584 | −8.020  | 17.946 | 7.912  | 1.00 | 128.70 | C |
| ATOM | 1420 | CG  | PHE | A | 584 | −7.055  | 17.011 | 7.222  | 1.00 | 128.85 | C |

TABLE 3-continued

Atomic coordinates of RSK2 model (pdb file)

| ATOM | 1421 | CD1 | PHE | A | 584 | −5.852 | 17.487 | 6.715 | 1.00 | 122.38 | C |
|---|---|---|---|---|---|---|---|---|---|---|---|
| ATOM | 1422 | CD2 | PHE | A | 584 | −7.356 | 15.665 | 7.066 | 1.00 | 128.23 | C |
| ATOM | 1423 | CE1 | PHE | A | 584 | −4.967 | 16.638 | 6.070 | 1.00 | 115.00 | C |
| ATOM | 1424 | CE2 | PHE | A | 584 | −6.475 | 14.811 | 6.422 | 1.00 | 123.55 | C |
| ATOM | 1425 | CZ | PHE | A | 584 | −5.279 | 15.299 | 5.924 | 1.00 | 117.76 | C |
| ATOM | 1426 | N | VAL | A | 585 | −8.560 | 18.973 | 4.569 | 1.00 | 95.84 | N |
| ATOM | 1427 | CA | VAL | A | 585 | −8.632 | 18.300 | 3.284 | 1.00 | 86.96 | C |
| ATOM | 1428 | C | VAL | A | 585 | −7.242 | 17.764 | 2.952 | 1.00 | 87.67 | C |
| ATOM | 1429 | O | VAL | A | 585 | −6.239 | 18.474 | 3.088 | 1.00 | 98.90 | O |
| ATOM | 1430 | CB | VAL | A | 585 | −9.155 | 19.225 | 2.149 | 1.00 | 117.47 | C |
| ATOM | 1431 | CG1 | VAL | A | 585 | −10.648 | 19.478 | 2.311 | 1.00 | 118.31 | C |
| ATOM | 1432 | CG2 | VAL | A | 585 | −8.383 | 20.538 | 2.104 | 1.00 | 116.04 | C |
| ATOM | 1433 | N | ALA | A | 586 | −7.186 | 16.498 | 2.550 | 1.00 | 82.15 | N |
| ATOM | 1434 | CA | ALA | A | 586 | −5.922 | 15.866 | 2.188 | 1.00 | 90.55 | C |
| ATOM | 1435 | C | ALA | A | 586 | −5.273 | 16.647 | 1.053 | 1.00 | 85.05 | C |
| ATOM | 1436 | O | ALA | A | 586 | −5.978 | 17.208 | 0.207 | 1.00 | 76.29 | O |
| ATOM | 1437 | CB | ALA | A | 586 | −6.154 | 14.417 | 1.780 | 1.00 | 91.08 | C |
| ATOM | 1438 | N | PRO | A | 587 | −3.932 | 16.696 | 1.036 | 1.00 | 90.13 | N |
| ATOM | 1439 | CA | PRO | A | 587 | −3.196 | 17.419 | −0.007 | 1.00 | 87.44 | C |
| ATOM | 1440 | C | PRO | A | 587 | −3.527 | 16.901 | −1.401 | 1.00 | 90.18 | C |
| ATOM | 1441 | O | PRO | A | 587 | −3.786 | 17.691 | −2.318 | 1.00 | 83.80 | O |
| ATOM | 1442 | CB | PRO | A | 587 | −1.729 | 17.111 | 0.323 | 1.00 | 83.19 | C |
| ATOM | 1443 | CG | PRO | A | 587 | −1.774 | 15.855 | 1.132 | 1.00 | 94.40 | C |
| ATOM | 1444 | CD | PRO | A | 587 | −3.021 | 15.989 | 1.953 | 1.00 | 92.48 | C |
| ATOM | 1445 | N | GLU | A | 588 | −3.534 | 15.580 | −1.547 | 1.00 | 91.91 | N |
| ATOM | 1446 | CA | GLU | A | 588 | −3.744 | 14.952 | −2.847 | 1.00 | 91.75 | C |
| ATOM | 1447 | C | GLU | A | 588 | −5.162 | 15.170 | −3.375 | 1.00 | 79.51 | C |
| ATOM | 1448 | O | GLU | A | 588 | −5.386 | 15.124 | −4.583 | 1.00 | 77.18 | O |
| ATOM | 1449 | CB | GLU | A | 588 | −3.417 | 13.456 | −2.776 | 1.00 | 99.66 | C |
| ATOM | 1450 | CG | GLU | A | 588 | −2.025 | 13.144 | −2.231 | 1.00 | 117.75 | C |
| ATOM | 1451 | CD | GLU | A | 588 | −0.909 | 13.456 | −3.219 | 1.00 | 128.93 | C |
| ATOM | 1452 | OE1 | GLU | A | 588 | −0.218 | 12.507 | −3.648 | 1.00 | 131.62 | O |
| ATOM | 1453 | OE2 | GLU | A | 588 | −0.710 | 14.644 | −3.558 | 1.00 | 131.28 | O |
| ATOM | 1454 | N | VAL | A | 589 | −6.111 | 15.411 | −2.473 | 1.00 | 75.49 | N |
| ATOM | 1455 | CA | VAL | A | 589 | −7.494 | 15.685 | −2.874 | 1.00 | 69.65 | C |
| ATOM | 1456 | C | VAL | A | 589 | −7.642 | 17.114 | −3.395 | 1.00 | 69.40 | C |
| ATOM | 1457 | O | VAL | A | 589 | −8.323 | 17.355 | −4.404 | 1.00 | 66.65 | O |
| ATOM | 1458 | CB | VAL | A | 589 | −8.497 | 15.421 | −1.722 | 1.00 | 95.71 | C |
| ATOM | 1459 | CG1 | VAL | A | 589 | −9.888 | 15.942 | −2.083 | 1.00 | 88.20 | C |
| ATOM | 1460 | CG2 | VAL | A | 589 | −8.549 | 13.934 | −1.395 | 1.00 | 91.67 | C |
| ATOM | 1461 | N | LEU | A | 590 | −6.988 | 18.057 | −2.721 | 1.00 | 78.16 | N |
| ATOM | 1462 | CA | LEU | A | 590 | −7.017 | 19.452 | −3.153 | 1.00 | 79.10 | C |
| ATOM | 1463 | C | LEU | A | 590 | −6.297 | 19.638 | −4.489 | 1.00 | 75.05 | C |
| ATOM | 1464 | O | LEU | A | 590 | −6.797 | 20.322 | −5.386 | 1.00 | 69.24 | O |
| ATOM | 1465 | CB | LEU | A | 590 | −6.383 | 20.353 | −2.092 | 1.00 | 84.90 | C |
| ATOM | 1466 | CG | LEU | A | 590 | −6.900 | 21.796 | −2.063 | 1.00 | 95.70 | C |
| ATOM | 1467 | CD1 | LEU | A | 590 | −8.394 | 21.832 | −1.734 | 1.00 | 97.39 | C |
| ATOM | 1468 | CD2 | LEU | A | 590 | −6.110 | 22.636 | −1.063 | 1.00 | 94.55 | C |
| ATOM | 1469 | N | GLU | A | 591 | −5.122 | 19.026 | −4.608 | 1.00 | 74.33 | N |
| ATOM | 1470 | CA | GLU | A | 591 | −4.328 | 19.097 | −5.829 | 1.00 | 74.46 | C |
| ATOM | 1471 | C | GLU | A | 591 | −5.095 | 18.523 | −7.010 | 1.00 | 67.55 | C |
| ATOM | 1472 | O | GLU | A | 591 | −5.150 | 19.127 | −8.086 | 1.00 | 69.41 | O |
| ATOM | 1473 | CB | GLU | A | 591 | −3.023 | 18.329 | −5.639 | 1.00 | 89.98 | C |
| ATOM | 1474 | CG | GLU | A | 591 | −2.142 | 18.269 | −6.868 | 1.00 | 100.67 | C |
| ATOM | 1475 | CD | GLU | A | 591 | −1.370 | 16.964 | −6.961 | 1.00 | 117.66 | C |
| ATOM | 1476 | OE1 | GLU | A | 591 | −1.960 | 15.955 | −7.405 | 1.00 | 125.15 | O |
| ATOM | 1477 | OE2 | GLU | A | 591 | −0.179 | 16.944 | −6.584 | 1.00 | 119.84 | O |
| ATOM | 1478 | N | ARG | A | 592 | −5.690 | 17.350 | −6.811 | 1.00 | 62.99 | N |
| ATOM | 1479 | CA | ARG | A | 592 | −6.460 | 16.720 | −7.871 | 1.00 | 68.24 | C |
| ATOM | 1480 | C | ARG | A | 592 | −7.640 | 17.598 | −8.236 | 1.00 | 64.35 | C |
| ATOM | 1481 | O | ARG | A | 592 | −8.059 | 17.645 | −9.395 | 1.00 | 55.08 | O |
| ATOM | 1482 | CB | ARG | A | 592 | −6.967 | 15.342 | −7.446 | 1.00 | 82.77 | C |
| ATOM | 1483 | CG | ARG | A | 592 | −7.580 | 14.562 | −8.598 | 1.00 | 99.82 | C |
| ATOM | 1484 | CD | ARG | A | 592 | −8.850 | 13.840 | −8.191 | 1.00 | 112.73 | C |
| ATOM | 1485 | NE | ARG | A | 592 | −9.224 | 12.835 | −9.180 | 1.00 | 117.18 | N |
| ATOM | 1486 | CZ | ARG | A | 592 | −8.790 | 11.578 | −9.161 | 1.00 | 119.78 | C |
| ATOM | 1487 | NH1 | ARG | A | 592 | −7.968 | 11.173 | −8.198 | 1.00 | 126.99 | N |
| ATOM | 1488 | NH2 | ARG | A | 592 | −9.176 | 10.724 | −10.101 | 1.00 | 110.34 | N |
| ATOM | 1489 | N | GLN | A | 593 | −8.193 | 18.294 | −7.246 | 1.00 | 54.28 | N |
| ATOM | 1490 | CA | GLN | A | 593 | −9.348 | 19.143 | −7.533 | 1.00 | 56.39 | C |
| ATOM | 1491 | C | GLN | A | 593 | −8.953 | 20.364 | −8.345 | 1.00 | 56.76 | C |
| ATOM | 1492 | O | GLN | A | 593 | −9.702 | 20.795 | −9.217 | 1.00 | 55.93 | O |
| ATOM | 1493 | CB | GLN | A | 593 | −10.055 | 19.564 | −6.259 | 1.00 | 73.64 | C |
| ATOM | 1494 | CG | GLN | A | 593 | −11.124 | 18.599 | −5.857 | 1.00 | 81.23 | C |
| ATOM | 1495 | CD | GLN | A | 593 | −12.487 | 19.043 | −6.308 | 1.00 | 51.73 | C |
| ATOM | 1496 | OE1 | GLN | A | 593 | −12.729 | 20.234 | −6.516 | 1.00 | 74.40 | O |
| ATOM | 1497 | NE2 | GLN | A | 593 | −13.405 | 18.096 | −6.430 | 1.00 | 71.53 | N |
| ATOM | 1498 | N | GLY | A | 594 | −7.784 | 20.919 | −8.042 | 1.00 | 55.58 | N |

TABLE 3-continued

Atomic coordinates of RSK2 model (pdb file)

| ATOM | 1499 | CA | GLY | A | 594 | −7.212 | 21.972 | −8.862 | 1.00 | 58.11 | C |
|------|------|-----|-----|---|-----|--------|--------|--------|------|-------|---|
| ATOM | 1500 | C | GLY | A | 594 | −7.010 | 21.518 | −10.300 | 1.00 | 50.74 | C |
| ATOM | 1501 | O | GLY | A | 594 | −7.381 | 22.230 | −11.242 | 1.00 | 49.48 | O |
| ATOM | 1502 | N | TYR | A | 595 | −6.422 | 20.334 | −10.472 | 1.00 | 55.75 | N |
| ATOM | 1503 | CA | TYR | A | 595 | −6.244 | 19.727 | −11.796 | 1.00 | 57.81 | C |
| ATOM | 1504 | C | TYR | A | 595 | −7.566 | 19.530 | −12.528 | 1.00 | 54.55 | C |
| ATOM | 1505 | O | TYR | A | 595 | −7.695 | 19.843 | −13.720 | 1.00 | 47.60 | O |
| ATOM | 1506 | CB | TYR | A | 595 | −5.553 | 18.367 | −11.669 | 1.00 | 60.23 | C |
| ATOM | 1507 | CG | TYR | A | 595 | −4.059 | 18.435 | −11.445 | 1.00 | 61.49 | C |
| ATOM | 1508 | CD1 | TYR | A | 595 | −3.301 | 19.472 | −11.976 | 1.00 | 63.68 | C |
| ATOM | 1509 | CD2 | TYR | A | 595 | −3.406 | 17.457 | −10.705 | 1.00 | 61.45 | C |
| ATOM | 1510 | CE1 | TYR | A | 595 | −1.917 | 19.534 | −11.771 | 1.00 | 66.70 | C |
| ATOM | 1511 | CE2 | TYR | A | 595 | −2.025 | 17.509 | −10.496 | 1.00 | 68.39 | C |
| ATOM | 1512 | CZ | TYR | A | 595 | −1.290 | 18.552 | −11.031 | 1.00 | 70.26 | C |
| ATOM | 1513 | OH | TYR | A | 595 | 0.075 | 18.608 | −10.830 | 1.00 | 74.62 | O |
| ATOM | 1514 | N | ASP | A | 596 | −8.547 | 18.977 | −11.826 | 1.00 | 46.37 | N |
| ATOM | 1515 | CA | ASP | A | 596 | −9.852 | 18.741 | −12.451 | 1.00 | 43.32 | C |
| ATOM | 1516 | C | ASP | A | 596 | −10.524 | 20.031 | −12.915 | 1.00 | 48.95 | C |
| ATOM | 1517 | O | ASP | A | 596 | −11.133 | 20.056 | −13.992 | 1.00 | 41.86 | O |
| ATOM | 1518 | CB | ASP | A | 596 | −10.789 | 17.980 | −11.504 | 1.00 | 62.25 | C |
| ATOM | 1519 | CG | ASP | A | 596 | −10.443 | 16.503 | −11.388 | 1.00 | 69.13 | C |
| ATOM | 1520 | OD1 | ASP | A | 596 | −9.778 | 15.967 | −12.294 | 1.00 | 66.47 | O |
| ATOM | 1521 | OD2 | ASP | A | 596 | −10.852 | 15.874 | −10.394 | 1.00 | 66.88 | O |
| ATOM | 1522 | N | ALA | A | 597 | −10.444 | 21.083 | −12.097 | 1.00 | 50.34 | N |
| ATOM | 1523 | CA | ALA | A | 597 | −11.049 | 22.369 | −12.454 | 1.00 | 45.57 | C |
| ATOM | 1524 | C | ALA | A | 597 | −10.353 | 22.983 | −13.667 | 1.00 | 45.67 | C |
| ATOM | 1525 | O | ALA | A | 597 | −11.001 | 23.546 | −14.535 | 1.00 | 43.11 | O |
| ATOM | 1526 | CB | ALA | A | 597 | −11.005 | 23.334 | −11.275 | 1.00 | 45.23 | C |
| ATOM | 1527 | N | ALA | A | 598 | −9.028 | 22.866 | −13.719 | 1.00 | 45.37 | N |
| ATOM | 1528 | CA | ALA | A | 598 | −8.284 | 23.323 | −14.892 | 1.00 | 42.10 | C |
| ATOM | 1529 | C | ALA | A | 598 | −8.695 | 22.562 | −16.139 | 1.00 | 42.16 | C |
| ATOM | 1530 | O | ALA | A | 598 | −8.701 | 23.120 | −17.234 | 1.00 | 44.71 | O |
| ATOM | 1531 | CB | ALA | A | 598 | −6.783 | 23.146 | −14.660 | 1.00 | 47.75 | C |
| ATOM | 1532 | N | CYS | A | 599 | −9.001 | 21.276 | −15.985 | 1.00 | 45.10 | N |
| ATOM | 1533 | CA | CYS | A | 599 | −9.384 | 20.462 | −17.136 | 1.00 | 39.69 | C |
| ATOM | 1534 | C | CYS | A | 599 | −10.748 | 20.924 | −17.631 | 1.00 | 40.49 | C |
| ATOM | 1535 | O | CYS | A | 599 | −11.002 | 20.967 | −18.846 | 1.00 | 39.90 | O |
| ATOM | 1536 | CB | CYS | A | 599 | −9.420 | 18.975 | −16.779 | 1.00 | 54.65 | C |
| ATOM | 1537 | SG | CYS | A | 599 | −9.642 | 17.893 | −18.221 | 1.00 | 64.69 | S |
| ATOM | 1538 | N | ASP | A | 600 | −11.622 | 21.293 | −16.696 | 1.00 | 37.31 | N |
| ATOM | 1539 | CA | ASP | A | 600 | −12.921 | 21.883 | −17.076 | 1.00 | 34.04 | C |
| ATOM | 1540 | C | ASP | A | 600 | −12.712 | 23.115 | −17.969 | 1.00 | 40.71 | C |
| ATOM | 1541 | O | ASP | A | 600 | −13.413 | 23.306 | −18.954 | 1.00 | 39.80 | O |
| ATOM | 1542 | CB | ASP | A | 600 | −13.721 | 22.350 | −15.843 | 1.00 | 42.30 | C |
| ATOM | 1543 | CG | ASP | A | 600 | −14.450 | 21.213 | −15.105 | 1.00 | 46.72 | C |
| ATOM | 1544 | OD1 | ASP | A | 600 | −14.522 | 20.079 | −15.618 | 1.00 | 43.07 | O |
| ATOM | 1545 | OD2 | ASP | A | 600 | −14.970 | 21.482 | −13.987 | 1.00 | 46.92 | O |
| ATOM | 1546 | N | ILE | A | 601 | −11.786 | 23.988 | −17.578 | 1.00 | 42.81 | N |
| ATOM | 1547 | CA | ILE | A | 601 | −11.541 | 25.212 | −18.344 | 1.00 | 43.69 | C |
| ATOM | 1548 | C | ILE | A | 601 | −10.938 | 24.894 | −19.720 | 1.00 | 39.83 | C |
| ATOM | 1549 | O | ILE | A | 601 | −11.266 | 25.540 | −20.720 | 1.00 | 38.17 | O |
| ATOM | 1550 | CB | ILE | A | 601 | −10.588 | 26.198 | −17.598 | 1.00 | 43.79 | C |
| ATOM | 1551 | CG1 | ILE | A | 601 | −11.162 | 26.590 | −16.224 | 1.00 | 45.62 | C |
| ATOM | 1552 | CG2 | ILE | A | 601 | −10.322 | 27.436 | −18.455 | 1.00 | 43.73 | C |
| ATOM | 1553 | CD1 | ILE | A | 601 | −12.677 | 26.973 | −16.279 | 1.00 | 46.88 | C |
| ATOM | 1554 | N | TRP | A | 602 | −10.045 | 23.906 | −19.771 | 1.00 | 40.40 | N |
| ATOM | 1555 | CA | TRP | A | 602 | −9.461 | 23.480 | −21.043 | 1.00 | 38.37 | C |
| ATOM | 1556 | C | TRP | A | 602 | −10.553 | 23.059 | −22.042 | 1.00 | 43.03 | C |
| ATOM | 1557 | O | TRP | A | 602 | −10.508 | 23.416 | −23.237 | 1.00 | 38.59 | O |
| ATOM | 1558 | CB | TRP | A | 602 | −8.463 | 22.335 | −20.779 | 1.00 | 36.70 | C |
| ATOM | 1559 | CG | TRP | A | 602 | −7.741 | 21.803 | −22.014 | 1.00 | 40.99 | C |
| ATOM | 1560 | CD1 | TRP | A | 602 | −6.523 | 22.213 | −22.506 | 1.00 | 42.29 | C |
| ATOM | 1561 | CD2 | TRP | A | 602 | −8.183 | 20.740 | −22.872 | 1.00 | 39.62 | C |
| ATOM | 1562 | NE1 | TRP | A | 602 | −6.202 | 21.479 | −23.643 | 1.00 | 39.75 | N |
| ATOM | 1563 | CE2 | TRP | A | 602 | −7.198 | 20.558 | −23.876 | 1.00 | 38.52 | C |
| ATOM | 1564 | CE3 | TRP | A | 602 | −9.318 | 19.913 | −22.893 | 1.00 | 41.60 | C |
| ATOM | 1565 | CZ2 | TRP | A | 602 | −7.303 | 19.586 | −24.875 | 1.00 | 40.29 | C |
| ATOM | 1566 | CZ3 | TRP | A | 602 | −9.431 | 18.955 | −23.892 | 1.00 | 47.49 | C |
| ATOM | 1567 | CH2 | TRP | A | 602 | −8.431 | 18.802 | −24.870 | 1.00 | 50.05 | C |
| ATOM | 1568 | N | SER | A | 603 | −11.555 | 22.326 | −21.556 | 1.00 | 40.07 | N |
| ATOM | 1569 | CA | SER | A | 603 | −12.659 | 21.924 | −22.439 | 1.00 | 41.40 | C |
| ATOM | 1570 | C | SER | A | 603 | −13.492 | 23.101 | −22.937 | 1.00 | 38.42 | C |
| ATOM | 1571 | O | SER | A | 603 | −14.011 | 23.071 | −24.048 | 1.00 | 36.41 | O |
| ATOM | 1572 | CB | SER | A | 603 | −13.580 | 20.897 | −21.781 | 1.00 | 39.90 | C |
| ATOM | 1573 | OG | SER | A | 603 | −12.946 | 19.630 | −21.757 | 1.00 | 47.31 | O |
| ATOM | 1574 | N | LEU | A | 604 | −13.639 | 24.126 | −22.109 | 1.00 | 35.38 | N |
| ATOM | 1575 | CA | LEU | A | 604 | −14.314 | 25.342 | −22.578 | 1.00 | 34.44 | C |
| ATOM | 1576 | C | LEU | A | 604 | −13.422 | 26.032 | −23.610 | 1.00 | 39.36 | C |

TABLE 3-continued

Atomic coordinates of RSK2 model (pdb file)

| ATOM | 1577 | O   | LEU | A | 604 | −13.910 | 26.684 | −24.535 | 1.00 | 40.12 | O |
|------|------|-----|-----|---|-----|---------|--------|---------|------|-------|---|
| ATOM | 1578 | CB  | LEU | A | 604 | −14.612 | 26.277 | −21.389 | 1.00 | 32.55 | C |
| ATOM | 1579 | CG  | LEU | A | 604 | −15.560 | 25.753 | −20.307 | 1.00 | 42.45 | C |
| ATOM | 1580 | CD1 | LEU | A | 604 | −15.781 | 26.821 | −19.233 | 1.00 | 42.37 | C |
| ATOM | 1581 | CD2 | LEU | A | 604 | −16.893 | 25.337 | −20.926 | 1.00 | 38.42 | C |
| ATOM | 1582 | N   | GLY | A | 605 | −12.107 | 25.894 | −23.453 | 1.00 | 37.05 | N |
| ATOM | 1583 | CA  | GLY | A | 605 | −11.192 | 26.380 | −24.484 | 1.00 | 36.81 | C |
| ATOM | 1584 | C   | GLY | A | 605 | −11.390 | 25.664 | −25.815 | 1.00 | 33.89 | C |
| ATOM | 1585 | O   | GLY | A | 605 | −11.399 | 26.289 | −26.886 | 1.00 | 38.11 | O |
| ATOM | 1586 | N   | VAL | A | 605 | −11.551 | 24.347 | −25.762 | 1.00 | 32.85 | N |
| ATOM | 1587 | CA  | VAL | A | 606 | −11.788 | 23.566 | −26.976 | 1.00 | 37.30 | C |
| ATOM | 1588 | C   | VAL | A | 606 | −13.099 | 24.010 | −27.620 | 1.00 | 39.21 | C |
| ATOM | 1589 | O   | VAL | A | 606 | −13.205 | 24.140 | −28.837 | 1.00 | 36.02 | O |
| ATOM | 1590 | CB  | VAL | A | 606 | −11.876 | 22.060 | −26.657 | 1.00 | 33.15 | C |
| ATOM | 1591 | CG1 | VAL | A | 606 | −12.374 | 21.284 | −27.895 | 1.00 | 36.87 | C |
| ATOM | 1592 | CG2 | VAL | A | 606 | −10.496 | 21.551 | −26.234 | 1.00 | 38.89 | C |
| ATOM | 1593 | N   | LEU | A | 607 | −14.093 | 24.237 | −26.776 | 1.00 | 31.77 | N |
| ATOM | 1594 | CA  | LEU | A | 607 | −15.379 | 24.758 | −27.245 | 1.00 | 34.96 | C |
| ATOM | 1595 | C   | LEU | A | 607 | −15.198 | 26.087 | −27.970 | 1.00 | 34.74 | C |
| ATOM | 1596 | O   | LEU | A | 607 | −15.711 | 26.283 | −29.063 | 1.00 | 35.94 | O |
| ATOM | 1597 | CB  | LEU | A | 607 | −16.333 | 24.935 | −26.063 | 1.00 | 34.20 | C |
| ATOM | 1598 | CG  | LEU | A | 607 | −17.713 | 25.530 | −26.417 | 1.00 | 34.74 | C |
| ATOM | 1599 | CD1 | LEU | A | 607 | −18.473 | 24.576 | −27.302 | 1.00 | 39.28 | C |
| ATOM | 1600 | CD2 | LEU | A | 607 | −18.504 | 25.808 | −25.131 | 1.00 | 43.29 | C |
| ATOM | 1601 | N   | LEU | A | 608 | −14.452 | 26.998 | −27.364 | 1.00 | 37.23 | N |
| ATOM | 1602 | CA  | LEU | A | 608 | −14.299 | 28.331 | −27.922 | 1.00 | 38.33 | C |
| ATOM | 1603 | C   | LEU | A | 608 | −13.599 | 28.283 | −29.269 | 1.00 | 38.75 | C |
| ATOM | 1604 | O   | LEU | A | 608 | −14.043 | 28.898 | −30.250 | 1.00 | 38.48 | O |
| ATOM | 1605 | CB  | LEU | A | 608 | −13.487 | 29.204 | −26.950 | 1.00 | 35.49 | C |
| ATOM | 1606 | CG  | LEU | A | 608 | −13.222 | 30.623 | −27.466 | 1.00 | 39.61 | C |
| ATOM | 1607 | CD1 | LEU | A | 608 | −14.537 | 31.282 | −27.856 | 1.00 | 40.71 | C |
| ATOM | 1608 | CD2 | LEU | A | 608 | −12.501 | 31.463 | −26.412 | 1.00 | 41.53 | C |
| ATOM | 1609 | N   | TYR | A | 609 | −12.480 | 27.565 | −29.305 | 1.00 | 42.21 | N |
| ATOM | 1610 | CA  | TYR | A | 609 | −11.697 | 27.397 | −30.528 | 1.00 | 41.67 | C |
| ATOM | 1611 | C   | TYR | A | 609 | −12.616 | 26.969 | −31.670 | 1.00 | 41.87 | C |
| ATOM | 1612 | O   | TYR | A | 609 | −12.604 | 27.533 | −32.780 | 1.00 | 40.73 | O |
| ATOM | 1613 | CB  | TYR | A | 609 | −10.618 | 26.320 | −30.284 | 1.00 | 36.02 | C |
| ATOM | 1614 | CG  | TYR | A | 609 | −9.573  | 26.195 | −31.382 | 1.00 | 38.82 | C |
| ATOM | 1615 | CD1 | TYR | A | 609 | −9.875  | 25.607 | −32.620 | 1.00 | 40.85 | C |
| ATOM | 1616 | CD2 | TYR | A | 609 | −8.287  | 26.661 | −31.181 | 1.00 | 43.06 | C |
| ATOM | 1617 | CE1 | TYR | A | 609 | −8.908  | 25.501 | −33.620 | 1.00 | 41.34 | C |
| ATOM | 1618 | CE2 | TYR | A | 609 | −7.324  | 26.545 | −32.152 | 1.00 | 37.60 | C |
| ATOM | 1619 | CZ  | TYR | A | 609 | −7.639  | 25.971 | −33.373 | 1.00 | 45.12 | C |
| ATOM | 1620 | OH  | TYR | A | 609 | −6.669  | 25.874 | −34.334 | 1.00 | 47.50 | O |
| ATOM | 1621 | N   | THR | A | 610 | −13.426 | 25.959 | −31.395 | 1.00 | 34.97 | N |
| ATOM | 1622 | CA  | THR | A | 610 | −14.273 | 25.364 | −32.421 | 1.00 | 39.28 | C |
| ATOM | 1623 | C   | THR | A | 610 | −15.412 | 26.308 | −32.842 | 1.00 | 41.33 | C |
| ATOM | 1624 | O   | THR | A | 610 | −15.728 | 26.405 | −34.025 | 1.00 | 38.62 | O |
| ATOM | 1625 | CB  | THR | A | 610 | −14.864 | 24.023 | −31.929 | 1.00 | 37.72 | C |
| ATOM | 1626 | OG1 | THR | A | 610 | −13.805 | 23.176 | −31.483 | 1.00 | 38.73 | O |
| ATOM | 1627 | CG2 | THR | A | 610 | −15.623 | 23.306 | −33.062 | 1.00 | 36.30 | C |
| ATOM | 1628 | N   | MET | A | 611 | −16.019 | 27.010 | −31.878 | 1.00 | 36.84 | N |
| ATOM | 1629 | CA  | MET | A | 611 | −17.049 | 28.007 | −32.208 | 1.00 | 36.11 | C |
| ATOM | 1630 | C   | MET | A | 611 | −16.498 | 29.077 | −33.124 | 1.00 | 41.78 | C |
| ATOM | 1631 | O   | MET | A | 611 | −17.187 | 29.545 | −34.035 | 1.00 | 39.78 | O |
| ATOM | 1632 | CB  | MET | A | 611 | −17.558 | 28.701 | −30.927 | 1.00 | 38.29 | C |
| ATOM | 1633 | CG  | MET | A | 611 | −18.547 | 27.899 | −30.107 | 1.00 | 46.31 | C |
| ATOM | 1634 | SD  | MET | A | 611 | −19.386 | 28.981 | −28.905 | 1.00 | 46.99 | S |
| ATOM | 1635 | CE  | MET | A | 611 | −18.000 | 29.407 | −27.841 | 1.00 | 44.33 | C |
| ATOM | 1636 | N   | LEU | A | 612 | −15.249 | 29.482 | −32.885 | 1.00 | 34.51 | N |
| ATOM | 1637 | CA  | LEU | A | 612 | −14.683 | 30.576 | −33.677 | 1.00 | 41.20 | C |
| ATOM | 1638 | C   | LEU | A | 612 | −14.320 | 30.200 | −35.119 | 1.00 | 47.98 | C |
| ATOM | 1639 | O   | LEU | A | 612 | −14.400 | 31.038 | −36.004 | 1.00 | 47.57 | O |
| ATOM | 1640 | CB  | LEU | A | 612 | −13.445 | 31.157 | −32.989 | 1.00 | 37.71 | C |
| ATOM | 1641 | CG  | LEU | A | 612 | −13.705 | 31.831 | −31.632 | 1.00 | 45.18 | C |
| ATOM | 1642 | CD1 | LEU | A | 612 | −12.394 | 32.222 | −30.916 | 1.00 | 44.55 | C |
| ATOM | 1643 | CD2 | LEU | A | 612 | −14.608 | 33.041 | −31.834 | 1.00 | 53.20 | C |
| ATOM | 1644 | N   | THR | A | 613 | −13.901 | 28.959 | −35.356 | 1.00 | 40.03 | N |
| ATOM | 1645 | CA  | THR | A | 613 | −13.348 | 28.598 | −36.669 | 1.00 | 41.06 | C |
| ATOM | 1646 | C   | THR | A | 613 | −14.053 | 27.457 | −37.385 | 1.00 | 49.27 | C |
| ATOM | 1647 | O   | THR | A | 613 | −13.802 | 27.217 | −38.565 | 1.00 | 42.00 | O |
| ATOM | 1648 | CB  | THR | A | 613 | −11.900 | 28.144 | −36.535 | 1.00 | 50.70 | C |
| ATOM | 1649 | OG1 | THR | A | 613 | −11.857 | 26.992 | −35.676 | 1.00 | 41.83 | O |
| ATOM | 1650 | CG2 | THR | A | 613 | −11.067 | 29.248 | −35.955 | 1.00 | 51.99 | C |
| ATOM | 1651 | N   | GLY | A | 614 | −14.891 | 26.719 | −36.672 | 1.00 | 40.55 | N |
| ATOM | 1652 | CA  | GLY | A | 614 | −15.555 | 25.576 | −37.279 | 1.00 | 40.35 | C |
| ATOM | 1653 | C   | GLY | A | 614 | −14.735 | 24.291 | −37.362 | 1.00 | 43.18 | C |
| ATOM | 1654 | O   | GLY | A | 614 | −15.154 | 23.330 | −38.000 | 1.00 | 41.14 | O |

TABLE 3-continued

Atomic coordinates of RSK2 model (pdb file)

| ATOM | 1655 | N | TYR | A | 615 | −13.554 | 24.265 | −36.751 | 1.00 | 35.81 | N |
|---|---|---|---|---|---|---|---|---|---|---|---|
| ATOM | 1656 | CA | TYR | A | 615 | −12.817 | 22.998 | −36.609 | 1.00 | 47.32 | C |
| ATOM | 1657 | C | TYR | A | 615 | −12.200 | 22.909 | −35.218 | 1.00 | 40.59 | C |
| ATOM | 1658 | O | TYR | A | 615 | −12.087 | 23.923 | −34.536 | 1.00 | 36.64 | O |
| ATOM | 1659 | CB | TYR | A | 615 | −11.772 | 22.810 | −37.723 | 1.00 | 48.08 | C |
| ATOM | 1660 | CG | TYR | A | 615 | −10.642 | 23.813 | −37.702 | 1.00 | 47.10 | C |
| ATOM | 1661 | CD2 | TYR | A | 615 | −9.424 | 23.511 | −37.095 | 1.00 | 44.54 | C |
| ATOM | 1662 | CD1 | TYR | A | 615 | −10.775 | 25.052 | −38.320 | 1.00 | 58.12 | C |
| ATOM | 1663 | CE2 | TYR | A | 615 | −8.373 | 24.432 | −37.083 | 1.00 | 48.95 | C |
| ATOM | 1664 | CE1 | TYR | A | 615 | −9.733 | 25.976 | −38.316 | 1.00 | 61.51 | C |
| ATOM | 1665 | CZ | TYR | A | 615 | −8.538 | 25.662 | −37.694 | 1.00 | 53.99 | C |
| ATOM | 1666 | OH | TYR | A | 615 | −7.505 | 26.577 | −37.690 | 1.00 | 59.16 | O |
| ATOM | 1667 | N | THR | A | 616 | −11.840 | 21.705 | −34.777 | 1.00 | 41.60 | N |
| ATOM | 1668 | CA | THR | A | 616 | −11.407 | 21.520 | −33.398 | 1.00 | 36.21 | C |
| ATOM | 1669 | C | THR | A | 616 | −9.878 | 21.630 | −33.343 | 1.00 | 37.56 | C |
| ATOM | 1670 | O | THR | A | 616 | −9.207 | 21.332 | −34.319 | 1.00 | 38.77 | O |
| ATOM | 1671 | CB | THR | A | 616 | −11.850 | 20.164 | −32.802 | 1.00 | 42.19 | C |
| ATOM | 1672 | OG1 | THR | A | 616 | −10.912 | 19.148 | −33.175 | 1.00 | 44.77 | O |
| ATOM | 1673 | CG2 | THR | A | 616 | −13.241 | 19.777 | −33.288 | 1.00 | 38.05 | C |
| ATOM | 1674 | N | PRO | A | 617 | −9.339 | 22.067 | −32.199 | 1.00 | 35.63 | N |
| ATOM | 1675 | CA | PRO | A | 617 | −7.898 | 22.386 | −32.180 | 1.00 | 35.60 | C |
| ATOM | 1676 | C | PRO | A | 617 | −6.927 | 21.220 | −32.313 | 1.00 | 41.74 | C |
| ATOM | 1677 | O | PRO | A | 617 | −5.765 | 21.444 | −32.703 | 1.00 | 41.40 | O |
| ATOM | 1678 | CB | PRO | A | 617 | −7.702 | 23.039 | −30.811 | 1.00 | 40.50 | C |
| ATOM | 1679 | CG | PRO | A | 617 | −8.896 | 22.601 | −29.975 | 1.00 | 41.15 | C |
| ATOM | 1680 | CD | PRO | A | 617 | −10.020 | 22.522 | −30.976 | 1.00 | 36.88 | C |
| ATOM | 1681 | N | PHE | A | 618 | −7.344 | 20.009 | −31.954 | 1.00 | 37.89 | N |
| ATOM | 1682 | CA | PHE | A | 618 | −6.379 | 18.898 | −31.875 | 1.00 | 41.43 | C |
| ATOM | 1683 | C | PHE | A | 618 | −6.725 | 17.699 | −32.736 | 1.00 | 45.00 | C |
| ATOM | 1684 | O | PHE | A | 618 | −6.032 | 16.687 | −32.705 | 1.00 | 39.01 | O |
| ATOM | 1685 | CB | PHE | A | 618 | −6.218 | 18.458 | −30.420 | 1.00 | 39.79 | C |
| ATOM | 1686 | CG | PHE | A | 618 | −5.808 | 19.580 | −29.500 | 1.00 | 37.50 | C |
| ATOM | 1687 | CD1 | PHE | A | 618 | −4.530 | 20.116 | −29.591 | 1.00 | 43.67 | C |
| ATOM | 1688 | CD2 | PHE | A | 618 | −6.697 | 20.100 | −28.573 | 1.00 | 42.43 | C |
| ATOM | 1689 | CE1 | PHE | A | 618 | −4.128 | 21.146 | −28.753 | 1.00 | 44.11 | C |
| ATOM | 1690 | CE2 | PHE | A | 618 | −6.318 | 21.144 | −27.731 | 1.00 | 41.53 | C |
| ATOM | 1691 | CZ | PHE | A | 618 | −5.012 | 21.662 | −27.823 | 1.00 | 41.24 | C |
| ATOM | 1692 | N | ALA | A | 619 | −7.808 | 17.791 | −33.496 | 1.00 | 37.40 | N |
| ATOM | 1693 | CA | ALA | A | 619 | −8.158 | 16.679 | −34.373 | 1.00 | 45.31 | C |
| ATOM | 1694 | C | ALA | A | 619 | −8.916 | 17.170 | −35.597 | 1.00 | 42.16 | C |
| ATOM | 1695 | O | ALA | A | 619 | −9.764 | 18.056 | −35.486 | 1.00 | 44.07 | O |
| ATOM | 1696 | CB | ALA | A | 619 | −8.981 | 15.641 | −33.609 | 1.00 | 40.24 | C |
| ATOM | 1697 | N | ASN | A | 620 | −8.623 | 16.575 | −36.751 | 1.00 | 39.96 | N |
| ATOM | 1698 | CA | ASN | A | 620 | −9.236 | 16.998 | −38.015 | 1.00 | 45.12 | C |
| ATOM | 1699 | C | ASN | A | 620 | −10.507 | 16.231 | −38.372 | 1.00 | 51.28 | C |
| ATOM | 1700 | O | ASN | A | 620 | −11.299 | 16.672 | −39.210 | 1.00 | 56.42 | O |
| ATOM | 1701 | CB | ASN | A | 620 | −8.227 | 16.908 | −39.156 | 1.00 | 51.26 | C |
| ATOM | 1702 | CG | ASN | A | 620 | −7.146 | 17.961 | −39.047 | 1.00 | 61.71 | C |
| ATOM | 1703 | OD1 | ASN | A | 620 | −7.429 | 19.126 | −38.751 | 1.00 | 65.77 | O |
| ATOM | 1704 | ND2 | ASN | A | 620 | −5.901 | 17.558 | −39.261 | 1.00 | 59.28 | N |
| ATOM | 1705 | N | GLY | A | 621 | −10.705 | 15.094 | −37.717 | 1.00 | 47.09 | N |
| ATOM | 1706 | CA | GLY | A | 621 | −11.819 | 14.218 | −38.032 | 1.00 | 46.86 | C |
| ATOM | 1707 | C | GLY | A | 621 | −11.792 | 12.997 | −37.139 | 1.00 | 51.13 | C |
| ATOM | 1708 | O | GLY | A | 621 | −10.860 | 12.843 | −36.339 | 1.00 | 48.36 | O |
| ATOM | 1709 | N | PRO | A | 622 | −12.802 | 12.116 | −37.282 | 1.00 | 47.62 | N |
| ATOM | 1710 | CA | PRO | A | 622 | −13.002 | 10.948 | −36.410 | 1.00 | 47.47 | C |
| ATOM | 1711 | C | PRO | A | 622 | −11.902 | 9.890 | −36.561 | 1.00 | 51.65 | C |
| ATOM | 1712 | O | PRO | A | 622 | −11.720 | 9.059 | −35.670 | 1.00 | 58.12 | O |
| ATOM | 1713 | CB | PRO | A | 622 | −14.341 | 10.375 | −36.896 | 1.00 | 54.68 | C |
| ATOM | 1714 | CG | PRO | A | 622 | −14.425 | 10.791 | −38.339 | 1.00 | 51.36 | C |
| ATOM | 1715 | CD | PRO | A | 622 | −13.761 | 12.146 | −38.407 | 1.00 | 51.93 | C |
| ATOM | 1716 | N | ASP | A | 623 | −11.176 | 9.932 | −37.670 | 1.00 | 50.49 | N |
| ATOM | 1717 | CA | ASP | A | 623 | −10.140 | 8.937 | −37.938 | 1.00 | 53.31 | C |
| ATOM | 1718 | C | ASP | A | 623 | −8.738 | 9.301 | −37.437 | 1.00 | 48.66 | C |
| ATOM | 1719 | O | ASP | A | 623 | −7.813 | 8.520 | −37.607 | 1.00 | 55.02 | O |
| ATOM | 1720 | CB | ASP | A | 623 | −10.063 | 8.630 | −39.434 | 1.00 | 55.94 | C |
| ATOM | 1721 | CG | ASP | A | 623 | −11.350 | 8.057 | −39.975 | 1.00 | 69.27 | C |
| ATOM | 1722 | OD1 | ASP | A | 623 | −12.088 | 7.414 | −39.193 | 1.00 | 67.92 | O |
| ATOM | 1723 | OD2 | ASP | A | 623 | −11.618 | 8.251 | −41.182 | 1.00 | 70.23 | O |
| ATOM | 1724 | N | ASP | A | 624 | −8.570 | 10.480 | −36.852 | 1.00 | 53.76 | N |
| ATOM | 1725 | CA | ASP | A | 624 | −7.271 | 10.841 | −36.279 | 1.00 | 57.84 | C |
| ATOM | 1726 | C | ASP | A | 624 | −6.872 | 9.841 | −35.189 | 1.00 | 53.13 | C |
| ATOM | 1727 | O | ASP | A | 624 | −7.676 | 9.485 | −34.331 | 1.00 | 58.46 | O |
| ATOM | 1728 | CB | ASP | A | 624 | −7.297 | 12.278 | −35.730 | 1.00 | 42.91 | C |
| ATOM | 1729 | CG | ASP | A | 624 | −7.124 | 13.329 | −36.830 | 1.00 | 51.74 | C |
| ATOM | 1730 | OD1 | ASP | A | 624 | −7.236 | 12.970 | −38.024 | 1.00 | 61.63 | O |
| ATOM | 1731 | OD2 | ASP | A | 624 | −6.867 | 14.510 | −36.501 | 1.00 | 50.02 | O |
| ATOM | 1732 | N | THR | A | 625 | −5.629 | 9.373 | −35.230 | 1.00 | 51.51 | N |

TABLE 3-continued

Atomic coordinates of RSK2 model (pdb file)

| ATOM | 1733 | CA | THR | A | 625 | −5.170 | 8.425 | −34.221 | 1.00 | 50.85 | C |
|---|---|---|---|---|---|---|---|---|---|---|---|
| ATOM | 1734 | C | THR | A | 625 | −5.144 | 9.097 | −32.856 | 1.00 | 48.47 | C |
| ATOM | 1735 | O | THR | A | 625 | −4.941 | 10.308 | −32.759 | 1.00 | 48.12 | O |
| ATOM | 1736 | CB | THR | A | 625 | −3.760 | 7.876 | −34.565 | 1.00 | 57.39 | C |
| ATOM | 1737 | OG1 | THR | A | 625 | −2.802 | 8.934 | −34.483 | 1.00 | 57.49 | O |
| ATOM | 1738 | CG2 | THR | A | 625 | −3.736 | 7.296 | −35.966 | 1.00 | 54.74 | C |
| ATOM | 1739 | N | PRO | A | 626 | −5.359 | 8.323 | −31.784 | 1.00 | 63.26 | N |
| ATOM | 1740 | CA | PRO | A | 626 | −5.284 | 8.901 | −30.438 | 1.00 | 56.91 | C |
| ATOM | 1741 | C | PRO | A | 626 | −3.858 | 9.391 | −30.127 | 1.00 | 49.12 | C |
| ATOM | 1742 | O | PRO | A | 626 | −3.656 | 10.363 | −29.392 | 1.00 | 49.12 | O |
| ATOM | 1743 | CB | PRO | A | 626 | −5.640 | 7.722 | −29.528 | 1.00 | 65.46 | C |
| ATOM | 1744 | CG | PRO | A | 626 | −6.265 | 6.703 | −30.419 | 1.00 | 66.88 | C |
| ATOM | 1745 | CD | PRO | A | 626 | −5.661 | 6.884 | −31.759 | 1.00 | 63.60 | C |
| ATOM | 1746 | N | GLU | A | 627 | −2.871 | 8.709 | −30.684 | 1.00 | 51.67 | N |
| ATOM | 1747 | CA | GLU | A | 627 | −1.500 | 9.134 | −30.464 | 1.00 | 57.04 | C |
| ATOM | 1748 | C | GLU | A | 627 | −1.228 | 10.515 | −31.055 | 1.00 | 62.40 | C |
| ATOM | 1749 | O | GLU | A | 627 | −0.584 | 11.337 | −30.409 | 1.00 | 52.50 | O |
| ATOM | 1750 | CB | GLU | A | 627 | −0.506 | 8.105 | −30.998 | 1.00 | 61.81 | C |
| ATOM | 1751 | CG | GLU | A | 627 | −0.521 | 6.791 | −30.252 | 1.00 | 73.05 | C |
| ATOM | 1752 | CD | GLU | A | 627 | −1.576 | 5.831 | −30.764 | 1.00 | 77.19 | C |
| ATOM | 1753 | OE1 | GLU | A | 627 | −2.341 | 6.198 | −31.678 | 1.00 | 75.58 | O |
| ATOM | 1754 | OE2 | GLU | A | 627 | −1.635 | 4.695 | −30.255 | 1.00 | 94.64 | O |
| ATOM | 1755 | N | GLU | A | 628 | −1.725 | 10.794 | −32.261 | 1.00 | 58.33 | N |
| ATOM | 1756 | CA | GLU | A | 628 | −1.438 | 12.101 | −32.840 | 1.00 | 50.13 | C |
| ATOM | 1757 | C | GLU | A | 628 | −2.207 | 13.204 | −32.159 | 1.00 | 46.32 | C |
| ATOM | 1758 | O | GLU | A | 628 | −1.721 | 14.325 | −32.049 | 1.00 | 48.46 | O |
| ATOM | 1759 | CB | GLU | A | 628 | −1.619 | 12.140 | −34.359 | 1.00 | 61.17 | C |
| ATOM | 1760 | CG | GLU | A | 628 | −3.019 | 12.009 | −34.870 | 1.00 | 56.88 | C |
| ATOM | 1761 | CD | GLU | A | 628 | −3.017 | 11.778 | −36.374 | 1.00 | 74.14 | C |
| ATOM | 1762 | OE1 | GLU | A | 628 | −3.942 | 11.116 | −36.886 | 1.00 | 63.22 | O |
| ATOM | 1763 | OE2 | GLU | A | 628 | −2.068 | 12.245 | −37.041 | 1.00 | 87.70 | O |
| ATOM | 1764 | N | ILE | A | 629 | −3.418 | 12.888 | −31.712 | 1.00 | 44.92 | N |
| ATOM | 1765 | CA | ILE | A | 629 | −4.203 | 13.854 | −30.969 | 1.00 | 47.51 | C |
| ATOM | 1766 | C | ILE | A | 629 | −3.496 | 14.207 | −29.662 | 1.00 | 54.71 | C |
| ATOM | 1767 | O | ILE | A | 629 | −3.332 | 15.384 | −29.339 | 1.00 | 44.71 | O |
| ATOM | 1768 | CB | ILE | A | 629 | −5.610 | 13.302 | −30.685 | 1.00 | 43.99 | C |
| ATOM | 1769 | CG1 | ILE | A | 629 | −6.401 | 13.198 | −31.998 | 1.00 | 41.00 | C |
| ATOM | 1770 | CG2 | ILE | A | 629 | −6.340 | 14.161 | −29.673 | 1.00 | 39.55 | C |
| ATOM | 1771 | CD1 | ILE | A | 629 | −7.750 | 12.510 | −31.804 | 1.00 | 45.24 | C |
| ATOM | 1772 | N | LEU | A | 630 | −3.065 | 13.187 | −28.924 | 1.00 | 44.82 | N |
| ATOM | 1773 | CA | LEU | A | 630 | −2.410 | 13.409 | −27.631 | 1.00 | 54.12 | C |
| ATOM | 1774 | C | LEU | A | 630 | −1.060 | 14.090 | −27.828 | 1.00 | 51.99 | C |
| ATOM | 1775 | O | LEU | A | 630 | −0.622 | 14.881 | −26.992 | 1.00 | 55.23 | O |
| ATOM | 1776 | CB | LEU | A | 630 | −2.222 | 12.084 | −26.888 | 1.00 | 56.06 | C |
| ATOM | 1777 | CG | LEU | A | 630 | −3.509 | 11.487 | −26.311 | 1.00 | 59.29 | C |
| ATOM | 1778 | CD1 | LEU | A | 630 | −3.249 | 10.101 | −25.745 | 1.00 | 65.17 | C |
| ATOM | 1779 | CD2 | LEU | A | 630 | −4.074 | 12.417 | −25.238 | 1.00 | 52.05 | C |
| ATOM | 1780 | N | ALA | A | 631 | −0.415 | 13.787 | −28.948 | 1.00 | 48.06 | N |
| ATOM | 1781 | CA | ALA | A | 631 | 0.870 | 14.407 | −29.276 | 1.00 | 49.42 | C |
| ATOM | 1782 | C | ALA | A | 631 | 0.667 | 15.907 | −29.463 | 1.00 | 61.57 | C |
| ATOM | 1783 | O | ALA | A | 631 | 1.445 | 16.705 | −28.950 | 1.00 | 54.26 | O |
| ATOM | 1784 | CB | ALA | A | 631 | 1.471 | 13.781 | −30.520 | 1.00 | 61.50 | C |
| ATOM | 1785 | N | ARG | A | 632 | −0.400 | 16.288 | −30.167 | 1.00 | 45.32 | N |
| ATOM | 1786 | CA | ARG | A | 632 | −0.746 | 17.699 | −30.331 | 1.00 | 44.69 | C |
| ATOM | 1787 | C | ARG | A | 632 | −1.099 | 18.395 | −29.015 | 1.00 | 49.06 | C |
| ATOM | 1788 | O | ARG | A | 632 | −0.600 | 19.487 | −28.732 | 1.00 | 57.94 | O |
| ATOM | 1789 | CB | ARG | A | 632 | −1.918 | 17.853 | −31.295 | 1.00 | 41.79 | C |
| ATOM | 1790 | CG | ARG | A | 632 | −1.580 | 17.475 | −32.722 | 1.00 | 45.58 | C |
| ATOM | 1791 | CD | ARG | A | 632 | −2.859 | 17.233 | −33.504 | 1.00 | 43.74 | C |
| ATOM | 1792 | NE | ARG | A | 632 | −2.568 | 16.711 | −34.831 | 1.00 | 51.29 | N |
| ATOM | 1793 | CZ | ARG | A | 632 | −3.416 | 15.985 | −35.551 | 1.00 | 61.59 | C |
| ATOM | 1794 | NH1 | ARG | A | 632 | −4.618 | 15.671 | −35.063 | 1.00 | 44.14 | N |
| ATOM | 1795 | NH2 | ARG | A | 632 | −3.054 | 15.566 | −36.749 | 1.00 | 60.04 | N |
| ATOM | 1796 | N | ILE | A | 633 | −1.990 | 17.777 | −28.239 | 1.00 | 46.55 | N |
| ATOM | 1797 | CA | ILE | A | 633 | −2.345 | 18.283 | −26.916 | 1.00 | 46.10 | C |
| ATOM | 1798 | C | ILE | A | 633 | −1.092 | 18.488 | −26.051 | 1.00 | 56.85 | C |
| ATOM | 1799 | O | ILE | A | 633 | −0.871 | 19.577 | −25.527 | 1.00 | 60.44 | O |
| ATOM | 1800 | CB | ILE | A | 633 | −3.329 | 17.344 | −26.205 | 1.00 | 47.27 | C |
| ATOM | 1801 | CG1 | ILE | A | 633 | −4.655 | 17.305 | −26.978 | 1.00 | 42.72 | C |
| ATOM | 1802 | CG2 | ILE | A | 633 | −3.553 | 17.796 | −24.740 | 1.00 | 42.26 | C |
| ATOM | 1803 | CD1 | ILE | A | 633 | −5.639 | 16.259 | −26.484 | 1.00 | 48.80 | C |
| ATOM | 1804 | N | GLY | A | 634 | −0.261 | 17.452 | −25.946 | 1.00 | 49.76 | N |
| ATOM | 1805 | CA | GLY | A | 634 | 0.926 | 17.491 | −25.104 | 1.00 | 53.13 | C |
| ATOM | 1806 | C | GLY | A | 634 | 1.948 | 18.537 | −25.507 | 1.00 | 63.85 | C |
| ATOM | 1807 | O | GLY | A | 634 | 2.716 | 19.028 | −24.677 | 1.00 | 68.73 | O |
| ATOM | 1808 | N | SER | A | 635 | 1.966 | 18.889 | −26.786 | 1.00 | 67.12 | N |
| ATOM | 1809 | CA | SER | A | 635 | 2.924 | 19.875 | −27.281 | 1.00 | 81.45 | C |
| ATOM | 1810 | C | SER | A | 635 | 2.477 | 21.290 | −26.928 | 1.00 | 75.64 | C |

TABLE 3-continued

Atomic coordinates of RSK2 model (pdb file)

| ATOM | 1811 | O | SER | A | 635 | 3.236 | 22.245 | −27.081 | 1.00 | 77.57 | O |
|---|---|---|---|---|---|---|---|---|---|---|---|
| ATOM | 1812 | CB | SER | A | 635 | 3.076 | 19.757 | −28.797 | 1.00 | 80.11 | C |
| ATOM | 1813 | OG | SER | A | 635 | 1.928 | 20.283 | −29.444 | 1.00 | 70.08 | O |
| ATOM | 1814 | N | GLY | A | 636 | 1.230 | 21.418 | −26.485 | 1.00 | 67.99 | N |
| ATOM | 1815 | CA | GLY | A | 636 | 0.656 | 22.715 | −26.177 | 1.00 | 82.88 | C |
| ATOM | 1816 | C | GLY | A | 636 | 0.624 | 23.665 | −27.362 | 1.00 | 86.28 | C |
| ATOM | 1817 | O | GLY | A | 636 | 0.681 | 24.885 | −27.195 | 1.00 | 83.58 | O |
| ATOM | 1818 | N | LYS | A | 637 | 0.532 | 23.109 | −28.565 | 1.00 | 82.89 | N |
| ATOM | 1819 | CA | LYS | A | 637 | 0.540 | 23.932 | −29.767 | 1.00 | 83.06 | C |
| ATOM | 1820 | C | LYS | A | 637 | −0.674 | 23.696 | −30.670 | 1.00 | 85.04 | C |
| ATOM | 1821 | O | LYS | A | 637 | −1.130 | 22.565 | −30.872 | 1.00 | 78.76 | O |
| ATOM | 1822 | CB | LYS | A | 637 | 1.854 | 23.760 | −30.539 | 1.00 | 93.82 | C |
| ATOM | 1823 | CG | LYS | A | 637 | 3.077 | 24.348 | −29.832 | 1.00 | 98.01 | C |
| ATOM | 1824 | CD | LYS | A | 637 | 3.226 | 25.843 | −30.091 | 1.00 | 99.04 | C |
| ATOM | 1825 | CE | LYS | A | 637 | 4.393 | 26.428 | −29.304 | 1.00 | 103.04 | C |
| ATOM | 1826 | NZ | LYS | A | 637 | 5.668 | 25.698 | −29.557 | 1.00 | 108.66 | N |
| ATOM | 1827 | N | PHE | A | 638 | −1.188 | 24.795 | −31.204 | 1.00 | 81.65 | N |
| ATOM | 1828 | CA | PHE | A | 638 | −2.398 | 24.797 | −32.005 | 1.00 | 70.28 | C |
| ATOM | 1829 | C | PHE | A | 638 | −2.359 | 26.113 | −32.774 | 1.00 | 74.22 | C |
| ATOM | 1830 | O | PHE | A | 638 | −1.810 | 27.101 | −32.282 | 1.00 | 74.38 | O |
| ATOM | 1831 | CB | PHE | A | 638 | −3.631 | 24.714 | −31.090 | 1.00 | 49.74 | C |
| ATOM | 1832 | CG | PHE | A | 638 | −3.505 | 25.543 | −29.847 | 1.00 | 57.12 | C |
| ATOM | 1833 | CD2 | PHE | A | 638 | −3.040 | 24.982 | −28.667 | 1.00 | 56.30 | C |
| ATOM | 1834 | CD1 | PHE | A | 638 | −3.825 | 26.891 | −29.861 | 1.00 | 56.39 | C |
| ATOM | 1835 | CE2 | PHE | A | 638 | −2.896 | 25.746 | −27.529 | 1.00 | 59.45 | C |
| ATOM | 1836 | CE1 | PHE | A | 638 | −3.692 | 27.658 | −28.718 | 1.00 | 55.61 | C |
| ATOM | 1837 | CZ | PHE | A | 638 | −3.221 | 27.086 | −27.554 | 1.00 | 64.35 | C |
| ATOM | 1838 | N | SER | A | 639 | −2.914 | 26.133 | −33.980 | 1.00 | 64.58 | N |
| ATOM | 1839 | CA | SER | A | 639 | −2.795 | 27.319 | −34.824 | 1.00 | 66.54 | C |
| ATOM | 1840 | C | SER | A | 639 | −3.786 | 28.411 | −34.442 | 1.00 | 54.44 | C |
| ATOM | 1841 | O | SER | A | 639 | −4.962 | 28.133 | −34.189 | 1.00 | 52.83 | O |
| ATOM | 1842 | CB | SER | A | 639 | −2.984 | 26.955 | −36.297 | 1.00 | 74.31 | C |
| ATOM | 1843 | OG | SER | A | 639 | −3.038 | 28.125 | −37.087 | 1.00 | 84.99 | O |
| ATOM | 1844 | N | LEU | A | 640 | −3.318 | 29.656 | −34.408 | 1.00 | 45.72 | N |
| ATOM | 1845 | CA | LEU | A | 640 | −4.218 | 30.782 | −34.184 | 1.00 | 51.12 | C |
| ATOM | 1846 | C | LEU | A | 640 | −4.031 | 31.849 | −35.245 | 1.00 | 54.88 | C |
| ATOM | 1847 | O | LEU | A | 640 | −4.370 | 33.011 | −35.031 | 1.00 | 56.32 | O |
| ATOM | 1848 | CB | LEU | A | 640 | −3.995 | 31.399 | −32.809 | 1.00 | 47.12 | C |
| ATOM | 1849 | CG | LEU | A | 640 | −4.381 | 30.540 | −31.610 | 1.00 | 54.66 | C |
| ATOM | 1850 | CD1 | LEU | A | 640 | −4.042 | 31.282 | −30.329 | 1.00 | 62.48 | C |
| ATOM | 1851 | CD2 | LEU | A | 640 | −5.852 | 30.197 | −31.670 | 1.00 | 53.46 | C |
| ATOM | 1852 | N | SER | A | 641 | −3.496 | 31.454 | −36.394 | 1.00 | 50.66 | N |
| ATOM | 1853 | CA | SER | A | 641 | −3.197 | 32.410 | −37.435 | 1.00 | 51.69 | C |
| ATOM | 1854 | C | SER | A | 641 | −3.482 | 31.792 | −38.792 | 1.00 | 69.42 | C |
| ATOM | 1855 | O | SER | A | 641 | −3.400 | 30.577 | −38.958 | 1.00 | 70.57 | O |
| ATOM | 1856 | CB | SER | A | 641 | −1.723 | 32.846 | −37.355 | 1.00 | 62.23 | C |
| ATOM | 1857 | OG | SER | A | 641 | −1.433 | 33.882 | −38.277 | 1.00 | 89.87 | O |
| ATOM | 1858 | N | GLY | A | 642 | −3.819 | 32.636 | −39.760 | 1.00 | 72.46 | N |
| ATOM | 1859 | CA | GLY | A | 642 | −4.095 | 32.172 | −41.105 | 1.00 | 68.07 | C |
| ATOM | 1860 | C | GLY | A | 642 | −5.486 | 31.599 | −41.292 | 1.00 | 60.40 | C |
| ATOM | 1861 | O | GLY | A | 642 | −6.186 | 31.297 | −40.322 | 1.00 | 57.26 | O |
| ATOM | 1862 | N | GLY | A | 643 | −5.874 | 31.460 | −42.555 | 1.00 | 67.88 | N |
| ATOM | 1863 | CA | GLY | A | 643 | −7.126 | 30.843 | −42.942 | 1.00 | 72.09 | C |
| ATOM | 1864 | C | GLY | A | 643 | −8.343 | 31.421 | −42.257 | 1.00 | 60.17 | C |
| ATOM | 1865 | O | GLY | A | 643 | −8.646 | 32.610 | −42.380 | 1.00 | 72.29 | O |
| ATOM | 1866 | N | TYR | A | 644 | −9.035 | 30.558 | −41.523 | 1.00 | 56.14 | N |
| ATOM | 1867 | CA | TYR | A | 644 | −10.231 | 30.929 | −40.790 | 1.00 | 56.29 | C |
| ATOM | 1868 | C | TYR | A | 644 | −9.938 | 31.858 | −39.623 | 1.00 | 60.20 | C |
| ATOM | 1869 | O | TYR | A | 644 | −10.846 | 32.485 | −39.088 | 1.00 | 67.82 | O |
| ATOM | 1870 | CB | TYR | A | 644 | −10.947 | 29.667 | −40.302 | 1.00 | 51.35 | C |
| ATOM | 1871 | CG | TYR | A | 644 | −11.372 | 28.758 | −41.442 | 1.00 | 59.52 | C |
| ATOM | 1872 | CD2 | TYR | A | 644 | −10.894 | 27.458 | −41.533 | 1.00 | 66.72 | C |
| ATOM | 1873 | CD1 | TYR | A | 644 | −12.244 | 29.209 | −42.430 | 1.00 | 63.70 | C |
| ATOM | 1874 | CE2 | TYR | A | 644 | −11.276 | 26.627 | −42.566 | 1.00 | 67.51 | C |
| ATOM | 1875 | CE1 | TYR | A | 644 | −12.634 | 28.379 | −43.477 | 1.00 | 65.36 | C |
| ATOM | 1876 | CZ | TYR | A | 644 | −12.143 | 27.090 | −43.538 | 1.00 | 70.37 | C |
| ATOM | 1877 | OH | TYR | A | 644 | −12.522 | 26.261 | −44.566 | 1.00 | 72.27 | O |
| ATOM | 1878 | N | TRP | A | 645 | −8.673 | 31.953 | −39.230 | 1.00 | 62.51 | N |
| ATOM | 1879 | CA | TRP | A | 645 | −8.301 | 32.818 | −38.111 | 1.00 | 57.05 | C |
| ATOM | 1880 | C | TRP | A | 645 | −8.035 | 34.265 | −38.556 | 1.00 | 64.36 | C |
| ATOM | 1881 | O | TRP | A | 645 | −7.883 | 35.157 | −37.720 | 1.00 | 63.24 | O |
| ATOM | 1882 | CB | TRP | A | 645 | −7.084 | 32.264 | −37.361 | 1.00 | 53.21 | C |
| ATOM | 1883 | CG | TRP | A | 645 | −7.390 | 31.108 | −36.455 | 1.00 | 51.15 | C |
| ATOM | 1884 | CD1 | TRP | A | 645 | −7.083 | 29.799 | −36.674 | 1.00 | 50.46 | C |
| ATOM | 1885 | CD2 | TRP | A | 645 | −8.062 | 31.158 | −35.192 | 1.00 | 47.73 | C |
| ATOM | 1886 | NE1 | TRP | A | 645 | −7.523 | 29.028 | −35.632 | 1.00 | 53.02 | N |
| ATOM | 1887 | CE2 | TRP | A | 645 | −8.120 | 29.836 | −34.701 | 1.00 | 47.51 | C |
| ATOM | 1888 | CE3 | TRP | A | 645 | −8.620 | 32.189 | −34.427 | 1.00 | 48.85 | C |

TABLE 3-continued

Atomic coordinates of RSK2 model (pdb file)

| ATOM | 1889 | CZ2 | TRP | A | 645 | −8.718 | 29.515 | −33.484 | 1.00 | 44.73 | C |
|---|---|---|---|---|---|---|---|---|---|---|---|
| ATOM | 1890 | CZ3 | TRP | A | 645 | −9.218 | 31.867 | −33.208 | 1.00 | 50.16 | C |
| ATOM | 1891 | CH2 | TRP | A | 645 | −9.259 | 30.539 | −32.750 | 1.00 | 47.68 | C |
| ATOM | 1892 | N | ASN | A | 646 | −7.983 | 34.501 | −39.863 | 1.00 | 69.85 | N |
| ATOM | 1893 | CA | ASN | A | 646 | −7.709 | 35.843 | −40.374 | 1.00 | 74.04 | C |
| ATOM | 1894 | C | ASN | A | 646 | −8.775 | 36.878 | −40.012 | 1.00 | 72.60 | C |
| ATOM | 1895 | O | ASN | A | 646 | −8.474 | 38.060 | −39.851 | 1.00 | 81.41 | O |
| ATOM | 1896 | CB | ASN | A | 646 | −7.493 | 35.823 | −41.891 | 1.00 | 79.53 | C |
| ATOM | 1897 | CG | ASN | A | 646 | −6.094 | 35.384 | −42.271 | 1.00 | 82.65 | C |
| ATOM | 1898 | OD1 | ASN | A | 646 | −5.190 | 35.348 | −41.430 | 1.00 | 76.66 | O |
| ATOM | 1899 | ND2 | ASN | A | 646 | −5.901 | 35.058 | −43.545 | 1.00 | 83.32 | N |
| ATOM | 1900 | N | SER | A | 647 | −10.020 | 36.433 | −39.887 | 1.00 | 76.98 | N |
| ATOM | 1901 | CA | SER | A | 647 | −11.118 | 37.346 | −39.589 | 1.00 | 83.02 | C |
| ATOM | 1902 | C | SER | A | 647 | −11.333 | 37.525 | −38.082 | 1.00 | 70.05 | C |
| ATOM | 1903 | O | SER | A | 647 | −12.094 | 38.390 | −37.654 | 1.00 | 73.28 | O |
| ATOM | 1904 | CB | SER | A | 647 | −12.408 | 36.859 | −40.255 | 1.00 | 85.08 | C |
| ATOM | 1905 | OG | SER | A | 647 | −13.404 | 37.866 | −40.223 | 1.00 | 95.16 | O |
| ATOM | 1906 | N | VAL | A | 648 | −10.635 | 36.722 | −37.288 | 1.00 | 53.98 | N |
| ATOM | 1907 | CA | VAL | A | 648 | −10.877 | 36.655 | −35.845 | 1.00 | 49.93 | C |
| ATOM | 1908 | C | VAL | A | 648 | −10.020 | 37.660 | −35.075 | 1.00 | 55.09 | C |
| ATOM | 1909 | O | VAL | A | 648 | −8.850 | 37.864 | −35.386 | 1.00 | 58.76 | O |
| ATOM | 1910 | CB | VAL | A | 648 | −10.664 | 35.216 | −35.342 | 1.00 | 54.96 | C |
| ATOM | 1911 | CG1 | VAL | A | 648 | −10.837 | 35.114 | −33.814 | 1.00 | 49.88 | C |
| ATOM | 1912 | CG2 | VAL | A | 648 | −11.613 | 34.284 | −36.093 | 1.00 | 52.35 | C |
| ATOM | 1913 | N | SER | A | 649 | −10.621 | 38.296 | −34.077 | 1.00 | 54.72 | N |
| ATOM | 1914 | CA | SER | A | 649 | −9.959 | 39.371 | −33.359 | 1.00 | 55.80 | C |
| ATOM | 1915 | C | SER | A | 649 | −8.798 | 38.856 | −32.519 | 1.00 | 64.19 | C |
| ATOM | 1916 | O | SER | A | 649 | −8.737 | 37.681 | −32.159 | 1.00 | 51.65 | O |
| ATOM | 1917 | CB | SER | A | 649 | −10.951 | 40.087 | −32.452 | 1.00 | 59.53 | C |
| ATOM | 1918 | OG | SER | A | 649 | −11.251 | 39.279 | −31.328 | 1.00 | 56.69 | O |
| ATOM | 1919 | N | ASP | A | 650 | −7.890 | 39.764 | −32.188 | 1.00 | 65.03 | N |
| ATOM | 1920 | CA | ASP | A | 650 | −6.731 | 39.430 | −31.384 | 1.00 | 62.27 | C |
| ATOM | 1921 | C | ASP | A | 650 | −7.115 | 39.123 | −29.959 | 1.00 | 60.66 | C |
| ATOM | 1922 | O | ASP | A | 650 | −6.490 | 38.283 | −29.306 | 1.00 | 63.51 | O |
| ATOM | 1923 | CB | ASP | A | 650 | −5.742 | 40.588 | −31.416 | 1.00 | 73.44 | C |
| ATOM | 1924 | CG | ASP | A | 650 | −4.447 | 40.213 | −32.070 | 1.00 | 71.61 | C |
| ATOM | 1925 | OD1 | ASP | A | 650 | −4.469 | 39.380 | −32.994 | 1.00 | 65.73 | O |
| ATOM | 1926 | OD2 | ASP | A | 650 | −3.401 | 40.739 | −31.645 | 1.00 | 74.01 | O |
| ATOM | 1927 | N | THR | A | 651 | −8.141 | 39.813 | −29.470 | 1.00 | 57.25 | N |
| ATOM | 1928 | CA | THR | A | 651 | −8.639 | 39.583 | −28.117 | 1.00 | 57.92 | C |
| ATOM | 1929 | C | THR | A | 651 | −9.103 | 38.139 | −27.967 | 1.00 | 55.31 | C |
| ATOM | 1930 | O | THR | A | 651 | −8.844 | 37.493 | −26.957 | 1.00 | 50.11 | O |
| ATOM | 1931 | CB | THR | A | 651 | −9.825 | 40.504 | −27.792 | 1.00 | 67.54 | C |
| ATOM | 1932 | OG1 | THR | A | 651 | −9.547 | 41.829 | −28.258 | 1.00 | 88.46 | O |
| ATOM | 1933 | CG2 | THR | A | 651 | −10.059 | 40.545 | −26.309 | 1.00 | 71.04 | C |
| ATOM | 1934 | N | ALA | A | 652 | −9.793 | 37.643 | −28.990 | 1.00 | 59.13 | N |
| ATOM | 1935 | CA | ALA | A | 652 | −10.317 | 36.282 | −28.990 | 1.00 | 44.58 | C |
| ATOM | 1936 | C | ALA | A | 652 | −9.190 | 35.260 | −28.987 | 1.00 | 45.16 | C |
| ATOM | 1937 | O | ALA | A | 652 | −9.224 | 34.282 | −28.239 | 1.00 | 46.28 | O |
| ATOM | 1938 | CB | ALA | A | 652 | −11.187 | 36.064 | −30.220 | 1.00 | 44.12 | C |
| ATOM | 1939 | N | LYS | A | 653 | −8.213 | 35.477 | −29.861 | 1.00 | 47.31 | N |
| ATOM | 1940 | CA | LYS | A | 653 | −7.091 | 34.563 | −29.981 | 1.00 | 45.21 | C |
| ATOM | 1941 | C | LYS | A | 653 | −6.345 | 34.513 | −28.655 | 1.00 | 52.74 | C |
| ATOM | 1942 | O | LYS | A | 653 | −5.925 | 33.444 | −28.205 | 1.00 | 46.73 | O |
| ATOM | 1943 | CB | LYS | A | 653 | −6.152 | 35.020 | −31.086 | 1.00 | 44.75 | C |
| ATOM | 1944 | CG | LYS | A | 653 | −6.747 | 34.910 | −32.507 | 1.00 | 47.33 | C |
| ATOM | 1945 | CD | LYS | A | 653 | −5.863 | 35.563 | −33.535 | 1.00 | 52.41 | C |
| ATOM | 1946 | CE | LYS | A | 653 | −6.554 | 35.569 | −34.890 | 1.00 | 55.94 | C |
| ATOM | 1947 | NZ | LYS | A | 653 | −5.672 | 36.072 | −35.966 | 1.00 | 57.08 | N |
| ATOM | 1948 | N | ASP | A | 654 | −6.194 | 35.672 | −28.025 | 1.00 | 52.11 | N |
| ATOM | 1949 | CA | ASP | A | 654 | −5.502 | 35.737 | −26.735 | 1.00 | 56.74 | C |
| ATOM | 1950 | C | ASP | A | 654 | −6.198 | 34.892 | −25.654 | 1.00 | 49.40 | C |
| ATOM | 1951 | O | ASP | A | 654 | −5.555 | 34.128 | −24.937 | 1.00 | 50.64 | O |
| ATOM | 1952 | CB | ASP | A | 654 | −5.333 | 37.187 | −26.285 | 1.00 | 59.68 | C |
| ATOM | 1953 | CG | ASP | A | 654 | −4.611 | 37.300 | −24.960 | 1.00 | 64.87 | C |
| ATOM | 1954 | OD2 | ASP | A | 654 | −5.288 | 37.575 | −23.952 | 1.00 | 56.40 | O |
| ATOM | 1955 | OD1 | ASP | A | 654 | −3.375 | 37.107 | −24.924 | 1.00 | 51.70 | O |
| ATOM | 1956 | N | LEU | A | 655 | −7.517 | 35.013 | −25.554 | 1.00 | 42.87 | N |
| ATOM | 1957 | CA | LEU | A | 655 | −8.280 | 34.247 | −24.569 | 1.00 | 38.45 | C |
| ATOM | 1958 | C | LEU | A | 655 | −8.162 | 32.753 | −24.855 | 1.00 | 43.67 | C |
| ATOM | 1959 | O | LEU | A | 655 | −7.944 | 31.951 | −23.946 | 1.00 | 43.22 | O |
| ATOM | 1960 | CB | LEU | A | 655 | −9.759 | 34.643 | −24.653 | 1.00 | 40.92 | C |
| ATOM | 1961 | CG | LEU | A | 655 | −10.701 | 34.528 | −23.456 | 1.00 | 52.76 | C |
| ATOM | 1962 | CD1 | LEU | A | 655 | −12.026 | 33.992 | −23.915 | 1.00 | 39.47 | C |
| ATOM | 1963 | CD2 | LEU | A | 655 | −10.153 | 33.750 | −22.238 | 1.00 | 45.57 | C |
| ATOM | 1964 | N | VAL | A | 656 | −8.302 | 32.389 | −26.128 | 1.00 | 39.89 | N |
| ATOM | 1965 | CA | VAL | A | 656 | −8.210 | 30.992 | −26.528 | 1.00 | 39.92 | C |
| ATOM | 1966 | C | VAL | A | 656 | −6.862 | 30.405 | −26.108 | 1.00 | 40.05 | C |

TABLE 3-continued

Atomic coordinates of RSK2 model (pdb file)

| ATOM | 1967 | O   | VAL | A | 656 | -6.799  | 29.318 | -25.536 | 1.00 | 44.62 | O |
|------|------|-----|-----|---|-----|---------|--------|---------|------|-------|---|
| ATOM | 1968 | CB  | VAL | A | 656 | -8.297  | 30.858 | -28.053 | 1.00 | 38.60 | C |
| ATOM | 1969 | CG1 | VAL | A | 656 | -7.939  | 29.447 | -28.467 | 1.00 | 45.48 | C |
| ATOM | 1970 | CG2 | VAL | A | 656 | -9.682  | 31.234 | -28.532 | 1.00 | 47.83 | C |
| ATOM | 1971 | N   | SER | A | 657 | -5.794  | 31.135 | -26.398 | 1.00 | 44.40 | N |
| ATOM | 1972 | CA  | SER | A | 657 | -4.449  | 30.659 | -26.089 | 1.00 | 44.43 | C |
| ATOM | 1973 | C   | SER | A | 657 | -4.273  | 30.406 | -24.590 | 1.00 | 51.36 | C |
| ATOM | 1974 | O   | SER | A | 657 | -3.559  | 29.487 | -24.185 | 1.00 | 47.55 | O |
| ATOM | 1975 | CB  | SER | A | 657 | -3.386  | 31.645 | -26.589 | 1.00 | 51.43 | C |
| ATOM | 1976 | OG  | SER | A | 657 | -3.424  | 32.875 | -25.867 | 1.00 | 53.90 | O |
| ATOM | 1977 | N   | LYS | A | 658 | -4.927  | 31.229 | -23.779 | 1.00 | 43.89 | N |
| ATOM | 1978 | CA  | LYS | A | 658 | -4.785  | 31.157 | -22.324 | 1.00 | 44.74 | C |
| ATOM | 1979 | C   | LYS | A | 658 | -5.714  | 30.117 | -21.684 | 1.00 | 47.50 | C |
| ATOM | 1980 | O   | LYS | A | 658 | -5.467  | 29.652 | -20.567 | 1.00 | 45.05 | O |
| ATOM | 1981 | CB  | LYS | A | 658 | -4.989  | 32.544 | -21.711 | 1.00 | 41.89 | C |
| ATOM | 1982 | CG  | LYS | A | 658 | -3.760  | 33.449 | -21.864 | 1.00 | 46.92 | C |
| ATOM | 1983 | CD  | LYS | A | 658 | -4.077  | 34.898 | -21.513 | 1.00 | 51.15 | C |
| ATOM | 1984 | CE  | LYS | A | 658 | -2.828  | 35.765 | -21.594 | 1.00 | 59.87 | C |
| ATOM | 1985 | NZ  | LYS | A | 658 | -3.213  | 37.201 | -21.621 | 1.00 | 65.90 | N |
| ATOM | 1986 | N   | MET | A | 659 | -6.760  | 29.744 | -22.416 | 1.00 | 45.79 | N |
| ATOM | 1987 | CA  | MET | A | 659 | -7.686  | 28.702 | -21.988 | 1.00 | 38.20 | C |
| ATOM | 1988 | C   | MET | A | 659 | -7.157  | 27.313 | -22.337 | 1.00 | 49.92 | C |
| ATOM | 1989 | O   | MET | A | 659 | -7.407  | 26.359 | -21.604 | 1.00 | 42.62 | O |
| ATOM | 1990 | CB  | MET | A | 659 | -9.072  | 28.933 | -22.594 | 1.00 | 40.10 | C |
| ATOM | 1991 | CG  | MET | A | 659 | -9.770  | 30.170 | -22.046 | 1.00 | 44.81 | C |
| ATOM | 1992 | SD  | MET | A | 659 | -11.463 | 30.356 | -22.674 | 1.00 | 42.14 | S |
| ATOM | 1993 | CE  | MET | A | 659 | -12.302 | 29.071 | -21.747 | 1.00 | 35.38 | C |
| ATOM | 1994 | N   | LEU | A | 660 | -6.411  | 27.212 | -23.441 | 1.00 | 44.18 | N |
| ATOM | 1995 | CA  | LEU | A | 660 | -5.856  | 25.935 | -23.907 | 1.00 | 39.14 | C |
| ATOM | 1996 | C   | LEU | A | 660 | -4.409  | 25.712 | -23.497 | 1.00 | 43.52 | C |
| ATOM | 1997 | O   | LEU | A | 660 | -3.798  | 24.723 | -23.924 | 1.00 | 47.80 | O |
| ATOM | 1998 | CB  | LEU | A | 660 | -5.928  | 25.841 | -25.438 | 1.00 | 37.09 | C |
| ATOM | 1999 | CG  | LEU | A | 660 | -7.337  | 25.742 | -25.990 | 1.00 | 30.90 | C |
| ATOM | 2000 | CD2 | LEU | A | 660 | -7.996  | 24.515 | -25.423 | 1.00 | 38.78 | C |
| ATOM | 2001 | CD1 | LEU | A | 660 | -7.278  | 25.677 | -27.547 | 1.00 | 33.76 | C |
| ATOM | 2002 | N   | HIS | A | 661 | -3.862  | 26.620 | -22.686 | 1.00 | 44.90 | N |
| ATOM | 2003 | CA  | HIS | A | 661 | -2.471  | 26.519 | -22.242 | 1.00 | 47.68 | C |
| ATOM | 2004 | C   | HIS | A | 661 | -2.240  | 25.111 | -21.701 | 1.00 | 51.69 | C |
| ATOM | 2005 | O   | HIS | A | 661 | -3.057  | 24.592 | -20.945 | 1.00 | 46.85 | O |
| ATOM | 2006 | CB  | HIS | A | 661 | -2.186  | 27.557 | -21.152 | 1.00 | 52.93 | C |
| ATOM | 2007 | CG  | HIS | A | 661 | -0.730  | 27.805 | -20.917 | 1.00 | 57.37 | C |
| ATOM | 2008 | ND1 | HIS | A | 661 | 0.161   | 26.796 | -20.614 | 1.00 | 57.09 | N |
| ATOM | 2009 | CD2 | HIS | A | 661 | -0.009  | 28.951 | -20.940 | 1.00 | 58.42 | C |
| ATOM | 2010 | CE1 | HIS | A | 661 | 1.370   | 27.312 | -20.464 | 1.00 | 57.67 | C |
| ATOM | 2011 | NE2 | HIS | A | 661 | 1.293   | 28.616 | -20.653 | 1.00 | 63.24 | N |
| ATOM | 2012 | N   | VAL | A | 662 | -1.156  | 24.469 | -22.110 | 1.00 | 47.58 | N |
| ATOM | 2013 | CA  | VAL | A | 662 | -0.941  | 23.076 | -21.729 | 1.00 | 55.82 | C |
| ATOM | 2014 | C   | VAL | A | 662 | -0.617  | 22.923 | -20.230 | 1.00 | 59.07 | C |
| ATOM | 2015 | O   | VAL | A | 662 | -0.859  | 21.876 | -19.630 | 1.00 | 62.39 | O |
| ATOM | 2016 | CB  | VAL | A | 662 | 0.164   | 22.424 | -22.595 | 1.00 | 56.28 | C |
| ATOM | 2017 | CG1 | VAL | A | 662 | 1.506   | 23.027 | -22.279 | 1.00 | 56.12 | C |
| ATOM | 2018 | CG2 | VAL | A | 662 | 0.185   | 20.924 | -22.382 | 1.00 | 70.78 | C |
| ATOM | 2019 | N   | ASP | A | 663 | -0.083  | 23.981 | -19.630 | 1.00 | 50.65 | N |
| ATOM | 2020 | CA  | ASP | A | 663 | 0.267   | 23.972 | -18.206 | 1.00 | 53.18 | C |
| ATOM | 2021 | C   | ASP | A | 663 | -0.942  | 24.429 | -17.386 | 1.00 | 55.66 | C |
| ATOM | 2022 | O   | ASP | A | 663 | -1.325  | 25.599 | -17.442 | 1.00 | 51.36 | O |
| ATOM | 2023 | CB  | ASP | A | 663 | 1.442   | 24.908 | -17.958 | 1.00 | 53.93 | C |
| ATOM | 2024 | CG  | ASP | A | 663 | 2.021   | 24.780 | -16.563 | 1.00 | 62.02 | C |
| ATOM | 2025 | OD1 | ASP | A | 663 | 1.336   | 24.286 | -15.640 | 1.00 | 63.51 | O |
| ATOM | 2026 | OD2 | ASP | A | 663 | 3.175   | 25.189 | -16.390 | 1.00 | 65.85 | O |
| ATOM | 2027 | N   | PRO | A | 664 | -1.541  | 23.511 | -16.614 | 1.00 | 54.83 | N |
| ATOM | 2028 | CA  | PRO | A | 664 | -2.747  | 23.885 | -15.864 | 1.00 | 59.58 | C |
| ATOM | 2029 | C   | PRO | A | 664 | -2.474  | 24.986 | -14.826 | 1.00 | 51.43 | C |
| ATOM | 2030 | O   | PRO | A | 664 | -3.394  | 25.723 | -14.479 | 1.00 | 62.68 | O |
| ATOM | 2031 | CB  | PRO | A | 664 | -3.155  | 22.576 | -15.183 | 1.00 | 57.35 | C |
| ATOM | 2032 | CG  | PRO | A | 664 | -1.907  | 21.779 | -15.108 | 1.00 | 58.47 | C |
| ATOM | 2033 | CD  | PRO | A | 664 | -1.143  | 22.115 | -16.358 | 1.00 | 59.05 | C |
| ATOM | 2034 | N   | HIS | A | 665 | -1.229  | 25.110 | -14.379 | 1.00 | 53.81 | N |
| ATOM | 2035 | CA  | HIS | A | 665 | -0.856  | 26.172 | -13.443 | 1.00 | 55.25 | C |
| ATOM | 2036 | C   | HIS | A | 665 | -0.920  | 27.540 | -14.113 | 1.00 | 67.94 | C |
| ATOM | 2037 | O   | HIS | A | 665 | -1.169  | 28.543 | -13.459 | 1.00 | 72.19 | O |
| ATOM | 2038 | CB  | HIS | A | 665 | 0.531   | 25.923 | -12.839 | 1.00 | 68.20 | C |
| ATOM | 2039 | CG  | HIS | A | 665 | 0.633   | 24.623 | -12.103 | 1.00 | 81.80 | C |
| ATOM | 2040 | ND1 | HIS | A | 665 | -0.048  | 24.379 | -10.930 | 1.00 | 93.49 | N |
| ATOM | 2041 | CD2 | HIS | A | 665 | 1.313   | 23.486 | -12.387 | 1.00 | 85.72 | C |
| ATOM | 2042 | CE1 | HIS | A | 665 | 0.217   | 23.153 | -10.515 | 1.00 | 98.26 | C |
| ATOM | 2043 | NE2 | HIS | A | 665 | 1.040   | 22.589 | -11.383 | 1.00 | 96.37 | N |
| ATOM | 2044 | N   | GLN | A | 666 | -0.729  | 27.575 | -15.428 | 1.00 | 61.34 | N |

TABLE 3-continued

Atomic coordinates of RSK2 model (pdb file)

| ATOM | 2045 | CA | GLN | A | 666 | −0.765 | 28.841 | −16.147 | 1.00 | 54.11 | C |
|---|---|---|---|---|---|---|---|---|---|---|---|
| ATOM | 2046 | C | GLN | A | 666 | −2.113 | 29.110 | −16.813 | 1.00 | 57.16 | C |
| ATOM | 2047 | O | GLN | A | 666 | −2.440 | 30.254 | −17.122 | 1.00 | 56.11 | O |
| ATOM | 2048 | CB | GLN | A | 666 | 0.357 | 28.897 | −17.183 | 1.00 | 63.23 | C |
| ATOM | 2049 | CG | GLN | A | 666 | 1.752 | 28.854 | −16.573 | 1.00 | 70.26 | C |
| ATOM | 2050 | CD | GLN | A | 666 | 2.839 | 28.808 | −17.635 | 1.00 | 84.33 | C |
| ATOM | 2051 | OE1 | GLN | A | 666 | 3.005 | 29.749 | −18.412 | 1.00 | 84.78 | O |
| ATOM | 2052 | NE2 | GLN | A | 666 | 3.572 | 27.701 | −17.684 | 1.00 | 84.31 | N |
| ATOM | 2053 | N | ARG | A | 667 | −2.884 | 28.054 | −17.041 | 1.00 | 47.33 | N |
| ATOM | 2054 | CA | ARG | A | 667 | −4.185 | 28.166 | −17.696 | 1.00 | 40.19 | C |
| ATOM | 2055 | C | ARG | A | 667 | −5.137 | 29.060 | −16.900 | 1.00 | 48.64 | C |
| ATOM | 2056 | O | ARG | A | 667 | −5.136 | 29.016 | −15.680 | 1.00 | 47.85 | O |
| ATOM | 2057 | CB | ARG | A | 667 | −4.793 | 26.767 | −17.839 | 1.00 | 48.02 | C |
| ATOM | 2058 | CG | ARG | A | 667 | −6.095 | 26.702 | −18.654 | 1.00 | 47.75 | C |
| ATOM | 2059 | CD | ARG | A | 667 | −6.497 | 25.239 | −18.853 | 1.00 | 41.86 | C |
| ATOM | 2060 | NE | ARG | A | 667 | −5.341 | 24.442 | −19.284 | 1.00 | 43.38 | N |
| ATOM | 2061 | CZ | ARG | A | 667 | −5.151 | 23.170 | −18.954 | 1.00 | 46.56 | C |
| ATOM | 2062 | NH1 | ARG | A | 667 | −6.055 | 22.546 | −18.216 | 1.00 | 48.07 | N |
| ATOM | 2063 | NH2 | ARG | A | 667 | −4.064 | 22.518 | −19.363 | 1.00 | 44.69 | N |
| ATOM | 2064 | N | LEU | A | 668 | −5.973 | 29.847 | −17.571 | 1.00 | 47.24 | N |
| ATOM | 2065 | CA | LEU | A | 668 | −6.899 | 30.700 | −16.823 | 1.00 | 55.91 | C |
| ATOM | 2066 | C | LEU | A | 668 | −7.881 | 29.865 | −16.001 | 1.00 | 53.76 | C |
| ATOM | 2067 | O | LEU | A | 668 | −8.220 | 28.744 | −16.378 | 1.00 | 48.48 | O |
| ATOM | 2068 | CB | LEU | A | 668 | −7.680 | 31.625 | −17.758 | 1.00 | 43.49 | C |
| ATOM | 2069 | CG | LEU | A | 668 | −6.901 | 32.617 | −18.614 | 1.00 | 55.61 | C |
| ATOM | 2070 | CD1 | LEU | A | 668 | −7.872 | 33.404 | −19.503 | 1.00 | 56.21 | C |
| ATOM | 2071 | CD2 | LEU | A | 668 | −6.041 | 33.548 | −17.756 | 1.00 | 56.05 | C |
| ATOM | 2072 | N | THR | A | 669 | −8.316 | 30.409 | −14.869 | 1.00 | 50.55 | N |
| ATOM | 2073 | CA | THR | A | 669 | −9.419 | 29.833 | −14.111 | 1.00 | 41.19 | C |
| ATOM | 2074 | C | THR | A | 669 | −10.717 | 30.396 | −14.693 | 1.00 | 43.84 | C |
| ATOM | 2075 | O | THR | A | 669 | −10.688 | 31.318 | −15.501 | 1.00 | 49.00 | O |
| ATOM | 2076 | CB | THR | A | 669 | −9.346 | 30.253 | −12.635 | 1.00 | 42.37 | C |
| ATOM | 2077 | OG1 | THR | A | 669 | −9.548 | 31.668 | −12.549 | 1.00 | 54.85 | O |
| ATOM | 2078 | CG2 | THR | A | 669 | −7.985 | 29.880 | −12.013 | 1.00 | 49.02 | C |
| ATOM | 2079 | N | ALA | A | 670 | −11.859 | 29.855 | −14.290 | 1.00 | 49.96 | N |
| ATOM | 2080 | CA | ALA | A | 670 | −13.140 | 30.411 | −14.742 | 1.00 | 46.87 | C |
| ATOM | 2081 | C | ALA | A | 670 | −13.286 | 31.883 | −14.334 | 1.00 | 48.16 | C |
| ATOM | 2082 | O | ALA | A | 670 | −13.844 | 32.698 | −15.076 | 1.00 | 41.97 | O |
| ATOM | 2083 | CB | ALA | A | 670 | −14.293 | 29.596 | −14.181 | 1.00 | 45.72 | C |
| ATOM | 2084 | N | ALA | A | 671 | −12.791 | 32.216 | −13.143 | 1.00 | 46.88 | N |
| ATOM | 2085 | CA | ALA | A | 671 | −12.832 | 33.585 | −12.647 | 1.00 | 46.92 | C |
| ATOM | 2086 | C | ALA | A | 671 | −12.064 | 34.542 | −13.553 | 1.00 | 53.00 | C |
| ATOM | 2087 | O | ALA | A | 671 | −12.542 | 35.632 | −13.846 | 1.00 | 50.46 | O |
| ATOM | 2088 | CB | ALA | A | 671 | −12.289 | 33.653 | −11.194 | 1.00 | 50.19 | C |
| ATOM | 2089 | N | LEU | A | 672 | −10.878 | 34.131 | −14.005 | 1.00 | 43.14 | N |
| ATOM | 2090 | CA | LEU | A | 672 | −10.063 | 34.976 | −14.868 | 1.00 | 54.99 | C |
| ATOM | 2091 | C | LEU | A | 672 | −10.615 | 35.053 | −16.294 | 1.00 | 52.36 | C |
| ATOM | 2092 | O | LEU | A | 672 | −10.449 | 36.066 | −16.979 | 1.00 | 49.83 | O |
| ATOM | 2093 | CB | LEU | A | 672 | −8.605 | 34.493 | −14.880 | 1.00 | 54.82 | C |
| ATOM | 2094 | CG | LEU | A | 672 | −7.638 | 35.186 | −13.913 | 1.00 | 62.76 | C |
| ATOM | 2095 | CD1 | LEU | A | 672 | −8.384 | 36.019 | −12.883 | 1.00 | 63.63 | C |
| ATOM | 2096 | CD2 | LEU | A | 672 | −6.744 | 34.166 | −13.233 | 1.00 | 61.37 | C |
| ATOM | 2097 | N | VAL | A | 673 | −11.266 | 33.987 | −16.748 | 1.00 | 48.68 | N |
| ATOM | 2098 | CA | VAL | A | 673 | −11.885 | 34.030 | −18.072 | 1.00 | 43.52 | C |
| ATOM | 2099 | C | VAL | A | 673 | −12.919 | 35.145 | −18.068 | 1.00 | 42.63 | C |
| ATOM | 2100 | O | VAL | A | 673 | −13.029 | 35.910 | −19.018 | 1.00 | 48.16 | O |
| ATOM | 2101 | CB | VAL | A | 673 | −12.586 | 32.707 | −18.441 | 1.00 | 43.17 | C |
| ATOM | 2102 | CG1 | VAL | A | 673 | −13.478 | 32.894 | −19.702 | 1.00 | 41.02 | C |
| ATOM | 2103 | CG2 | VAL | A | 673 | −11.559 | 31.613 | −18.670 | 1.00 | 43.87 | C |
| ATOM | 2104 | N | LEU | A | 674 | −13.633 | 35.267 | −16.958 | 1.00 | 47.18 | N |
| ATOM | 2105 | CA | LEU | A | 674 | −14.726 | 36.227 | −16.887 | 1.00 | 49.17 | C |
| ATOM | 2106 | C | LEU | A | 674 | −14.240 | 37.679 | −16.818 | 1.00 | 56.65 | C |
| ATOM | 2107 | O | LEU | A | 674 | −15.028 | 38.602 | −17.035 | 1.00 | 54.70 | O |
| ATOM | 2108 | CB | LEU | A | 674 | −15.655 | 35.895 | −15.720 | 1.00 | 55.45 | C |
| ATOM | 2109 | CG | LEU | A | 674 | −16.445 | 34.591 | −15.880 | 1.00 | 47.01 | C |
| ATOM | 2110 | CD1 | LEU | A | 674 | −17.008 | 34.160 | −14.552 | 1.00 | 46.57 | C |
| ATOM | 2111 | CD2 | LEU | A | 674 | −17.584 | 34.757 | −16.910 | 1.00 | 45.02 | C |
| ATOM | 2112 | N | ARG | A | 675 | −12.952 | 37.889 | −16.537 | 1.00 | 47.08 | N |
| ATOM | 2113 | CA | ARG | A | 675 | −12.413 | 39.254 | −16.523 | 1.00 | 51.19 | C |
| ATOM | 2114 | C | ARG | A | 675 | −11.549 | 39.536 | −17.748 | 1.00 | 52.92 | C |
| ATOM | 2115 | O | ARG | A | 675 | −10.895 | 40.571 | −17.821 | 1.00 | 52.21 | O |
| ATOM | 2116 | CB | ARG | A | 675 | −11.621 | 39.564 | −15.242 | 1.00 | 59.37 | C |
| ATOM | 2117 | CG | ARG | A | 675 | −11.916 | 38.677 | −14.060 | 1.00 | 64.55 | C |
| ATOM | 2118 | CD | ARG | A | 675 | −13.322 | 38.849 | −13.507 | 1.00 | 75.27 | C |
| ATOM | 2119 | NE | ARG | A | 675 | −13.744 | 37.639 | −12.799 | 0.55 | 73.03 | N |
| ATOM | 2120 | CZ | ARG | A | 675 | −14.961 | 37.435 | −12.305 | 0.49 | 75.82 | C |
| ATOM | 2121 | NH1 | ARG | A | 675 | −15.903 | 38.362 | −12.428 | 0.78 | 83.63 | N |
| ATOM | 2122 | NH2 | ARG | A | 675 | −15.235 | 36.297 | −11.685 | 0.59 | 72.11 | N |

TABLE 3-continued

Atomic coordinates of RSK2 model (pdb file)

| ATOM | 2123 | N | HIS | A | 676 | −11.542 | 38.617 | −18.710 | 1.00 | 52.34 | N |
|---|---|---|---|---|---|---|---|---|---|---|---|
| ATOM | 2124 | CA | HIS | A | 676 | −10.830 | 38.853 | −19.966 | 1.00 | 57.41 | C |
| ATOM | 2125 | C | HIS | A | 676 | −11.646 | 39.855 | −20.783 | 1.00 | 46.57 | C |
| ATOM | 2126 | O | HIS | A | 676 | −12.878 | 39.792 | −20.785 | 1.00 | 51.95 | O |
| ATOM | 2127 | CB | HIS | A | 676 | −10.651 | 37.538 | −20.735 | 1.00 | 57.21 | C |
| ATOM | 2128 | CG | HIS | A | 676 | −9.639 | 37.605 | −21.841 | 1.00 | 50.23 | C |
| ATOM | 2129 | ND1 | HIS | A | 676 | −9.939 | 38.081 | −23.099 | 1.00 | 51.23 | N |
| ATOM | 2130 | CD2 | HIS | A | 676 | −8.335 | 37.240 | −21.878 | 1.00 | 49.23 | C |
| ATOM | 2131 | CE1 | HIS | A | 676 | −8.861 | 38.013 | −23.862 | 1.00 | 51.68 | C |
| ATOM | 2132 | NE2 | HIS | A | 676 | −7.875 | 37.501 | −23.148 | 1.00 | 48.78 | N |
| ATOM | 2133 | N | PRO | A | 677 | −10.967 | 40.796 | −21.456 | 1.00 | 51.37 | N |
| ATOM | 2134 | CA | PRO | A | 677 | −11.651 | 41.837 | −22.232 | 1.00 | 59.74 | C |
| ATOM | 2135 | C | PRO | a | 677 | −12.593 | 41.291 | −23.316 | 1.00 | 61.98 | C |
| ATOM | 2136 | O | PRO | A | 677 | −13.564 | 41.966 | −23.660 | 1.00 | 57.68 | O |
| ATOM | 2137 | CB | PRO | A | 677 | −10.498 | 42.643 | −22.851 | 1.00 | 65.29 | C |
| ATOM | 2138 | CG | PRO | A | 677 | −9.248 | 41.854 | −22.581 | 1.00 | 66.58 | C |
| ATOM | 2139 | CD | PRO | A | 677 | −9.515 | 41.024 | −21.377 | 1.00 | 56.29 | C |
| ATOM | 2140 | N | TRP | A | 678 | −12.319 | 40.093 | −23.830 | 1.00 | 49.37 | N |
| ATOM | 2141 | CA | TRP | A | 678 | −13.188 | 39.477 | −24.827 | 1.00 | 49.33 | C |
| ATOM | 2142 | C | TRP | A | 678 | −14.549 | 39.184 | −24.203 | 1.00 | 46.95 | C |
| ATOM | 2143 | O | TRP | A | 678 | −15.573 | 39.242 | −24.878 | 1.00 | 50.60 | O |
| ATOM | 2144 | CB | TRP | A | 678 | −12.565 | 38.189 | −25.393 | 1.00 | 51.10 | C |
| ATOM | 2145 | CG | TRP | A | 678 | −13.241 | 37.712 | −26.658 | 1.00 | 50.50 | C |
| ATOM | 2146 | CD1 | TRP | A | 678 | −13.133 | 38.262 | −27.904 | 1.00 | 49.25 | C |
| ATOM | 2147 | CD2 | TRP | A | 678 | −14.121 | 36.589 | −26.789 | 1.00 | 46.49 | C |
| ATOM | 2148 | NE1 | TRP | A | 678 | −13.901 | 37.555 | −28.808 | 1.00 | 50.52 | N |
| ATOM | 2149 | CE2 | TRP | A | 678 | −14.513 | 36.520 | −28.147 | 1.00 | 45.86 | C |
| ATOM | 2150 | CE3 | TRP | A | 678 | −14.618 | 35.635 | −25.892 | 1.00 | 44.19 | C |
| ATOM | 2151 | CZ2 | TRP | A | 678 | −15.378 | 35.535 | −28.629 | 1.00 | 41.37 | C |
| ATOM | 2152 | CZ3 | TRP | A | 678 | −15.472 | 34.659 | −26.369 | 1.00 | 39.50 | C |
| ATOM | 2153 | CH2 | TRP | A | 678 | −15.843 | 34.617 | −27.737 | 1.00 | 38.18 | C |
| ATOM | 2154 | N | ILE | A | 679 | −14.559 | 38.875 | −22.908 | 1.00 | 47.39 | N |
| ATOM | 2155 | CA | ILE | A | 679 | −15.822 | 38.633 | −22.221 | 1.00 | 50.01 | C |
| ATOM | 2156 | C | ILE | A | 679 | −16.446 | 39.933 | −21.715 | 1.00 | 59.26 | C |
| ATOM | 2157 | O | ILE | A | 679 | −17.625 | 40.193 | −21.966 | 1.00 | 58.60 | O |
| ATOM | 2158 | CB | ILE | A | 679 | −15.673 | 37.644 | −21.049 | 1.00 | 48.59 | C |
| ATOM | 2159 | CG1 | ILE | A | 679 | −15.306 | 36.246 | −21.571 | 1.00 | 43.63 | C |
| ATOM | 2160 | CG2 | ILE | A | 679 | −16.955 | 37.613 | −20.215 | 1.00 | 53.80 | C |
| ATOM | 2161 | CD1 | ILE | A | 679 | −16.434 | 35.493 | −22.258 | 1.00 | 42.91 | C |
| ATOM | 2162 | N | VAL | A | 680 | −15.672 | 40.758 | −21.013 | 1.00 | 57.00 | N |
| ATOM | 2163 | CA | VAL | A | 680 | −16.265 | 41.964 | −20.422 | 1.00 | 65.55 | C |
| ATOM | 2164 | C | VAL | A | 680 | −16.593 | 43.054 | −21.446 | 1.00 | 62.55 | C |
| ATOM | 2165 | O | VAL | A | 680 | −17.602 | 43.739 | −21.306 | 1.00 | 62.99 | O |
| ATOM | 2166 | CB | VAL | A | 680 | −15.469 | 42.551 | −19.193 | 1.00 | 63.88 | C |
| ATOM | 2167 | CG2 | VAL | A | 680 | −14.741 | 43.836 | −19.555 | 1.00 | 69.05 | C |
| ATOM | 2168 | CG1 | VAL | A | 680 | −14.514 | 41.532 | −18.603 | 1.00 | 57.19 | C |
| ATOM | 2169 | N | HIS | A | 681 | −15.762 | 43.210 | −22.475 | 1.00 | 59.59 | N |
| ATOM | 2170 | CA | HIS | A | 681 | −16.032 | 44.225 | −23.493 | 1.00 | 65.61 | C |
| ATOM | 2171 | C | HIS | A | 681 | −16.571 | 43.605 | −24.767 | 1.00 | 68.83 | C |
| ATOM | 2172 | O | HIS | A | 681 | −16.104 | 43.906 | −25.868 | 1.00 | 66.24 | O |
| ATOM | 2173 | CB | HIS | A | 681 | −14.789 | 45.065 | −23.781 | 1.00 | 69.47 | C |
| ATOM | 2174 | CG | HIS | A | 681 | −14.379 | 45.934 | −22.634 | 1.00 | 75.31 | C |
| ATOM | 2175 | ND1 | HIS | A | 681 | −13.214 | 45.732 | −21.925 | 1.00 | 77.96 | N |
| ATOM | 2176 | CD2 | HIS | A | 681 | −14.992 | 46.995 | −22.057 | 1.00 | 76.75 | C |
| ATOM | 2177 | CE1 | HIS | A | 681 | −13.120 | 46.640 | −20.969 | 1.00 | 80.37 | C |
| ATOM | 2178 | NE2 | HIS | A | 681 | −14.186 | 47.418 | −21.027 | 1.00 | 82.13 | N |
| ATOM | 2179 | N | TRP | A | 682 | −17.562 | 42.736 | −24.598 | 1.00 | 71.01 | N |
| ATOM | 2180 | CA | TRP | A | 682 | −18.200 | 42.052 | −25.712 | 1.00 | 72.61 | C |
| ATOM | 2181 | C | TRP | A | 682 | −18.759 | 43.045 | −26.729 | 1.00 | 74.21 | C |
| ATOM | 2182 | O | TRP | A | 682 | −18.725 | 42.790 | −27.931 | 1.00 | 60.27 | O |
| ATOM | 2183 | CB | TRP | A | 682 | −19.320 | 41.145 | −25.194 | 1.00 | 72.71 | C |
| ATOM | 2184 | CG | TRP | A | 682 | −20.286 | 41.873 | −24.320 | 1.00 | 80.28 | C |
| ATOM | 2185 | CD1 | TRP | A | 682 | −20.185 | 42.065 | −22.974 | 1.00 | 78.92 | C |
| ATOM | 2186 | CD2 | TRP | A | 682 | −21.495 | 42.527 | −24.731 | 1.00 | 87.73 | C |
| ATOM | 2187 | NE1 | TRP | A | 682 | −21.259 | 42.794 | −22.518 | 1.00 | 86.91 | N |
| ATOM | 2188 | CE2 | TRP | A | 682 | −22.077 | 43.091 | −23.577 | 1.00 | 91.60 | C |
| ATOM | 2189 | CE3 | TRP | A | 682 | −22.142 | 42.689 | −25.960 | 1.00 | 86.59 | C |
| ATOM | 2190 | CZ2 | TRP | A | 682 | −23.275 | 43.802 | −23.616 | 1.00 | 94.47 | C |
| ATOM | 2191 | CZ3 | TRP | A | 682 | −23.333 | 43.397 | −25.997 | 1.00 | 90.03 | C |
| ATOM | 2192 | CH2 | TRP | A | 682 | −23.885 | 43.943 | −24.833 | 1.00 | 94.42 | C |
| ATOM | 2193 | N | ASP | A | 683 | −19.246 | 44.186 | −26.245 | 1.00 | 83.47 | N |
| ATOM | 2194 | CA | ASP | A | 683 | −19.921 | 45.159 | −27.105 | 1.00 | 87.33 | C |
| ATOM | 2195 | C | ASP | A | 683 | −18.992 | 45.884 | −28.076 | 1.00 | 85.58 | C |
| ATOM | 2196 | O | ASP | A | 683 | −19.428 | 46.767 | −28.809 | 1.00 | 92.15 | O |
| ATOM | 2197 | CB | ASP | A | 683 | −20.719 | 46.173 | −26.274 | 1.00 | 97.20 | C |
| ATOM | 2198 | CG | ASP | A | 683 | −19.848 | 46.967 | −25.318 | 1.00 | 98.57 | C |
| ATOM | 2199 | OD1 | ASP | A | 683 | −19.209 | 47.942 | −25.765 | 1.00 | 96.90 | O |
| ATOM | 2200 | OD2 | ASP | A | 683 | −19.813 | 46.622 | −24.116 | 1.00 | 101.60 | O |

TABLE 3-continued

Atomic coordinates of RSK2 model (pdb file)

| ATOM | 2201 | N   | GLN | A | 684 | −17.717 | 45.509 | −28.080 | 1.00 | 83.20  | N |
|------|------|-----|-----|---|-----|---------|--------|---------|------|--------|---|
| ATOM | 2202 | CA  | GLN | A | 684 | −16.762 | 46.061 | −29.033 | 1.00 | 82.42  | C |
| ATOM | 2203 | C   | GLN | A | 684 | −16.307 | 45.002 | −30.028 | 1.00 | 82.55  | C |
| ATOM | 2204 | O   | GLN | A | 684 | −15.550 | 45.284 | −30.956 | 1.00 | 76.88  | O |
| ATOM | 2205 | CB  | GLN | A | 684 | −15.560 | 46.643 | −28.302 | 1.00 | 81.31  | C |
| ATOM | 2206 | CG  | GLN | A | 684 | −15.943 | 47.708 | −27.311 | 1.00 | 88.27  | C |
| ATOM | 2207 | CD  | GLN | A | 684 | −14.809 | 48.652 | −27.033 | 1.00 | 96.97  | C |
| ATOM | 2208 | OE1 | GLN | A | 684 | −13.844 | 48.297 | −26.357 | 1.00 | 100.26 | O |
| ATOM | 2209 | NE2 | GLN | A | 684 | −14.904 | 49.864 | −27.569 | 1.00 | 104.02 | N |
| ATOM | 2210 | N   | LEU | A | 685 | −16.779 | 43.780 | −29.822 | 1.00 | 74.58  | N |
| ATOM | 2211 | CA  | LEU | A | 685 | −16.458 | 42.675 | −30.709 | 1.00 | 69.60  | C |
| ATOM | 2212 | C   | LEU | A | 685 | −17.117 | 42.849 | −32.075 | 1.00 | 71.19  | C |
| ATOM | 2213 | O   | LEU | A | 685 | −18.215 | 43.394 | −32.179 | 1.00 | 74.92  | O |
| ATOM | 2214 | CB  | LEU | A | 685 | −16.902 | 41.352 | −30.081 | 1.00 | 65.22  | C |
| ATOM | 2215 | CG  | LEU | A | 685 | −15.896 | 40.585 | −29.215 | 1.00 | 66.91  | C |
| ATOM | 2216 | CD1 | LEU | A | 685 | −14.894 | 41.500 | −28.532 | 1.00 | 63.39  | C |
| ATOM | 2217 | CD2 | LEU | A | 685 | −16.641 | 39.756 | −28.186 | 1.00 | 60.15  | C |
| ATOM | 2218 | N   | PRO | A | 686 | −16.439 | 42.387 | −33.129 | 1.00 | 65.37  | N |
| ATOM | 2219 | CA  | PRO | A | 686 | −17.017 | 42.403 | −34.478 | 1.00 | 74.70  | C |
| ATOM | 2220 | C   | PRO | A | 686 | −18.329 | 41.621 | −34.529 | 1.00 | 77.05  | C |
| ATOM | 2221 | O   | PRO | A | 686 | −18.463 | 40.568 | −33.892 | 1.00 | 64.79  | O |
| ATOM | 2222 | CB  | PRO | A | 686 | −15.945 | 41.717 | −35.334 | 1.00 | 76.95  | C |
| ATOM | 2223 | CG  | PRO | A | 686 | −14.993 | 41.071 | −34.359 | 1.00 | 77.08  | C |
| ATOM | 2224 | CD  | PRO | A | 686 | −15.058 | 41.881 | −33.114 | 1.00 | 63.78  | C |
| ATOM | 2225 | N   | GLN | A | 687 | −19.299 | 42.144 | −35.266 | 1.00 | 81.56  | N |
| ATOM | 2226 | CA  | GLN | A | 687 | −20.589 | 41.482 | −35.364 | 1.00 | 83.98  | C |
| ATOM | 2227 | C   | GLN | A | 687 | −20.827 | 40.931 | −36.761 | 1.00 | 83.77  | C |
| ATOM | 2228 | O   | GLN | A | 687 | −21.890 | 40.372 | −37.043 | 1.00 | 78.95  | O |
| ATOM | 2229 | CB  | GLN | A | 687 | −21.716 | 42.425 | −34.952 | 1.00 | 85.08  | C |
| ATOM | 2230 | CG  | GLN | A | 687 | −21.761 | 43.718 | −35.731 | 1.00 | 88.67  | C |
| ATOM | 2231 | CD  | GLN | A | 687 | −22.860 | 44.626 | −35.231 | 1.00 | 101.14 | C |
| ATOM | 2232 | OE1 | GLN | A | 687 | −23.276 | 44.527 | −34.076 | 1.00 | 103.37 | O |
| ATOM | 2233 | NE2 | GLN | A | 687 | −23.351 | 45.505 | −36.099 | 1.00 | 106.49 | N |
| ATOM | 2234 | N   | TYR | A | 688 | −19.839 | 41.085 | −37.637 | 1.00 | 91.08  | N |
| ATOM | 2235 | CA  | TYR | A | 688 | −19.916 | 40.425 | −38.934 | 1.00 | 93.40  | C |
| ATOM | 2236 | C   | TYR | A | 688 | −19.684 | 38.930 | −38.763 | 1.00 | 79.26  | C |
| ATOM | 2237 | O   | TYR | A | 688 | −19.143 | 38.480 | −37.737 | 1.00 | 67.66  | O |
| ATOM | 2238 | CB  | TYR | A | 688 | −18.965 | 41.033 | −39.975 | 1.00 | 107.92 | C |
| ATOM | 2239 | CG  | TYR | A | 688 | −17.581 | 41.405 | −39.489 | 1.00 | 111.64 | C |
| ATOM | 2240 | CD2 | TYR | A | 688 | −16.537 | 40.484 | −39.511 | 1.00 | 107.11 | C |
| ATOM | 2241 | CD1 | TYR | A | 688 | −17.309 | 42.693 | −39.044 | 1.00 | 114.52 | C |
| ATOM | 2242 | CE2 | TYR | A | 688 | −15.267 | 40.835 | −39.082 | 1.00 | 106.69 | C |
| ATOM | 2243 | CE1 | TYR | A | 688 | −16.045 | 43.051 | −38.615 | 1.00 | 111.32 | C |
| ATOM | 2244 | CZ  | TYR | A | 688 | −15.030 | 42.119 | −38.636 | 1.00 | 109.36 | C |
| ATOM | 2245 | OH  | TYR | A | 688 | −13.773 | 42.477 | −38.207 | 1.00 | 110.11 | O |
| ATOM | 2246 | N   | GLN | A | 689 | −20.112 | 38.163 | −39.757 | 1.00 | 73.77  | N |
| ATOM | 2247 | CA  | GLN | A | 689 | −20.100 | 36.716 | −39.637 | 1.00 | 79.23  | C |
| ATOM | 2248 | C   | GLN | A | 689 | −18.671 | 36.195 | −39.534 | 1.00 | 74.30  | C |
| ATOM | 2249 | O   | GLN | A | 689 | −17.738 | 36.761 | −40.108 | 1.00 | 74.48  | O |
| ATOM | 2250 | CB  | GLN | A | 689 | −20.854 | 36.065 | −40.805 | 1.00 | 79.78  | C |
| ATOM | 2251 | CG  | GLN | A | 689 | −20.135 | 36.124 | −42.122 | 1.00 | 77.67  | C |
| ATOM | 2252 | CD  | GLN | A | 689 | −20.971 | 35.572 | −43.270 | 1.00 | 92.82  | C |
| ATOM | 2253 | OE1 | GLN | A | 689 | −21.862 | 34.746 | −43.068 | 1.00 | 98.94  | O |
| ATOM | 2254 | NE2 | GLN | A | 689 | −20.691 | 36.036 | −44.479 | 1.00 | 87.48  | N |
| ATOM | 2255 | N   | LEU | A | 690 | −18.501 | 35.135 | −38.760 | 1.00 | 70.97  | N |
| ATOM | 2256 | CA  | LEU | A | 690 | −17.220 | 34.469 | −38.697 | 1.00 | 66.42  | C |
| ATOM | 2257 | C   | LEU | A | 690 | −17.010 | 33.707 | −39.997 | 1.00 | 66.87  | C |
| ATOM | 2258 | O   | LEU | A | 690 | −17.971 | 33.287 | −40.644 | 1.00 | 70.72  | O |
| ATOM | 2259 | CB  | LEU | A | 690 | −17.183 | 33.532 | −37.493 | 1.00 | 52.53  | C |
| ATOM | 2260 | CG  | LEU | A | 690 | −17.039 | 34.279 | −36.170 | 1.00 | 52.75  | C |
| ATOM | 2261 | CD1 | LEU | A | 690 | −17.606 | 33.454 | −35.038 | 1.00 | 47.15  | C |
| ATOM | 2262 | CD2 | LEU | A | 690 | −15.578 | 34.604 | −35.921 | 1.00 | 55.33  | C |
| ATOM | 2263 | N   | ASN | A | 691 | −15.757 | 33.555 | −40.401 | 1.00 | 62.78  | N |
| ATOM | 2264 | CA  | ASN | A | 691 | −15.450 | 32.746 | −41.574 | 1.00 | 66.14  | C |
| ATOM | 2265 | C   | ASN | A | 691 | −14.975 | 31.390 | −41.081 | 1.00 | 60.68  | C |
| ATOM | 2266 | O   | ASN | A | 691 | −13.886 | 31.268 | −40.530 | 1.00 | 57.19  | O |
| ATOM | 2267 | CB  | ASN | A | 691 | −14.379 | 33.418 | −42.426 | 1.00 | 70.58  | C |
| ATOM | 2268 | CG  | ASN | A | 691 | −14.138 | 32.694 | −43.738 | 1.00 | 76.01  | C |
| ATOM | 2269 | OD1 | ASN | A | 691 | −15.078 | 32.317 | −44.442 | 1.00 | 76.86  | O |
| ATOM | 2270 | ND2 | ASN | A | 691 | −12.868 | 32.485 | −44.068 | 1.00 | 79.59  | N |
| ATOM | 2271 | N   | ARG | A | 692 | −15.801 | 30.369 | −41.250 | 1.00 | 56.68  | N |
| ATOM | 2272 | CA  | ARG | A | 692 | −15.528 | 29.093 | −40.611 | 1.00 | 59.75  | C |
| ATOM | 2273 | C   | ARG | A | 692 | −15.632 | 27.926 | −41.566 | 1.00 | 48.83  | C |
| ATOM | 2274 | O   | ARG | A | 692 | −16.299 | 28.013 | −42.590 | 1.00 | 52.06  | O |
| ATOM | 2275 | CB  | ARG | A | 692 | −16.506 | 28.880 | −39.450 | 1.00 | 49.16  | C |
| ATOM | 2276 | CG  | ARG | A | 692 | −16.454 | 29.998 | −38.413 | 1.00 | 46.46  | C |
| ATOM | 2277 | CD  | ARG | A | 692 | −17.401 | 29.766 | −37.242 | 1.00 | 40.65  | C |
| ATOM | 2278 | NE  | ARG | A | 692 | −18.799 | 29.688 | −37.673 | 1.00 | 42.47  | N |

TABLE 3-continued

Atomic coordinates of RSK2 model (pdb file)

| ATOM | 2279 | CZ | ARG | A | 692 | −19.796 | 29.295 | −36.892 | 1.00 | 47.28 | C |
|---|---|---|---|---|---|---|---|---|---|---|---|
| ATOM | 2280 | NH1 | ARG | A | 692 | −19.551 | 28.949 | −35.621 | 1.00 | 45.32 | N |
| ATOM | 2281 | NH2 | ARG | A | 692 | −21.026 | 29.252 | −37.369 | 1.00 | 43.58 | N |
| ATOM | 2282 | N | GLN | A | 693 | −14.986 | 26.820 | −41.212 | 1.00 | 50.21 | N |
| ATOM | 2283 | CA | GLN | A | 693 | −15.235 | 25.578 | −41.916 | 1.00 | 56.23 | C |
| ATOM | 2284 | C | GLN | A | 693 | −16.710 | 25.247 | −41.709 | 1.00 | 54.07 | C |
| ATOM | 2285 | O | GLN | A | 693 | −17.266 | 25.494 | −40.636 | 1.00 | 60.31 | O |
| ATOM | 2286 | CB | GLN | A | 693 | −14.372 | 24.451 | −41.354 | 1.00 | 47.88 | C |
| ATOM | 2287 | CG | GLN | A | 693 | −14.459 | 23.161 | −42.164 | 1.00 | 59.77 | C |
| ATOM | 2288 | CD | GLN | A | 693 | −13.816 | 21.972 | −41.458 | 1.00 | 63.23 | C |
| ATOM | 2289 | OE1 | GLN | A | 693 | −13.894 | 21.830 | −40.226 | 1.00 | 59.28 | O |
| ATOM | 2290 | NE2 | GLN | A | 693 | −13.189 | 21.104 | −42.240 | 1.00 | 58.73 | N |
| ATOM | 2291 | N | ASP | A | 694 | −17.352 | 24.710 | −42.728 | 1.00 | 50.88 | N |
| ATOM | 2292 | CA | ASP | A | 694 | −18.714 | 24.238 | −42.542 | 1.00 | 63.17 | C |
| ATOM | 2293 | C | ASP | A | 694 | −18.729 | 22.725 | −42.647 | 1.00 | 53.78 | C |
| ATOM | 2294 | O | ASP | A | 694 | −19.055 | 22.187 | −43.676 | 1.00 | 54.33 | O |
| ATOM | 2295 | CB | ASP | A | 694 | −19.655 | 24.854 | −43.576 | 1.00 | 63.70 | C |
| ATOM | 2296 | CG | ASP | A | 694 | −21.082 | 24.305 | −43.480 | 1.00 | 77.85 | C |
| ATOM | 2297 | OD1 | ASP | A | 694 | −21.504 | 23.904 | −42.373 | 1.00 | 78.38 | O |
| ATOM | 2298 | OD2 | ASP | A | 694 | −21.782 | 24.274 | −44.519 | 1.00 | 85.75 | O |
| ATOM | 2299 | N | ALA | A | 695 | −18.336 | 22.037 | −41.580 | 1.00 | 57.64 | N |
| ATOM | 2300 | CA | ALA | A | 695 | −18.420 | 20.576 | −41.585 | 1.00 | 52.13 | C |
| ATOM | 2301 | C | ALA | A | 695 | −18.775 | 20.101 | −40.187 | 1.00 | 55.53 | C |
| ATOM | 2302 | O | ALA | A | 695 | −17.937 | 19.513 | −39.499 | 1.00 | 48.32 | O |
| ATOM | 2303 | CB | ALA | A | 695 | −17.102 | 19.950 | −42.056 | 1.00 | 57.90 | C |
| ATOM | 2304 | N | PRO | A | 696 | −20.018 | 20.377 | −39.754 | 1.00 | 46.52 | N |
| ATOM | 2305 | CA | PRO | A | 696 | −20.417 | 20.092 | −38.368 | 1.00 | 49.65 | C |
| ATOM | 2306 | C | PRO | A | 696 | −20.313 | 18.600 | −38.047 | 1.00 | 50.37 | C |
| ATOM | 2307 | O | PRO | A | 696 | −19.947 | 18.249 | −36.925 | 1.00 | 48.19 | O |
| ATOM | 2308 | CB | PRO | A | 696 | −21.887 | 20.559 | −38.322 | 1.00 | 43.86 | C |
| ATOM | 2309 | CG | PRO | A | 696 | −22.339 | 20.512 | −39.775 | 1.00 | 48.27 | C |
| ATOM | 2310 | CD | PRO | A | 696 | −21.125 | 20.951 | −40.541 | 1.00 | 55.36 | C |
| ATOM | 2311 | N | HIS | A | 697 | −20.621 | 17.737 | −39.011 | 1.00 | 45.13 | N |
| ATOM | 2312 | CA | HIS | A | 697 | −20.530 | 16.305 | −38.762 | 1.00 | 46.88 | C |
| ATOM | 2313 | C | HIS | A | 697 | −19.079 | 15.835 | −38.635 | 1.00 | 48.11 | C |
| ATOM | 2314 | O | HIS | A | 697 | −18.784 | 14.959 | −37.827 | 1.00 | 48.57 | O |
| ATOM | 2315 | CB | HIS | A | 697 | −21.223 | 15.491 | −39.839 | 1.00 | 52.98 | C |
| ATOM | 2316 | CG | HIS | A | 697 | −21.254 | 14.027 | −39.543 | 1.00 | 54.49 | C |
| ATOM | 2317 | ND1 | HIS | A | 697 | −22.011 | 13.490 | −38.522 | 1.00 | 54.53 | N |
| ATOM | 2318 | CD2 | HIS | A | 697 | −20.601 | 12.988 | −40.117 | 1.00 | 52.96 | C |
| ATOM | 2319 | CE1 | HIS | A | 697 | −21.830 | 12.180 | −38.489 | 1.00 | 56.64 | C |
| ATOM | 2320 | NE2 | HIS | A | 697 | −20.982 | 11.851 | −39.448 | 1.00 | 52.41 | N |
| ATOM | 2321 | N | LEU | A | 698 | −18.183 | 16.403 | −39.434 | 1.00 | 48.37 | N |
| ATOM | 2322 | CA | LEU | A | 698 | −16.750 | 16.113 | −39.277 | 1.00 | 47.22 | C |
| ATOM | 2323 | C | LEU | A | 698 | −16.260 | 16.503 | −37.879 | 1.00 | 43.55 | C |
| ATOM | 2324 | O | LEU | A | 698 | −15.517 | 15.761 | −37.229 | 1.00 | 42.17 | O |
| ATOM | 2325 | CB | LEU | A | 698 | −15.944 | 16.877 | −40.318 | 1.00 | 53.59 | C |
| ATOM | 2326 | CG | LEU | A | 698 | −14.492 | 16.436 | −40.501 | 1.00 | 56.43 | C |
| ATOM | 2327 | CD1 | LEU | A | 698 | −14.442 | 14.992 | −40.966 | 1.00 | 59.45 | C |
| ATOM | 2328 | CD2 | LEU | A | 698 | −13.816 | 17.326 | −41.523 | 1.00 | 60.63 | C |
| ATOM | 2329 | N | VAL | A | 699 | −16.653 | 17.695 | −37.442 | 1.00 | 42.57 | N |
| ATOM | 2330 | CA | VAL | A | 699 | −16.301 | 18.194 | −36.114 | 1.00 | 41.25 | C |
| ATOM | 2331 | C | VAL | A | 699 | −16.811 | 17.265 | −35.014 | 1.00 | 42.67 | C |
| ATOM | 2332 | O | VAL | A | 699 | −16.134 | 17.016 | −34.016 | 1.00 | 39.23 | O |
| ATOM | 2333 | CB | VAL | A | 699 | −16.867 | 19.618 | −35.873 | 1.00 | 45.97 | C |
| ATOM | 2334 | CG1 | VAL | A | 699 | −16.806 | 19.988 | −34.383 | 1.00 | 45.19 | C |
| ATOM | 2335 | CG2 | VAL | A | 699 | −16.106 | 20.639 | −36.702 | 1.00 | 44.68 | C |
| ATOM | 2336 | N | LYS | A | 700 | −18.024 | 16.765 | −35.179 | 1.00 | 41.11 | N |
| ATOM | 2337 | CA | LYS | A | 700 | −18.587 | 15.896 | −34.160 | 1.00 | 37.52 | C |
| ATOM | 2338 | C | LYS | A | 700 | −17.716 | 14.650 | −34.033 | 1.00 | 50.22 | C |
| ATOM | 2339 | O | LYS | A | 700 | −17.480 | 14.158 | −32.930 | 1.00 | 44.41 | O |
| ATOM | 2340 | CB | LYS | A | 700 | −20.037 | 15.546 | −34.507 | 1.00 | 39.31 | C |
| ATOM | 2341 | CG | LYS | A | 700 | −20.680 | 14.502 | −33.620 | 1.00 | 50.27 | C |
| ATOM | 2342 | CD | LYS | A | 700 | −22.162 | 14.304 | −34.025 | 1.00 | 56.34 | C |
| ATOM | 2343 | CE | LYS | A | 700 | −22.874 | 13.297 | −33.141 | 1.00 | 72.50 | C |
| ATOM | 2344 | NZ | LYS | A | 700 | −24.303 | 13.110 | −33.568 | 1.00 | 83.14 | N |
| ATOM | 2345 | N | GLY | A | 701 | −17.212 | 14.161 | −35.162 | 1.00 | 41.48 | N |
| ATOM | 2346 | CA | GLY | A | 701 | −16.330 | 13.011 | −35.143 | 1.00 | 49.62 | C |
| ATOM | 2347 | C | GLY | A | 701 | −14.963 | 13.349 | −34.555 | 1.00 | 47.68 | C |
| ATOM | 2348 | O | GLY | A | 701 | −14.369 | 12.541 | −33.837 | 1.00 | 43.98 | O |
| ATOM | 2349 | N | ALA | A | 702 | −14.461 | 14.540 | −34.866 | 1.00 | 43.33 | N |
| ATOM | 2350 | CA | ALA | A | 702 | −13.153 | 14.955 | −34.361 | 1.00 | 43.89 | C |
| ATOM | 2351 | C | ALA | A | 702 | −13.213 | 15.151 | −32.850 | 1.00 | 43.46 | C |
| ATOM | 2352 | O | ALA | A | 702 | −12.260 | 14.857 | −32.138 | 1.00 | 43.27 | O |
| ATOM | 2353 | CB | ALA | A | 702 | −12.689 | 16.238 | −35.041 | 1.00 | 38.33 | C |
| ATOM | 2354 | N | MET | A | 703 | −14.333 | 15.670 | −32.373 | 1.00 | 36.37 | N |
| ATOM | 2355 | CA | MET | A | 703 | −14.534 | 15.900 | −30.938 | 1.00 | 39.77 | C |
| ATOM | 2356 | C | MET | A | 703 | −14.583 | 14.550 | −30.196 | 1.00 | 43.31 | C |

TABLE 3-continued

Atomic coordinates of RSK2 model (pdb file)

| ATOM | 2357 | O | MET | A | 703 | −13.898 | 14.358 | −29.194 | 1.00 | 43.02 | O |
|---|---|---|---|---|---|---|---|---|---|---|---|
| ATOM | 2358 | CB | MET | A | 703 | −15.844 | 16.690 | −30.721 | 1.00 | 44.38 | C |
| ATOM | 2359 | CG | MET | A | 703 | −15.849 | 17.573 | −29.490 | 1.00 | 53.92 | C |
| ATOM | 2360 | SD | MET | A | 703 | −14.584 | 18.863 | −29.530 | 1.00 | 42.25 | S |
| ATOM | 2361 | CE | MET | A | 703 | −15.423 | 20.170 | −30.423 | 1.00 | 45.73 | C |
| ATOM | 2362 | N | ALA | A | 704 | −15.403 | 13.620 | −30.696 | 1.00 | 44.48 | N |
| ATOM | 2363 | CA | ALA | A | 704 | −15.441 | 12.255 | −30.164 | 1.00 | 44.67 | C |
| ATOM | 2364 | C | ALA | A | 704 | −14.036 | 11.631 | −30.088 | 1.00 | 48.00 | C |
| ATOM | 2365 | O | ALA | A | 704 | −13.663 | 11.045 | −29.067 | 1.00 | 41.38 | O |
| ATOM | 2366 | CB | ALA | A | 704 | −16.359 | 11.377 | −31.007 | 1.00 | 45.29 | C |
| ATOM | 2367 | N | ALA | A | 705 | −13.268 | 11.757 | −31.168 | 1.00 | 45.63 | N |
| ATOM | 2368 | CA | ALA | A | 705 | −11.902 | 11.229 | −31.196 | 1.00 | 44.28 | C |
| ATOM | 2369 | C | ALA | A | 705 | −11.016 | 11.892 | −30.135 | 1.00 | 43.64 | C |
| ATOM | 2370 | O | ALA | A | 705 | −10.166 | 11.247 | −29.500 | 1.00 | 43.42 | O |
| ATOM | 2371 | CB | ALA | A | 705 | −11.281 | 11.421 | −32.589 | 1.00 | 45.67 | C |
| ATOM | 2372 | N | THR | A | 706 | −11.198 | 13.193 | −29.962 | 1.00 | 38.93 | N |
| ATOM | 2373 | CA | THR | A | 706 | −10.394 | 13.949 | −29.014 | 1.00 | 42.52 | C |
| ATOM | 2374 | C | THR | A | 706 | −10.657 | 13.479 | −27.572 | 1.00 | 41.02 | C |
| ATOM | 2375 | O | THR | A | 706 | −9.728 | 13.260 | −26.792 | 1.00 | 39.98 | O |
| ATOM | 2376 | CB | THR | A | 706 | −10.705 | 15.453 | −29.100 | 1.00 | 40.12 | C |
| ATOM | 2377 | OG1 | THR | A | 706 | −10.236 | 15.965 | −30.355 | 1.00 | 38.36 | O |
| ATOM | 2378 | CG2 | THR | A | 706 | −9.991 | 16.200 | −27.968 | 1.00 | 45.07 | C |
| ATOM | 2379 | N | TYR | A | 707 | −11.930 | 13.306 | −27.233 | 1.00 | 38.07 | N |
| ATOM | 2380 | CA | TYR | A | 707 | −12.281 | 12.919 | −25.868 | 1.00 | 38.98 | C |
| ATOM | 2381 | C | TYR | A | 707 | −12.061 | 11.442 | −25.591 | 1.00 | 53.44 | C |
| ATOM | 2382 | O | TYR | A | 707 | −11.775 | 11.052 | −24.459 | 1.00 | 46.93 | O |
| ATOM | 2383 | CB | TYR | A | 707 | −13.691 | 13.400 | −25.487 | 1.00 | 38.72 | C |
| ATOM | 2384 | CG | TYR | A | 707 | −13.664 | 14.882 | −25.209 | 1.00 | 38.67 | C |
| ATOM | 2385 | CD1 | TYR | A | 707 | −13.263 | 15.361 | −23.963 | 1.00 | 44.25 | C |
| ATOM | 2386 | CD2 | TYR | A | 707 | −13.961 | 15.806 | −26.212 | 1.00 | 39.38 | C |
| ATOM | 2387 | CE1 | TYR | A | 707 | −13.196 | 16.721 | −23.707 | 1.00 | 41.35 | C |
| ATOM | 2388 | CE2 | TYR | A | 707 | −13.903 | 17.179 | −25.966 | 1.00 | 39.98 | C |
| ATOM | 2389 | CZ | TYR | A | 707 | −13.515 | 17.624 | −24.705 | 1.00 | 46.61 | C |
| ATOM | 2390 | OH | TYR | A | 707 | −13.441 | 18.970 | −24.441 | 1.00 | 44.20 | O |
| ATOM | 2391 | N | SER | A | 708 | −12.168 | 10.627 | −26.631 | 1.00 | 43.35 | N |
| ATOM | 2392 | CA | SER | A | 708 | −11.809 | 9.223 | −26.515 | 1.00 | 46.79 | C |
| ATOM | 2393 | C | SER | A | 708 | −10.328 | 9.088 | −26.171 | 1.00 | 52.37 | C |
| ATOM | 2394 | O | SER | A | 708 | −9.938 | 8.263 | −25.333 | 1.00 | 52.51 | O |
| ATOM | 2395 | CB | SER | A | 708 | −12.092 | 8.491 | −27.820 | 1.00 | 47.88 | C |
| ATOM | 2396 | OG | SER | A | 708 | −11.710 | 7.136 | −27.708 | 1.00 | 55.30 | O |
| ATOM | 2397 | N | ALA | A | 709 | −9.503 | 9.896 | −26.829 | 1.00 | 47.45 | N |
| ATOM | 2398 | CA | ALA | A | 709 | −8.065 | 9.845 | −26.598 | 1.00 | 51.97 | C |
| ATOM | 2399 | C | ALA | A | 709 | −7.764 | 10.282 | −25.162 | 1.00 | 54.76 | C |
| ATOM | 2400 | O | ALA | A | 709 | −6.956 | 9.662 | −24.478 | 1.00 | 60.45 | O |
| ATOM | 2401 | CB | ALA | A | 709 | −7.321 | 10.722 | −27.609 | 1.00 | 47.60 | C |
| ATOM | 2402 | N | LEU | A | 710 | −8.434 | 11.339 | −24.718 | 1.00 | 56.74 | N |
| ATOM | 2403 | CA | LEU | A | 710 | −8.270 | 11.878 | −23.366 | 1.00 | 64.72 | C |
| ATOM | 2404 | C | LEU | A | 710 | −8.610 | 10.895 | −22.243 | 1.00 | 76.00 | C |
| ATOM | 2405 | O | LEU | A | 710 | −7.797 | 10.658 | −21.348 | 1.00 | 77.82 | O |
| ATOM | 2406 | CB | LEU | A | 710 | −9.112 | 13.134 | −23.206 | 1.00 | 57.59 | C |
| ATOM | 2407 | CG | LEU | A | 710 | −8.593 | 14.345 | −23.967 | 1.00 | 61.96 | C |
| ATOM | 2408 | CD1 | LEU | A | 710 | −9.561 | 15.486 | −23.808 | 1.00 | 61.59 | C |
| ATOM | 2409 | CD2 | LEU | A | 710 | −7.222 | 14.726 | −23.457 | 1.00 | 63.32 | C |
| ATOM | 2410 | N | ASN | A | 711 | −9.809 | 10.325 | −22.284 | 1.00 | 76.30 | N |
| ATOM | 2411 | CA | ASN | A | 711 | −10.221 | 9.357 | −21.268 | 1.00 | 82.11 | C |
| ATOM | 2412 | C | ASN | A | 711 | −9.406 | 8.064 | −21.358 | 1.00 | 85.04 | C |
| ATOM | 2413 | O | ASN | A | 711 | −9.437 | 7.229 | −20.457 | 1.00 | 96.57 | O |
| ATOM | 2414 | CB | ASN | A | 711 | −11.721 | 9.073 | −21.382 | 1.00 | 86.23 | C |
| ATOM | 2415 | CG | ASN | A | 711 | −12.547 | 10.344 | −21.558 | 1.00 | 85.56 | C |
| ATOM | 2416 | OD1 | ASN | A | 711 | −12.104 | 11.442 | −21.215 | 1.00 | 79.16 | O |
| ATOM | 2417 | ND2 | ASN | A | 711 | −13.752 | 10.197 | −22.100 | 1.00 | 90.49 | N |
| ATOM | 2418 | N | ARG | A | 712 | −8.674 | 7.929 | −22.459 | 1.00 | 80.63 | N |
| ATOM | 2419 | CA | ARG | A | 712 | −7.774 | 6.810 | −22.710 | 1.00 | 88.96 | C |
| ATOM | 2420 | C | ARG | A | 712 | −8.471 | 5.452 | −22.639 | 1.00 | 105.31 | C |
| ATOM | 2421 | O | ARG | A | 712 | −8.541 | 4.829 | −21.580 | 1.00 | 116.64 | O |
| ATOM | 2422 | CB | ARG | A | 712 | −6.574 | 6.857 | −21.762 | 1.00 | 90.39 | C |
| ATOM | 2423 | CG | ARG | A | 712 | −5.254 | 6.573 | −22.447 | 1.00 | 96.35 | C |
| ATOM | 2424 | CD | ARG | A | 712 | −4.803 | 7.740 | −23.311 | 1.00 | 97.25 | C |
| ATOM | 2425 | NE | ARG | A | 712 | −3.768 | 8.538 | −22.656 | 1.00 | 98.51 | N |
| ATOM | 2426 | CZ | ARG | A | 712 | −3.974 | 9.724 | −22.090 | 1.00 | 86.82 | C |
| ATOM | 2427 | NH1 | ARG | A | 712 | −5.184 | 10.268 | −22.102 | 1.00 | 78.33 | N |
| ATOM | 2428 | NH2 | ARG | A | 712 | −2.964 | 10.367 | −21.515 | 1.00 | 76.84 | N |
| TER | | | | | | | | | | | |
| HETATM | 2429 | NA | NA | B | 1 | −31.488 | 24.535 | −13.655 | 1.00 | 39.63 | NA |
| TER | | | | | | | | | | | |
| HETATM | 2430 | O | HOH | C | 1 | −32.636 | 25.820 | −15.386 | 1.00 | 40.55 | O |
| HETATM | 2431 | O | HOH | C | 2 | −26.467 | 14.643 | −14.746 | 1.00 | 51.27 | O |
| HETATM | 2432 | O | HOH | C | 3 | −19.767 | 14.943 | −14.926 | 1.00 | 44.57 | O |

TABLE 3-continued

Atomic coordinates of RSK2 model (pdb file)

| HETATM | 2433 | O | HOH | C | 5  | −21.928 | 18.736 | −29.891 | 1.00 | 55.29 | O |
|---|---|---|---|---|---|---|---|---|---|---|---|
| HETATM | 2434 | O | HOH | C | 6  | −21.977 | 21.032 | −28.134 | 1.00 | 54.67 | O |
| HETATM | 2435 | O | HOH | C | 7  | −27.024 | 31.068 | −27.661 | 1.00 | 56.54 | O |
| HETATM | 2436 | O | HOH | C | 8  | −17.662 | 23.130 | −38.884 | 1.00 | 41.46 | O |
| HETATM | 2437 | O | HOH | C | 11 | −14.203 | 18.516 | −17.953 | 1.00 | 46.09 | O |
| HETATM | 2438 | O | HOH | C | 12 | −18.349 | 16.392 | −27.389 | 1.00 | 49.93 | O |
| HETATM | 2439 | O | HOH | C | 14 | −28.723 | 32.234 | −18.348 | 1.00 | 53.25 | O |
| HETATM | 2440 | O | HOH | C | 15 | −26.956 | 32.248 | −38.301 | 1.00 | 59.35 | O |
| HETATM | 2441 | O | HOH | C | 16 | −20.720 | 12.766 | −10.061 | 1.00 | 55.94 | O |
| HETATM | 2442 | O | HOH | C | 17 | −9.647  | 18.691 | −30.771 | 1.00 | 42.06 | O |
| HETATM | 2443 | O | HOH | C | 18 | −4.993  | 19.226 | −35.870 | 1.00 | 64.44 | O |
| HETATM | 2444 | O | HOH | C | 19 | −4.979  | 23.550 | −34.509 | 1.00 | 49.96 | O |
| HETATM | 2445 | O | HOH | C | 20 | −11.079 | 11.645 | −39.981 | 1.00 | 65.65 | O |
| HETATM | 2446 | O | HOH | C | 21 | −9.097  | 8.971  | −30.113 | 1.00 | 51.44 | O |
| HETATM | 2447 | O | HOH | C | 23 | −11.894 | 27.746 | −12.255 | 1.00 | 41.17 | O |
| HETATM | 2448 | O | HOH | C | 24 | −19.401 | 38.292 | −22.877 | 1.00 | 44.74 | O |
| HETATM | 2449 | O | HOH | C | 25 | −20.395 | 17.757 | −41.859 | 1.00 | 50.55 | O |
| HETATM | 2450 | O | HOH | C | 26 | −23.910 | 14.925 | −37.256 | 1.00 | 57.58 | O |
| HETATM | 2451 | O | HOH | C | 27 | −18.823 | 14.617 | −30.578 | 1.00 | 45.53 | O |
| HETATM | 2452 | O | HOH | C | 28 | −38.818 | 18.785 | −19.917 | 1.00 | 50.45 | O |
| HETATM | 2453 | O | HOH | C | 29 | −32.416 | 15.673 | −22.286 | 1.00 | 58.96 | O |
| HETATM | 2454 | O | HOH | C | 30 | −32.355 | 18.247 | −28.169 | 1.00 | 57.23 | O |
| HETATM | 2455 | O | HOH | C | 31 | −20.446 | 18.396 | −32.356 | 1.00 | 55.83 | O |
| HETATM | 2456 | O | HOH | C | 32 | −19.578 | 17.127 | −30.036 | 1.00 | 52.70 | O |
| HETATM | 2457 | O | HOH | C | 33 | −17.570 | 14.311 | −27.991 | 1.00 | 48.55 | O |
| HETATM | 2458 | O | HOH | C | 34 | −23.389 | 17.282 | −36.853 | 1.00 | 50.44 | O |
| HETATM | 2459 | O | HOH | C | 35 | −25.031 | 31.785 | −16.358 | 1.00 | 55.02 | O |
| HETATM | 2460 | O | HOH | C | 36 | −9.594  | 26.313 | −12.794 | 1.00 | 47.26 | O |
| HETATM | 2461 | O | HOH | C | 37 | −7.739  | 26.687 | −14.929 | 1.00 | 48.92 | O |
| HETATM | 2462 | O | HOH | C | 38 | −12.583 | 30.135 | −10.948 | 1.00 | 49.79 | O |
| HETATM | 2463 | O | HOH | C | 39 | −13.577 | 17.248 | −19.943 | 1.00 | 53.44 | O |
| HETATM | 2464 | O | HOH | C | 40 | −18.751 | 20.391 | −2.679  | 1.00 | 61.13 | O |
| HETATM | 2465 | O | HOH | C | 41 | −21.946 | 15.441 | −3.885  | 1.00 | 58.51 | O |
| HETATM | 2466 | O | HOH | C | 42 | −11.866 | 19.681 | −36.557 | 1.00 | 44.87 | O |
| HETATM | 2467 | O | HOH | C | 43 | −17.480 | 12.603 | −38.174 | 1.00 | 47.32 | O |
| HETATM | 2468 | O | HOH | C | 44 | −8.876  | 12.675 | −40.019 | 1.00 | 63.50 | O |
| HETATM | 2469 | O | HOH | C | 45 | −17.253 | 38.072 | −35.996 | 1.00 | 65.87 | O |
| HETATM | 2470 | O | HOH | C | 46 | −21.247 | 19.449 | −34.579 | 1.00 | 55.33 | O |
| HETATM | 2471 | O | HOH | C | 48 | −22.870 | 9.738  | −16.223 | 1.00 | 72.56 | O |
| HETATM | 2472 | O | HOH | C | 51 | −49.842 | 19.919 | −18.763 | 1.00 | 60.38 | O |
| HETATM | 2473 | O | HOH | C | 52 | −43.587 | 19.075 | −22.180 | 1.00 | 64.83 | O |
| HETATM | 2474 | O | HOH | C | 53 | −17.308 | 14.190 | −2.774  | 1.00 | 59.16 | O |
| HETATM | 2475 | O | HOH | C | 54 | −35.681 | 26.001 | −12.054 | 1.00 | 67.34 | O |
| HETATM | 2476 | O | HOH | C | 55 | −26.972 | 34.204 | −19.854 | 1.00 | 64.53 | O |
| HETATM | 2477 | O | HOH | C | 56 | −19.188 | 25.775 | −38.874 | 1.00 | 48.60 | O |
| HETATM | 2478 | O | HOH | C | 57 | −21.244 | 26.964 | −41.091 | 1.00 | 88.31 | O |
| HETATM | 2479 | O | HOH | C | 58 | −28.278 | 26.066 | −36.583 | 1.00 | 51.80 | O |
| HETATM | 2480 | O | HOH | C | 60 | −14.487 | 37.972 | −36.305 | 1.00 | 59.45 | O |
| HETATM | 2481 | O | HOH | C | 61 | −13.392 | 32.614 | −38.250 | 1.00 | 63.91 | O |
| HETATM | 2482 | O | HOH | C | 62 | −22.124 | 38.745 | −22.968 | 1.00 | 61.38 | O |
| HETATM | 2483 | O | HOH | C | 63 | −23.296 | 31.666 | −12.070 | 1.00 | 63.18 | O |
| HETATM | 2484 | O | HOH | C | 65 | −14.717 | 29.989 | −9.096  | 1.00 | 50.67 | O |
| HETATM | 2485 | O | HOH | C | 66 | −11.620 | 16.033 | −7.873  | 1.00 | 59.76 | O |
| HETATM | 2486 | O | HOH | C | 68 | −38.192 | 20.735 | −22.286 | 1.00 | 60.14 | O |
| HETATM | 2487 | O | HOH | C | 69 | −11.945 | 19.550 | −39.318 | 1.00 | 47.67 | O |
| HETATM | 2488 | O | HOH | C | 70 | −2.996  | 20.835 | −33.270 | 1.00 | 58.09 | O |
| HETATM | 2489 | O | HOH | C | 71 | −7.135  | 20.747 | −36.193 | 1.00 | 54.72 | O |
| HETATM | 2490 | O | HOH | C | 73 | −0.997  | 29.188 | −24.899 | 1.00 | 62.24 | O |
| HETATM | 2491 | O | HOH | C | 74 | −3.914  | 43.077 | −30.195 | 1.00 | 57.15 | O |
| HETATM | 2492 | O | HOH | C | 75 | −5.344  | 27.127 | −13.672 | 1.00 | 50.75 | O |
| HETATM | 2493 | O | HOH | C | 76 | −7.783  | 24.771 | −11.206 | 1.00 | 51.65 | O |
| HETATM | 2494 | O | HOH | C | 77 | −23.854 | 22.679 | −42.214 | 1.00 | 58.39 | O |
| HETATM | 2495 | O | HOH | C | 78 | −16.649 | 12.176 | −40.600 | 1.00 | 53.20 | O |
| HETATM | 2496 | O | HOH | C | 80 | −9.654  | 8.030  | −32.912 | 1.00 | 68.94 | O |
| HETATM | 2497 | O | HOH | C | 81 | −15.431 | 10.244 | −27.128 | 1.00 | 47.83 | O |
| HETATM | 2498 | O | HOH | C | 84 | −13.596 | 23.230 | −6.760  | 1.00 | 58.68 | O |
| HETATM | 2499 | O | HOH | C | 85 | −11.286 | 24.450 | −7.321  | 1.00 | 74.31 | O |
| HETATM | 2500 | O | HOH | C | 86 | −9.137  | 6.881  | −28.733 | 1.00 | 57.50 | O |
| HETATM | 2501 | O | HOH | C | 87 | 1.326   | 10.634 | −28.584 | 1.00 | 70.53 | O |
| HETATM | 2502 | O | HOH | C | 88 | −9.015  | 42.504 | −30.755 | 1.00 | 60.43 | O |
| HETATM | 2503 | O | HOH | C | 89 | −17.667 | 39.129 | −16.837 | 1.00 | 61.70 | O |
| HETATM | 2504 | O | HOH | C | 90 | −34.491 | 28.815 | −20.223 | 1.00 | 65.43 | O |
| HETATM | 2505 | O | HOH | C | 91 | −27.739 | 15.059 | −17.377 | 1.00 | 61.15 | O |
| HETATM | 2506 | O | HOH | C | 93 | −5.543  | 19.404 | −15.606 | 1.00 | 73.05 | O |
| HETATM | 2507 | O | HOH | C | 95 | −33.642 | 21.164 | −32.087 | 1.00 | 61.04 | O |
| HETATM | 2508 | O | HOH | C | 96 | −30.337 | 15.575 | −20.884 | 1.00 | 75.39 | O |
| HETATM | 2509 | O | HOH | C | 97 | −37.806 | 5.711  | −5.034  | 1.00 | 71.43 | O |
| HETATM | 2510 | O | HOH | C | 98 | −38.023 | 22.719 | −23.836 | 1.00 | 51.12 | O |

TABLE 3-continued

Atomic coordinates of RSK2 model (pdb file)

| | | | | | | | | | | | |
|---|---|---|---|---|---|---|---|---|---|---|---|
| HETATM | 2511 | O | HOH | C | 99 | −31.891 | 24.700 | −31.405 | 1.00 | 67.52 | O |
| HETATM | 2512 | O | HOH | C | 100 | −28.164 | 19.674 | −32.197 | 1.00 | 72.74 | O |
| HETATM | 2513 | O | HOH | C | 101 | −31.095 | 26.965 | −29.990 | 1.00 | 68.13 | O |
| HETATM | 2514 | O | HOH | C | 102 | −27.648 | 17.774 | −31.259 | 1.00 | 56.34 | O |
| HETATM | 2515 | O | HOH | C | 103 | −19.464 | 27.980 | −42.348 | 1.00 | 82.08 | O |
| HETATM | 2516 | O | HOH | C | 104 | −25.287 | 33.732 | −28.534 | 1.00 | 68.00 | O |
| HETATM | 2517 | O | HOH | C | 105 | −20.548 | 32.547 | −11.654 | 1.00 | 81.80 | O |
| HETATM | 2518 | O | HOH | C | 106 | −11.274 | 14.461 | −16.053 | 1.00 | 68.12 | O |
| HETATM | 2519 | O | HOH | C | 107 | −16.813 | 22.101 | −23.823 | 1.00 | 45.10 | O |
| HETATM | 2520 | O | HOH | C | 108 | −17.466 | 11.687 | −26.812 | 1.00 | 47.26 | O |
| HETATM | 2521 | O | HOH | C | 109 | −16.227 | 11.401 | −22.646 | 1.00 | 79.59 | O |
| HETATM | 2522 | O | HOH | C | 110 | −22.352 | 17.010 | −32.208 | 1.00 | 86.48 | O |
| HETATM | 2523 | O | HOH | C | 111 | −32.150 | 29.849 | −17.637 | 1.00 | 58.70 | O |
| HETATM | 2524 | O | HOH | C | 112 | −11.387 | 16.284 | 7.657 | 1.00 | 66.65 | O |
| HETATM | 2525 | O | HOH | C | 113 | −3.661 | 22.013 | −24.672 | 1.00 | 50.02 | O |
| HETATM | 2526 | O | HOH | C | 114 | −42.439 | 11.599 | −29.637 | 1.00 | 70.82 | O |
| HETATM | 2527 | O | HOH | C | 115 | −42.938 | 8.633 | −29.627 | 1.00 | 69.44 | O |
| HETATM | 2528 | O | HOH | C | 116 | −42.939 | 16.456 | −28.113 | 1.00 | 60.92 | O |
| HETATM | 2529 | O | HOH | C | 117 | 0.102 | 27.067 | −30.339 | 1.00 | 74.26 | O |
| HETATM | 2530 | O | HOH | C | 118 | −7.692 | 42.195 | −33.970 | 1.00 | 68.44 | O |
| HETATM | 2531 | O | HOH | C | 119 | −8.862 | 32.773 | −10.234 | 1.00 | 54.83 | O |
| HETATM | 2532 | O | HOH | C | 120 | −10.735 | 30.983 | −8.916 | 1.00 | 53.95 | O |
| HETATM | 2533 | O | HOH | C | 121 | −8.303 | 37.787 | −17.388 | 1.00 | 61.11 | O |
| HETATM | 2534 | O | HOH | C | 122 | −20.041 | 31.220 | −39.780 | 1.00 | 70.76 | O |
| HETATM | 2535 | O | HOH | C | 123 | −20.168 | 29.089 | −40.470 | 1.00 | 56.82 | O |
| TER | | | | | | | | | | | |
| HETATM | 2536 | C01 | LIG | D | 1 | −6.612 | 14.457 | −17.611 | 1.00 | 76.64 | A C |
| HETATM | 2537 | O02 | LIG | D | 1 | −7.363 | 15.243 | −18.461 | 1.00 | 66.93 | A O |
| HETATM | 2538 | C03 | LIG | D | 1 | −7.297 | 16.617 | −18.392 | 1.00 | 72.43 | A C |
| HETATM | 2539 | O04 | LIG | D | 1 | −6.466 | 17.159 | −17.679 | 1.00 | 74.34 | A O |
| HETATM | 2540 | C05 | LIG | D | 1 | −8.022 | 17.443 | −19.403 | 1.00 | 64.52 | A C |
| HETATM | 2541 | C06 | LIG | D | 1 | −7.375 | 18.741 | −19.759 | 1.00 | 55.65 | A C |
| HETATM | 2542 | C07 | LIG | D | 1 | −6.102 | 18.623 | −20.529 | 1.00 | 45.83 | A C |
| HETATM | 2543 | O08 | LIG | D | 1 | −5.801 | 17.548 | −21.029 | 1.00 | 57.00 | A O |
| HETATM | 2544 | O09 | LIG | D | 1 | −5.297 | 19.713 | −20.751 | 1.00 | 55.39 | A O |
| HETATM | 2545 | C10 | LIG | D | 1 | −4.201 | 19.565 | −21.590 | 1.00 | 49.72 | A C |
| TER | | | | | | | | | | | |
| END | | | | | | | | | | | |

Example 5

Mass Spectrometric Analysis

RSK2 samples were reduced and alkylated with iodoacetamide, i.e. carbamidomethylated, and subsequently digested with chymotrypsin. The resulting peptides were concentrated on a ZipTip micropurification column and eluted onto an anchorchip target for analysis on a Bruker Autoflex Speed MALDI TOF/TOF instrument. The peptide mixture was analyzed in positive reflector mode for accurate peptide mass determination. MALDI MS/MS was performed on 15 peptides for peptide fragmentation analysis, i.e partial sequencing. The MS and MS/MS spectra were combined and used for database searching using the Mascot software. The data was searched against RSK2 sequence and identified based on a probability-scoring algorithm (www.matrixscience.com).

Example 6

Analysis of Mutants

Mutational analysis of MSK1 was performed in a mammalian expression vector (pEBG2T) in which a glutathione S-transferase (GST) domain and FLAG-tag (Asp-Tyr-Lys-Asp-Asp-Asp-Asp-Lys) was fused to the N-terminus of human MSK1 (GST-FLAG-MSK1)[6]. The positions corresponding to C436, T579 and C599 in murine RSK2 (SEQ ID NO: 1) of human MSK1 (C440, T583 and C603) were mutated to Val, Ser and Thr (For T583 only an Ala mutation was performed) using the QuikChange Lightning Kit (Agilent Technologies).

Human embryonic kidney cells (HEK-293) were cultured in tissue culture flasks (150 cm$^2$) to 60% confluence in Dulbecco's modified Eagle's medium (DMEM) (Gibco) supplemented with 50 units/ml penicillin G (Gibco), 50 Mg/ml streptomycin (Invitrogen), 5 µg/ml gentamycin (Gibco), 10% (v/v) foetal bovine serum (FBS) (Gibco) and 2.5% HEPES (Gibco). Cells were trypsinated and seeded in 10 cm petri dishes at a density of 6.5×10$^6$ cells per dish in 10 ml DMEM supplemented with 50 µg/ml bovine pituitary growth hormone (BGH) (Gibco), antibiotics (penicillin G, streptomycin, gentamycin) and 2% FBS and 2.5% HEPES and were incubated for 2 days. The culture medium was changed to 7 ml DMEM supplemented with 2.5% Hepes for 16 hours. Transfection with plasmids was performed as previously described Jensen et al. 1999[57] with modifications. HEK-293 cells were transfected using 3.5 µg plasmid DNA/dish dissolved in 250 µl Optimem (Invitrogen) and 30 µl Lipofectamine 2000 (Invitrogen) dissolved in 250 µl Optimem added together for 20 minutes before transferred to cells. The Lipofectamine and DNA complexes were incubated with cells for 6 hours at 37° C. and 5% CO$_2$. Cell culture medium was then changed back to 7 ml DMEM special growth medium with BGH, antibiotics, 2% FCS and 2.5% HEPES for 48 hours.

Dimethylfumarate (DMF) (Sigma-Aldrich) was dissolved in dimethylsulfoxide (DMSO) (Merck) resulting in a 70 mM stock solution and diluted to 7 mM (4% v/v DMSO) in culture medium. All stock solutions were freshly made 10 min before use. HEK 293 cells were stimulated like keratinocytes, as previously described Gesser et al. 2011[46]. Cells were either left untreated or were pre-incubated with 140 µM of DMF for 1 hour and stimulated for 15 minutes for RSK2 and 30 minutes for MSK1 plasmids with 1 ng/ml of human recombinant Epidermal growth factor (EGF) (PeproTech UK). Cells were stopped after one wash with ice-cold PBS and snap-frozen in liquid nitrogen. Whole-cell extracts were prepared by adding 400 µl of 1× cell lysis sample buffer (Cell Signalling Technology) to each 10 cm dish. The 1× lysis buffer was supplemented with 22 µl protease inhibitor cocktail (EDTA-free complete, Roche Diagnostics), and 10 µl of 100 mM PMSF/ml buffer. The collected samples were sonicated and centrifuged for 10 minutes at 4° C. at 10.000 g and the supernatants were saved for protein determination. Equal loads of protein (50 µg) were separated on pre-cast gels, SDS-Page 8-16% (Invitrogen). Proteins were blotted onto Hybond nitrocellulose membrane (Amersham) and tested with antibodies as previously described (Gesser et al. 2007, 2011). Antibodies for Western Blotting: Primary antibodies were rabbit anti-phospho-MSK1 (Ser376) and rabbit anti-phospho-RSK2 (Ser386) and mouse anti-GST (26H1); Secondary antibodies were HRP anti-rabbit #7074, HRP anti-mouse #7076 (all from Cell Signalling). Densitometry analysis of the band intensity was performed on a flatbed scanner (Epson PERFECTION V750PRO) and quantitated by Jelly Quant.

For affinity purification 1 mg protein/sample, in about 300 µl/well were added to a GST affinity MultiTrap 4B 96-well filter plate (GE Healthcare). After two washes with binding buffer, proteins were eluted in 200 µl of 50 mM Tris-HCl buffer added 20 mM reduced glutathione (Sigma-Aldrich) pH 8.0 and were concentrated by freeze drying. The proteins were re-dissolved in 28 µl of 1× lysis buffer plus 14 µl of 3×SDS lysis buffer/sample and 21 µl/sample was separated on SDS-PAGE 8-16% gels. Mutational studies identified the cysteine C603, in MSK1 corresponding to C599 in murine RSK2 as vital for the inhibition of the RSK and MSK kinases by DMF.

Example 7

Docking and in Silico Screening

Two grids is calculated using Maestro version 8.0 with Exhaustive Sampling of Optimize H-bonds, one grid with Minimize structure within 0.3 Å and one without Minimize for the refined structure of DMF bound to RSK2. The bounding box is defined as the centroid of residue C599 with standard value dimensions.

Ligands are built in Maestro as fumaric acid ester derivatives, resulting in 100 compounds. Ligands are energy minimized in MacroModel with the OPLS_2005 force field and maximum iterations set to 10000.

Docking is performed into all the grids generated using the XP scoring function. Constraints are applied so that a C—S bond was formed between the ligand and RSK2. Derivatives are chosen for synthesis and in vitro testing based on both G-score and manual inspection of the docking pose. Additionally, consistently poorly scoring/docking ligands that are very similar to those chosen for synthesis are also synthesized as negative controls. Docking and in silico screening identifies potential drug candidates.

Example 8

In Vitro Test of Drug Candidates 1

Normal adult human keratinocytes were obtained by trypsinization of skin samples from patients undergoing surgery as described earlier (Kragballe et al. 1985[61]) First passage keratinocytes are grown in keratinocyte serum-free medium (Invitrogen) added supplement (Gibco 37000-15) and 5 µg/ml gentamycin (Gibco) to 60% confluence. Cells are then trypsinated and seeded in 6-well plates at 400×10³ cells/well in keratinocyte basal medium (Gibco 37000-015), supplemented with only bovine pituitary growth hormone (Gibco 15710), 50 µg/ml bovine pituitary extract (Gibco), 5 µg/ml gentamycin and 2% FCS (Gibco) as described before[51]. After 24 h, cells are pre-incubated with vehicle or drug candidates (1, 10 and 100 µM) for 1 hour and stimulated with 2 ng/ml human recombinant EGF (AF-100-15, PeproTech EC, London, UK) for 5, 15 and 30 min as described before[51]. cells were collected after wash with ice-cold PBS and snap-frozen in liquid nitrogen. Whole cell extracts are prepared in 100 µl of sample buffer as previously described[39] Alternatively, cells are left alone or pre-incubated with drug candidates for 1 h and then stimulated with IL-1β (20 ng/ml)(Pepro Tech INC) or rh-TNF-α (10 ng/ml) (R&D Systems, Minneapolis) for 0, 5, 15 or 30 min as described before[39]

Equal loads of proteins (50 µg/lane) are separated on 8-16% SDS-PAGE Tris-glycine gels (Invitrogen) and after Western Blotting probed with anti-p-MSK1 (S376) and anti-p-RSK2 (S386) antibodies as previously described[51].

Drug candidates are solubilised in DMSO 100 mM (Sigma-Aldrich) and diluted to 1 mM stock solution (2% v/v DMSO) in keratinocyte basal medium 10 minutes before use. Drug candidates are directly added to cell culture medium to final concentration of 1, 10 and 100 µM.

Example 9

In Vitro Test of Drug Candidates 2

Peripheral blood mononuclear cells (PBMCs) are purified by Lymphoprep density gradient media (Axis-Shield) from EDTA blood of normal human donors as described before. Cells are washed with cold sterile Dulbecco's PBS (Gibco) and seeded at 6×10⁶ cells/petri dish in 10 ml RPMI 1640 (Gibco) supplemented with penicillin (10,000 units/mil), streptomycin (10 mg/ml) (Gibco) and gentamycin (2.5 mg/ml) in 10² cm petri dishes. Cells are pre-incubated with vehicle or drug candidates (1, 10 100 µM) for 1 h and either left alone or stimulated with 10 ng/ml IL-1β (R&D Systems) or 2 ng/ml EGF (Gibco) for 0, 10 and 20 minutes. After stimulation, petri dishes are placed on ice and cells are collected by ice cold Dulbecco's PBS and centrifuged 1400 rpm for 10 minutes. Supernatants are removed and cells are added 100 µl of 1× cell Lysis sample buffer (Cell Signalling Technology)/sample. After protein determination, 20 µg protein/lane is separated on 8-16% SDS-PAGE Tris-glycin gels (Invitrogen) and after Western Blotting probed with anti-p-MSK1 (S376) and anti-p-RSK2 (S386) antibodies as previously described[51]. Drug candidates are solubilised in DMSO (Sigma-Aldrich) 100 mM and diluted to 1 mM stock solution (2% v/v DMSO) in RPMI 1640 medium 10 minutes before use. Drug candidates are directly added to cell culture medium to final concentration of 1, 10 and 100 µM.

Example 10

In Vivo Test of Drug Candidates

Experimental autoimmune encephalomyelitis (EAE), a reliable and widely used mouse-model of multiple sclerosis (MS) and is similarly to Schilling et al. 2006[7] carried out. EAE is induced in mice by s.c. injections in the flanks and tail base of 50 μg MOG 35-55 peptide in PBS emulsified in an equal volume of complete Freund's adjuvant (CFA) containing *Mycobacterium tuberculosis* H37RA (Difco) at a final concentration of 0.5 mg/ml. Two injections of 200 ng per mouse i.p of pertussis toxin (List Biological Laboratories Inc.) are given on days 0 and 2. Animals are weighed and scored for clinical signs of disease on a daily basis as previously described. Drug candidates are freshly diluted in 200 μl 0.08% Methocel (DOW)/$H_2O$ (before use) and is used as vehicle and administered by oral gavage starting from day 3 post immunization (p.i) until termination. Each treatment group consists of 8 animals: vehicle alone as a negative control, 5 mg/kg body weight drug candidate twice a day, 15 mg/kg body weight drug candidate twice a day. The lower drug candidate dose is correlated to the dose used in human psoriasis in clinical trials. The threefold higher dosage of drug candidate was used to compensate for body surface disparity of mice. Oral gavage is used to ensure exact dosing and to avoid compound degradation. Mice are deeply anaesthesized with ketamine/xylazine hydrochloride in the early chronic phase and perfused with saline followed by 4% of paraformaldehyde. The complete spinal cord is carefully removed and axial sections were paraffin embedded. Paraffin sections are subjected to haematoxylin/eosin (H&E) staining to assess parameters of inflammatory infiltrates.

REFERENCES

1 Altmeyer, P. J. et al. Antipsoriatic effect of fumaric acid derivatives. Results of a multicenter double-blind study in 100 patients. *J Am Acad Dermatol* 30, 977-981 (1994).
2 Brewer, L. & Rogers, S. Fumaric acid esters in the management of severe psoriasis. *Clin Exp Dermatol* 32, 246-249, doi:10.1111/j.1365-2230.2007.02389.x (2007).
3 Hoefnagel, J. J., Thio, H. B., Willemze, R. & Bouwes Bavinck, J. N. Long-term safety aspects of systemic therapy with fumaric acid esters in severe psoriasis. *Br J Dermatol* 149, 363-369 (2003).
4 Kolbach, D. N. & Nieboer, C. Fumaric acid therapy in psoriasis: results and side effects of 2 years of treatment. *J Am Acad Dermatol* 27, 769-771 (1992).
5 Mrowietz, U., Christophers, E. & Altmeyer, P. Treatment of psoriasis with fumaric acid esters: results of a prospective multicentre study. German Multicentre Study. *Br J Dermatol* 138, 456-460 (1998).
6 Thio, H. B., van der Schroeff, J. G., Nugteren-Huying, W. M. & Vermeer, B. J. Long-term systemic therapy with dimethylfumarate and monoethylfumarate (fumaderm ¬/-E) in psoriasis. *Journal of the European Academy of Dermatology and Venereology* 4, 35-40, doi:10.1016/0926-9959(94)00056-6 (1995).
7 Schilling, S., Goelz, S., Linker, R., Luehder, F. & Gold, R. Fumaric acid esters are effective in chronic experimental autoimmune encephalomyelitis and suppress macrophage infiltration. *Clinical & Experimental Immunology* 145, 101-107 (2006).
8 Schimrigk, S. et al. Oral fumaric acid esters for the treatment of active multiple sclerosis: an open-label, baseline-controlled pilot study. *Eur J Neurol* 13, 604-610, doi:10.1111/j.1468-1331.2006.01292.x (2006).
9 Kappos, L. et al. Efficacy and safety of oral fumarate in patients with relapsing-remitting multiple sclerosis: a multicentre, randomised, double-blind, placebo-controlled phase IIb study. *Lancet* 372, 1463-1472, doi: 10.1016/S0140-6736(08)61619-0 (2008).
10 Schweckendiek, W. [Treatment of psoriasis vulgaris]. *Med Monatsschr* 13, 103-104 (1959).
11 Mrowietz, U. & Asadullah, K. Dimethylfumarate for psoriasis: more than a dietary curiosity. *Trends Mol Med* 11, 43-48, doi:10.1016/j.molmed.2004.11.003 (2005).
12 Nieboer, C., de Hoop, D., van Loenen, A. C., Langendijk, P. N. & van Dijk, E. Systemic therapy with fumaric acid derivates: new possibilities in the treatment of psoriasis. *J Am Acad Dermatol* 20, 601-608 (1989).
13 BG 12: BG 00012, BG 12/Oral Fumarate, FAG-201, second-generation fumarate derivative—Fumapharm/Biogen Idec. *Drugs R D* 6, 229-230 (2005).
14 Kappos, L. et al. Effect of BG-12 on contrast-enhanced lesions in patients with relapsing, Äi remitting multiple sclerosis: subgroup analyses from the phase 2b study. *Multiple Sclerosis Journal* 18, 314-321, doi:10.1177/1352458511421054 (2012).
15 http://www.medscape.com/viewarticle/752287. (Accessed on Feb. 1, 2012.).
16 Gambichler, T. et al. Clearance of necrobiosis lipoidica with fumaric acid esters. *Dermatology* 207, 422-424, doi:74133 (2003).
17 Kreuter, A. et al. Fumaric acid esters in necrobiosis lipoidica: results of a prospective noncontrolled study. *Br J Dermatol* 153, 802-807, doi:10.1111/j.1365-2133.2005.06762.x (2005).
18 Breuer, K., Gutzmer, R., Volker, B., Kapp, A. & Werfel, T. Therapy of noninfectious granulomatous skin diseases with fumaric acid esters. *Br J Dermatol* 152, 1290-1295, doi:10.1111/j.1365-2133.2005.06585.x (2005).
19 Eberle, F. C., Ghoreschi, K. & Hertl, M. Fumaric acid esters in severe ulcerative necrobiosis lipoidica: a case report and evaluation of current therapies. *Acta Derm Venereol* 90, 104-106, doi:10.2340/00015555-0757 (2010).
20 Eberlein-Konig, B. et al. Disseminated granuloma annulare—treatment with fumaric acid esters. *Dermatology* 210, 223-226, doi:10.1159/000083514 (2005).
21 Weber, H. O., Borelli, C., Rocken, M. & Schaller, M. Treatment of disseminated granuloma annulare with low-dose fumaric acid. *Acta Derm Venereol* 89, 295-298, doi:10.2340/00015555-0647 (2009).
22 Schulze-Dirks, A. & Petzoldt, D. [Granuloma annulare disseminatum: successful therapy with fumaric acid ester]. *Hautarzt* 52, 228-230 (2001).
23 Venten, I., Hess, N., Hirschmuller, A., Altmeyer, P. & Brockmeyer, N. Treatment of therapy-resistant Alopecia areata with fumaric acid esters. *Eur J Med Res* 11, 300-305 (2006).
24 Kleine, R., Brohl, L. & Amon, U. [Treatment of granulomatous cheilitis with fumaric acid esters in a young woman]. *Hautarzt* 62, 940-942, doi:10.1007/s00105-011-2174-1 (2011).
25 Guenova, E. & Hoetzenecker, W. Treatment of recurrent aphthous stomatitis with fumaric acid esters. *Arch Dermatol* 147, 282-284, doi:10.1001/archdermatol.2011.27 (2011).

26. Gutzmer, R., Kapp, A. & Werfel, T. [Successful treatment of skin and lung sarcoidosis with fumaric acid ester]. *Hautarzt* 55, 553-557, doi:10.1007/s00105-004-0728-1 (2004).
27. Heinz, C. & Heiligenhaus, A. Improvement of noninfectious uveitis with fumaric acid esters: results of a pilot study. *Arch Ophthalmol* 125, 569-571, doi:10.1001/archopht.125.4.569 (2007).
28. Loewe, R. et al. Dimethylfumarate impairs melanoma growth and metastasis. *Cancer Res* 66, 11888-11896, doi:10.1158/0008-5472.CAN-06-2397 (2006).
29. Valero, T. et al. Combination of dacarbazine and dimethylfumarate efficiently reduces melanoma lymph node metastasis. *J Invest Dermatol* 130, 1087-1094, doi: 10.1038/jid.2009.368 (2010).
30. Yamazoe, Y. et al. Dimethylfumarate inhibits tumor cell invasion and metastasis by suppressing the expression and activities of matrix metalloproteinases in melanoma cells. *Cell Biol Int* 33, 1087-1094, doi:10.1016/j.cellbi.2009.06.027 (2009).
31. Ellrichmann, G. et al. Efficacy of fumaric acid esters in the R6/2 and YAC128 models of Huntington's disease. *PLoS One* 6, e16172, doi:10.1371/journal.pone.0016172 (2011).
32. Ghashghaeinia, M. et al. Targeting glutathione by dimethylfumarate protects against experimental malaria by enhancing erythrocyte cell membrane scrambling. *Am J Physiol Cell Physiol* 299, C791-804, doi:10.1152/ajpcell.00014.2010 (2010).
33. Cross, S. A. et al. Dimethyl fumarate, an immune modulator and inducer of the antioxidant response, suppresses HIV replication and macrophage-mediated neurotoxicity: a novel candidate for HIV neuroprotection. *J Immunol* 187, 5015-5025, doi:10.4049/jimmunol.1101868 (2011).
34. Seidel, P., Goulet, S., Hostettler, K., Tamm, M. & Roth, M. DMF inhibits PDGF-BB induced airway smooth muscle cell proliferation through induction of heme-oxygenase-1. *Respir Res* 11, 145, doi:10.1186/1465-9921-11-145 (2010).
35. Meili-Butz, S. et al. Dimethyl fumarate, a small molecule drug for psoriasis, inhibits Nuclear Factor-kappaB and reduces myocardial infarct size in rats. *Eur J Pharmacol* 586, 251-258, doi:10.1016/j.ejphar.2008.02.038 (2008).
36. Seidel, P. et al. Dimethylfumarate inhibits NF-{kappa}B function at multiple levels to limit airway smooth muscle cell cytokine secretion. *Am J Physiol Lung Cell Mol Physiol* 297, L326-339, doi:10.1152/ajplung.90624.2008 (2009).
37. Vandermeeren, M., Janssens, S., Borgers, M. & Geysen, J. Dimethylfumarate is an inhibitor of cytokine-induced E-selectin, VCAM-1, and ICAM-1 expression in human endothelial cells. *Biochem Biophys Res Commun* 234, 19-23, doi:10.1006/bbrc.1997.6570 (1997).
38. Wilms, H. et al. Dimethylfumarate inhibits microglial and astrocytic inflammation by suppressing the synthesis of nitric oxide, IL-1beta, TNF-alpha and IL-6 in an in-vitro model of brain inflammation. *J Neuroinflammation* 7, 30, doi:10.1186/1742-2094-7-30 (2010).
39. Gesser, B. et al. Dimethylfumarate specifically inhibits the mitogen and stress-activated kinases 1 and 2 (MSK1/2): possible role for its anti-psoriatic effect. *J Invest Dermatol* 127, 2129-2137, doi:10.1038/sj.jid.5700859 (2007).
40. Otkjaer, K. et al. IL-20 gene expression is induced by IL-1beta through mitogen-activated protein kinase and NF-kappaB-dependent mechanisms. *J Invest Dermatol* 127, 1326-1336, doi:10.1038/sj.jid.5700713 (2007).
41. Meissner, M. et al. Suppression of VEGFR2 expression in human endothelial cells by dimethylfumarate treatment: evidence for anti-angiogenic action. *J Invest Dermatol* 131, 1356-1364, doi:10.1038/jid.2011.46 (2011).
42. Treumer, F., Zhu, K., Glaser, R. & Mrowietz, U. Dimethylfumarate is a potent inducer of apoptosis in human T cells. *J Invest Dermatol* 121, 1383-1388, doi:10.1111/j.1523-1747.2003.12605.x (2003).
43. de Jong, R. et al. Selective stimulation of T helper 2 cytokine responses by the anti-psoriasis agent monomethylfumarate. *Eur J Immunol* 26, 2067-2074, doi: 10.1002/eji.1830260916 (1996).
44. Rostami-Yazdi, M., Clement, B., Schmidt, T. J., Schinor, D. & Mrowietz, U. Detection of metabolites of fumaric acid esters in human urine: implications for their mode of action. *J Invest Dermatol* 129, 231-234, doi:10.1038/jid.2008.197 (2009).
45. Ghoreschi, K. et al. Fumarates improve psoriasis and multiple sclerosis by inducing type II dendritic cells. *J Exp Med* 208, 2291-2303, doi:10.1084/jem.20100977 (2011).
46. Gesser, B. et al. Dimethylfumarate inhibits MIF-induced proliferation of keratinocytes by inhibiting MSK1 and RSK1 activation and by inducing nuclear p-c-Jun (S63) and p-p53 (S15) expression. *Inflamm Res* 60, 643-653 (2011).
47. Malakhova, M. et al. Structural basis for activation of the autoinhibitory C-terminal kinase domain of p90 RSK2. *Nat Struct Mol Biol* 15, 112-113, doi:10.1038/nsmb1347 (2008).
48. Alessi, D. R. The protein kinase C inhibitors Ro 318220 and GF 109203X are equally potent inhibitors of MAP-KAP kinase-1beta (Rsk-2) and p70 S6 kinase. *FEBS Lett* 402, 121-123 (1997).
49. Smith, J. A. et al. Identification of the first specific inhibitor of p90 ribosomal S6 kinase (RSK) reveals an unexpected role for RSK in cancer cell proliferation. *Cancer Res* 65, 1027-1034 (2005).
50. Nguyen, T. L. et al. Homology model of RSK2 N-terminal kinase domain, structure-based identification of novel RSK2 inhibitors, and preliminary common pharmacophore. *Bioorg Med Chem* 14, 6097-6105, doi: 10.1016/j.bmc.2006.05.001 (2006).
51. Cohen, M. S., Zhang, C., Shokat, K. M. & Taunton, J. Structural bioinformatics-based design of selective, irreversible kinase inhibitors. *Science* 308, 1318-1321, doi: 10.1126/science1108367 (2005).
52. Serafimova, I. M. et al. Reversible targeting of noncatalytic cysteines with chemically tuned electrophiles. *Nat Chem Biol* 8, 471-476, doi:10.1038/nchembio.925 (2012).
53. Kabsch, W. Automatic processing of rotation diffraction data from crystals of initially unknown symmetry and cell constants. *Journal of Applied Crystallography* 26, 795-800 (1993).
54. McCoy, A. J. et al. Phaser crystallographic software. *Journal of Applied Crystallography* 40, 658-674 (2007).
55. Afonine, P. V., Grosse-Kunstleve, R. W. & Adams, P. D. The Phenix refinement framework. CCP4 *NewsI.* 42, contribution 8 (2005).

56 Emsley, P. & Cowtan, K. Coot: model-building tools for molecular graphics. *Acta Crystallographica Section D* 60, 2126-2132 (2004).

57 Jensen, C. J. et al. 90-kDa ribosomal S6 kinase is phosphorylated and activated by 3-phosphoinositide-dependent protein kinase-1. *J Biol Chem* 274, 27168-27176 (1999).

58 Kragballe, K., Desjarlais, L. & Marcelo, C. L. Increased DNA synthesis of uninvolved psoriatic epidermis is maintained in vitro. *Br J Dermatol* 112, 263-270 (1985).

59 Peng H, Guerau-de-Arellano, Mehta V. H. et al. Dimethyl Fumarate Inhibits Dendritic Cell Maturation via Nuclear Factor κB (NF-κB) and Extracellular Signal-regulated Kinase 1 and 2 (ERK1/2) and Mitogen Stress-activated Kinase 1 (MSK1) Signaling. J Biol. Chem. Vol 1287, No. 33 pp. 28017-28026 (2012).

60 Edgar R C (2004) MUSCLE: multiple sequence alignment with high accuracy and high throughput. Nucl Acids Res 32, 1792-1797

---

The invention claimed is:
1. A three dimensional crystal of a complex between:
 a) dimethyl fumarate (DMF) ligand, and
 b) a polypeptide consisting of the sequence of SEQ ID NO: 1 (C-terminal kinase domain of murine ribosomal S6 kinase 2), wherein said crystal is of a tetragonal space group having unit cell parameters of a=b=47 Å±3 Å, c=292 Å±5 Å and α=β=γ=90°±2°.

2. The crystal according to claim 1 wherein the ligand is located in a binding site comprising amino acid residues Y197, A200, C201, W204, I235, H263, V264, R269 or L312 of SEQ ID NO: 1.

3. The crystal according to claim 1, wherein the polypeptide further comprises an affinity tag.

4. The crystal according to claim 3, wherein the polypeptide comprises a protease cleavage site allowing the affinity tag to be removed.

5. The crystal according to claim 1, wherein said crystal is of space group $P4_12_12$.

6. A method for growing a crystal according to claim 1, comprising the steps of:
 a) obtaining a composition comprising 5 to 15 mg/mL of a polypeptide consisting of SEQ ID NO: 1, in a suitable buffer
 b) contacting the composition of a) with a dimethyl fumarate (DMF) ligand,
 c) allowing time for formation of a protein-ligand complex in solution,
 d) mixing the solution comprising the protein-ligand complex of c) with a reservoir solution comprising a precipitant and a buffer,
 e) incubating a drop of the mixture of d) under vapour diffusion conditions versus the reservoir solution, and
 f) obtaining crystals of the protein-ligand complex.

7. The method according to claim 6, further comprising pre-treating the polypeptide with a reducing agent.

8. The method according to claim 7, wherein the reducing agent is tris(2-carboxyethyl)phosphine (TCEP).

9. The method according to claim 6, wherein the reservoir solution is an aqueous solution of:
 a) 0.1 M Bis-Tris pH 6.5, HEPES pH=7.0, or
 b) TrisHCl pH=8.5 and 25% (w/v) polyethylene glycol (PEG) 3350.

10. The method according to claim 6, wherein equal volumes of protein-ligand complex and reservoir solution are mixed in step d).

11. The method according to claim 6, further comprising a step of optimizing the crystal size and diffraction properties by contacting the crystal with an additive.

12. The method according to claim 6, further comprising the steps of:
 a) isolating an initial precipitate; and
 b) growing these by vapour diffusion from hanging or sitting drops.

13. A method for identifying a ligand capable of binding to the binding site of a polypeptide selected from the group consisting of SEQ ID NO: 1, 2, 3, 4, 5, 6, 7, 8, 9, 10, 11, 12, 13, 14, 15, 16, 17, 18, 19 and 20, said method comprising the steps of:
 a) obtaining the crystal of claim 1;
 b) subjecting the crystal obtained in step (a) to X-ray diffraction to obtain an X-ray diffraction pattern;
 c) solving a three dimensional structure of a binding site from the diffraction pattern obtained in step (b), thereby obtaining three dimensional structure of the binding site; and,
 d) identifying ligands that can bind to at least 1 amino acid residue of the binding sites located in any of SEQ ID NO: 1-20 based on the obtained three dimensional structure of the binding site of SEQ ID NO: 1.

14. The method according to claim 13, wherein the atomic coordinates are determined to a resolution selected from the group consisting of at least 5 Å, at least 4 Å, at least 3 Å, at least 2 Å, and at least 1.5 Å.

15. The method according to claim 13, wherein the ligand is selected from the group consisting of non-hydrolyzable peptides and peptide analogues, organic compounds and inorganic compounds.

16. The method according to claim 13, wherein a library of small organic molecules or a library of potential peptide ligands are screened.

17. The method according to claim 13, wherein the one or more ligand(s) is located in a binding site comprising amino acid residues:
 a) Y197, A200, C201, W204, I235, H263, V264, R269 or L312 of SEQ ID NO. 1;
 b) Y196, A199, C200, W203, I234, H262, V263, R268 or L311 of SEQ ID NO. 2;
 c) Y591, G594, C595, W598, I629, H657, V658, R663 or L705 of SEQ ID NO. 3;
 d) Y595, A598, C599, W602, I633, H661, V662, R667 or L710 of SEQ ID NO. 4;
 e) Y588, A591, C592, W595, 626, H654, V655, R660 or L702 of SEQ ID NO. 5;
 f) Y599, A602, C603, W606, I637, H665, M666, R671 or L714 of SEQ ID NO. 6;
 g) Y599, 5602, C603, W606, I641, T669, V670, R675 or F722 of SEQ ID NO. 7;
 h) Y586, 5589, C590, W593, I628, T656, V657, R662 or F709 of SEQ ID NO. 8;
 i) Y580, G583, C584, W587, I618, H646, V647, R652 or L694 of SEQ ID NO. 9;
 j) Y595, A598, C599, W602, I633, H661, V662, R667, L710 of SEQ ID NO. 10;
 k) Y588, A591, C592, W595, I626, H654, V655, R660 or L702 of SEQ ID NO. 11;
 l) Y619, A622, C623, W626, I657, H685, M686, R691 or L731 of SEQ ID NO. 12;
 m) Y663, 5666, C667, W670, I705, T733, V734, R739 or F786 of SEQ ID NO. 13;
 n) Y591, G594, C595, W598, I629, H657, V658, R663 or L705 of SEQ ID NO. 15;
 o) Y595, A598, C599, W602, I633, H661, V662, R667 or L710 of SEQ ID NO. 16;
 p) Y588, A591, C592, W595, I626, H654, V655, R660 or L702 of SEQ ID NO. 17;
 q) Y716, A719, C720, W723, I754 or H782 or M783 or R788 or L828 of SEQ ID NO. 18;
 r) Y575, A578, C579, W582, I617, T645, V646, R651 and F698 of SEQ ID NO. 19 or;
 s) Y586, S589, C590, W593, I628, T656, V657, R662 or F709 of SEQ ID NO. 20.

18. A computer-implemented method for rational drug design comprising:
 a) obtaining the crystal of claim 1;
 b) subjecting the crystal obtained in step (a) to X-ray diffraction to obtain an X-ray diffraction pattern;
 c) solving the three dimensional structure of the polypeptide from the diffraction pattern obtained in step (b), thereby obtaining three dimensional structure of the polypeptide as defined in table 3;
 d) providing on a computer the atomic coordinates of the polypeptide as defined by table 3;

e) providing the structure of a candidate inhibitor molecule; and
f) fitting the structure of the candidate inhibitor molecule to the atomic coordinates of the polypeptide of said table 3.

* * * * *